US006562591B1

(12) United States Patent
Luo et al.

(10) Patent No.: US 6,562,591 B1
(45) Date of Patent: May 13, 2003

(54) GERMINAL CENTER KINASE CELL CYCLE PROTEINS, COMPOSITIONS AND METHODS OF USE

(75) Inventors: Ying Luo, Los Altos, CA (US); C. Alan Fu, San Mateo, CA (US); Mary Shen, Newark, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/425,324

(22) Filed: Oct. 21, 1999

(51) Int. Cl.[7] .......................... C12P 21/06; C12N 1/20; C12N 15/74; C12N 15/00; C07H 21/04

(52) U.S. Cl. .................. 435/69.1; 435/320.1; 435/471; 435/252.3; 536/23.5

(58) Field of Search .............................. 435/69.1, 70.1, 435/71.1, 71.2, 252.3, 320.1, 325, 471; 536/23.5

(56) References Cited

U.S. PATENT DOCUMENTS 6,277,979 B1 * 8/2001 Bingham et al.

FOREIGN PATENT DOCUMENTS

WO WO 94/01548 * 1/1994
WO WO 95/33819 A2 12/1995
WO WO 00/14212 A1 3/2000
WO WO 00/15805 A1 3/2000
WO WO 00/36124 A2 6/2000
WO WO 01/21799 A1 3/2001

OTHER PUBLICATIONS

Su Y–C, et al. NIK is a new Ste20–related kinase that binds NCK and MEKK1 and activates ths SAPK/JNK cascade via a conserved regulatory domain. EMBO J. 16:1279–1290, 1997.*

Ohara O, et al. GenBank Accession No. AB011123. Apr. 10, 1998.*

Nagase T, et al. DNA Res 5:31–39, 1998.*

Herskowitz, "MAP Kinase Pathways in Yeast: For Mating and More," *Cell*, 80:187–197 (1995).

Bagrodia et al., "Cdc42 and PAK–mediated Signaling Leads to Jun Kinase and p38 Mitogen–activated Protein Kinase Activation", *J. Biol. Chem.*, 270:27995–27998 (1995).

Kyriakis et al., "Sounding the Alarm: Protein Kinase Cascades Activated by Stress and Inflammation", *J. Biol. Chem.*, 271:24313–24316 (1996).

Ip et al., "Signal transduction by the c–Jun N–terminal kinase (JNK)—from inflammation to development", *Curr. Opin. Cell Biol.*, 10:205:219 (1998).

Sells et al. "Human p21–activated kinase (Pak1) regulates actin organization in mammalian cells", *Curr. Biol.*, 7:202–210 (1997).

Kyriakis, J., "Signaling by the Germinal Center Kinase Family of Protein Kinases", *J. Biol. Chem.*, 274:5259–5262 (1999).

Pombo et al., "Activation of the SAPK pathway by the human STE20 homologue germinal centre kinase", *Nature*, 377750:754 (1995).

Shi et al., "Activation of Stress–activated Protein Kinase/c–Jun N–terminal Kinase, but not NF–κB, by the Tumor Necrosis Factor (TNF) Receptor 1 through a TNF Receptor–associated Factor 2– and Germinal Center Kinase Related–dependent Pathway", *J. Biol. Chem.*, 272:32102–32107 (1997).

Kiefer et al., "HPK1, a hematopoietic protein kinase activating the SAPK/JNK pathway", *EMBO J.*, 15:7013–7025 (1996).

Diener et al, "Activation of the c–Jun N–terminal kinase pathway by a novel protein kinase related to human germinal center kinase", *Proc. Natl. Acad. Sci.* USA, 94:9687–9692 (1997).

Yao et al., "A Novel Human STE20–related Protein Kinase, HGK, That Specifically Activates the c–Jun N–terminal Kinase Signaling Pathway", *J. Biol. Chem.*, 274:2118–2125 (1999).

Su et al., "NIK is a new Ste20–related kinase that binds NCK and MEKK1 and activates the SAPK/JNK cascade via a conserved regulatory domain", *EMBO J.*, 16:1279–1290 (1997).

Yuasa et al., "Tumor Necrosis Factor Signaling to Stress–activated Prrtein Kinase (SAPK)/Jun $NH_2$–terminal Kinase (JNK) and p38", *J. Biol. Chem.*, 273:22681–22692 (1998).

Eichinger et al., "Characterization and Cloning of a Dictyostelium Ste20–like Protein Kinase That Phosphorylates the Actin–binding Protein Severin", *J. Biol. Chem.*, 273:12952–12959 (1998).

Fu, et al., "TNIK, a Novel Member of the Germinal Center Kinase Family That Activates the c–Jun N–terminal Kinase Pathway and Regulates the Cytoskeleton," *J. Biol Chem* 274(43):30729–30737 (1999).

Kitamura, et al., "Molecular Cloning of $p125^{NAP1}$,a Protein That Associates with an SH3 Domain of Nck," *Biochem Biophys Res Comm* 219:509–514 (1996).

Nagase et al., "Prediction of the Coding Sequences of Unidentified Human Genes. IX. The Complete Sequences of 100 New cDNA Clones from Brain Which Can Code for Large Proteins in vitro," *DNA Research* 5:31–39 (1998).

Rothe et al., "I–TRAF is a novel TRAF–interacting protein that regulates TRAF–mediated signal transduction," *Proc. Natl. Acad. Sci. USA* 93:8241–8246 (Aug. 1996).

Shi et al., "TNF–Mediated Activation of the Stress–Activated Protein Kinase Pathway: TNF Receptor–Associated Factor 2 Recruits and Activates Germinal Center Kinase Related," *J Immunol* 163:3279–3285 (Sep. 1999).

Suzuki et al., "Down–regulation of the INK4 Family of Cyclin–Dependent Kinase Inhibitors by Tax Protein of HTLV–1 through Two Distinct Mechanisms," *Virology* 259:384–391 (1999).

* cited by examiner

*Primary Examiner*—Gary Kunz
*Assistant Examiner*—Robert S. Landsman
(74) *Attorney, Agent, or Firm*—Townsend and Townsend and Crew LLP

(57) ABSTRACT

The present invention is directed to polypeptides, nucleic acids and related molecules which have an effect on or are related to the cell cycle. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention. Further provided by the present invention are methods for identifying novel compositions which mediate cell cycle bioactivity, and the use of such compositions in diagnosis and treatment of disease.

23 Claims, 35 Drawing Sheets

```
TNIK   1 MASDSPARSLDEIDLSALRDPAGIFELVELVGNGTYGQVYKGRHVKTGQLAAIKVMDVTGDEEEEIKQEINMLKKYSHHR
NIK    1 MANDSPAKSLVDIDLSSLRDPAGIFELVEVVGNGTYGQVYKGRHVKT-VTAAIKVMDVTEDEEEEITLEINMLKKYSHHR

TNIK  81 NIATYYGAFIKKNPPGMDDQLWLVMEFCGAGSVTDLIKNTKGNTLKEEWIAYICREILRGLSHLHQHKVIHRDIKGQNVL
NIK   80 NIATYYGAFIKKSPPGHDDQLWLVMEFCGAGSITDLVKNTKGNTLKEDWIAYISREILRGLAHLHIHEVIHRDIKGQNVL

TNIK 161 LTENAEVKLVDFGVSAQLDRTVGRRNTFIGTPYWMAPEVIACDENPDATYDFKSDLWSLGITAIEMAEGAPPLCDMHPMR
NIK  160 LTENAEVKLVDFGVSAQLDRTVGRRNTFIGTPYWMAPEVIACDENPDATYDYRSDLWSCGITAIEMAEGGPPLCDMHPMR

TNIK 241 ALFLIPRNPAPRLKSKKWSKKFQSFIESCLVKNHSQRPATEQLMKHPFIRDQPNERQVRIQLKDHIDRTKKKRGEKDETE
NIK  240 ALFLIPRNPPPRLKSKKWSKKFFSFIEGCLVKNYMQRPSTEQLLKHPFIRDQPNERQVRIQLKDHIDRTRKKRGEKDETE

TNIK 321 YEYSGSEEEEEEN--DSGEPSSILNLPGESTLRRDFLRLQLANKERSEALRRQQLEQQQ--RENEEHKRQLLAERQKRIE
NIK  320 YEYSGSEEEEEEVPEQEGEPSSIVNVPGESTLRRDFLRLQQENKERSEALRRQQLLQEQQLREQEEYKRQLLAERQKRIE

TNIK 397 EQKEQRRRLEEQQRREKELRKQQEREQRR---------------HYEEQMRR--EEERRRAEHEQEYIRRQLEEEQRQLE
NIK  400 QQKEQRRRLEEQQRREREARRQQEREQRRREQEEKRRLEELERRRKEEEERRRAEEEKRRVEREQEYIRRQLEEEQRHLE

TNIK 460 ILQQQLLHEQALLLEYKRKQLEEQRQAERLQRQLKQERDYLVSLQHQRQEQRPVEKKPLYHYKEGMSPSEKPAWAKEVEE
NIK  480 ILQQQLLQEQAMLLHDHRRPHAQQ-QPPPPQQQDRS--------------------KPSFHAPE---P--KP--HYDPAD

TNIK 540 RSRLNRQSSPAMPHKVANRISDPNIPPRSESFSISGVQPARTPPMLRPVDPQIPHLVAVKSQGPALTASQSVHEQPTKGL
NIK  532 RAREVQWS-----HLASLKN---NVSPVSRSHSFSDPSPKFAHHHLRSQDPCPP---SR-----------------SEGL

TNIK 620 SGFQEALNVTSHRVEMPRQNSDPTSENPPLPTRIEKFDRSSWLRQEED-IPPKVPQRTTSISPALARKNSPGNGSALGPR
NIK  584 S-----------------QSSDSKSE-VPEPT------QKAWSRSDSDEVPPRVPVRTTSRSPVLSRRDSPLQGGGQQNS

TNIK 699 LGSQPIRASNPDLRRTEPILESPLQRTSSGSSSSSSTPSSQPSSQGGSQPGSQAGSSERTRVRANSKSEGSPVLPHEPAK
NIK  640 QAGQRNSTSSIEPRLLWERVEKLVPRPGSGSSSGSSNSGSQP----GSHPGSQSGSGERFRVRSSSKSEGSPSPRQESAA
```

FIG._1A

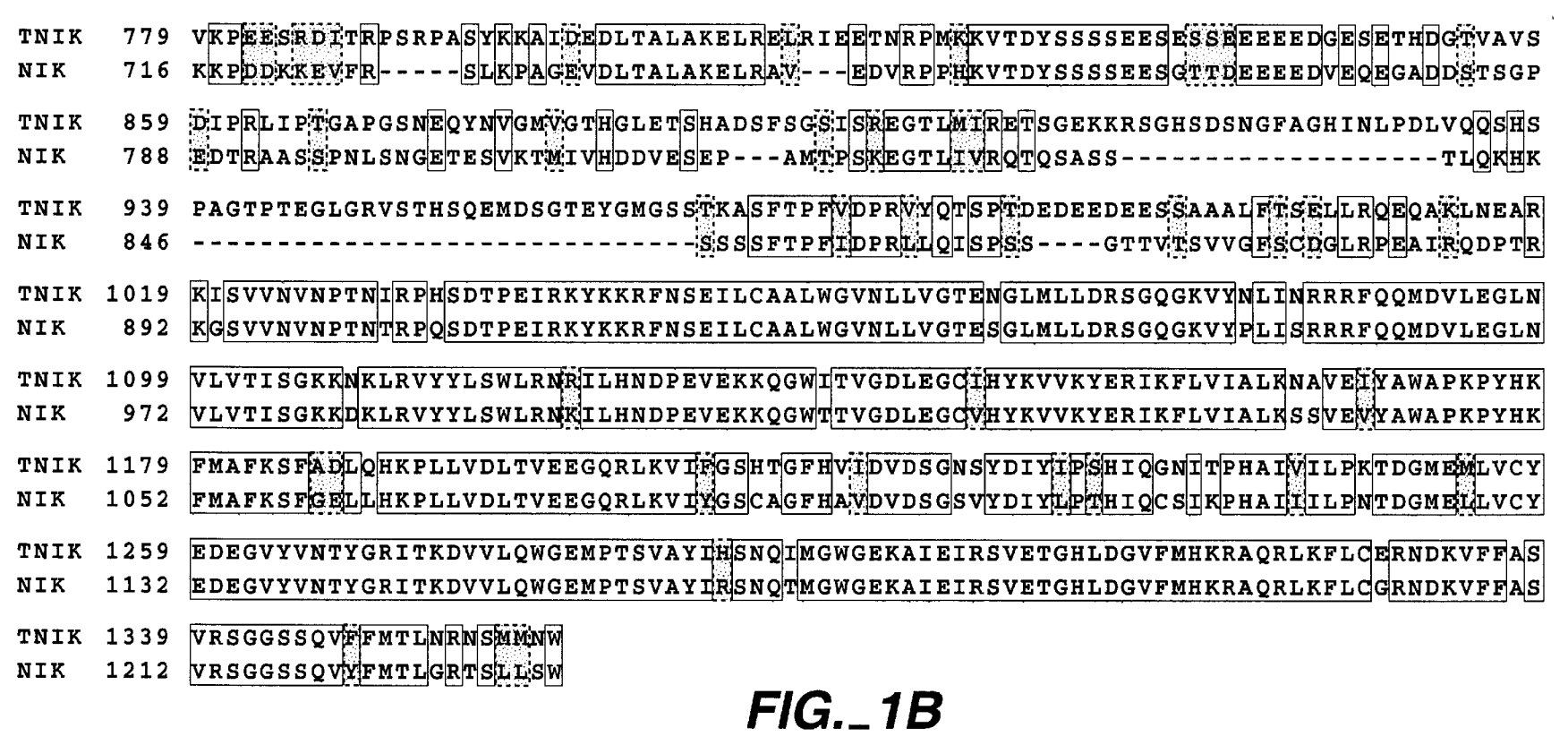

```
TNIK   779  VKPEESRDITRPSRPASYKKAIDEDLTALAKELRELRIEETNRPMKKVTDYSSSSEESESSEEEEEDGESETHDGTVAVS
NIK    716  KKPDDKKEVFR-----SLKPAGEVDLTALAKELRAV---EDVRPPHKVTDYSSSSEESGTTDEEEEDVEQEGADDSTSGP

TNIK   859  DIPRLIPTGAPGSNEQYNVGMVGTHGLETSHADSFSGSISREGTLMIRETSGEKKRSGHSDSNGFAGHINLPDLVQQSHS
NIK    788  EDTRAASSPNLSNGETESVKTMIVHDDVESEP---AMTPSKEGTLIVRQTQSASS-------------------TLQKHK

TNIK   939  PAGTPTEGLGRVSTHSQEMDSGTEYGMGSSTKASFTPFVDPRVYQTSPTDEDEEDEESSAAALFTSELLRQEQAKLNEAR
NIK    846  ------------------------------SSSSFTPFIDPRLLQISPSS----GTTVTSVVGFSCDGLRPEAIRQDPTR

TNIK  1019  KISVVNVNPTNIRPHSDTPEIRKYKKRFNSEILCAALWGVNLLVGTENGLMLLDRSGQGKVYNLINRRRFQQMDVLEGLN
NIK    892  KGSVVNVNPTNTRPQSDTPEIRKYKKRFNSEILCAALWGVNLLVGTESGLMLLDRSGQGKVYPLISRRRFQQMDVLEGLN

TNIK  1099  VLVTISGKKNKLRVYYLSWLRNRILHNDPEVEKKQGWITVGDLEGCIHYKVVKYERIKFLVIALKNAVEIYAWAPKPYHK
NIK    972  VLVTISGKKDKLRVYYLSWLRNKILHNDPEVEKKQGWTTVGDLEGCVHYKVVKYERIKFLVIALKSSVEVYAWAPKPYHK

TNIK  1179  FMAFKSFADLQHKPLLVDLTVEEGQRLKVIFGSHTGFHVIDVDSGNSYDIYIPSHIQGNITPHAIVILPKTDGMEMLVCY
NIK   1052  FMAFKSFGELLHKPLLVDLTVEEGQRLKVIYGSCAGFHAVDVDSGSVYDIYLPTHIQCSIKPHAIIILPNTDGMELLVCY

TNIK  1259  EDEGVYVNTYGRITKDVVLQWGEMPTSVAYIHSNQIMGWGEKAIEIRSVETGHLDGVFMHKRAQRLKFLCERNDKVFFAS
NIK   1132  EDEGVYVNTYGRITKDVVLQWGEMPTSVAYIRSNQTMGWGEKAIEIRSVETGHLDGVFMHKRAQRLKFLCGRNDKVFFAS

TNIK  1339  VRSGGSSQVFFMTLNRNSMMNW
NIK   1212  VRSGGSSQVYFMTLGRTSLLSW
```

FIG._1B

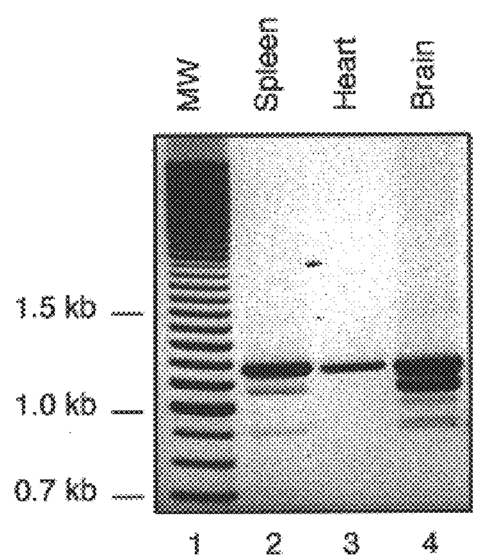
FIG._2
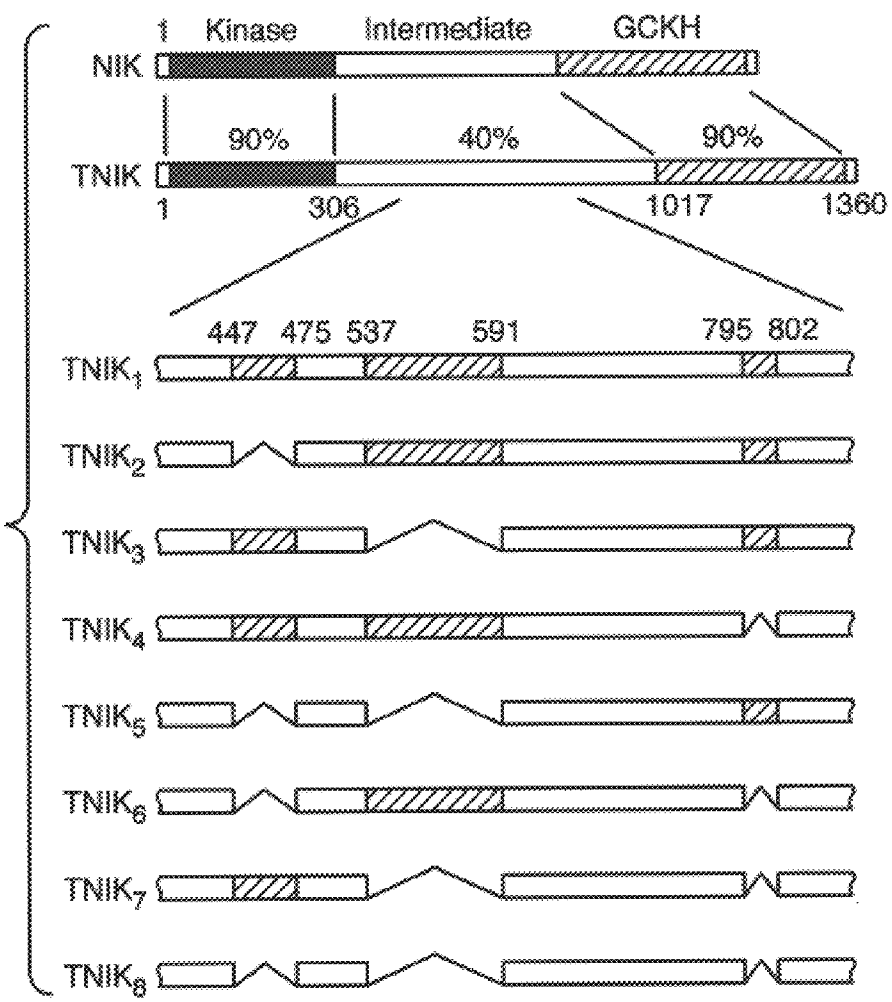
FIG._3

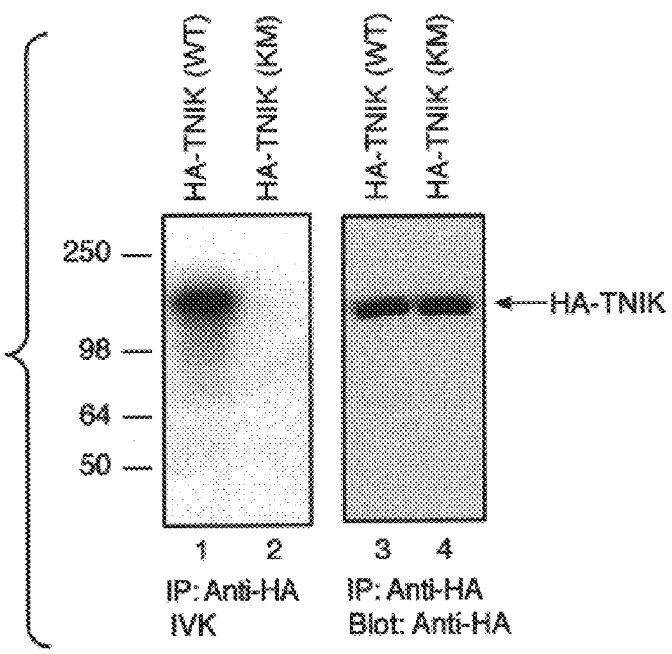
FIG._4
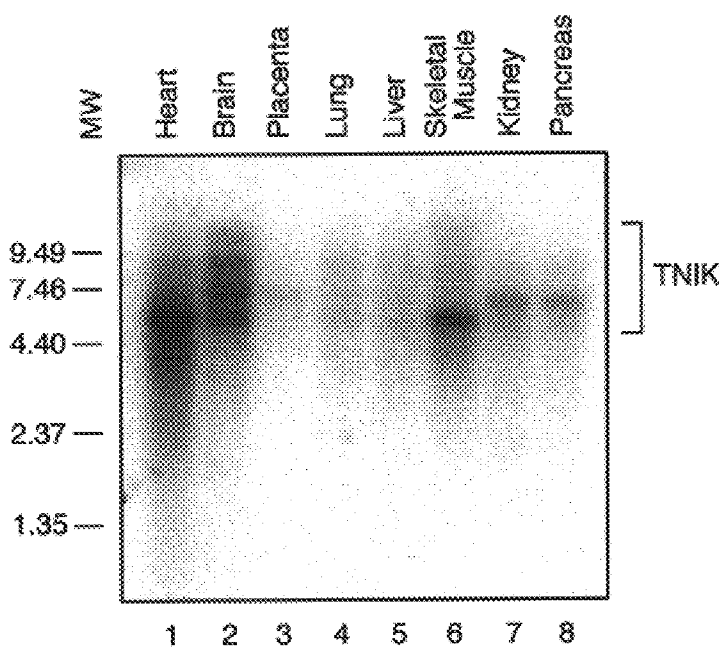
FIG._5A
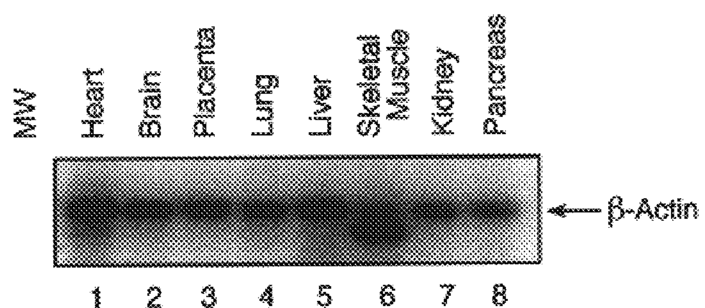
FIG._5B

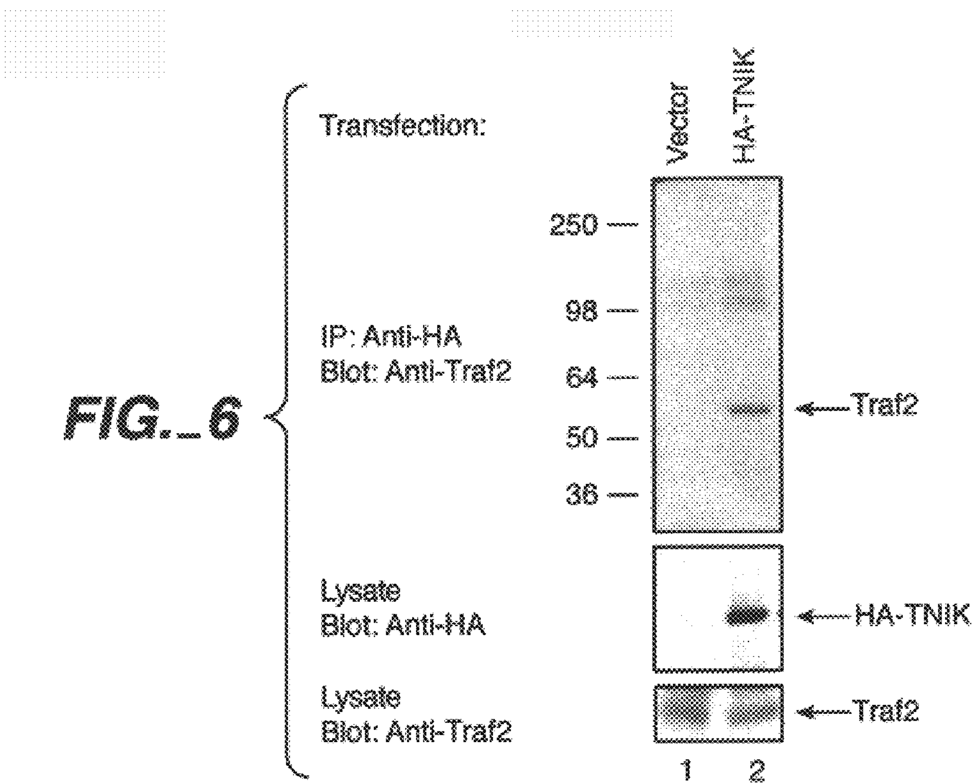
FIG._6
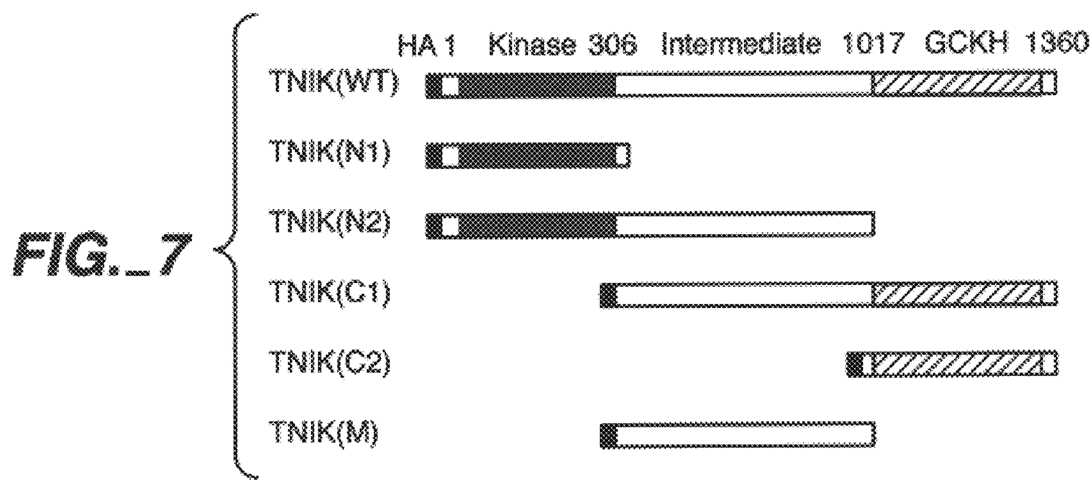
FIG._7

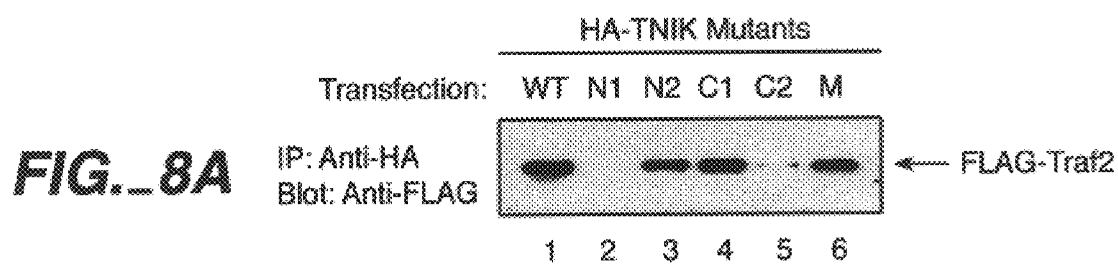
FIG._8A
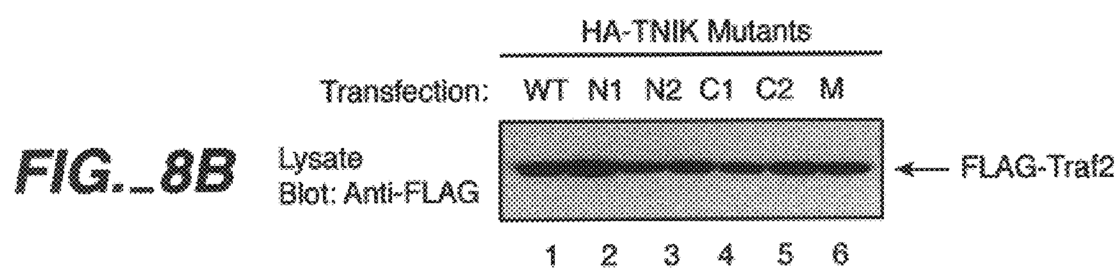
FIG._8B
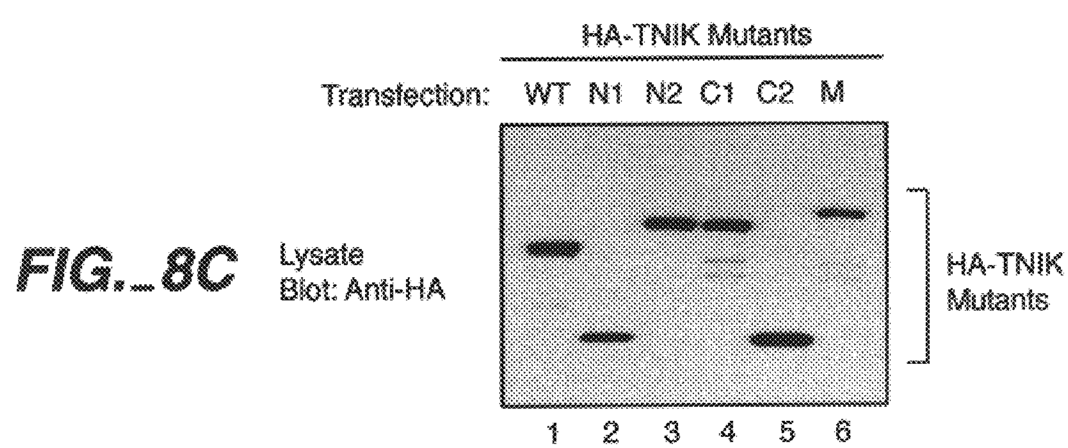
FIG._8C
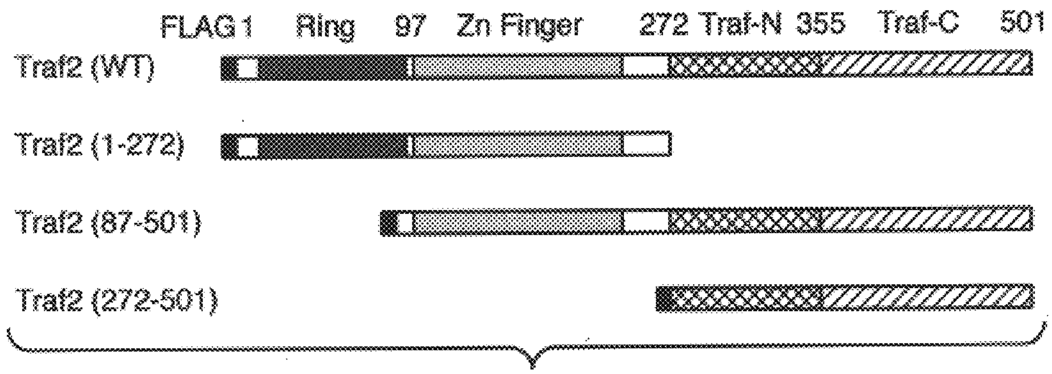
FIG._9

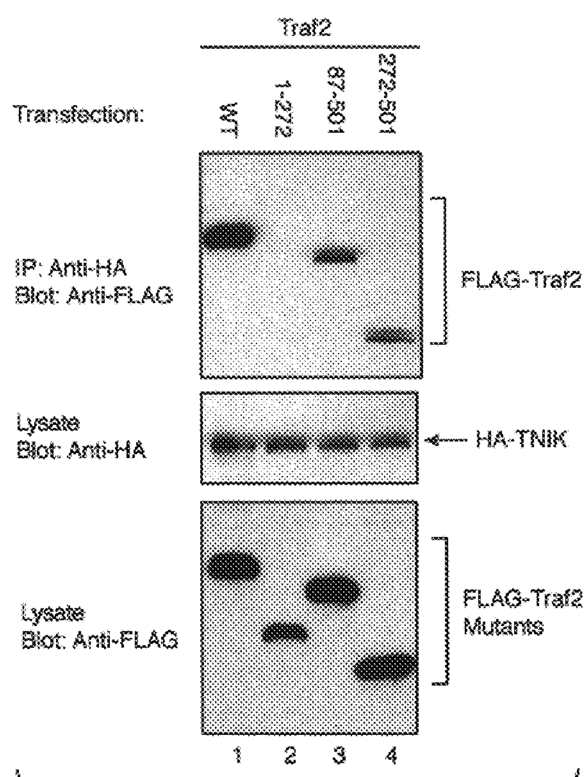
FIG._10
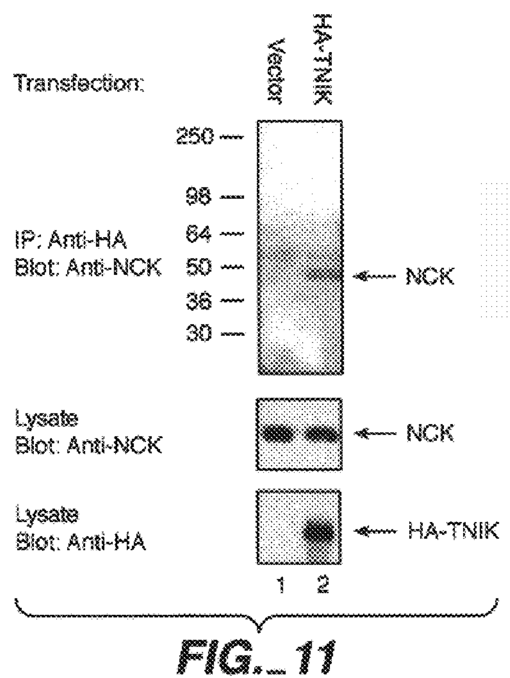
FIG._11

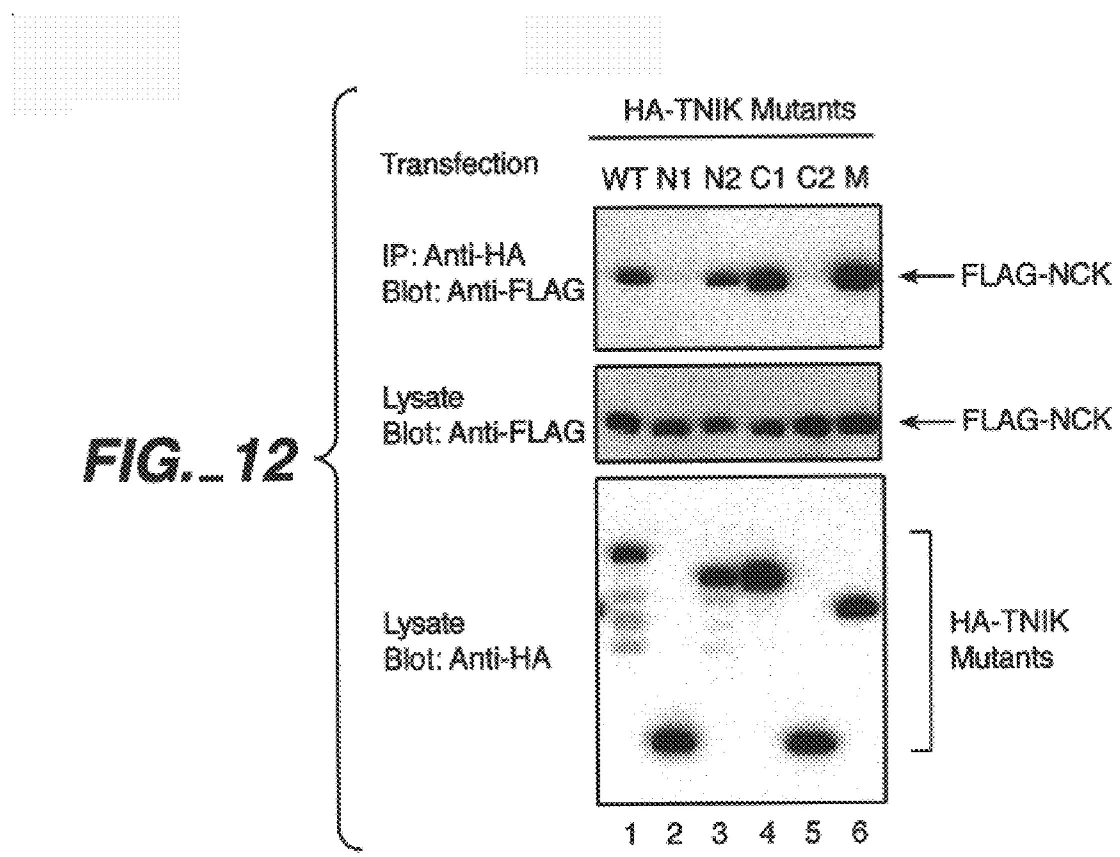
FIG._12
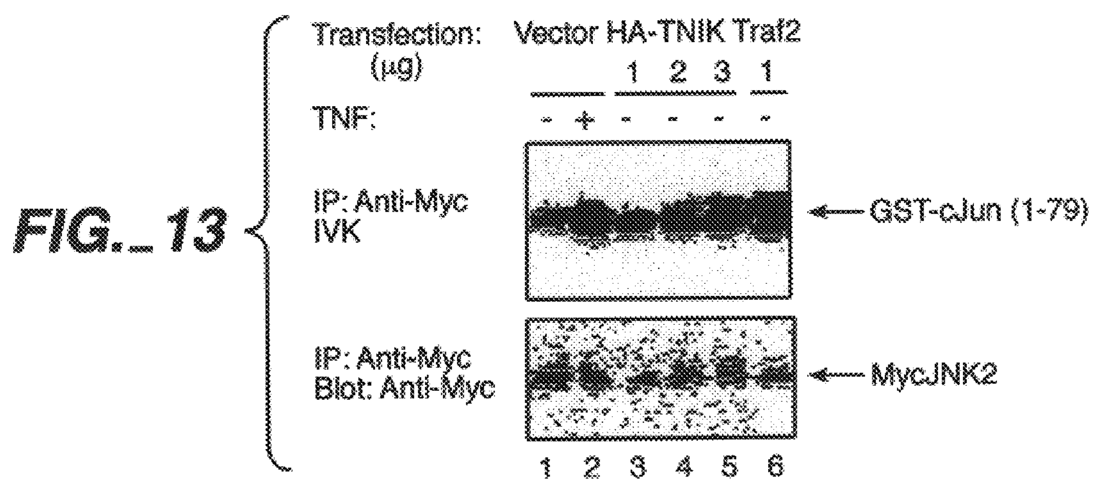
FIG._13

FIG._14
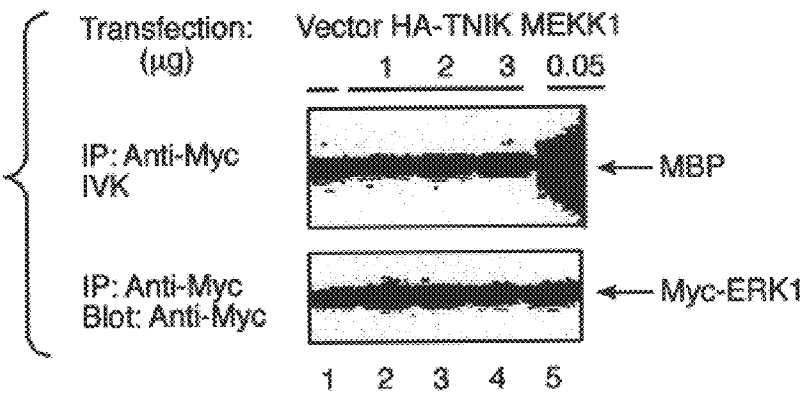
FIG._15
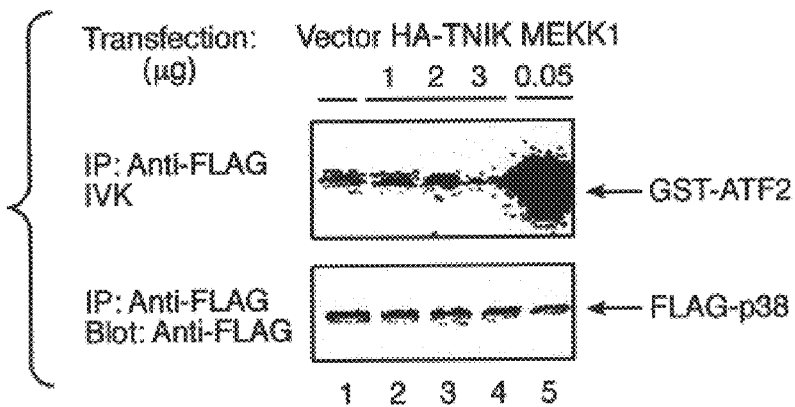
FIG._16
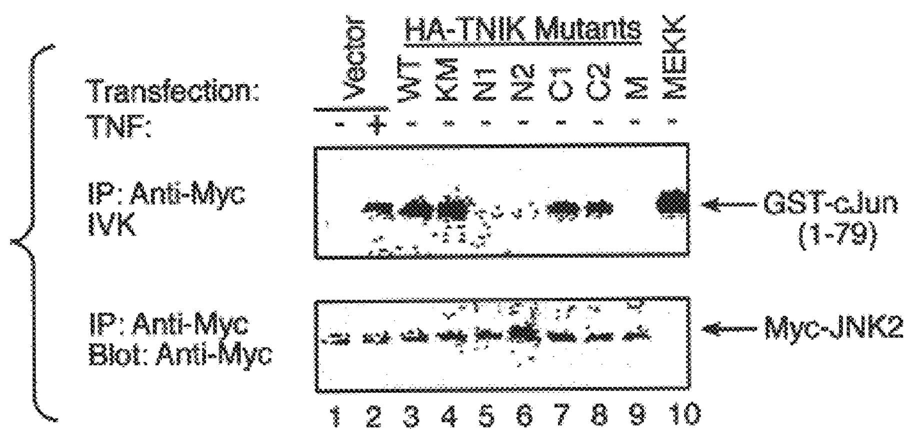

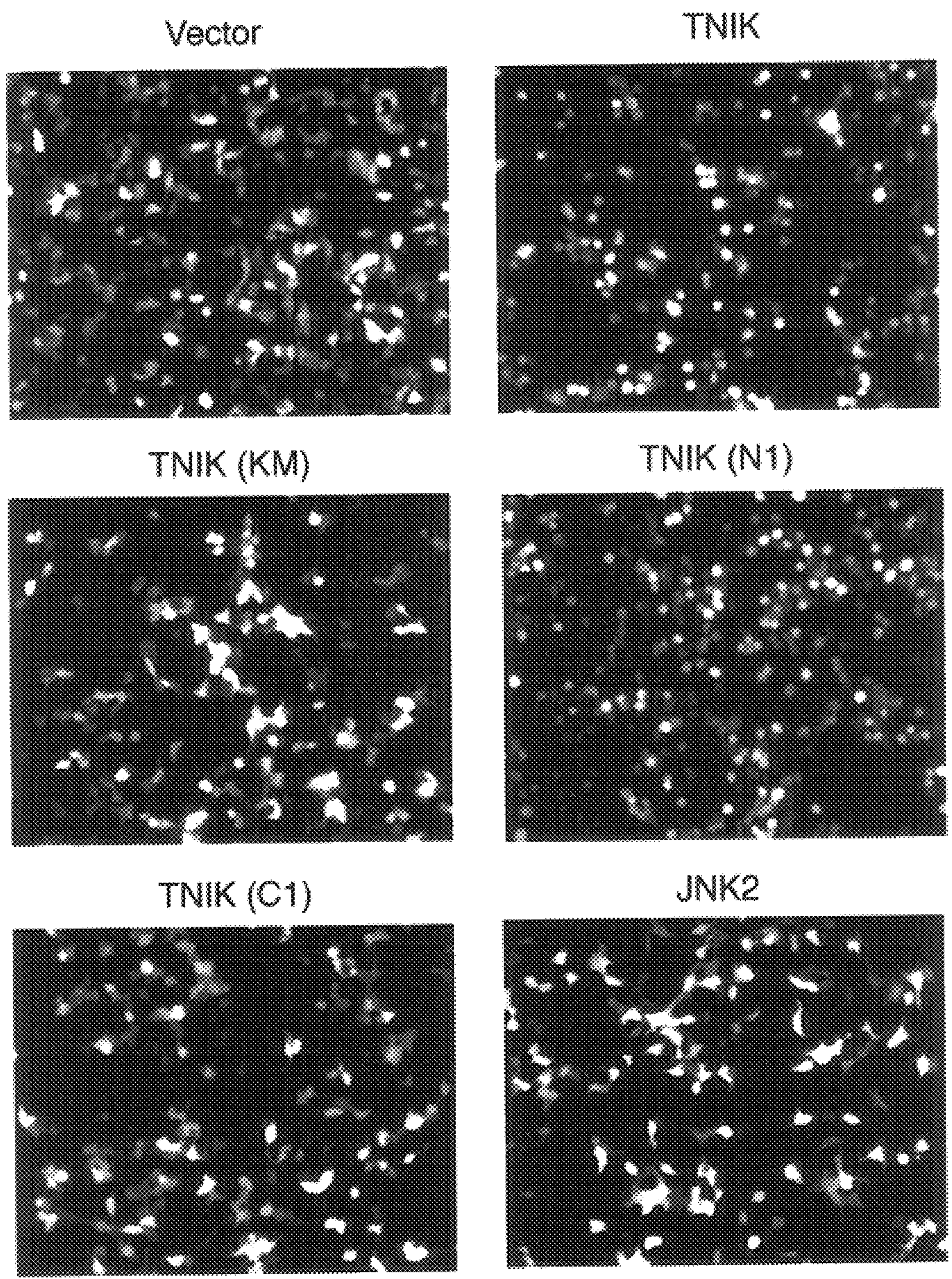
FIG._17

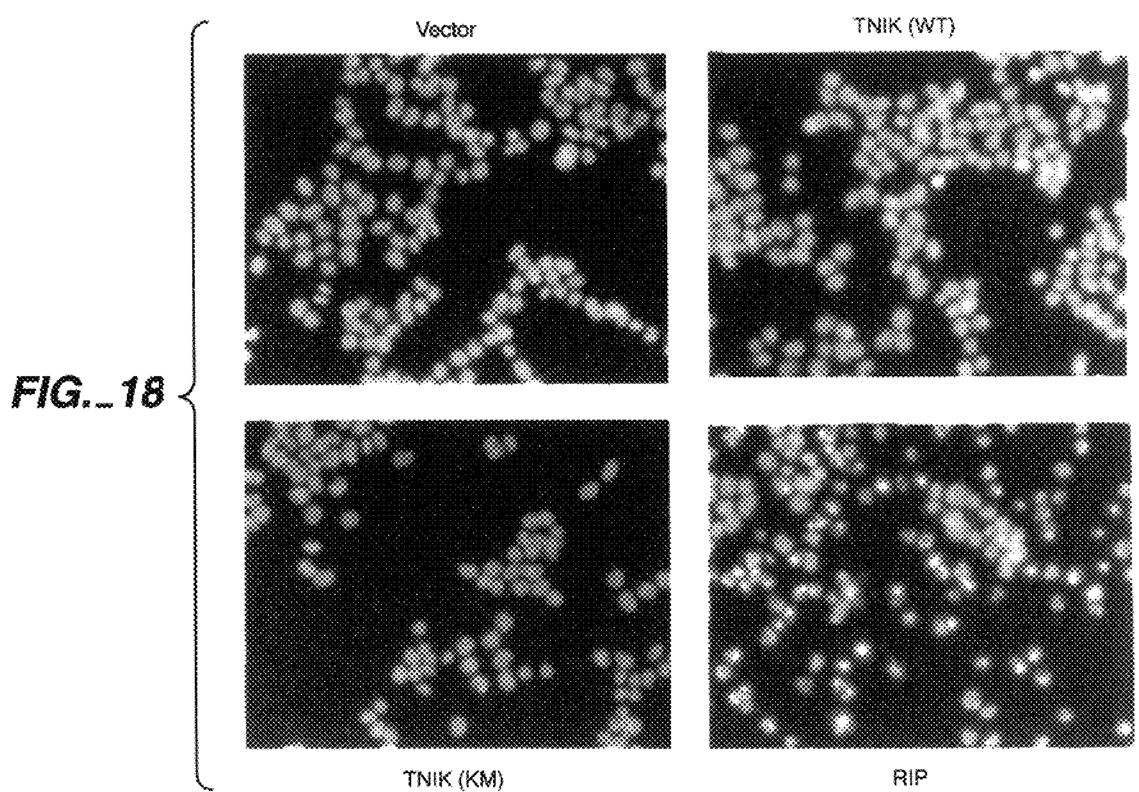
FIG._18

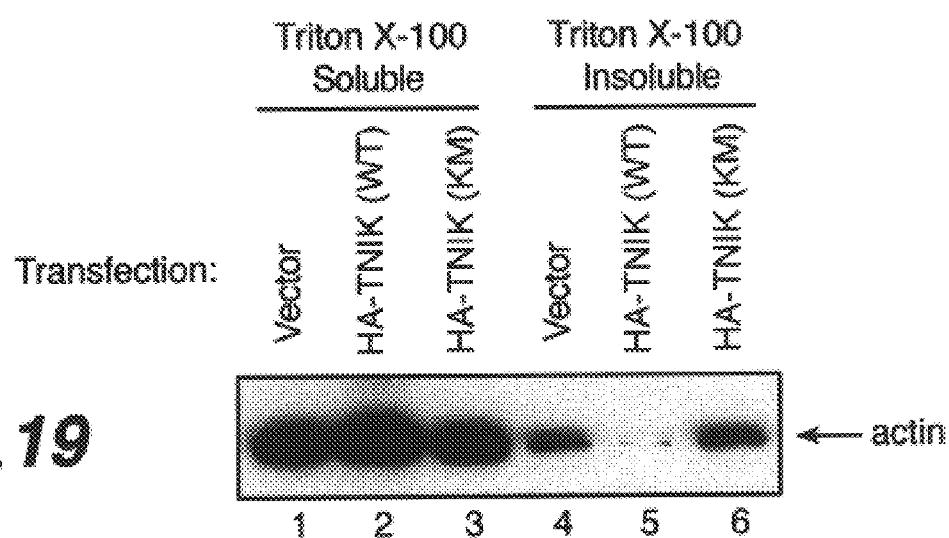
FIG._19
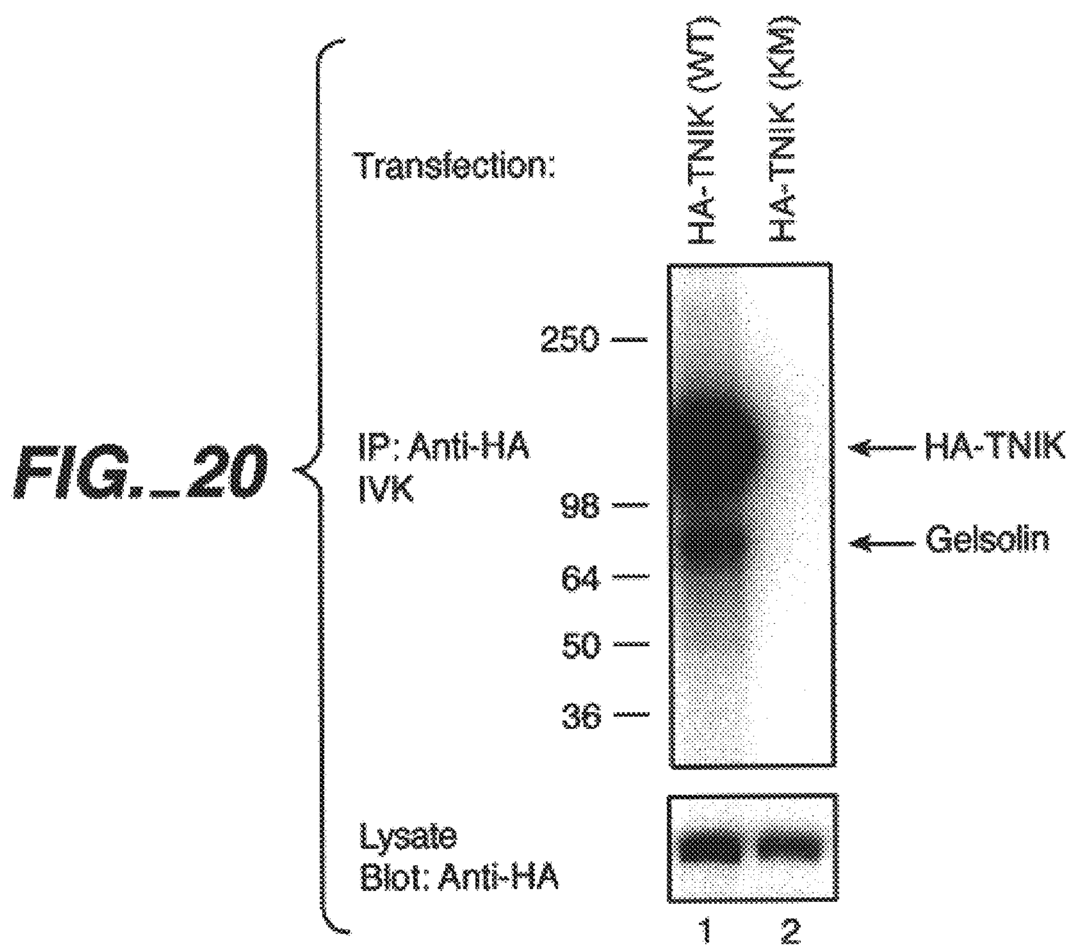
FIG._20

ATGGCGAGCGACTCCCCGGCTCGAAGCCTGGATGAAATAGATCTCTCGGCTCTGAGGGACCCTGCAGGGATCTTT
GAATTGGTGGAACTTGTTGGAAATGGAACATACGGGCAAGTTTATAAGGGTCGTCATGTCAAAACGGGCCAGCTT
GCAGCCATCAAGGTTATGGATGTCACAGGGGATGAAGAGGAAGAAATCAAACAAGAAATTAACATGTTGAAGAAA
TATTCTCATCACCGGAATATTGCTACATACTATGGTGCTTTTATCAAAAAGAACCCACCAGGCATGGATGACCAA
CTTTGGTTGGTGATGGAGTTTTGTGGTGCTGGCTCTGTCACCGACCTGATCAAGAACACAAAAGGTAACACGTTG
AAAGAGGAGTGGATTGCATACATCTGCAGGGAAATCTTACGGGGGCTGAGTCACCTGCACCAGCATAAAGTGATT
CATCGAGATATTAAAGGGCAAAATGTCTTGCTGACTGAAAATGCAGAAGTTAAACTAGTGGACTTTGGAGTCAGT
GCTCAGCTTGATCGAACAGTGGGCAGGAGGAATACTTTCATTGGAACTCCCTACTGGATGGCACCAGAAGTTATT
GCCTGTGATGAAAACCCAGATGCCACATATGATTTCAAGAGTGACTTGTGGTCTTTGGGTATCACCGCCATTGAA
ATGGCAGAAGGTGCTCCCCCTCTCTGTGACATGCACCCCATGAGAGCTCTCTTCCTCATCCCCCGGAATCCAGCG
CCTCGGCTGAAGTCTAAGAAGTGGTCAAAAAAATTCCAGTCATTTATTGAGAGCTGCTTGGTAAAGAATCACAGC
CAGCGACCAGCAACAGAACAATTGATGAAGCATCCATTTATACGAGACCAACCTAATGAGCGACAGGTCCGCATT
CAACTCAAGGACCATATTGATAGAACAAAGAAGAAGCGAGGAGAAAAAGATGAGACAGAGTATGAGTACAGTGGA
AGTGAGGAAGAAGAGGAGGAGAATGACTCAGGAGAGCCCAGCTCCATCCTGAATCTGCCAGGGGAGTCGACGCTG
CGGAGGGACTTTCTGAGGCTGCAGCTGGCCAACAAGGAGCGTTCTGAGGCCCTACGGAGGCAGCAGCTGGAGCAG
CAGCAGCGGGAGAATGAGGAGCACAAGCGGCAGCTGCTGGCCGAGCGTCAGAAGCGCATCGAGGAGCAGAAAGAG
CAGAGGCGGCGGCTGGAGGAGCAACAAAGGCGAGAGAAGGAGCTGCGGAAGCAGCAGGAGAGGGAGCAGCGCCGG
CACTATGAGGAGCAGATGCGCCGGGAGGAGGAGAGGAGGCGTGCGGAGCATGAACAGGAATACATCAGGCGACAG
TTAGAGGAGGAGCAGAGACAGTTAGAGATCTTGCAGCAGCAGCTACTGCATGAACAAGCTCTACTTCTGGAATAT
AAGCGCAAACAATTGGAAGAACAGAGACAAGCAGAAAGACTGCAGAGGCAGCTAAAGCAAGAAAGAGACTACTTA
GTTTCCCTTCAGCATCAGCGGCAGGAGCAGAGGCCTGTGGAGAAGAAGCCACTGTACCATTACAAAGAAGGAATG
AGTCCTAGTGAGAAGCCAGCATGGGCCAAGGAGGTAGAAGAACGGTCAAGGCTCAACCGGCAAAGTTCCCCTGCC
ATGCCTCACAAGGTTGCCAACAGGATATCTGACCCCAACCTGCCCCCAAGGTCGGAGTCCTTCAGCATTAGTGGA
GTTCAGCCTGCTCGAACACCCCCCATGCTCAGACCAGTCGATCCCCAGATCCCACATCTGGTAGCTGTAAAATCC
CAGGGACCTGCCTTGACCGCCTCCCAGTCAGTGCACGAGCAGCCCACAAAGGGCCTCTCTGGGTTTCAGGAGGCT
CTGAACGTGACCTCCCACCGCGTGGAGATGCCACGCCAGAACTCAGATCCCACCTCGGAAAATCCTCCTCTCCCC
ACTCGCATTGAAAAGTTTGACCGAAGCTCTTGGTTACGACAGGAAGAAGACATTCCACCAAAGGTGCCTCAAAGA

FIG._21A

ACAACTTCTATATCCCCAGCATTAGCCAGAAAGAATTCTCCTGGGAATGGTAGTGCTCTGGGACCCAGACTAGGA
TCTCAACCCATCAGAGCAAGCAACCCTGATCTCCGGAGAACTGAGCCCATCTTGGAGAGCCCCTTGCAGAGGACC
AGCAGTGGCAGTTCCTCCAGCTCCAGCACCCCTAGCTCCCAGCCCAGCTCCCAAGGAGGCTCCCAGCCTGGATCA
CAAGCAGGATCCAGTGAACGCACCAGAGTTCGAGCCAACAGTAAGTCAGAAGGATCACCTGTGCTTCCCCATGAG
CCTGCCAAGGTGAAACCAGAAGAATCCAGGGACATTACCCGGCCCAGTCGACCAGCTAGCTACAAAAAAGCTATA
GATGAGGATCTGACGGCATTAGCCAAAGAACTAAGAGAACTCCGGATTGAAGAAACAAACCGCCCAATGAAGAAG
GTGACTGATTACTCCTCCTCCAGTGAGGAGTCAGAAAGTAGCGAGGAAGAGGAGGAAGATGGAGAGAGCGAGACC
CATGATGGGACAGTGGCTGTCAGCGACATACCCAGACTGATACCAACAGGAGCTCCAGGCAGCAACGAGCAGTAC
AATGTGGGAATGGTGGGGACGCATGGGCTGGAGACCTCTCATGCGGACAGTTTCAGCGGCAGTATTTCAAGAGAA
GGAACCTTGATGATTAGAGAGACGTCTGGAGAGAAGAAGCGATCTGGCCACAGTGACAGCAATGGCTTTGCTGGC
CACATCAACCTCCCTGACCTGGTGCAGCAGAGCCATTCTCCAGCTGGAACCCCGACTGAGGGACTGGGGCGCGTC
TCAACCCATTCCCAGGAGATGGACTCTGGGACTGAATATGGCATGGGGAGCAGCACCAAAGCCTCCTTCACCCCC
TTTGTGGACCCCAGAGTATACCAGACGTCTCCCACTGATGAAGATGAAGAGGATGAGGAATCATCAGCCGCAGCT
CTGTTTACTAGCGAACTTCTTAGGCAAGAACAGGCCAAACTCAATGAAGCAAGAAAGATTTCGGTGGTAAATGTA
AACCCAACCAACATTCGGCCTCATAGCGACACACCAGAAATCAGAAAATACAAGAAACGATTCAACTCAGAAATA
CTTTGTGCAGCTCTGTGGGGTGTAAACCTTCTGGTGGGGACTGAAAATGGCCTGATGCTTTTGGACCGAAGTGGG
CAAGGCAAAGTCTATAATCTGATCAACCGGAGGCGATTTCAGCAGATGGATGTGCTAGAGGGACTGAATGTCCTT
GTGACAATTTCAGGAAAGAAGAATAAGCTACGAGTTTACTATCTTTCATGGTTAAGAAACAGAATACTACATAAT
GACCCAGAAGTAGAAAAGAAACAAGGCTGGATCACTGTTGGGGACTTGGAAGGCTGTATACATTATAAAGTTGTT
AAATATGAAAGGATCAAATTTTTGGTGATTGCCTTAAAGAATGCTGTGGAAATATATGCTTGGGCTCCTAAACCG
TATCATAAATTCATGGCATTTAAGTCTTTTGCAGATCTCCAGCACAAGCCTCTGCTAGTTGATCTCACGGTAGAA
GAAGGTCAAAGATTAAAGGTTATTTTTGGTTCACACACTGGTTTCCATGTAATTGATGTTGATTCAGGAAACTCT
TATGATATCTACATACCATCTCATATTCAGGGCAATATCACTCCTCATGCTATTGTCATCTTGCCTAAAACAGAT
GGAATGGAAATGCTTGTTTGCTATGAGGATGAGGGGGTGTATGTAAACACCTATGGCCGGATAACTAAGGATGTG
GTGCTCCAATGGGGAGAAATGCCCACGTCTGTGGCCTACATTCATTCCAATCAGATAATGGCTGGGGCGAGAAA
GCTATTGAGATCCGGTCAGTGGAAACAGGACATTTGGATGGAGTATTTATGCATAAGCGAGCTCAAAGGTTAAAG
TTTCTATGTGAAAGAAATGATAAGGTATTTTTTGCATCCGTGCGATCTGGAGGAAGTAGCCAAGTGTTTTTCATG
ACCCTCAACAGAAATTCCATGATGAACTGGTAA

FIG._21B

ATGGCGAGCGACTCCCCGGCTCGAAGCCTGGATGAAATAGATCTCTCGGCTCTGAGGGACCCTGCAGGGATCTTT
GAATTGGTGGAACTTGTTGGAAATGGAACATACGGGCAAGTTTATAAGGGTCGTCATGTCAAAACGGGCCAGCTT
GCAGCCATCAAGGTTATGGATGTCACAGGGGATGAAGAGGAAGAAATCAAACAAGAAATTAACATGTTGAAGAAA
TATTCTCATCACCGGAATATTGCTACATACTATGGTGCTTTTATCAAAAAGAACCCACCAGGCATGGATGACCAA
CTTTGGTTGGTGATGGAGTTTTGTGGTGCTGGCTCTGTCACCGACCTGATCAAGAACACAAAAGGTAACACGTTG
AAAGAGGAGTGGATTGCATACATCTGCAGGGAAATCTTACGGGGGCTGAGTCACCTGCACCAGCATAAAGTGATT
CATCGAGATATTAAAGGGCAAAATGTCTTGCTGACTGAAAATGCAGAAGTTAAACTAGTGGACTTTGGAGTCAGT
GCTCAGCTTGATCGAACAGTGGGCAGGAGGAATACTTTCATTGGAACTCCCTACTGGATGGCACCAGAAGTTATT
GCCTGTGATGAAAACCCAGATGCCACATATGATTTCAAGAGTGACTTGTGGTCTTTGGGTATCACCGCCATTGAA
ATGGCAGAAGGTGCTCCCCCTCTCTGTGACATGCACCCCATGAGAGCTCTCTTCCTCATCCCCCGGAATCCAGCG
CCTCGGCTGAAGTCTAAGAAGTGGTCAAAAAAATTCCAGTCATTTATTGAGAGCTGCTTGGTAAAGAATCACAGC
CAGCGACCAGCAACAGAACAATTGATGAAGCATCCATTTATACGAGACCAACCTAATGAGCGACAGGTCCGCATT
CAACTCAAGGACCATATTGATAGAACAAAGAAGAAGCGAGGAGAAAAAGATGAGACAGAGTATGAGTACAGTGGA
AGTGAGGAAGAAGAGGAGGAGAATGACTCAGGAGAGCCCAGCTCCATCCTGAATCTGCCAGGGGAGTCGACGCTG
CGGAGGGACTTTCTGAGGCTGCAGCTGGCCAACAAGGAGCGTTCTGAGGCCCTACGGAGGCAGCAGCTGGAGCAG
CAGCAGCGGGAGAATGAGGAGCACAAGCGGCAGCTGCTGGCCGAGCGTCAGAAGCGCATCGAGGAGCAGAAAGAG
CAGAGGCGGCGGCTGGAGGAGCAACAAAGGCGAGAGAAGGAGCTGCGGAAGCAGCAGGAGAGGGAGCAGCGCCGG
CACTATGAGGAGCAGATGCGCCGGGAGGAGGAGAGGAGGCGTGCGGAGCATGAACAGGAATATAAGCGCAAACAA
TTGGAAGAACAGAGACAAGCAGAAAGACTGCAGAGGCAGCTAAAGCAAGAAAGAGACTACTTAGTTTCCCTTCAG
CATCAGCGGCAGGAGCAGAGGCCTGTGGAGAAGAAGCCACTGTACCATTACAAAGAAGGAATGAGTCCTAGTGAG
AAGCCAGCATGGGCCAAGGAGGTAGAAGAACGGTCAAGGCTCAACCGGCAAAGTTCCCCTGCCATGCCTCACAAG
GTTGCCAACAGGATATCTGACCCCAACCTGCCCCCAAGGTCGGAGTCCTTCAGCATTAGTGGAGTTCAGCCTGCT
CGAACACCCCCCATGCTCAGACCAGTCGATCCCCAGATCCCACATCTGGTAGCTGTAAAATCCCAGGGACCTGCC
TTGACCGCCTCCCAGTCAGTGCACGAGCAGCCCACAAAGGGCCTCTCTGGGTTTCAGGAGGCTCTGAACGTGACC
TCCCACCGCGTGGAGATGCCACGCCAGAACTCAGATCCCACCTCGGAAAATCCTCCTCTCCCCACTCGCATTGAA
AAGTTTGACCGAAGCTCTTGGTTACGACAGGAAGAAGACATTCCACCAAAGGTGCCTCAAAGAACAACTTCTATA
TCCCCAGCATTAGCCAGAAAGAATTCTCCTGGGAATGGTAGTGCTCTGGGACCCAGACTAGGATCTCAACCCATC
AGAGCAAGCAACCCTGATCTCCGGAGAACTGAGCCCATCTTGGAGAGCCCCTTGCAGAGGACCAGCAGTGGCAGT

FIG._22A

TCCCCAGCATTAGCCAGAAAGAATTCTCCTGGGAATGGTAGTGCTCTGGGACCCAGACTAGGATCTCAACCCATC
AGAGCAAGCAACCCTGATCTCCGGAGAACTGAGCCCATCTTGGAGAGCCCCTTGCAGAGGACCAGCAGTGGCAGT
TCCTCCAGCTCCAGCACCCCTAGCTCCCAGCCCAGCTCCCAAGGAGGCTCCCAGCCTGGATCACAAGCAGGATCC
AGTGAACGCACCAGAGTTCGAGCCAACAGTAAGTCAGAAGGATCACCTGTGCTTCCCCATGAGCCTGCCAAGGTG
AAACCAGAAGAATCCAGGGACATTACCCGGCCCAGTCGACCAGCTAGCTACAAAAAAGCTATAGATGAGGATCTG
ACGGCATTAGCCAAAGAACTAAGAGAACTCCGGATTGAAGAAACAAACCGCCCAATGAAGAAGGTGACTGATTAC
TCCTCCTCCAGTGAGGAGTCAGAAAGTAGCGAGGAAGAGGAGGAAGATGGAGAGAGCGAGACCCATGATGGGACA
GTGGCTGTCAGCGACATACCCAGACTGATACCAACAGGAGCTCCAGGCAGCAACGAGCAGTACAATGTGGGAATG
GTGGGGACGCATGGGCTGGAGACCTCTCATGCGGACAGTTTCAGCGGCAGTATTTCAAGAGAAGGAACCTTGATG
ATTAGAGAGACGTCTGGAGAGAAGAAGCGATCTGGCCACAGTGACAGCAATGGCTTTGCTGGCCACATCAACCTC
CCTGACCTGGTGCAGCAGAGCCATTCTCCAGCTGGAACCCCGACTGAGGGACTGGGGCGCGTCTCAACCCATTCC
CAGGAGATGGACTCTGGGACTGAATATGGCATGGGGAGCAGCACCAAAGCCTCCTTCACCCCCTTTGTGGACCCC
AGAGTATACCAGACGTCTCCCACTGATGAAGATGAAGAGGATGAGGAATCATCAGCCGCAGCTCTGTTTACTAGC
GAACTTCTTAGGCAAGAACAGGCCAAACTCAATGAAGCAAGAAAGATTTCGGTGGTAAATGTAAACCCAACCAAC
ATTCGGCCTCATAGCGACACACCAGAAATCAGAAAATACAAGAAACGATTCAACTCAGAAATACTTTGTGCAGCT
CTGTGGGGTGTAAACCTTCTGGTGGGGACTGAAAATGGCCTGATGCTTTTGGACCGAAGTGGGCAAGGCAAAGTC
TATAATCTGATCAACCGGAGGCGATTTCAGCAGATGGATGTGCTAGAGGGACTGAATGTCCTTGTGACAATTTCA
GGAAAGAAGAATAAGCTACGAGTTTACTATCTTTCATGGTTAAGAAACAGAATACTACATAATGACCCAGAAGTA
GAAAAGAAACAAGGCTGGATCACTGTTGGGGACTTGGAAGGCTGTATACATTATAAAGTTGTTAAATATGAAAGG
ATCAAATTTTTGGTGATTGCCTTAAAGAATGCTGTGGAAATATATGCTTGGGCTCCTAAACCGTATCATAAATTC
ATGGCATTTAAGTCTTTTGCAGATCTCCAGCACAAGCCTCTGCTAGTTGATCTCACGGTAGAAGAAGGTCAAAGA
TTAAAGGTTATTTTTGGTTCACACACTGGTTTCCATGTAATTGATGTTGATTCAGGAAACTCTTATGATATCTAC
ATACCATCTCATATTCAGGGCAATATCACTCCTCATGCTATTGTCATCTTGCCTAAAACAGATGGAATGGAAATG
CTTGTTTGCTATGAGGATGAGGGGGTGTATGTAAACACCTATGGCCGGATAACTAAGGATGTGGTGCTCCAATGG
GGAGAAATGCCCACGTCTGTGGCCTACATTCATTCCAATCAGATAATGGGCTGGGGCGAGAAAGCTATTGAGATC
CGGTCAGTGGAAACAGGACATTTGGATGGAGTATTTATGCATAAGCGAGCTCAAAGGTTAAAGTTTCTATGTGAA
AGAAATGATAAGGTATTTTTTGCATCCGTGCGATCTGGAGGAAGTAGCCAAGTGTTTTTCATGACCCTCAACAGA
AATTCCATGATGAACTGGTAA

FIG._22B

ATGGCGAGCGACTCCCCGGCTCGAAGCCTGGATGAAATAGATCTCTCGGCTCTGAGGGACCCTGCAGGGATCTTT
GAATTGGTGGAACTTGTTGGAAATGGAACATACGGGCAAGTTTATAAGGGTCGTCATGTCAAAACGGGCCAGCTT
GCAGCCATCAAGGTTATGGATGTCACAGGGGATGAAGAGGAAGAAATCAAACAAGAAATTAACATGTTGAAGAAA
TATTCTCATCACCGGAATATTGCTACATACTATGGTGCTTTTATCAAAAAGAACCCACCAGGCATGGATGACCAA
CTTTGGTTGGTGATGGAGTTTTGTGGTGCTGGCTCTGTCACCGACCTGATCAAGAACACAAAAGGTAACACGTTG
AAAGAGGAGTGGATTGCATACATCTGCAGGGAAATCTTACGGGGGCTGAGTCACCTGCACCAGCATAAAGTGATT
CATCGAGATATTAAAGGGCAAAATGTCTTGCTGACTGAAAATGCAGAAGTTAAACTAGTGGACTTTGGAGTCAGT
GCTCAGCTTGATCGAACAGTGGGCAGGAGGAATACTTTCATTGGAACTCCCTACTGGATGGCACCAGAAGTTATT
GCCTGTGATGAAAACCCAGATGCCACATATGATTTCAAGAGTGACTTGTGGTCTTTGGGTATCACCGCCATTGAA
ATGGCAGAAGGTGCTCCCCCTCTCTGTGACATGCACCCCATGAGAGCTCTCTTCCTCATCCCCCGGAATCCAGCG
CCTCGGCTGAAGTCTAAGAAGTGGTCAAAAAAATTCCAGTCATTTATTGAGAGCTGCTTGGTAAAGAATCACAGC
CAGCGACCAGCAACAGAACAATTGATGAAGCATCCATTTATACGAGACCAACCTAATGAGCGACAGGTCCGCATT
CAACTCAAGGACCATATTGATAGAACAAAGAAGAAGCGAGGAGAAAAAGATGAGACAGAGTATGAGTACAGTGGA
AGTGAGGAAGAAGAGGAGGAGAATGACTCAGGAGAGCCCAGCTCCATCCTGAATCTGCCAGGGGAGTCGACGCTG
CGGAGGGACTTTCTGAGGCTGCAGCTGGCCAACAAGGAGCGTTCTGAGGCCCTACGGAGGCAGCAGCTGGAGCAG
CAGCAGCGGGAGAATGAGGAGCACAAGCGGCAGCTGCTGGCCGAGCGTCAGAAGCGCATCGAGGAGCAGAAAGAG
CAGAGGCGGCGGCTGGAGGAGCAACAAAGGCGAGAGAAGGAGCTGCGGAAGCAGCAGGAGAGGGAGCAGCGCCGG
CACTATGAGGAGCAGATGCGCCGGGAGGAGGAGAGGAGGCGTGCGGAGCATGAACAGGAATACATCAGGCGACAG
TTAGAGGAGGAGCAGAGACAGTTAGAGATCTTGCAGCAGCAGCTACTGCATGAACAAGCTCTACTTCTGGAATAT
AAGCGCAAACAATTGGAAGAACAGAGACAAGCAGAAAGACTGCAGAGGCAGCTAAAGCAAGAAAGAGACTACTTA
GTTTCCCTTCAGCATCAGCGGCAGGAGCAGAGGCCTGTGGAGAAGAAGCCACTGTACCATTACAAAGAAGGAATG
AGTCCTAGTGAGAAGCCAGCATGGGCCAAGGAGATCCCACATCTGGTAGCTGTAAAATCCCAGGGACCTGCCTTG
ACCGCCTCCCAGTCAGTGCACGAGCAGCCCACAAAGGGCCTCTCTGGGTTTCAGGAGGCTCTGAACGTGACCTCC
CACCGCGTGGAGATGCCACGCCAGAACTCAGATCCCACCTCGGAAAATCCTCCTCTCCCCACTCGCATTGAAAAG
TTTGACCGAAGCTCTTGGTTACGACAGGAAGAAGACATTCCACCAAAGGTGCCTCAAAGAACAACTTCTATATCC
CCAGCATTAGCCAGAAAGAATTCTCCTGGGAATGGTAGTGCTCTGGGACCCAGACTAGGATCTCAACCCATCAGA
GCAAGCAACCCTGATCTCCGGAGAACTGAGCCCATCTTGGAGAGCCCCTTGCAGAGGACCAGCAGTGGCAGTTCC

FIG._23A

TCCAGCTCCAGCACCCCTAGCTCCCAGCCCAGCTCCCAAGGAGGCTCCCAGCCTGGATCACAAGCAGGATCCAGT
GAACGCACCAGAGTTCGAGCCAACAGTAAGTCAGAAGGATCACCTGTGCTTCCCCATGAGCCTGCCAAGGTGAAA
CCAGAAGAATCCAGGGACATTACCCGGCCCAGTCGACCAGCTAGCTACAAAAAAGCTATAGATGAGGATCTGACG
GCATTAGCCAAAGAACTAAGAGAACTCCGGATTGAAGAAACAAACCGCCCAATGAAGAAGGTGACTGATTACTCC
TCCTCCAGTGAGGAGTCAGAAAGTAGCGAGGAAGAGGAGGAAGATGGAGAGAGCGAGACCCATGATGGGACAGTG
GCTGTCAGCGACATACCCAGACTGATACCAACAGGAGCTCCAGGCAGCAACGAGCAGTACAATGTGGGAATGGTG
GGGACGCATGGGCTGGAGACCTCTCATGCGGACAGTTTCAGCGGCAGTATTTCAAGAGAAGGAACCTTGATGATT
AGAGAGACGTCTGGAGAGAAGAAGCGATCTGGCCACAGTGACAGCAATGGCTTTGCTGGCCACATCAACCTCCCT
GACCTGGTGCAGCAGAGCCATTCTCCAGCTGGAACCCCGACTGAGGGACTGGGGCGCGTCTCAACCCATTCCCAG
GAGATGGACTCTGGGACTGAATATGGCATGGGGAGCAGCACCAAAGCCTCCTTCACCCCCTTTGTGGACCCCAGA
GTATACCAGACGTCTCCCACTGATGAAGATGAAGAGGATGAGGAATCATCAGCCGCAGCTCTGTTTACTAGCGAA
CTTCTTAGGCAAGAACAGGCCAAACTCAATGAAGCAAGAAAGATTTCGGTGGTAAATGTAAACCCAACCAACATT
CGGCCTCATAGCGACACACCAGAAATCAGAAAATACAAGAAACGATTCAACTCAGAAATACTTTGTGCAGCTCTG
TGGGGTGTAAACCTTCTGGTGGGGACTGAAAATGGCCTGATGCTTTTGGACCGAAGTGGGCAAGGCAAAGTCTAT
AATCTGATCAACCGGAGGCGATTTCAGCAGATGGATGTGCTAGAGGGACTGAATGTCCTTGTGACAATTTCAGGA
AAGAAGAATAAGCTACGAGTTTACTATCTTTCATGGTTAAGAAACAGAATACTACATAATGACCCAGAAGTAGAA
AAGAAACAAGGCTGGATCACTGTTGGGGACTTGGAAGGCTGTATACATTATAAAGTTGTTAAATATGAAAGGATC
AAATTTTTGGTGATTGCCTTAAAGAATGCTGTGGAAATATATGCTTGGGCTCCTAAACCGTATCATAAATTCATG
GCATTTAAGTCTTTTGCAGATCTCCAGCACAAGCCTCTGCTAGTTGATCTCACGGTAGAAGAAGGTCAAAGATTA
AAGGTTATTTTTGGTTCACACACTGGTTTCCATGTAATTGATGTTGATTCAGGAAACTCTTATGATATCTACATA
CCATCTCATATTCAGGGCAATATCACTCCTCATGCTATTGTCATCTTGCCTAAAACAGATGGAATGGAAATGCTT
GTTTGCTATGAGGATGAGGGGGTGTATGTAAACACCTATGGCCGGATAACTAAGGATGTGGTGCTCCAATGGGGA
GAAATGCCCACGTCTGTGGCCTACATTCATTCCAATCAGATAATGGGCTGGGGCGAGAAAGCTATTGAGATCCGG
TCAGTGGAAACAGGACATTTGGATGGAGTATTTATGCATAAGCGAGCTCAAAGGTTAAAGTTTCTATGTGAAAGA
AATGATAAGGTATTTTTTGCATCCGTGCGATCTGGAGGAAGTAGCCAAGTGTTTTTCATGACCCTCAACAGAAAT
TCCATGATGAACTGGTAA

FIG._23B

ATGGCGAGCGACTCCCCGGCTCGAAGCCTGGATGAAATAGATCTCTCGGCTCTGAGGGACCCTGCAGGGATCTTT
GAATTGGTGGAACTTGTTGGAAATGGAACATACGGGCAAGTTTATAAGGGTCGTCATGTCAAAACGGGCCAGCTT
GCAGCCATCAAGGTTATGGATGTCACAGGGGATGAAGAGGAAGAAATCAAACAAGAAATTAACATGTTGAAGAAA
TATTCTCATCACCGGAATATTGCTACATACTATGGTGCTTTTATCAAAAAGAACCCACCAGGCATGGATGACCAA
CTTTGGTTGGTGATGGAGTTTTGTGGTGCTGGCTCTGTCACCGACCTGATCAAGAACACAAAAGGTAACACGTTG
AAAGAGGAGTGGATTGCATACATCTGCAGGGAAATCTTACGGGGGCTGAGTCACCTGCACCAGCATAAAGTGATT
CATCGAGATATTAAAGGGCAAAATGTCTTGCTGACTGAAAATGCAGAAGTTAAACTAGTGGACTTTGGAGTCAGT
GCTCAGCTTGATCGAACAGTGGGCAGGAGGAATACTTTCATTGGAACTCCCTACTGGATGGCACCAGAAGTTATT
GCCTGTGATGAAAACCCAGATGCCACATATGATTTCAAGAGTGACTTGTGGTCTTTGGGTATCACCGCCATTGAA
ATGGCAGAAGGTGCTCCCCCTCTCTGTGACATGCACCCCATGAGAGCTCTCTTCCTCATCCCCCGGAATCCAGCG
CCTCGGCTGAAGTCTAAGAAGTGGTCAAAAAAATTCCAGTCATTTATTGAGAGCTGCTTGGTAAAGAATCACAGC
CAGCGACCAGCAACAGAACAATTGATGAAGCATCCATTTATACGAGACCAACCTAATGAGCGACAGGTCCGCATT
CAACTCAAGGACCATATTGATAGAACAAAGAAGAAGCGAGGAGAAAAAGATGAGACAGAGTATGAGTACAGTGGA
AGTGAGGAAGAAGAGGAGGAGAATGACTCAGGAGAGCCCAGCTCCATCCTGAATCTGCCAGGGGAGTCGACGCTG
CGGAGGGACTTTCTGAGGCTGCAGCTGGCCAACAAGGAGCGTTCTGAGGCCCTACGGAGGCAGCAGCTGGAGCAG
CAGCAGCGGGAGAATGAGGAGCACAAGCGGCAGCTGCTGGCCGAGCGTCAGAAGCGCATCGAGGAGCAGAAAGAG
CAGAGGCGGCGGCTGGAGGAGCAACAAAGGCGAGAGAAGGAGCTGCGGAAGCAGCAGGAGAGGGAGCAGCGCCGG
CACTATGAGGAGCAGATGCGCCGGGAGGAGGAGAGGAGGCGTGCGGAGCATGAACAGGAATACATCAGGCGACAG
TTAGAGGAGGAGCAGAGACAGTTAGAGATCTTGCAGCAGCAGCTACTGCATGAACAAGCTCTACTTCTGGAATAT
AAGCGCAAACAATTGGAAGAACAGAGACAAGCAGAAAGACTGCAGAGGCAGCTAAAGCAAGAAAGAGACTACTTA
GTTTCCCTTCAGCATCAGCGGCAGGAGCAGAGGCCTGTGGAGAAGAAGCCACTGTACCATTACAAAGAAGGAATG
AGTCCTAGTGAGAAGCCAGCATGGGCCAAGGAGGTAGAAGAACGGTCAAGGCTCAACCGGCAAAGTTCCCCTGCC
ATGCCTCACAAGGTTGCCAACAGGATATCTGACCCCAACCTGCCCCCAAGGTCGGAGTCCTTCAGCATTAGTGGA
GTTCAGCCTGCTCGAACACCCCCCATGCTCAGACCAGTCGATCCCCAGATCCCACATCTGGTAGCTGTAAAATCC
CAGGGACCTGCCTTGACCGCCTCCCAGTCAGTGCACGAGCAGCCCACAAAGGGCCTCTCTGGGTTTCAGGAGGCT
CTGAACGTGACCTCCCACCGCGTGGAGATGCCACGCCAGAACTCAGATCCCACCTCGGAAAATCCTCCTCTCCCC
ACTCGCATTGAAAAGTTTGACCGAAGCTCTTGGTTACGACAGGAAGAAGACATTCCACCAAAGGTGCCTCAAAGA
ACAACTTCTATATCCCCAGCATTAGCCAGAAAGAATTCTCCTGGGAATGGTAGTGCTCTGGGACCCAGACTAGGA

FIG._24A

TCTCAACCCATCAGAGCAAGCAACCCTGATCTCCGGAGAACTGAGCCCATCTTGGAGAGCCCCTTGCAGAGGACC
AGCAGTGGCAGTTCCTCCAGCTCCAGCACCCCTAGCTCCCAGCCCAGCTCCCAAGGAGGCTCCCAGCCTGGATCA
CAAGCAGGATCCAGTGAACGCACCAGAGTTCGAGCCAACAGTAAGTCAGAAGGATCACCTGTGCTTCCCCATGAG
CCTGCCAAGGTGAAACCAGAAGAATCCAGGGACATTACCCGGCCCAGTCGACCAGCTGATCTGACGGCATTAGCC
AAAGAACTAAGAGAACTCCGGATTGAAGAAACAAACCGCCCAATGAAGAAGGTGACTGATTACTCCTCCTCCAGT
GAGGAGTCAGAAAGTAGCGAGGAAGAGGAGGAAGATGGAGAGAGCGAGACCCATGATGGGACAGTGGCTGTCAGC
GACATACCCAGACTGATACCAACAGGAGCTCCAGGCAGCAACGAGCAGTACAATGTGGGAATGGTGGGGACGCAT
GGGCTGGAGACCTCTCATGCGGACAGTTTCAGCGGCAGTATTTCAAGAGAAGGAACCTTGATGATTAGAGAGACG
TCTGGAGAGAAGAAGCGATCTGGCCACAGTGACAGCAATGGCTTTGCTGGCCACATCAACCTCCCTGACCTGGTG
CAGCAGAGCCATTCTCCAGCTGGAACCCCGACTGAGGGACTGGGGCGCGTCTCAACCCATTCCCAGGAGATGGAC
TCTGGGACTGAATATGGCATGGGGAGCAGCACCAAAGCCTCCTTCACCCCCTTTGTGGACCCCAGAGTATACCAG
ACGTCTCCCACTGATGAAGATGAAGAGGATGAGGAATCATCAGCCGCAGCTCTGTTTACTAGCGAACTTCTTAGG
CAAGAACAGGCCAAACTCAATGAAGCAAGAAAGATTTCGGTGGTAAATGTAAACCCAACCAACATTCGGCCTCAT
AGCGACACACCAGAAATCAGAAAATACAAGAAACGATTCAACTCAGAAATACTTTGTGCAGCTCTGTGGGGTGTA
AACCTTCTGGTGGGGACTGAAAATGGCCTGATGCTTTTGGACCGAAGTGGGCAAGGCAAAGTCTATAATCTGATC
AACCGGAGGCGATTTCAGCAGATGGATGTGCTAGAGGGACTGAATGTCCTTGTGACAATTTCAGGAAAGAAGAAT
AAGCTACGAGTTTACTATCTTTCATGGTTAAGAAACAGAATACTACATAATGACCCAGAAGTAGAAAAGAAACAA
GGCTGGATCACTGTTGGGGACTTGGAAGGCTGTATACATTATAAAGTTGTTAAATATGAAAGGATCAAATTTTTG
GTGATTGCCTTAAAGAATGCTGTGGAAATATATGCTTGGGCTCCTAAACCGTATCATAAATTCATGGCATTTAAG
TCTTTTGCAGATCTCCAGCACAAGCCTCTGCTAGTTGATCTCACGGTAGAAGAAGGTCAAAGATTAAAGGTTATT
TTTGGTTCACACACTGGTTTCCATGTAATTGATGTTGATTCAGGAAACTCTTATGATATCTACATACCATCTCAT
ATTCAGGGCAATATCACTCCTCATGCTATTGTCATCTTGCCTAAAACAGATGGAATGGAAATGCTTGTTTGCTAT
GAGGATGAGGGGGTGTATGTAAACACCTATGGCCGGATAACTAAGGATGTGGTGCTCCAATGGGGAGAAATGCCC
ACGTCTGTGGCCTACATTCATTCCAATCAGATAATGGCTGGGGCGAGAAAGCTATTGAGATCCGGTCAGTGGAA
ACAGGACATTTGGATGGAGTATTTATGCATAAGCGAGCTCAAAGGTTAAAGTTTCTATGTGAAAGAAATGATAAG
GTATTTTTTGCATCCGTGCGATCTGGAGGAAGTAGCCAAGTGTTTTTCATGACCCTCAACAGAAATTCCATGATG
AACTGGTAA

FIG._24B

ATGGCGAGCGACTCCCCGGCTCGAAGCCTGGATGAAATAGATCTCTCGGCTCTGAGGGACCCTGCAGGGATCTTT
GAATTGGTGGAACTTGTTGGAAATGGAACATACGGGCAAGTTTATAAGGGTCGTCATGTCAAAACGGGCCAGCTT
GCAGCCATCAAGGTTATGGATGTCACAGGGGATGAAGAGGAAGAAATCAAACAAGAAATTAACATGTTGAAGAAA
TATTCTCATCACCGGAATATTGCTACATACTATGGTGCTTTTATCAAAAAGAACCCACCAGGCATGGATGACCAA
CTTTGGTTGGTGATGGAGTTTTGTGGTGCTGGCTCTGTCACCGACCTGATCAAGAACACAAAAGGTAACACGTTG
AAAGAGGAGTGGATTGCATACATCTGCAGGGAAATCTTACGGGGGCTGAGTCACCTGCACCAGCATAAAGTGATT
CATCGAGATATTAAAGGGCAAAATGTCTTGCTGACTGAAAATGCAGAAGTTAAACTAGTGGACTTTGGAGTCAGT
GCTCAGCTTGATCGAACAGTGGGCAGGAGGAATACTTTCATTGGAACTCCCTACTGGATGGCACCAGAAGTTATT
GCCTGTGATGAAAACCCAGATGCCACATATGATTTCAAGAGTGACTTGTGGTCTTTGGGTATCACCGCCATTGAA
ATGGCAGAAGGTGCTCCCCCTCTCTGTGACATGCACCCCATGAGAGCTCTCTTCCTCATCCCCCGGAATCCAGCG
CCTCGGCTGAAGTCTAAGAAGTGGTCAAAAAAATTCCAGTCATTTATTGAGAGCTGCTTGGTAAAGAATCACAGC
CAGCGACCAGCAACAGAACAATTGATGAAGCATCCATTTATACGAGACCAACCTAATGAGCGACAGGTCCGCATT
CAACTCAAGGACCATATTGATAGAACAAAGAAGAAGCGAGGAGAAAAAGATGAGACAGAGTATGAGTACAGTGGA
AGTGAGGAAGAAGAGGAGGAGAATGACTCAGGAGAGCCCAGCTCCATCCTGAATCTGCCAGGGGAGTCGACGCTG
CGGAGGGACTTTCTGAGGCTGCAGCTGGCCAACAAGGAGCGTTCTGAGGCCCTACGGAGGCAGCAGCTGGAGCAG
CAGCAGCGGGAGAATGAGGAGCACAAGCGGCAGCTGCTGGCCGAGCGTCAGAAGCGCATCGAGGAGCAGAAAGAG
CAGAGGCGGCGGCTGGAGGAGCAACAAAGGCGAGAGAAGGAGCTGCGGAAGCAGCAGGAGAGGGAGCAGCGCCGG
CACTATGAGGAGCAGATGCGCCGGGAGGAGGAGAGGAGGCGTGCGGAGCATGAACAGGAATATAAGCGCAAACAA
TTGGAAGAACAGAGACAAGCAGAAAGACTGCAGAGGCAGCTAAAGCAAGAAAGAGACTACTTAGTTTCCCTTCAG
CATCAGCGGCAGGAGCAGAGGCCTGTGGAGAAGAAGCCACTGTACCATTACAAAGAAGGAATGAGTCCTAGTGAG
AAGCCAGCATGGGCCAAGGAGATCCCACATCTGGTAGCTGTAAAATCCCAGGGACCTGCCTTGACCGCCTCCCAG
TCAGTGCACGAGCAGCCCACAAAGGGCCTCTCTGGGTTTCAGGAGGCTCTGAACGTGACCTCCCACCGCGTGGAG
ATGCCACGCCAGAACTCAGATCCCACCTCGGAAAATCCTCCTCTCCCCACTCGCATTGAAAAGTTTGACCGAAGC
TCTTGGTTACGACAGGAAGAAGACATTCCACCAAAGGTGCCTCAAAGAACAACTTCTATATCCCCAGCATTAGCC
AGAAAGAATTCTCCTGGGAATGGTAGTGCTCTGGGACCCAGACTAGGATCTCAACCCATCAGAGCAAGCAACCCT
GATCTCCGGAGAACTGAGCCCATCTTGGAGAGCCCCTTGCAGAGGACCAGCAGTGGCAGTTCCTCCAGCTCCAGC
ACCCCTAGCTCCCAGCCCAGCTCCCAAGGAGGCTCCCAGCCTGGATCACAAGCAGGATCCAGTGAACGCACCAGA

FIG._25A

GTTCGAGCCAACAGTAAGTCAGAAGGATCACCTGTGCTTCCCCATGAGCCTGCCAAGGTGAAACCAGAAGAATCC
AGGGACATTACCCGGCCCAGTCGACCAGCTAGCTACAAAAAAGCTATAGATGAGGATCTGACGGCATTAGCCAAA
GAACTAAGAGAACTCCGGATTGAAGAAACAAACCGCCCAATGAAGAAGGTGACTGATTACTCCTCCTCCAGTGAG
GAGTCAGAAAGTAGCGAGGAAGAGGAGGAAGATGGAGAGAGCGAGACCCATGATGGGACAGTGGCTGTCAGCGAC
ATACCCAGACTGATACCAACAGGAGCTCCAGGCAGCAACGAGCAGTACAATGTGGGAATGGTGGGGACGCATGGG
CTGGAGACCTCTCATGCGGACAGTTTCAGCGGCAGTATTTCAAGAGAAGGAACCTTGATGATTAGAGAGACGTCT
GGAGAGAAGAAGCGATCTGGCCACAGTGACAGCAATGGCTTTGCTGGCCACATCAACCTCCCTGACCTGGTGCAG
CAGAGCCATTCTCCAGCTGGAACCCCGACTGAGGGACTGGGGCGCGTCTCAACCCATTCCCAGGAGATGGACTCT
GGGACTGAATATGGCATGGGGAGCAGCACCAAAGCCTCCTTCACCCCCTTTGTGGACCCCAGAGTATACCAGACG
TCTCCCACTGATGAAGATGAAGAGGATGAGGAATCATCAGCCGCAGCTCTGTTTACTAGCGAACTTCTTAGGCAA
GAACAGGCCAAACTCAATGAAGCAAGAAAGATTTCGGTGGTAAATGTAAACCCAACCAACATTCGGCCTCATAGC
GACACACCAGAAATCAGAAAATACAAGAAACGATTCAACTCAGAAATACTTTGTGCAGCTCTGTGGGGTGTAAAC
CTTCTGGTGGGGACTGAAAATGGCCTGATGCTTTTGGACCGAAGTGGCAAGGCAAAGTCTATAATCTGATCAAC
CGGAGGCGATTTCAGCAGATGGATGTGCTAGAGGGACTGAATGTCCTTGTGACAATTTCAGGAAAGAAGAATAAG
CTACGAGTTTACTATCTTTCATGGTTAAGAAACAGAATACTACATAATGACCCAGAAGTAGAAAAGAAACAAGGC
TGGATCACTGTTGGGGACTTGGAAGGCTGTATACATTATAAAGTTGTTAAATATGAAAGGATCAAATTTTTGGTG
ATTGCCTTAAAGAATGCTGTGGAAATATATGCTTGGGCTCCTAAACCGTATCATAAATTCATGGCATTTAAGTCT
TTTGCAGATCTCCAGCACAAGCCTCTGCTAGTTGATCTCACGGTAGAAGAAGGTCAAAGATTAAAGGTTATTTTT
GGTTCACACACTGGTTTCCATGTAATTGATGTTGATTCAGGAAACTCTTATGATATCTACATACCATCTCATATT
CAGGGCAATATCACTCCTCATGCTATTGTCATCTTGCCTAAAACAGATGGAATGGAAATGCTTGTTTGCTATGAG
GATGAGGGGGTGTATGTAAACACCTATGGCCGGATAACTAAGGATGTGGTGCTCCAATGGGGAGAAATGCCCACG
TCTGTGGCCTACATTCATTCCAATCAGATAATGGGCTGGGGCGAGAAAGCTATTGAGATCCGGTCAGTGGAAACA
GGACATTTGGATGGAGTATTTATGCATAAGCGAGCTCAAAGGTTAAAGTTTCTATGTGAAAGAAATGATAAGGTA
TTTTTTGCATCCGTGCGATCTGGAGGAAGTAGCCAAGTGTTTTTCATGACCCTCAACAGAAATTCCATGATGAAC
TGGTAA

FIG._25B

ATGGCGAGCGACTCCCCGGCTCGAAGCCTGGATGAAATAGATCTCTCGGCTCTGAGGGACCCTGCAGGGATCTTT
GAATTGGTGGAACTTGTTGGAAATGGAACATACGGGCAAGTTTATAAGGGTCGTCATGTCAAAACGGGCCAGCTT
GCAGCCATCAAGGTTATGGATGTCACAGGGGATGAAGAGGAAGAAATCAAACAAGAAATTAACATGTTGAAGAAA
TATTCTCATCACCGGAATATTGCTACATACTATGGTGCTTTTATCAAAAAGAACCCACCAGGCATGGATGACCAA
CTTTGGTTGGTGATGGAGTTTTGTGGTGCTGGCTCTGTCACCGACCTGATCAAGAACACAAAAGGTAACACGTTG
AAAGAGGAGTGGATTGCATACATCTGCAGGGAAATCTTACGGGGGCTGAGTCACCTGCACCAGCATAAAGTGATT
CATCGAGATATTAAAGGGCAAAATGTCTTGCTGACTGAAAATGCAGAAGTTAAACTAGTGGACTTTGGAGTCAGT
GCTCAGCTTGATCGAACAGTGGGCAGGAGGAATACTTTCATTGGAACTCCCTACTGGATGGCACCAGAAGTTATT
GCCTGTGATGAAAACCCAGATGCCACATATGATTTCAAGAGTGACTTGTGGTCTTTGGGTATCACCGCCATTGAA
ATGGCAGAAGGTGCTCCCCCTCTCTGTGACATGCACCCCATGAGAGCTCTCTTCCTCATCCCCCGGAATCCAGCG
CCTCGGCTGAAGTCTAAGAAGTGGTCAAAAAAATTCCAGTCATTTATTGAGAGCTGCTTGGTAAAGAATCACAGC
CAGCGACCAGCAACAGAACAATTGATGAAGCATCCATTTATACGAGACCAACCTAATGAGCGACAGGTCCGCATT
CAACTCAAGGACCATATTGATAGAACAAAGAAGAAGCGAGGAGAAAAAGATGAGACAGAGTATGAGTACAGTGGA
AGTGAGGAAGAAGAGGAGGAGAATGACTCAGGAGAGCCCAGCTCCATCCTGAATCTGCCAGGGGAGTCGACGCTG
CGGAGGGACTTTCTGAGGCTGCAGCTGGCCAACAAGGAGCGTTCTGAGGCCCTACGGAGGCAGCAGCTGGAGCAG
CAGCAGCGGGAGAATGAGGAGCACAAGCGGCAGCTGCTGGCCGAGCGTCAGAAGCGCATCGAGGAGCAGAAAGAG
CAGAGGCGGCGGCTGGAGGAGCAACAAAGGCGAGAGAAGGAGCTGCGGAAGCAGCAGGAGAGGGAGCAGCGCCGG
CACTATGAGGAGCAGATGCGCCGGGAGGAGGAGAGGAGGCGTGCGGAGCATGAACAGGAATATAAGCGCAAACAA
TTGGAAGAACAGAGACAAGCAGAAAGACTGCAGAGGCAGCTAAAGCAAGAAAGAGACTACTTAGTTTCCCTTCAG
CATCAGCGGCAGGAGCAGAGGCCTGTGGAGAAGAAGCCACTGTACCATTACAAAGAAGGAATGAGTCCTAGTGAG
AAGCCAGCATGGGCCAAGGAGGTAGAAGAACGGTCAAGGCTCAACCGGCAAAGTTCCCCTGCCATGCCTCACAAG
GTTGCCAACAGGATATCTGACCCCAACCTGCCCCCAAGGTCGGAGTCCTTCAGCATTAGTGGAGTTCAGCCTGCT
CGAACACCCCCCATGCTCAGACCAGTCGATCCCCAGATCCCACATCTGGTAGCTGTAAAATCCCAGGGACCTGCC
TTGACCGCCTCCCAGTCAGTGCACGAGCAGCCCACAAAGGGCCTCTCTGGGTTTCAGGAGGCTCTGAACGTGACC
TCCCACCGCGTGGAGATGCCACGCCAGAACTCAGATCCCACCTCGGAAAATCCTCCTCTCCCCACTCGCATTGAA
AAGTTTGACCGAAGCTCTTGGTTACGACAGGAAGAAGACATTCCACCAAAGGTGCCTCAAAGAACAACTTCTATA
TCCCCAGCATTAGCCAGAAAGAATTCTCCTGGGAATGGTAGTGCTCTGGGACCCAGACTAGGATCTCAACCCATC

FIG._26A

AGAGCAAGCAACCCTGATCTCCGGAGAACTGAGCCCATCTTGGAGAGCCCCTTGCAGAGGACCAGCAGTGGCAGT
TCCTCCAGCTCCAGCACCCCTAGCTCCCAGCCCAGCTCCCAAGGAGGCTCCCAGCCTGGATCACAAGCAGGATCC
AGTGAACGCACCAGAGTTCGAGCCAACAGTAAGTCAGAAGGATCACCTGTGCTTCCCCATGAGCCTGCCAAGGTG
AAACCAGAAGAATCCAGGGACATTACCCGGCCCAGTCGACCAGCTGATCTGACGGCATTAGCCAAAGAACTAAGA
GAACTCCGGATTGAAGAAACAAACCGCCCAATGAAGAAGGTGACTGATTACTCCTCCTCCAGTGAGGAGTCAGAA
AGTAGCGAGGAAGAGGAGGAAGATGGAGAGAGCGAGACCCATGATGGGACAGTGGCTGTCAGCGACATACCCAGA
CTGATACCAACAGGAGCTCCAGGCAGCAACGAGCAGTACAATGTGGGAATGGTGGGGACGCATGGGCTGGAGACC
TCTCATGCGGACAGTTTCAGCGGCAGTATTTCAAGAGAAGGAACCTTGATGATTAGAGAGACGTCTGGAGAGAAG
AAGCGATCTGGCCACAGTGACAGCAATGGCTTTGCTGGCCACATCAACCTCCCTGACCTGGTGCAGCAGAGCCAT
TCTCCAGCTGGAACCCCGACTGAGGGACTGGGGCGCGTCTCAACCCATTCCCAGGAGATGGACTCTGGGACTGAA
TATGGCATGGGGAGCAGCACCAAAGCCTCCTTCACCCCCTTTGTGGACCCCAGAGTATACCAGACGTCTCCCACT
GATGAAGATGAAGAGGATGAGGAATCATCAGCCGCAGCTCTGTTTACTAGCGAACTTCTTAGGCAAGAACAGGCC
AAACTCAATGAAGCAAGAAAGATTTCGGTGGTAAATGTAAACCCAACCAACATTCGGCCTCATAGCGACACACCA
GAAATCAGAAAATACAAGAAACGATTCAACTCAGAAATACTTTGTGCAGCTCTGTGGGGTGTAAACCTTCTGGTG
GGGACTGAAAATGGCCTGATGCTTTTGGACCGAAGTGGGCAAGGCAAAGTCTATAATCTGATCAACCGGAGGCGA
TTTCAGCAGATGGATGTGCTAGAGGGACTGAATGTCCTTGTGACAATTTCAGGAAAGAAGAATAAGCTACGAGTT
TACTATCTTTCATGGTTAAGAAACAGAATACTACATAATGACCCAGAAGTAGAAAAGAAACAAGGCTGGATCACT
GTTGGGGACTTGGAAGGCTGTATACATTATAAAGTTGTTAAATATGAAAGGATCAAATTTTTGGTGATTGCCTTA
AAGAATGCTGTGGAAATATATGCTTGGGCTCCTAAACCGTATCATAAATTCATGGCATTTAAGTCTTTTGCAGAT
CTCCAGCACAAGCCTCTGCTAGTTGATCTCACGGTAGAAGAAGGTCAAAGATTAAAGGTTATTTTTGGTTCACAC
ACTGGTTTCCATGTAATTGATGTTGATTCAGGAAACTCTTATGATATCTACATACCATCTCATATTCAGGGCAAT
ATCACTCCTCATGCTATTGTCATCTTGCCTAAAACAGATGGAATGGAAATGCTTGTTTGCTATGAGGATGAGGGG
GTGTATGTAAACACCTATGGCCGGATAACTAAGGATGTGGTGCTCCAATGGGGAGAAATGCCCACGTCTGTGGCC
TACATTCATTCCAATCAGATAATGGCTGGGGCGAGAAAGCTATTGAGATCCGGTCAGTGGAAACAGGACATTTG
GATGGAGTATTTATGCATAAGCGAGCTCAAAGGTTAAAGTTTCTATGTGAAAGAAATGATAAGGTATTTTTTGCA
TCCGTGCGATCTGGAGGAAGTAGCCAAGTGTTTTTCATGACCCTCAACAGAAATTCCATGATGAACTGGTAA>

*FIG._26B*

ATGGCGAGCGACTCCCCGGCTCGAAGCCTGGATGAAATAGATCTCTCGGCTCTGAGGGACCCTGCAGGGATCTTT
GAATTGGTGGAACTTGTTGGAAATGGAACATACGGGCAAGTTTATAAGGGTCGTCATGTCAAAACGGGCCAGCTT
GCAGCCATCAAGGTTATGGATGTCACAGGGGATGAAGAGGAAGAAATCAAACAAGAAATTAACATGTTGAAGAAA
TATTCTCATCACCGGAATATTGCTACATACTATGGTGCTTTTATCAAAAAGAACCCACCAGGCATGGATGACCAA
CTTTGGTTGGTGATGGAGTTTTGTGGTGCTGGCTCTGTCACCGACCTGATCAAGAACACAAAAGGTAACACGTTG
AAAGAGGAGTGGATTGCATACATCTGCAGGGAAATCTTACGGGGGCTGAGTCACCTGCACCAGCATAAAGTGATT
CATCGAGATATTAAAGGGCAAAATGTCTTGCTGACTGAAAATGCAGAAGTTAAACTAGTGGACTTTGGAGTCAGT
GCTCAGCTTGATCGAACAGTGGGCAGGAGGAATACTTTCATTGGAACTCCCTACTGGATGGCACCAGAAGTTATT
GCCTGTGATGAAAACCCAGATGCCACATATGATTTCAAGAGTGACTTGTGGTCTTTGGGTATCACCGCCATTGAA
ATGGCAGAAGGTGCTCCCCCTCTCTGTGACATGCACCCCATGAGAGCTCTCTTCCTCATCCCCCGGAATCCAGCG
CCTCGGCTGAAGTCTAAGAAGTGGTCAAAAAAATTCCAGTCATTTATTGAGAGCTGCTTGGTAAAGAATCACAGC
CAGCGACCAGCAACAGAACAATTGATGAAGCATCCATTTATACGAGACCAACCTAATGAGCGACAGGTCCGCATT
CAACTCAAGGACCATATTGATAGAACAAAGAAGAAGCGAGGAGAAAAAGATGAGACAGAGTATGAGTACAGTGGA
AGTGAGGAAGAAGAGGAGGAGAATGACTCAGGAGAGCCCAGCTCCATCCTGAATCTGCCAGGGGAGTCGACGCTG
CGGAGGGACTTTCTGAGGCTGCAGCTGGCCAACAAGGAGCGTTCTGAGGCCCTACGGAGGCAGCAGCTGGAGCAG
CAGCAGCGGGAGAATGAGGAGCACAAGCGGCAGCTGCTGGCCGAGCGTCAGAAGCGCATCGAGGAGCAGAAAGAG
CAGAGGCGGCGGCTGGAGGAGCAACAAAGGCGAGAGAAGGAGCTGCGGAAGCAGCAGGAGAGGGAGCAGCGCCGG
CACTATGAGGAGCAGATGCGCCGGGAGGAGGAGAGGAGGCGTGCGGAGCATGAACAGGAATACATCAGGCGACAG
TTAGAGGAGGAGCAGAGACAGTTAGAGATCTTGCAGCAGCAGCTACTGCATGAACAAGCTCTACTTCTGGAATAT
AAGCGCAAACAATTGGAAGAACAGAGACAAGCAGAAAGACTGCAGAGGCAGCTAAAGCAAGAAAGAGACTACTTA
GTTTCCCTTCAGCATCAGCGGCAGGAGCAGAGGCCTGTGGAGAAGAAGCCACTGTACCATTACAAAGAAGGAATG
AGTCCTAGTGAGAAGCCAGCATGGGCCAAGGAGATCCCACATCTGGTAGCTGTAAAATCCCAGGGACCTGCCTTG
ACCGCCTCCCAGTCAGTGCACGAGCAGCCCACAAAGGGCCTCTCTGGGTTTCAGGAGGCTCTGAACGTGACCTCC
CACCGCGTGGAGATGCCACGCCAGAACTCAGATCCCACCTCGGAAAATCCTCCTCTCCCCACTCGCATTGAAAAG
TTTGACCGAAGCTCTTGGTTACGACAGGAAGAAGACATTCCACCAAAGGTGCCTCAAAGAACAACTTCTATATCC
CCAGCATTAGCCAGAAAGAATTCTCCTGGGAATGGTAGTGCTCTGGGACCCAGACTAGGATCTCAACCCATCAGA
GCAAGCAACCCTGATCTCCGGAGAACTGAGCCCATCTTGGAGAGCCCCTTGCAGAGGACCAGCAGTGGCAGTTCC

FIG._27A

TCCAGCTCCAGCACCCCTAGCTCCCAGCCCAGCTCCCAAGGAGGCTCCCAGCCTGGATCACAAGCAGGATCCAGT
GAACGCACCAGAGTTCGAGCCAACAGTAAGTCAGAAGGATCACCTGTGCTTCCCCATGAGCCTGCCAAGGTGAAA
CCAGAAGAATCCAGGGACATTACCCGGCCCAGTCGACCAGCTGATCTGACGGCATTAGCCAAAGAACTAAGAGAA
CTCCGGATTGAAGAAACAAACCGCCCAATGAAGAAGGTGACTGATTACTCCTCCTCCAGTGAGGAGTCAGAAAGT
AGCGAGGAAGAGGAGGAAGATGGAGAGAGCGAGACCCATGATGGGACAGTGGCTGTCAGCGACATACCCAGACTG
ATACCAACAGGAGCTCCAGGCAGCAACGAGCAGTACAATGTGGGAATGGTGGGGACGCATGGGCTGGAGACCTCT
CATGCGGACAGTTTCAGCGGCAGTATTTCAAGAGAAGGAACCTTGATGATTAGAGAGACGTCTGGAGAGAAGAAG
CGATCTGGCCACAGTGACAGCAATGGCTTTGCTGGCCACATCAACCTCCCTGACCTGGTGCAGCAGAGCCATTCT
CCAGCTGGAACCCCGACTGAGGGACTGGGGCGCGTCTCAACCCATTCCCAGGAGATGGACTCTGGGACTGAATAT
GGCATGGGGAGCAGCACCAAAGCCTCCTTCACCCCCTTTGTGGACCCCAGAGTATACCAGACGTCTCCCACTGAT
GAAGATGAAGAGGATGAGGAATCATCAGCCGCAGCTCTGTTTACTAGCGAACTTCTTAGGCAAGAACAGGCCAAA
CTCAATGAAGCAAGAAAGATTTCGGTGGTAAATGTAAACCCAACCAACATTCGGCCTCATAGCGACACACCAGAA
ATCAGAAAATACAAGAAACGATTCAACTCAGAAATACTTTGTGCAGCTCTGTGGGGTGTAAACCTTCTGGTGGGG
ACTGAAAATGGCCTGATGCTTTTGGACCGAAGTGGGCAAGGCAAAGTCTATAATCTGATCAACCGGAGGCGATTT
CAGCAGATGGATGTGCTAGAGGGACTGAATGTCCTTGTGACAATTTCAGGAAAGAAGAATAAGCTACGAGTTTAC
TATCTTTCATGGTTAAGAAACAGAATACTACATAATGACCCAGAAGTAGAAAAGAAACAAGGCTGGATCACTGTT
GGGGACTTGGAAGGCTGTATACATTATAAAGTTGTTAAATATGAAAGGATCAAATTTTGGTGATTGCCTTAAAG
AATGCTGTGGAAATATATGCTTGGGCTCCTAAACCGTATCATAAATTCATGGCATTTAAGTCTTTTGCAGATCTC
CAGCACAAGCCTCTGCTAGTTGATCTCACGGTAGAAGAAGGTCAAAGATTAAAGGTTATTTTTGGTTCACACACT
GGTTTCCATGTAATTGATGTTGATTCAGGAAACTCTTATGATATCTACATACCATCTCATATTCAGGGCAATATC
ACTCCTCATGCTATTGTCATCTTGCCTAAAACAGATGGAATGGAAATGCTTGTTTGCTATGAGGATGAGGGGGTG
TATGTAAACACCTATGGCCGGATAACTAAGGATGTGGTGCTCCAATGGGGAGAAATGCCCACGTCTGTGGCCTAC
ATTCATTCCAATCAGATAATGGGCTGGGGCGAGAAAGCTATTGAGATCCGGTCAGTGGAAACAGGACATTTGGAT
GGAGTATTTATGCATAAGCGAGCTCAAAGGTTAAAGTTTCTATGTGAAAGAAATGATAAGGTATTTTTTGCATCC
GTGCGATCTGGAGGAAGTAGCCAAGTGTTTTTCATGACCCTCAACAGAAATTCCATGATGAACTGGTAA

FIG._27B

ATGGCGAGCGACTCCCCGGCTCGAAGCCTGGATGAAATAGATCTCTCGGCTCTGAGGGACCCTGCAGGGATCTTT
GAATTGGTGGAACTTGTTGGAAATGGAACATACGGGCAAGTTTATAAGGGTCGTCATGTCAAAACGGGCCAGCTT
GCAGCCATCAAGGTTATGGATGTCACAGGGGATGAAGAGGAAGAAATCAAACAAGAAATTAACATGTTGAAGAAA
TATTCTCATCACCGGAATATTGCTACATACTATGGTGCTTTTATCAAAAAGAACCCACCAGGCATGGATGACCAA
CTTTGGTTGGTGATGGAGTTTTGTGGTGCTGGCTCTGTCACCGACCTGATCAAGAACACAAAAGGTAACACGTTG
AAAGAGGAGTGGATTGCATACATCTGCAGGGAAATCTTACGGGGGCTGAGTCACCTGCACCAGCATAAAGTGATT
CATCGAGATATTAAAGGGCAAAATGTCTTGCTGACTGAAAATGCAGAAGTTAAACTAGTGGACTTTGGAGTCAGT
GCTCAGCTTGATCGAACAGTGGGCAGGAGGAATACTTTCATTGGAACTCCCTACTGGATGGCACCAGAAGTTATT
GCCTGTGATGAAAACCCAGATGCCACATATGATTTCAAGAGTGACTTGTGGTCTTTGGGTATCACCGCCATTGAA
ATGGCAGAAGGTGCTCCCCCTCTCTGTGACATGCACCCCATGAGAGCTCTCTTCCTCATCCCCCGGAATCCAGCG
CCTCGGCTGAAGTCTAAGAAGTGGTCAAAAAAATTCCAGTCATTTATTGAGAGCTGCTTGGTAAAGAATCACAGC
CAGCGACCAGCAACAGAACAATTGATGAAGCATCCATTTATACGAGACCAACCTAATGAGCGACAGGTCCGCATT
CAACTCAAGGACCATATTGATAGAACAAAGAAGAAGCGAGGAGAAAAAGATGAGACAGAGTATGAGTACAGTGGA
AGTGAGGAAGAAGAGGAGGAGAATGACTCAGGAGAGCCCAGCTCCATCCTGAATCTGCCAGGGGAGTCGACGCTG
CGGAGGGACTTTCTGAGGCTGCAGCTGGCCAACAAGGAGCGTTCTGAGGCCCTACGGAGGCAGCAGCTGGAGCAG
CAGCAGCGGGAGAATGAGGAGCACAAGCGGCAGCTGCTGGCCGAGCGTCAGAAGCGCATCGAGGAGCAGAAAGAG
CAGAGGCGGCGGCTGGAGGAGCAACAAAGGCGAGAGAAGGAGCTGCGGAAGCAGCAGGAGAGGGAGCAGCGCCGG
CACTATGAGGAGCAGATGCGCCGGGAGGAGGAGAGGAGGCGTGCGGAGCATGAACAGGAATATAAGCGCAAACAA
TTGGAAGAACAGAGACAAGCAGAAAGACTGCAGAGGCAGCTAAAGCAAGAAAGAGACTACTTAGTTTCCCTTCAG
CATCAGCGGCAGGAGCAGAGGCCTGTGGAGAAGAAGCCACTGTACCATTACAAAGAAGGAATGAGTCCTAGTGAG
AAGCCAGCATGGGCCAAGGAGATCCCACATCTGGTAGCTGTAAAATCCCAGGGACCTGCCTTGACCGCCTCCCAG
TCAGTGCACGAGCAGCCCACAAAGGGCCTCTCTGGGTTTCAGGAGGCTCTGAACGTGACCTCCCACCGCGTGGAG
ATGCCACGCCAGAACTCAGATCCCACCTCGGAAAATCCTCCTCTCCCCACTCGCATTGAAAAGTTTGACCGAAGC
TCTTGGTTACGACAGGAAGAAGACATTCCACCAAAGGTGCCTCAAAGAACAACTTCTATATCCCCAGCATTAGCC
AGAAAGAATTCTCCTGGGAATGGTAGTGCTCTGGGACCCAGACTAGGATCTCAACCCATCAGAGCAAGCAACCCT
GATCTCCGGAGAACTGAGCCCATCTTGGAGAGCCCCTTGCAGAGGACCAGCAGTGGCAGTTCCTCCAGCTCCAGC
ACCCCTAGCTCCCAGCCCAGCTCCCAAGGAGGCTCCCAGCCTGGATCACAAGCAGGATCCAGTGAACGCACCAGA

FIG._28A

GTTCGAGCCAACAGTAAGTCAGAAGGATCACCTGTGCTTCCCCATGAGCCTGCCAAGGTGAAACCAGAAGAATCC
AGGGACATTACCCGGCCCAGTCGACCAGCTGATCTGACGGCATTAGCCAAAGAACTAAGAGAACTCCGGATTGAA
GAAACAAACCGCCCAATGAAGAAGGTGACTGATTACTCCTCCTCCAGTGAGGAGTCAGAAAGTAGCGAGGAAGAG
GAGGAAGATGGAGAGAGCGAGACCCATGATGGGACAGTGGCTGTCAGCGACATACCCAGACTGATACCAACAGGA
GCTCCAGGCAGCAACGAGCAGTACAATGTGGGAATGGTGGGGACGCATGGGCTGGAGACCTCTCATGCGGACAGT
TTCAGCGGCAGTATTTCAAGAGAAGGAACCTTGATGATTAGAGAGACGTCTGGAGAGAAGAAGCGATCTGGCCAC
AGTGACAGCAATGGCTTTGCTGGCCACATCAACCTCCCTGACCTGGTGCAGCAGAGCCATTCTCCAGCTGGAACC
CCGACTGAGGGACTGGGGCGCGTCTCAACCCATTCCCAGGAGATGGACTCTGGGACTGAATATGGCATGGGGAGC
AGCACCAAAGCCTCCTTCACCCCCTTTGTGGACCCCAGAGTATACCAGACGTCTCCCACTGATGAAGATGAAGAG
GATGAGGAATCATCAGCCGCAGCTCTGTTTACTAGCGAACTTCTTAGGCAAGAACAGGCCAAACTCAATGAAGCA
AGAAAGATTTCGGTGGTAAATGTAAACCCAACCAACATTCGGCCTCATAGCGACACACCAGAAATCAGAAAATAC
AAGAAACGATTCAACTCAGAAATACTTTGTGCAGCTCTGTGGGGTGTAAACCTTCTGGTGGGGACTGAAAATGGC
CTGATGCTTTTGGACCGAAGTGGGCAAGGCAAAGTCTATAATCTGATCAACCGGAGGCGATTTCAGCAGATGGAT
GTGCTAGAGGGACTGAATGTCCTTGTGACAATTTCAGGAAAGAAGAATAAGCTACGAGTTTACTATCTTTCATGG
TTAAGAAACAGAATACTACATAATGACCCAGAAGTAGAAAAGAAACAAGGCTGGATCACTGTTGGGGACTTGGAA
GGCTGTATACATTATAAAGTTGTTAAATATGAAAGGATCAAATTTTTGGTGATTGCCTTAAAGAATGCTGTGGAA
ATATATGCTTGGGCTCCTAAACCGTATCATAAATTCATGGCATTTAAGTCTTTTGCAGATCTCCAGCACAAGCCT
CTGCTAGTTGATCTCACGGTAGAAGAAGGTCAAAGATTAAAGGTTATTTTTGGTTCACACACTGGTTTCCATGTA
ATTGATGTTGATTCAGGAAACTCTTATGATATCTACATACCATCTCATATTCAGGGCAATATCACTCCTCATGCT
ATTGTCATCTTGCCTAAAACAGATGGAATGGAAATGCTTGTTTGCTATGAGGATGAGGGGGTGTATGTAAACACC
TATGGCCGGATAACTAAGGATGTGGTGCTCCAATGGGGAGAAATGCCCACGTCTGTGGCCTACATTCATTCCAAT
CAGATAATGGGCTGGGGCGAGAAAGCTATTGAGATCCGGTCAGTGGAAACAGGACATTTGGATGGAGTATTTATG
CATAAGCGAGCTCAAAGGTTAAAGTTTCTATGTGAAAGAAATGATAAGGTATTTTTTGCATCCGTGCGATCTGGA
GGAAGTAGCCAAGTGTTTTTCATGACCCTCAACAGAAATTCCATGATGAACTGGTAA

FIG._28B

```
1     MASDSPARSLDEIDLSALRDPAGIFELVELVGNGTYGQVYKGRHVKTGQLAAIKVMDVTG
61    DEEEEIKQEINMLKKYSHHRNIATYYGAFIKKNPPGMDDQLWLVMEFCGAGSVTDLIKNT
121   KGNTLKEEWIAYICREILRGLSHLHQHKVIHRDIKGQNVLLTENAEVKLVDFGVSAQLDR
181   TVGRRNTFIGTPYWMAPEVIACDENPDATYDFKSDLWSLGITAIEMAEGAPPLCDMHPMR
241   ALFLIPRNPAPRLKSKKWSKKFQSFIESCLVKNHSQRPATEQLMKHPFIRDQPNERQVRI
301   QLKDHIDRTKKKRGEKDETEYEYSGSEEEEEENDSGEPSSILNLPGESTLRRDFLRLQLA
361   NKERSEALRRQQLEQQQRENEEHKRQLLAERQKRIEEQKEQRRRLEEQQRREKELRKQQE
421   REQRRHYEEQMRREEERRRAEHEQEYKRKQLEEQRQAERLQRQLKQERDYLVSLQHQRQE
481   QRPVEKKPLYHYKEGMSPSEKPAWAKEVEERSRLNRQSSPAMPHKVANRISDPNLPPRSE
541   SFSISGVQPARTPPMLRPVDPQIPHLVAVKSQGPALTASQSVHEQPTKGLSGFQEALNVT
601   SHRVEMPRQNSDPTSENPPLPTRIEKFDRSSWLRQEEDIPPKVPQRTTSISPALARKNSP
661   GNGSALGPRLGSQPIRASNPDLRRTEPILESPLQRTSSGSSSSSSTPSSQPSSQGGSQPG
721   SQAGSSERTRVRANSKSEGSPVLPHEPAKVKPEESRDITRPSRPASYKKAIDEDLTALAK
781   ELRELRIEETNRPMKKVTDYSSSSEESESSEEEEEDGESETHDGTVAVSDIPRLIPTGAP
841   GSNEQYNVGMVGTHGLETSHADSFSGSISREGTLMIRETSGEKKRSGHSDSNGFAGHINL
901   PDLVQQSHSPAGTPTEGLGRVSTHSQEMDSGTEYGMGSSTKASFTPFVDPRVYQTSPTDE
961   DEEDEESSAAALFTSELLRQEQAKLNEARKISVVNVNPTNIRPHSDTPEIRKYKKRFNSE
1021  ILCAALWGVNLLVGTENGLMLLDRSGQGKVYNLINRRRFQQMDVLEGLNVLVTISGKKNK
1081  LRVYYLSWLRNRILHNDPEVEKKQGWITVGDLEGCIHYKVVKYERIKFLVIALKNAVEIY
1141  AWAPKPYHKFMAFKSFADLQHKPLLVDLTVEEGQRLKVIFGSHTGFHVIDVDSGNSYDIY
1201  IPSHIQGNITPHAIVILPKTDGMEMLVCYEDEGVYVNTYGRITKDVVLQWGEMPTSVAYI
1261  HSNQIMGWGEKAIEIRSVETGHLDGVFMHKRAQRLKFLCERNDKVFFASVRSGGSSQVFF
1321  MTLNRNSMMNWZ
```

FIG._29

```
1    MASDSPARSLDEIDLSALRDPAGIFELVELVGNGTYGQVYKGRHVKTGQLAAIKVMDVTG
61   DEEEEIKQEINMLKKYSHHRNIATYYGAFIKKNPPGMDDQLWLVMEFCGAGSVTDLIKNT
121  KGNTLKEEWIAYICREILRGLSHLHQHKVIHRDIKGQNVLLTENAEVKLVDFGVSAQLDR
181  TVGRRNTFIGTPYWMAPEVIACDENPDATYDFKSDLWSLGITAIEMAEGAPPLCDMHPMR
241  ALFLIPRNPAPRLKSKKWSKKFQSFIESCLVKNHSQRPATEQLMKHPFIRDQPNERQVRI
301  QLKDHIDRTKKKRGEKDETEYEYSGSEEEEEENDSGEPSSILNLPGESTLRRDFLRLQLA
361  NKERSEALRRQQLEQQQRENEEHKRQLLAERQKRIEEQKEQRRRLEEQQRREKELRKQQE
421  REQRRHYEEQMRREEERRRAEHEQEYIRRQLEEEQRQLEILQQQLLHEQALLLEYKRKQL
481  EEQRQAERLQRQLKQERDYLVSLQHQRQEQRPVEKKPLYHYKEGMSPSEKPAWAKEIPHL
541  VAVKSQGPALTASQSVHEQPTKGLSGFQEALNVTSHRVEMPRQNSDPTSENPPLPTRIEK
601  FDRSSWLRQEEDIPPKVPQRTTSISPALARKNSPGNGSALGPRLGSQPIRASNPDLRRTE
661  PILESPLQRTSSGSSSSSSTPSSQPSSQGGSQPGSQAGSSERTRVRANSKSEGSPVLPHE
721  PAKVKPEESRDITRPSRPASYKKAIDEDLTALAKELRELRIEETNRPMKKVTDYSSSSEE
781  SESSEEEEEDGESETHDGTVAVSDIPRLIPTGAPGSNEQYNVGMVGTHGLETSHADSFSG
841  SISREGTLMIRETSGEKKRSGHSDSNGFAGHINLPDLVQQSHSPAGTPTEGLGRVSTHSQ
901  EMDSGTEYGMGSSTKASFTPFVDPRVYQTSPTDEDEEDEESSAAALFTSELLRQEQAKLN
961  EARKISVVNVNPTNIRPHSDTPEIRKYKKRFNSEILCAALWGVNLLVGTENGLMLLDRSG
1021 QGKVYNLINRRRFQQMDVLEGLNVLVTISGKKNKLRVYYLSWLRNRILHNDPEVEKKQGW
1081 ITVGDLEGCIHYKVVKYERIKFLVIALKNAVEIYAWAPKPYHKFMAFKSFADLQHKPLLV
1141 DLTVEEGQRLKVIFGSHTGFHVIDVDSGNSYDIYIPSHIQGNITPHAIVILPKTDGMEML
1201 VCYEDEGVYVNTYGRITKDVVLQWGEMPTSVAYIHSNQIMGWGEKAIEIRSVETGHLDGV
1261 FMHKRAQRLKFLCERNDKVFFASVRSGGSSQVFFMTLNRNSMMNWZ
```

FIG._30

```
1    MASDSPARSLDEIDLSALRDPAGIFELVELVGNGTYGQVYKGRHVKTGQLAAIKVMDVTG
61   DEEEEIKQEINMLKKYSHHRNIATYYGAFIKKNPPGMDDQLWLVMEFCGAGSVTDLIKNT
121  KGNTLKEEWIAYICREILRGLSHLHQHKVIHRDIKGQNVLLTENAEVKLVDFGVSAQLDR
181  TVGRRNTFIGTPYWMAPEVIACDENPDATYDFKSDLWSLGITAIEMAEGAPPLCDMHPMR
241  ALFLIPRNPAPRLKSKKWSKKFQSFIESCLVKNHSQRPATEQLMKHPFIRDQPNERQVRI
301  QLKDHIDRTKKKRGEKDETEYEYSGSEEEEEENDSGEPSSILNLPGESTLRRDFLRLQLA
361  NKERSEALRRQQLEQQQRENEEHKRQLLAERQKRIEEQKEQRRRLEEQQRREKELRKQQE
421  REQRRHYEEQMRREEERRRAEHEQEYIRRQLEEEQRQLEILQQQLLHEQALLLEYKRKQL
481  EEQRQAERLQRQLKQERDYLVSLQHQRQEQRPVEKKPLYHYKEGMSPSEKPAWAKEVEER
541  SRLNRQSSPAMPHKVANRISDPNLPPRSESFSISGVQPARTPPMLRPVDPQIPHLVAVKS
601  QGPALTASQSVHEQPTKGLSGFQEALNVTSHRVEMPRQNSDPTSENPPLPTRIEKFDRSS
661  WLRQEEDIPPKVPQRTTSISPALARKNSPGNGSALGPRLGSQPIRASNPDLRRTEPILES
721  PLQRTSSGSSSSSSTPSSQPSSQGGSQPGSQAGSSERTRVRANSKSEGSPVLPHEPAKVK
781  PEESRDITRPSRPADLTALAKELRELRIEETNRPMKKVTDYSSSSEESESSEEEEEDGES
841  ETHDGTVAVSDIPRLIPTGAPGSNEQYNVGMVGTHGLETSHADSFSGSISREGTLMIRET
901  SGEKKRSGHSDSNGFAGHINLPDLVQQSHSPAGTPTEGLGRVSTHSQEMDSGTEYGMGSS
961  TKASFTPFVDPRVYQTSPTDEDEEDEESSAAALFTSELLRQEQAKLNEARKISVVNVNPT
1021 NIRPHSDTPEIRKYKKRFNSEILCAALWGVNLLVGTENGLMLLDRSGQGKVYNLINRRRF
1081 QQMDVLEGLNVLVTISGKKNKLRVYYLSWLRNRILHNDPEVEKKQGWITVGDLEGCIHYK
1141 VVKYERIKFLVIALKNAVEIYAWAPKPYHKFMAFKSFADLQHKPLLVDLTVEEGQRLKVI
1201 FGSHTGFHVIDVDSGNSYDIYIPSHIQGNITPHAIVILPKTDGMEMLVCYEDEGVYVNTY
1261 GRITKDVVLQWGEMPTSVAYIHSNQIMGWGEKAIEIRSVETGHLDGVFMHKRAQRLKFLC
1321 ERNDKVFFASVRSGGSSQVFFMTLNRNSMMNWZ
```

FIG._31

```
1    MASDSPARSLDEIDLSALRDPAGIFELVELVGNGTYGQVYKGRHVKTGQLAAIKVMDVTG
61   DEEEEIKQEINMLKKYSHHRNIATYYGAFIKKNPPGMDDQLWLVMEFCGAGSVTDLIKNT
121  KGNTLKEEWIAYICREILRGLSHLHQHKVIHRDIKGQNVLLTENAEVKLVDFGVSAQLDR
181  TVGRRNTFIGTPYWMAPEVIACDENPDATYDFKSDLWSLGITAIEMAEGAPPLCDMHPMR
241  ALFLIPRNPAPRLKSKKWSKKFQSFIESCLVKNHSQRPATEQLMKHPFIRDQPNERQVRI
301  QLKDHIDRTKKKRGEKDETEYEYSGSEEEEEENDSGEPSSILNLPGESTLRRDFLRLQLA
361  NKERSEALRRQQLEQQQRENEEHKRQLLAERQKRIEEQKEQRRRLEEQQRREKELRKQQE
421  REQRRHYEEQMRREEERRRAEHEQEYKRKQLEEQRQAERLQRQLKQERDYLVSLQHQRQE
481  QRPVEKKPLYHYKEGMSPSEKPAWAKEIPHLVAVKSQGPALTASQSVHEQPTKGLSGFQE
541  ALNVTSHRVEMPRQNSDPTSENPPLPTRIEKFDRSSWLRQEEDIPPKVPQRTTSISPALA
601  RKNSPGNGSALGPRLGSQPIRASNPDLRRTEPILESPLQRTSSGSSSSSSTPSSQPSSQG
661  GSQPGSQAGSSERTRVRANSKSEGSPVLPHEPAKVKPEESRDITRPSRPASYKKAIDEDL
721  TALAKELRELRIEETNRPMKKVTDYSSSSEESESSEEEEEDGESETHDGTVAVSDIPRLI
781  PTGAPGSNEQYNVGMVGTHGLETSHADSFSGSISREGTLMIRETSGEKKRSGHSDSNGFA
841  GHINLPDLVQQSHSPAGTPTEGLGRVSTHSQEMDSGTEYGMGSSTKASFTPFVDPRVYQT
901  SPTDEDEEDEESSAAALFTSELLRQEQAKLNEARKISVVNVNPTNIRPHSDTPEIRKYKK
961  RFNSEILCAALWGVNLLVGTENGLMLLDRSGQGKVYNLINRRRFQQMDVLEGLNVLVTIS
1021 GKKNKLRVYYLSWLRNRILHNDPEVEKKQGWITVGDLEGCIHYKVVKYERIKFLVIALKN
1081 AVEIYAWAPKPYHKFMAFKSFADLQHKPLLVDLTVEEGQRLKVIFGSHTGFHVIDVDSGN
1141 SYDIYIPSHIQGNITPHAIVILPKTDGMEMLVCYEDEGVYVNTYGRITKDVVLQWGEMPT
1201 SVAYIHSNQIMGWGEKAIEIRSVETGHLDGVFMHKRAQRLKFLCERNDKVFFASVRSGGS
1261 SQVFFMTLNRNSMMNWZ
```

*FIG._32*

1 MASDSPARSLDEIDLSALRDPAGIFELVELVGNGTYGQVYKGRHVKTGQLAAIKVMDVTG

61 DEEEEIKQEINMLKKYSHHRNIATYYGAFIKKNPPGMDDQLWLVMEFCGAGSVTDLIKNT

121 KGNTLKEEWIAYICREILRGLSHLHQHKVIHRDIKGQNVLLTENAEVKLVDFGVSAQLDR

181 TVGRRNTFIGTPYWMAPEVIACDENPDATYDFKSDLWSLGITAIEMAEGAPPLCDMHPMR

241 ALFLIPRNPAPRLKSKKWSKKFQSFIESCLVKNHSQRPATEQLMKHPFIRDQPNERQVRI

301 QLKDHIDRTKKKRGEKDETEYEYSGSEEEEEENDSGEPSSILNLPGESTLRRDFLRLQLA

361 NKERSEALRRQQLEQQQRENEEHKRQLLAERQKRIEEQKEQRRRLEEQQRREKELRKQQE

421 REQRRHYEEQMRREEERRRAEHEQEYKRKQLEEQRQAERLQRQLKQERDYLVSLQHQRQE

481 QRPVEKKPLYHYKEGMSPSEKPAWAKEVEERSRLNRQSSPAMPHKVANRISDPNLPPRSE

541 SFSISGVQPARTPPMLRPVDPQIPHLVAVKSQGPALTASQSVHEQPTKGLSGFQEALNVT

601 SHRVEMPRQNSDPTSENPPLPTRIEKFDRSSWLRQEEDIPPKVPQRTTSISPALARKNSP

661 GNGSALGPRLGSQPIRASNPDLRRTEPILESPLQRTSSGSSSSSSTPSSQPSSQGGSQPG

721 SQAGSSERTRVRANSKSEGSPVLPHEPAKVKPEESRDITRPSRPADLTALAKELRELRIE

781 ETNRPMKKVTDYSSSSEESESSEEEEEDGESETHDGTVAVSDIPRLIPTGAPGSNEQYNV

841 GMVGTHGLETSHADSFSGSISREGTLMIRETSGEKKRSGHSDSNGFAGHINLPDLVQQSH

901 SPAGTPTEGLGRVSTHSQEMDSGTEYGMGSSTKASFTPFVDPRVYQTSPTDEDEEDEESS

961 AAALFTSELLRQEQAKLNEARKISVVNVNPTNIRPHSDTPEIRKYKKRFNSEILCAALWG

1021 VNLLVGTENGLMLLDRSGQGKVYNLINRRRFQQMDVLEGLNVLVTISGKKNKLRVYYLSW

1081 LRNRILHNDPEVEKKQGWITVGDLEGCIHYKVVKYERIKFLVIALKNAVEIYAWAPKPYH

1141 KFMAFKSFADLQHKPLLVDLTVEEGQRLKVIFGSHTGFHVIDVDSGNSYDIYIPSHIQGN

1201 ITPHAIVILPKTDGMEMLVCYEDEGVYVNTYGRITKDVVLQWGEMPTSVAYIHSNQIMGW

1261 GEKAIEIRSVETGHLDGVFMHKRAQRLKFLCERNDKVFFASVRSGGSSQVFFMTLNRNSM

1321 MNWZ

FIG._33

```
1    MASDSPARSLDEIDLSALRDPAGIFELVELVGNGTYGQVYKGRHVKTGQLAAIKVMDVTG
61   DEEEEIKQEINMLKKYSHHRNIATYYGAFIKKNPPGMDDQLWLVMEFCGAGSVTDLIKNT
121  KGNTLKEEWIAYICREILRGLSHLHQHKVIHRDIKGQNVLLTENAEVKLVDFGVSAQLDR
181  TVGRRNTFIGTPYWMAPEVIACDENPDATYDFKSDLWSLGITAIEMAEGAPPLCDMHPMR
241  ALFLIPRNPAPRLKSKKWSKKFQSFIESCLVKNHSQRPATEQLMKHPFIRDQPNERQVRI
301  QLKDHIDRTKKKRGEKDETEYEYSGSEEEEEENDSGEPSSILNLPGESTLRRDFLRLQLA
361  NKERSEALRRQQLEQQQRENEEHKRQLLAERQKRIEEQKEQRRRLEEQQRREKELRKQQE
421  REQRRHYEEQMRREEERRRAEHEQEYIRRQLEEEQRQLEILQQQLLHEQALLLEYKRKQL
481  EEQRQAERLQRQLKQERDYLVSLQHQRQEQRPVEKKPLYHYKEGMSPSEKPAWAKEIPHL
541  VAVKSQGPALTASQSVHEQPTKGLSGFQEALNVTSHRVEMPRQNSDPTSENPPLPTRIEK
601  FDRSSWLRQEEDIPPKVPQRTTSISPALARKNSPGNGSALGPRLGSQPIRASNPDLRRTE
661  PILESPLQRTSSGSSSSSSTPSSQPSSQGGSQPGSQAGSSERTRVRANSKSEGSPVLPHE
721  PAKVKPEESRDITRPSRPADLTALAKELRELRIEETNRPMKKVTDYSSSSEESESSEEEE
781  EDGESETHDGTVAVSDIPRLIPTGAPGSNEQYNVGMVGTHGLETSHADSFSGSISREGTL
841  MIRETSGEKKRSGHSDSNGFAGHINLPDLVQQSHSPAGTPTEGLGRVSTHSQEMDSGTEY
901  GMGSSTKASFTPFVDPRVYQTSPTDEDEEDEESSAAALFTSELLRQEQAKLNEARKISVV
961  NVNPTNIRPHSDTPEIRKYKKRFNSEILCAALWGVNLLVGTENGLMLLDRSGQGKVYNLI
1021 NRRRFQQMDVLEGLNVLVTISGKKNKLRVYYLSWLRNRILHNDPEVEKKQGWITVGDLEG
1081 CIHYKVVKYERIKFLVIALKNAVEIYAWAPKPYHKFMAFKSFADLQHKPLLVDLTVEEGQ
1141 RLKVIFGSHTGFHVIDVDSGNSYDIYIPSHIQGNITPHAIVILPKTDGMEMLVCYEDEGV
1201 YVNTYGRITKDVVLQWGEMPTSVAYIHSNQIMGWGEKAIEIRSVETGHLDGVFMHKRAQR
1261 LKFLCERNDKVFFASVRSGGSSQVFFMTLNRNSMMNWZ
```

FIG._34

```
1    MASDSPARSLDEIDLSALRDPAGIFELVELVGNGTYGQVYKGRHVKTGQLAAIKVMDVTG
61   DEEEEIKQEINMLKKYSHHRNIATYYGAFIKKNPPGMDDQLWLVMEFCGAGSVTDLIKNT
121  KGNTLKEEWIAYICREILRGLSHLHQHKVIHRDIKGQNVLLTENAEVKLVDFGVSAQLDR
181  TVGRRNTFIGTPYWMAPEVIACDENPDATYDFKSDLWSLGITAIEMAEGAPPLCDMHPMR
241  ALFLIPRNPAPRLKSKKWSKKFQSFIESCLVKNHSQRPATEQLMKHPFIRDQPNERQVRI
301  QLKDHIDRTKKKRGEKDETEYEYSGSEEEEEENDSGEPSSILNLPGESTLRRDFLRLQLA
361  NKERSEALRRQQLEQQQRENEEHKRQLLAERQKRIEEQKEQRRRLEEQQRREKELRKQQE
421  REQRRHYEEQMRREEERRRAEHEQEYKRKQLEEQRQAERLQRQLKQERDYLVSLQHQRQE
481  QRPVEKKPLYHYKEGMSPSEKPAWAKEIPHLVAVKSQGPALTASQSVHEQPTKGLSGFQE
541  ALNVTSHRVEMPRQNSDPTSENPPLPTRIEKFDRSSWLRQEEDIPPKVPQRTTSISPALA
601  RKNSPGNGSALGPRLGSQPIRASNPDLRRTEPILESPLQRTSSGSSSSSTPSSQPSSQG
661  GSQPGSQAGSSERTRVRANSKSEGSPVLPHEPAKVKPEESRDITRPSRPADLTALAKELR
721  ELRIEETNRPMKKVTDYSSSSEESESSEEEEEDGESETHDGTVAVSDIPRLIPTGAPGSN
781  EQYNVGMVGTHGLETSHADSFSGSISREGTLMIRETSGEKKRSGHSDSNGFAGHINLPDL
841  VQQSHSPAGTPTEGLGRVSTHSQEMDSGTEYGMGSSTKASFTPFVDPRVYQTSPTDEDEE
901  DEESSAAALFTSELLRQEQAKLNEARKISVVNVNPTNIRPHSDTPEIRKYKKRFNSEILC
961  AALWGVNLLVGTENGLMLLDRSGQGKVYNLINRRRFQQMDVLEGLNVLVTISGKKNKLRV
1021 YYLSWLRNRILHNDPEVEKKQGWITVGDLEGCIHYKVVKYERIKFLVIALKNAVEIYAWA
1081 PKPYHKFMAFKSFADLQHKPLLVDLTVEEGQRLKVIFGSHTGFHVIDVDSGNSYDIYIPS
1141 HIQGNITPHAIVILPKTDGMEMLVCYEDEGVYVNTYGRITKDVVLQWGEMPTSVAYIHSN
1201 QIMGWGEKAIEIRSVETGHLDGVFMHKRAQRLKFLCERNDKVFFASVRSGGSSQVFFMTL
1261 NRNSMMNWZ
```

FIG._35

GERMINAL CENTER KINASE CELL CYCLE PROTEINS, COMPOSITIONS AND METHODS OF USE

FIELD OF THE INVENTION

The present invention is directed to compositions involved in cell cycle regulation and methods of use. More particularly, the present invention is directed to genes encoding proteins and proteins involved in cell cycle regulation. Methods of use include use in assays screening for modulators of the cell cycle and use as therapeutics.

BACKGROUND OF THE INVENTION

Cells cycle through various stages of growth, starting with the M phase, where mitosis and cytoplasmic division (cytokinesis) occurs. The M phase is followed by the G1 phase, in which the cells resume a high rate of biosynthesis and growth. The S phase begins with DNA synthesis, and ends when the DNA content of the nucleus has doubled. The cell then enters G2 phase, which ends when mitosis starts, signaled by the appearance of condensed chromosomes. Terminally differentiated cells are arrested in the G1 phase, and no longer undergo cell division.

The hallmark of a malignant cell is uncontrolled proliferation. This phenotype is acquired through the accumulation of gene mutations, the majority of which promote passage through the cell cycle. Cancer cells ignore growth regulatory signals and remain committed to cell division. Classic oncogenes, such as ras, lead to inappropriate transition from G1 to S phase of the cell cycle, mimicking proliferative extracellular signals. Cell cycle checkpoint controls ensure faithful replication and segregation of the genome. The loss of cell cycle checkpoint control results in genomic instability, greatly accelerating the accumulation of mutations which drive malignant transformation. Thus, modulating cell cycle checkpoint pathways and other such pathways with therapeutic agents could exploit the differences between normal and tumor cells, both improving the selectivity of radio- and chemotherapy, and leading to novel cancer treatments. As another example, it would be useful to control entry into apoptosis.

On the other hand, it is also sometimes desirable to enhance proliferation of cells in a controlled manner. For example, proliferation of cells is useful in wound healing and where growth of tissue is desirable. Thus, identifying modulators which promote, enhance or deter the inhibition of proliferation is desirable.

Proteins of general interest that have been reported on include kinases. The Ste20 family of kinases can be divided into two structurally distinct subfamilies. The first subfamily contains a C-terminal catalytic domain and an N-terminal binding site for the small G proteins Rac1 and Cdc42 (Herskowitz, *Cell*, 80:187–197 (1995)). The yeast serine/threonine kinase Ste20 and its mammalian homologue, p21 Activated Kinase 1 (PAK1), belong to this subfamily. Ste20 initiates a mitogen-activated protein kinase (MAPK) cascade that includes Ste11 (MAPKKK), Ste7 (MAPKK), and FUS3/KSS1 (MAPK) in response to activation of the small G protein Cdc42, as well as signals from the hetero-trimeric G proteins coupled to pheromone receptors (Herskowitz, *Cell*, 80:187–197 (1995)). Similar to Ste20, PAK1 has been reported to be a Cdc42 and Rac1 effector molecule and specifically regulates the c-Jun N-terminal kinase (JNK) pathway, one of the mammalian MAPK pathways (Bagrodia, et. al., *J. Biol. Chem.*, 270:27995–27998 (1995); Kyriakis, et al., *J. Biol. Chem.*, 271:24313–24316 (1996)). The JNK pathway is activated by a variety of stress inducing agents, including osmotic and heat shock, UV irradiation, protein inhibitors and pro-inflammatory cytokines such as tumor necrosis factor (TNF) (Ip, et al., *Curr. Opin. Cell Biol.*, 10:205–219 (1998)). JNKs are activated through threonine and tyrosine phosphorylation by MEK4 and MEK7 (MAPKK), which are in turn phosphorylated and activated by MAPKKKs including MEK kinase 1 (MEKK1), and mixed lineage kinases MLK2 and MLK3 (Ip, et al., *Curr. Opin. Cell Biol*., 10:205–219 (1998)). In addition to the activation of the JNK pathway, PAK1 has also been reported to be a regulator of the actin cytoskeleton (Sells, et al., *Curr. Biol.*, 7:202–210 (1997)).

The second subgroup of Ste20 family of kinases is represented by the family of germinal center kinases (GCK) (Kyriakis, *J. Biol. Chem.*, 274:5259–5262 (1999)). In contrast to Ste20 and PAK1, GCK family members have an N-terminal kinase domain and a C-terminal regulatory region. Many GCK family members, including GCK, germinal center kinase related protein (GCKR), meatopoietic protein kinase (HPK) 1, GCK-like kinase (GLK), HPK/GCK-like kinase (HGK) and NCK interacting kinase (NIK), have also been reported to activate the JNK pathway when overexpressed in 293 cells (Pombo, et al., *Nature*, 377:750–754 (1995); Shi, et al., *J. Biol. Chem.*, 272:32102–32107 (1997); Kiefer, et al., *EMBO J.*, 15:7013–7025 (1996); Diener, et al., *Proc. Natl. Acad. Sci. USA*, 94:9687–9692 (1997); Yao, et al., *J. Biol. Chem.*, 274:2118–2125 (1999); Su, et al., *EMBO J.*, 16:1279–1290 (1997)). Among those, GCK and GCKR have been implicated in mediating TNF-induced JNK activation through TNF receptor associated factor 2 (Traf2) (Pombo, et al., *Nature*, 377:750–754 (1995); Diener, et al., *Proc. Natl. Acad. Sci. USA*, 94:9687–9692 (1997); Yuasa, et al., *J. Biol. Chem.*, 273:22681–22692 (1998)). NCK interacting kinase (NIK) interacts with the SH2–SH3 domain containing adapter protein NCK and has been proposed to link protein tyrosine kinase signals to JNK activation (Su, et al., EMBO J., 16:1279–1290 (1997)).

One study reports on a GCK family kinase from Dictyostelium that can phosphorylate Severin in vitro. (Eichinger, et al., *J. Biol. Chem.*, 273:12952–12959 (1998)). Severin is an F-actin fragmenting and capping enzyme that regulates Dictyostelium motility. However, there has not been any studies indicating the involvement of mammalian GCKs in cytoskeleton regulation.

Despite the desirability of identifying cell cycle components and modulators, there is a deficit in the field of such compounds. Accordingly, it would be advantageous to provide compositions and methods useful in screening for modulators of the cell cycle. It would also be advantageous to provide novel compositions which are involved in the cell cycle.

SUMMARY OF THE INVENTION

The present invention provides cell cycle proteins and nucleic acids which encode such proteins. Also provided are methods for screening for a bioactive agent capable of modulating the cell cycle. The method comprises combining a cell cycle protein and a candidate bioactive agent and a cell or a population of cells, and determining the effect on the cell in the presence and absence of the candidate agent. Therapeutics for regulating or modulating the cell cycle are also provided.

In one aspect, a recombinant nucleic acid encoding a cell cycle protein of the present invention comprises a nucleic acid that hybridizes under high stringency conditions to a sequence complementary to that set forth in FIGS. 21, 22, 23, 24, 25, 26, 27 or 28. In a preferred embodiment, the cell cycle protein provided herein binds to Traf2 or Nck. Most preferably, the cell cycle protein binds to Traf2 and binds to Nck.

In one embodiment, a recombinant nucleic acid is provided which comprises a nucleic acid sequence as set forth in FIG. 21 (SEQ ID NO:1), 22 (SEQ ID NO:2), 23 (SEQ ID NO:3), 24 (SEQ ID NO:4), 25 (SEQ ID NO:5), 26 (SEQ ID NO:6), 27 (SEQ ID NO:7) or 28 (SEQ ID NO:8). In another embodiment, a recombinant nucleic acid encoding a cell cycle protein is provided which comprises a nucleic acid sequence having at least 85% sequence identity to a sequence as set forth in FIG. 21 (SEQ ID NO:1), 22 (SEQ ID NO:2), 23 (SEQ ID NO:3), 24 (SEQ ID NO:4), 25 (SEQ ID NO:5), 26 (SEQ ID NO:6), 27 (SEQ ID NO:7) or 28 (SEQ ID NO:8). In a further embodiment, provided herein is a recombinant nucleic acid encoding an amino acid sequence as depicted in FIG. 1 for Tnik, (SEQ ID NO:34) or FIG. 29 (SEQ ID NO:9), 30 (SEQ ID NO: 10), 31 (SEQ ID NO: 11), 32 (SEQ ID NO: 12), 33 (SEQ ID NO:13), 34 (SEQ ID NO:14) or 35 (SEQ ID NO:15).

In another aspect of the invention, expression vectors are provided. The expression vectors comprise one or more of the recombinant nucleic acids provided herein operably linked to regulatory sequences recognized by a host cell transformed with the nucleic acid. Further provided herein are host cells comprising the vectors and recombinant nucleic acids provided herein. Moreover, provided herein are processes for producing a cell cycle protein comprising culturing a host cell as described herein under conditions suitable for expression of the cell cycle protein. In one embodiment, the process includes recovering the cell cycle protein.

Also provided herein are recombinant cell cycle proteins encoded by the nucleic acids of the present invention. In one aspect, a recombinant polypeptide is provided herein which comprises an amino acid sequence having at least 80% sequence identity with a sequence as set forth in FIG. 21 (SEQ ID NO:1), 22 (SEQ ID NO:2), 23 (SEQ ID NO:3), 24 (SEQ ID NO:4), 25 (SEQ ID NO:5), 26 (SEQ ID NO:6), 27 (SEQ ID NO:7) or 28 (SEQ ID NO:8). In one embodiment, a recombinant cell cycle protein is provided which comprises an amino acid sequence as set forth in FIG. 1 for Tnik (SEQ ID NO:34), or FIG. 29 (SEQ ID NO:9), 30 (SEQ ID NO:10), 31 (SEQ ID NO:11), 32 (SEQ ID NO:12), 33 (SEQ ID NO:34 (SEQ ID NO:14) or 35 (SEQ ID NO:15).

In another aspect, the present invention provides isolated polypeptides which specifically bind to a cell cycle protein as described herein. Examples of such isolated polypeptides include antibodies. Such an antibody can be a monoclonal antibody. In one embodiment, such an antibody reduces or eliminates the biological function of said cell cycle protein.

Further provided herein are methods for screening for a bioactive agent capable of binding to a cell cycle protein. In one embodiment the method comprises combining a cell cycle protein and a candidate bioactive agent, and determining the binding of said candidate bioactive agent to said cell cycle protein.

In another aspect, provided herein is a method for screening for a bioactive agent capable of interfering with the binding of a cell cycle protein and a Traf, preferably Traf2, or Nck protein. In one embodiment, such a method comprises combining a cell cycle protein, a candidate bioactive agent and a Traf or Nck protein, and determining the binding of the cell cycle protein and the Traf or Nck protein. If desired, the cell cycle protein and the Traf or Nck protein can be combined first.

Further provided herein are methods for screening for a bioactive agent capable of modulating the activity of cell cycle protein. In one embodiment the method comprises adding a candidate bioactive agent to a cell comprising a recombinant nucleic acid encoding a cell cycle protein, and determining the effect of the candidate bioactive agent on the cell. In a preferred embodiment, a library of candidate bioactive agents is added to a plurality of cells comprising a recombinant nucleic acid encoding a cell cycle protein.

Other aspects of the invention will become apparent to the skilled artisan by the following description of the invention.

BRIEF DESCRIPTION OF THE DRAWINGS

FIG. 1 shows a sequence alignment of Tnik (top sequence (SEQ ID NO:34)) to NIK (bottom sequence (SEQ ID NO:35)). Identical residues are shaded with black and homologous residues are shaded with gray and dotted below. The three alternatively spliced exons are marked by (–) above the Tnik sequence (SEQ ID NO:34). residues are shaded with black and homologous residues are shaded with gray and dotted below. The three alternatively spliced exons are marked by (–) above the Tnik sequence.

FIG. 2 shows a picture of a gel showing polymerase chain reaction (PCR) products of Tnik fragments from human spleen, heart and brain cDNAs. Oligos corresponding to nucleotides 1264–1281 and nucleotides 2427–2410 were used as primers.

FIG. 3 shows a diagram of NIK and Tnik spliced isoforms. The percent homology between Tnik and NIK in individual domains is indicated. The three alternatively spliced exons are hatched and the amino acid boundaries corresponding to the three exons are indicated.

FIG. 4 shows a picture of a gel with the results of an in vitro kinase assay of Tnik. Phoenix-A cells in 6-well plates were transiently transfected with 3 $\mu$g of HA-Tnik(WT) (lanes 1 and 3) or HA-Tnik(KM) (lane 2 and 4). Expressed proteins were immunoprecipitated with an anti-HA antibody. Immune complexes were subjected to in vitro kinase assay (lanes 1, 2) or immunoblotting with an anti-HA antibody (lanes 3, 4).

FIG. 5 shows a picture of the results of expression of Tnik message in human tissues. FIG. 5A: Human multi-tissue Northern blot (Clontech) was hybridized with a probe corresponding to nts 1264–2427 in the Tnik coding region. FIG. 5B: The same blot was stripped and re-blotted with an β-actin probe to control for the amount of mRNA on each lane.

FIG. 6 shows the interaction of Tnik with Traf2 by a gel showing co-immunoprecipitation of Tnik with endogenous Traf2. Phoenix-A cells in 100 mm dishes were transiently transfected with 10 $\mu$g of vector (lane 1) or HA-Tnik (lane 2). Top panel: Cell lysates were immunoprecipitated with an anti-HA mAb and blotted with an anti-Traf2 pAb. Middle and bottom panels: One tenth of cell lysates were blotted with an anti-HA mAb or an anti-Traf2 pAb to control for protein expression.

FIG. 7 shows a schematic diagram of Tnik mutants.

FIGS. 8A–8C show results which show the mapping of domains on Tnik that mediated its interaction with Traf2. FLAG-Traf2 was co-transfected into Phoenix-A cells with HA-Tnik mutants. Top panel (FIG. 8A): Cell lysates were immunoprecipitated with an anti-HA pAb and blotted with an anti-FLAG mAb. Middle and bottom panels (FIGS. 8B and 8C): Cell lysates were immunoblotted with an anti-FLAG mAb or an anti-HA mAb.

FIG. 9 shows a schematic diagram of Traf2 mutants.

FIG. 10 shows the mapping of domains on Traf2 that mediated its interaction with Tnik. HA-Tnik was co-transfected into Phoenix-A cells with FLAG-Traf2 mutants and the cell lysates were analyzed as in FIG. 8.

FIG. 11 shows the results showing interaction of Tnik with NCK by co-immunoprecipitation of Tnik with endogenous NCK. Phoenix-A cells in 100 mm dishes were transiently transfected with 10 μg of vector (lane 1) or HA-Tnik (lane 2). Top panel: Cell lysates were immunoprecipitated with an anti-HA pAb and blotted with an anti-NCK mAb. Middle and bottom panels: One tenth of cell lysates were blotted with an anti-NCK mAb or an anti-HA mAb.

FIG. 12 shows the mapping of domains on Tnik that mediated its interaction with NCK. FLAG-NCK was co-transfected into Phoenix-A cells with HA-Tnik mutants. Top panel: Cell lysates were immunoprecipitated with an anti-HA pAb and blotted with an anti-FLAG mAb. Middle and bottom panels: Cell lysates were immunoblotted with an anti-FLAG mAb or an anti-HA mAb to control for protein expression.

FIG. 13 shows the results showing specific activation of the JNK pathway by Tnik by overexpression of Tnik activated JNK2. 1 μg of Myc-JNK2 was co-transfected into Phoenix-A cells in 6-well plates with 3 μg of vector (lanes 1–2), 1, 2 or 3 μg of Tnik plus 2, 1 or 0 μg of vector (lanes 3–5), or 1 μg of Traf2 plus 2 μg of vector (lane 6). Top panel: Myc-JNK2 was immunoprecipitated from cell lysates by an anti-Myc mAb and subjected to an in vitro kinase assay with GST-cJun as an exogenous substrate. In lane 2, 100 ng/ml of TNFα was added for 15 min before the cells were lysed. Bottom panel: One tenth of cell lysates were immunoblotted with an anti-Myc mAb to control for expression levels of Myc-JNK2.

FIG. 14 shows overexpression of Tnik did not activate extracellular signal regulated kinase (ERK) 1. 1 μg of Myc-ERK1 was co-transfected into Phoenix-A cells in 6-well plates with 3 μg of vector (lane 1), 1, 2 or 3 μg of Tnik plus 2, 1 or 0 μg of vector (lanes 2–4), or 0.05 μg of MEKK1 plus 2.95 μg of vector (lane 5). Top panel: Myc-ERK1 was immunoprecipitated from cell lysates by an anti-Myc mAb and subjected to an in vitro kinase assay with MBP as an exogenous substrate. Bottom panel: One tenth of the cell lysates were immunoblotted with an anti-Myc mAb to control for expression levels of Myc-ERK1.

FIG. 15 shows overexpression of Tnik did not activate p38. 1 μg of FLAG-p38 was co-transfected into Phoenix-A cells in 6-well plates with 3 μg of vector (lane 1), 1, 2 or 3 μg of Tnik plus 2, 1 or 0 μg of vector (lanes 2–4), or 0.05 μg of MEKK1 plus 2.95 μg of vector (lane 5). Top panel: FLAG-p38 was immunoprecipitated from cell lysates by an anti-FLAG mAb and subjected to an in vitro kinase assay with GST-ATF2 as an exogenous substrate. Bottom panel: One tenth of cell lysates were immunoblotted with an anti-FLAG mAb to control for expression levels of FLAG-p38.

FIG. 16 shows that the C-terminal GCKH (germinal center kinase homology region) domain of Tnik is both necessary and sufficient for JNK activation. 1 μg of Myc-JNK2 was co-transfected into Phoenix-A cells in 6-well plates with 3 μg of vector (lanes 1, 2), 3 μg of the indicated Tnik mutants (lanes 3–9) or 0.05 μg of MEKK1 plus 2.95 μg of vector (lane 10). In vitro kinase assay and immunoblotting were performed as described in A. These experiments were repeated at least three times.

FIG. 17 shows cytoskeletal regulation and inhibition of cell spreading by TNIK 0.4 μg of GFP was cotransfected into Phoenix A cells with 3 μg of vector, Tnik(WT), Tnik (KM), Tnik (C1) or JNK2. 24 hours following transfection, cells were examined using fluorescence microscopy.

FIG. 18 shows the results showing Tnik overexpression did not induce apoptosis. 3 μg of Vector, Tnik(VT), Tnik (KM) or RIP was transfected into Phoenix-A cells for 24 hours. Transfected cells were stained with Hoechst 33258 and examined under fluorescent microscope.

FIG. 19 shows a picture of a gel showing Tnik overexpression induced redistribution of actin. Phoenix-A cells were transfected with 3 μg of vector, HA-Tnik(WT) or HA-Tnik(KM) and lysed with 1% Triton X-100 as described in EXPERIMENTAL PROCEDURES. Top panel: Cell lysates ($4\times10^4$cells) from either Triton X-100 soluble (lanes 1–3) or insoluble (lanes 4–6) fractions were resolved on SDS-PAGE and immunoblotted with an anti-β-actin mAb. Bottom panel: Total cell lysates were blotted with an anti-HA mAb to control for expression levels of Tnik(WT) and Tnik(KM).

FIG. 20 shows a picture of a gel showing phosphorylation of Gelsolin by Tnik in vitro. Phoenix-A cells were transiently transfected with 3 μg of HA-Tnik(WT) (lane 1) or HA-Tnik(KM) (lane 2). Cell lysates were subjected to anti-HA immunoprecipitation and an in vitro kinase assay using Gelsolin (Sigma) as an exogenous substrate.

FIG. 21 shows the nucleic acid sequence of SEQ ID NO:1, encoding a cell cycle protein, Tnik, isoform 1.

FIG. 22 shows the nucleic acid sequence of SEQ ID NO:2, encoding a cell cycle protein, Tnik, isoform 2.

FIG. 23 shows the nucleic acid sequence of SEQ ID NO:3, encoding a cell cycle protein, Tnik, isoform 3.

FIG. 24 shows the nucleic acid sequence of SEQ ID NO:4, encoding a cell cycle protein, Tnik, isoform 4.

FIG. 25 shows the nucleic acid sequence of SEQ ID NO:5, encoding a cell cycle protein, Tnik, isoform 5.

FIG. 26 shows the nucleic acid sequence of SEQ ID NO:6, encoding a cell cycle protein, Tnik, isoform 6.

FIG. 27 shows the nucleic acid sequence of SEQ ID NO:7, encoding a cell cycle protein, Tnik, isoform 7.

FIG. 28 shows the nucleic acid sequence of SEQ ID NO:8, encoding a cell cycle protein, Tnik, isoform 8.

FIG. 29 shows the amino acid sequence of SEQ ID NO:9, of Tnik, isoform 2.

FIG. 30 shows the amino acid sequence of SEQ ID NO:10, of Tnik, isoform 3.

FIG. 31 shows the amino acid sequence of SEQ ID NO:11, of Tnik, isoform 4.

FIG. 32 shows the amino acid sequence of SEQ ID NO:12, of Tnik, isoform 5.

FIG. 33 shows the amino acid sequence of SEQ ID NO.13, of Tnik, isoform 6.

FIG. 34 shows the amino acid sequence of SEQ ID NO:14, of Tnik, isoform 7.

FIG. 35 shows the amino acid sequence of SEQ ID NO:15, of Tnik, isoform 8.

DETAILED DESCRIPTION OF THE INVENTION

The present invention provides cell cycle proteins and nucleic acids which encode such proteins. Also provided are methods for screening for a bioactive agent capable of modulating the cell cycle. The method comprises combining a cell cycle protein and a candidate bioactive agent and a cell or a population of cells, and determining the effect on the cell in the presence and absence of the candidate agent. Other screening assays including binding assays are also provided herein as described below. Therapeutics for regulating or modulating the cell cycle are also provided and described herein. Diagnostics, as further described below, are also provided herein.

A cell cycle protein of the present invention may be identified in several ways. "Protein" in this sense includes proteins, polypeptides, and peptides. The cell cycle proteins of the invention fall into two general classes: proteins that are completely novel, i.e. are not part of a public database as of the time of discovery, although they may have homology to either known proteins or peptides encoded by expressed sequence tags (ESTs). Alternatively, the cell cycle proteins are known proteins, but that were not known to be involved in the cell cycle; i.e. they are identified herein as having a novel biological function. Accordingly, a cell cycle protein may be initially identified by its association with a protein known to be involved in the cell cycle. Wherein the cell cycle proteins and nucleic acids are novel, compositions and methods of use are provided herein. In the case that the cell cycle proteins and nucleic acids were known but not known to be involved in cell cycle activity as described herein, methods of use, i.e. functional screens, are provided.

In one embodiment provided herein, a cell cycle protein as defined herein has one or more of the following characteristics: binding to Traf, preferably Traf2, binding to Nck; and cell cycle protein activity as described herein.

In one embodiment, the cell cycle protein is termed Tnik herein. One or more of the characteristics described below can apply to any of the cell cycle proteins provided herein, however, Tnik is used for illustrative purposes. Tnik is a member of the germinal center kinases. Preferably, Tnik binds to Traf or Nck. Preferably, the Traf protein is Traf2. In a preferred embodiment, Tnik binds to Traf and Nck.

Regarding Traf, regulation of CD40 signaling through multiple Traf binding sites and Traf hetero-oligomerization is described in, e.g., Pullen, et al., *Biochemistry*, 37(34):11836–45 (1998); Pullen, et al., *J Biol Chem*., 274(20):14246–54 (1999); Ishida, et al., *PNAS USA*, 93(18):9437–42 (1996); Kashiwada, et al., *J Exp Med*, 187(2):237–44(1998). Additionally, cell cycle and apoptosis-related proteins, kinases, and carcinomas are described in Muzio, et al., *J Dent Res*., 78(7):1345–53 (1999); Jimenez, et al., *Nature*, 400(6739):81–83 (1999); and Hsieh, Int *J Oncol*., 15(2):245–252 (1999). Moreover, Traf2 mediated activation of NF-kappa B by TNF receptor 2 and CD40 has been reported on. Rothe, et al., *Science*, 269(5229):1424–7 (1995). Regarding Traf2, also see, Takeuchi, et al., *JBC*, 271(33):19935–42 (1996) and Natoli, et al., *J Biol Chem*, 272(42):26079–82 (1997).

Regarding Nck, Nck has been reported on. For example, it has been reported that the adaptor protein Nck links receptor tyrosine kinases with the serine-threonine kinase Pak1. Nck is an adaptor protein composed of a single SH2 domain and three SH3 domains. Upon growth factor stimulation, Nck is recruited to receptor tyrosine kinases via its SH2 domain, probably initiating one or more signaling cascades. Galisteo, et al., *J Biol Chem*, 271(35):20997–1000 (1996). Also see, Chen, et al., *J Biol Chem*., 273(39):25171–8 (1998) which reports on Nck family genes, chromosomal localization and expression.

As indicated below, Tnik shares homology with fragments of clone K1AA0551, GENBANK Accession number AB011123. Preferred embodiments of Tnik herein include the full length protein. In another preferred embodiment, Tnik comprises one or more cell cycle bioactivities as described below. In yet other embodiments wherein bioactivities are not required, Tnik excludes portions of the sequence which overlap with K1AA0551.

Thus, in some embodiments, the portions of homology with K1AA0551 may be excluded. For example, in Tnik Isoform number 1, the KIAA5501 fragment begins about with base pair number 1 at about position number 82 on Tnik and ends about with base pair number 4002 at about position number 4083 on Tnik. In Tnik isoform number 2, the KIAA5501 fragment begins about with base pair number 1338 at about position number 1332 on Tnik and ends about with base pair number 4002 at about position number 3996 on Tnik. In Tnik Isoform number 3, the KIAA5501 fragment begins about with base pair number 1691 at about position number 1607 on Tnik and ends about with base pair number 4002 at about position number 3918 on Tnik. In the Tnik isoform number 4, the KIAA5501 fragment begins about with base pair number 1 at about position number 82 on Tnik and ends about with base pair number 2301 at about position number 2382 on Tnik. In Tnik isoform number 5, the KIAA5501 fragment begins about with base pair number 1691 at about position number 1520 on Tnik and ends about with base pair number 4002 at about position number 3831 on Tnik. In Tnik isoform number 6, the KIAA5501 fragment begins about with base pair number 2326 at about position number 2296 on Tnik and ends about with base pair number 4002 at about position number 3972 on Tnik. In Tnik isoform number 7, the KIAA5501 fragment begins about with base pair number 2326 at about position number 2218 on Tnik and ends about with base pair number 4002 at about position number 3894 on Tnik. In Tnik isoform number 8, the KIAA5501 fragment begins about with base pair number 2326 at about position number 2131 on Tnik and ends about with base pair number 4002 at about position number 3807 on Tnik.

In a preferred embodiment, the cell cycle protein has a N-terminal kinase domain corresponding approximately to positions 1–305 of Tnik shown in the figures, an intermediate region, corresponding approximately to amino acid positions 306 through 1017 of Tnik as shown in the figures, and a C-terminal germinal center kinase homology region corresponding approximately to amino acids 1018 through 1360 of Tnik as shown in the figures. In one embodiment herein, the cell cycle protein consists essentially of one or more of the N-terminal kinase domain, intermediate region, and C-terminal germinal center kinase homology region.

In one embodiment, the cell cycle protein has one or more of the following characteristics: an intermediate region which shares greater than 40%, more preferably greater than 65%, more preferably, greater than 75%, more preferably greater than 85%, more preferably greater than 95% homology to the corresponding amino acids as shown in FIG. 1 or encoded by any of the nucleic acids of FIGS. 21–28; an N-terminal kinase domain of the cell cycle protein which shares greater than 90%, more preferably 95% homology to the corresponding amino acids as shown in FIG. 1 or encoded by any one of the nucleic acids of FIGS. 21–28; a C-terminal genminal center kinase homology region which has greater than 90%, more preferably 95% homology to the corresponding amino acids as shown in any one of FIGS. 1 and 29–35. The embodiments provided herein explicitly include any combination of these characteristics. Moreover, the homology of the cell cycle protein may be greater in one region corresponding to one or more of the isoforms but not the other.

The homology to, for example, NIK can be found as described below. In one embodiment, homology is found using the following database and parameters homology. The method used to generate 90% and 40% homology is: Program: DNA Star Windows 32 version 3.18; Method: Jotun Hein; Multiple Alignment Parameters: Gap Penalty=11, Gap Length Penalty=3; Pairwise Alignment Parameters: K tuple=2.

In a preferred embodiment, a protein is a "cell cycle protein" as defined herein if the overall sequence identity of the amino acid sequence of FIG. 1 for Tnik (SEQ ID NO:34), or FIG. 29 (SEQ ID NO:9), 30 (SEQ ID NO: 10), 31 (SEQ ID NO:I 1), 32 (SEQ ID NO: 12), 33 (SEQ ID NO: 13), 34 (SEQ ID NO: 14) or 35 (SEQ ID NO: 15) is preferably greater than about 75%, more preferably greater than about 80%, even more preferably greater than about 85% and most preferably greater than 90%. In some embodiments the sequence identity will be as high as about 93 to 95 or 98%.

In a preferred embodiment, a protein is a "cell cycle protein" as defined herein if the overall sequence identity of the amino acid sequence of FIG. 1 for Tnik, or FIGS. 29, 30, 31, 32, 33, 34 or 35 is preferably greater than about 75%, more preferably greater than about 80%, even more preferably greater than about 85% and most preferably greater than 90%. In some embodiments the sequence identity will be as high as about 93 to 95 or 98%.

In another preferred embodiment, a cell cycle protein has an overall sequence similarity with the amino acid sequence of FIG. 1 for Tnik (SEQ ID NO:34), or FIG. 29 (SEQ ID NO:9), 30 (SEQ ID NO:10), 31 (SEQ ID NO:11), 32 (SEQ ID NO:12), 33 (SEQ ID NO:13), 34 (SEQ ID NO:14) or 35 (SEQ ID NO:15), of greater than about 80%, more preferably greater than about 85%, even more preferably greater than about 90% and most preferably greater than 93%. In some embodiments the sequence identity will be as high as about 95 to 98 or 99%.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith, et al., *Adv. Appl. Math.* 2:482 (1981), by the sequence identity alignment algorithm of Needleman, et al., *J. Mol. Biol.*, 48:443 (1970), by the search for similarity method of Pearson, et al., *PNAS USA*, 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux, et al., *Nucl. Acid Res.*, 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng, et al., *J. Mol. Evol.*, 35:351–360 (1987); the method is similar to that described by Higgins, et al., *CABIOS*, 5:151–153 (1989). Useful PILEUP parameters including a default gap weight of 3.00, a default gap length weight of 0.10, and weighted end gaps.

Another example of a useful algorithm is the BLAST algorithm, described in Altschul, et al., *J. Mol. Biol*,. 215:403–410, (1990) and Karlin, et al., *PNAS USA*, 90:5873–5787 (1993). A particularly useful BLAST program is the WU-BLAST-2 program which was obtained from Altschul, et al., *Methods in Enzymology*, 266:460–480 (1996). WU-BLAST-2 uses several search parameters, most of which are set to the default values. The adjustable pameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul, et al., *Nucleic Acids Res.*, 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequences in the Figures, it is understood that in one embodiment, the percentage of sequence identity will be determined based on the number of identical amino acids in relation to the total number of amino acids. Thus, for example, sequence identity of sequences shorter than that shown in the Figure, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein.

Cell cycle proteins of the present invention may be shorter or longer than the amino acid sequence encoded by the nucleic acid shown in the Figure. Thus, in a preferred embodiment, included within the definition of cell cycle proteins are portions or fragments of the amino acid sequence encoded by the nucleic acid sequence provided herein. In one embodiment herein, fragments of cell cycle proteins are considered cell cycle proteins if a) they share at least one antigenic epitope; b) have at least the indicated sequence identity; c) and preferably have cell cycle biological activity as further defined herein. In some cases, where the sequence is used diagnostically, that is, when the presence or absence of cell cycle protein nucleic acid is determined, only the indicated sequence identity is required. The nucleic acids of the present invention may also be shorter or longer than the sequence in the Figure. The nucleic acid fragments include any portion of the nucleic acids provided herein which have a sequence not exactly previously identified; fragments having sequences with the indicated sequence identity to that portion not previously identified are provided in an embodiment herein.

In addition, as is more fully outlined below, cell cycle proteins can be made that are longer than those depicted in the Figure; for example, by the addition of epitope or purification tags, the addition of other fusion sequences, or the elucidation of additional coding and non-coding sequences. As described below, the fusion of a cell cycle peptide to a fluorescent peptide, such as Green Fluorescent Peptide (GFP), is particularly preferred.

Cell cycle proteins may also be identified as encoded by cell cycle nucleic acids which hybridize to the sequence depicted in the Figure, or the complement thereof, as outlined herein. Hybridization conditions are further described below.

In a preferred embodiment, when a cell cycle protein is to be used to generate antibodies, a cell cycle protein must share at least one epitope or determinant with the full length protein. By "epitope" or "determinant" herein is meant a portion of a protein which will generate and/or bind an antibody. Thus, in most instances, antibodies made to a smaller cell cycle protein will be able to bind to the full length protein. In a preferred embodiment, the epitope is unique; that is, antibodies generated to a unique epitope show little or no cross-reactivity. The term "antibody" includes antibody fragments, as are known in the art, including Fab $Fab_2$, single chain antibodies (Fv for example), chimeric antibodies, etc., either produced by the modification of whole antibodies or those synthesized de novo using recombinant DNA technologies.

In a preferred embodiment, the antibodies to a cell cycle protein are capable of reducing or eliminating the biological function of the cell cycle proteins described herein, as is described below. That is, the addition of anti-cell cycle protein antibodies (either polyclonal or preferably monoclonal) to cell cycle proteins (or cells containing cell cycle proteins) may reduce or eliminate the cell cycle activity. Generally, at least a 25% decrease in activity is preferred, with at least about 50% being particularly preferred and about a 95–100% decrease being especially preferred.

The cell cycle antibodies of the invention specifically bind to cell cycle proteins. In a preferred embodiment, the antibodies specifically bind to cell cycle proteins. By "specifically bind" herein is meant that the antibodies bind to the protein with a binding constant in the range of at least $10^{-4}$–$10^{-6}M^{-1}$, with a preferred range being $10^{-7}$–$10^{-9}M^{-1}$. Antibodies are further described below.

In the case of the nucleic acid, the overall sequence identity of the nucleic acid sequence is commensurate with amino acid sequence identity but takes into account the degeneracy in the genetic code and codon bias of different organisms. Accordingly, the nucleic acid sequence identity may be either lower or higher than that of the protein sequence. Thus the sequence identity of the nucleic acid sequence as compared to the nucleic acid sequence of the Figure is preferably greater than 75%, more preferably greater than about 80%, particularly greater than about 85% and most preferably greater than 90%. In some embodiments the sequence identity will be as high as about 93 to 95 or 98%.

In a preferred embodiment, a cell cycle nucleic acid encodes a cell cycle protein. As will be appreciated by those in the art, due to the degeneracy of the genetic code, an extremely large number of nucleic acids may be made, all of which encode the cell cycle proteins of the present invention. Thus, having identified a particular amino acid sequence, those skilled in the art could make any number of different nucleic acids, by simply modifying the sequence of one or more codons in a way which does not change the amino acid sequence of the cell cycle protein.

In one embodiment, the nucleic acid is determined through hybridization studies. Thus, for example, nucleic acids which hybridize under high stringency to the nucleic acid sequence shown in the Figure, or its complement is considered a cell cycle nucleic acid. High stringency conditions are known in the art; see for example Maniatis, et al., *Molecular Cloning: A Laboratory Manual*, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art, see Maniatis and Ausubel, supra, and Tijssen, supra.

The cell cycle proteins and nucleic acids of the present invention are preferably recombinant. As used herein and further defined below, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequences depicted in the Figures also include the complement of the sequence. By the term "recombinant nucleic acid" herein is meant nucleic acid, originally formed in vitro, in general, by the manipulation of nucleic acid by endonucleases, in a form not normally found in nature. Thus an isolated cell cycle nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a cell cycle protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In one embodiment, the present invention provides cell cycle protein variants. These variants fall into one or more of three classes: substitutional, insertional or deletional variants. These variants ordinarily are prepared by site specific mutagenesis of nucleotides in the DNA encoding a cell cycle protein, using cassette or PCR mutagenesis or other techniques well known in the art, to produce DNA encoding the variant, and thereafter expressing the DNA in recombinant cell culture as outlined above. However, variant cell cycle protein fragments having up to about 100–150 residues may be prepared by in vitro synthesis using established techniques. Amino acid sequence variants are characterized by the predetermined nature of the variation, a feature that sets them apart from naturally occurring alielic or interspecies variation of the cell cycle protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed cell cycle variants screened for the optimal combination of desired activity. Techniques for making substitution mutations at predetermined sites in DNA having a known sequence are well known, for example, M13 primer mutagenesis and PCR mutagenesis. Screening of the mutants is done using assays of cell cycle protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the cell cycle protein are desired, substitutions are generally made in accordance with the following chart:

CHART I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the cell cycle proteins as needed. Alternatively, the variant may be designed such that the biological activity of the cell cycle protein is altered. For example, glycosylation sites may be altered or removed.

Covalent modifications of cell cycle polypeptides are included within the scope of this invention. One type of covalent modification includes reacting targeted amino acid residues of a cell cycle polypeptide with an organic derivatizing agent that is capable of reacting with selected side chains or the N- or C-terminal residues of a cell cycle polypeptide. Derivatization with bifunctional agents is useful, for instance, for crosslinking cell cycle to a water-insoluble support matrix or surface for use in the method for purifying anti-cell cycle antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azido-salicylic acid, homobifunctional imidoesters, including disuccinimidyl esters such as 3,3'-dithiobis-(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of the cell cycle polypeptide included within the scope of this invention comprises altering the native glycosylation pattern of the polypeptide. "Altering the native glycosylation pattern" is intended for purposes herein to mean deleting one or more carbohydrate moieties found in native sequence cell cycle polypeptide, and/or adding one or more glycosylation sites that are not present in the native sequence cell cycle polypeptide.

Addition of glycosylation sites to cell cycle polypeptides may be accomplished by altering the amino acid sequence thereof. The alteration may be made, for example, by the addition of, or substitution by, one or more serine or threonine residues to the native sequence cell cycle polypeptide (for O-linked glycosylation sites). The cell cycle amino acid sequence may optionally be altered through changes at the DNA level, particularly by mutating the DNA encoding the cell cycle polypeptide at preselected bases such that codons are generated that will translate into the desired amino acids.

Another means of increasing the number of carbohydrate moieties on the cell cycle polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem*., pp. 259–306 (1981).

Removal of carbohydrate moieties present on the cell cycle polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys*., 259:52 (1987) and by Edge, et al., *Anal. Biochem*., 118:131 (1981). Enzymatic cleavage of carbohydrate moieties on polypeptides can be achieved by the use of a variety of endo-and exo-glycosidases as described by Thotakura, et al., *Meth. Enzymol*., 138:350 (1987).

Another type of covalent modification of cell cycle comprises linking the cell cycle polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Cell cycle polypeptides of the present invention may also be modified in a way to form chimeric molecules comprising a cell cycle polypeptide fused to another, heterologous polypeptide or amino acid sequence. In one embodiment, such a chimeric molecule comprises a fusion of a cell cycle polypeptide with a tag polypeptide which provides an epitope to which an anti-tag antibody can selectively bind. The epitope tag is generally placed at the amino-or carboxyl-terminus of the cell cycle polypeptide. The presence of such epitope-tagged forms of a cell cycle polypeptide can be detected using an antibody against the tag polypeptide. Also, provision of the epitope tag enables the cell cycle polypeptide to be readily purified by affinity purification using an anti-tag antibody or another type of affinity matrix that binds to the epitope tag. In an alternative embodiment, the chimeric molecule may comprise a fusion of a cell cycle polypeptide with an immunoglobulin or a particular region of an immunoglobulin. For a bivalent form of the chimeric molecule, such a fusion could be to the Fc region of an IgG molecule as discussed further below.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field, et al., *Mol. Cell. Biol*., 8:2159–2165 (1988)]; the c-myc tag and the 8F9, 3C7, 6E10, G4, B7 and 9E10 antibodies thereto [Evan, et al., *Molecular and Cellular Biology*, 5:3610–3616 (1985)]; and the Herpes Simplex virus glycoprotein D (gD) tag and its antibody [Paborsky, et al., *Protein Engineering*, 3(6):547–553 (1990)]. Other tag polypeptides include the Flag-peptide [Hopp, et al., *Bio Technology*, 6:1204–1210 (1988)]; the KT3 epitope peptide [Martin, et al., *Science*, 255:192–194 (1992)]; tubulin epitope peptide [Skinner, et al., *J. Biol. Chem*., 266:15163–15166 (1991)]; and the T7 gene 10 protein peptide tag [Lutz-Freyermuth, et al., *Proc. Natl. Acad. Sci. USA*, 87:6393–6397 (1990)].

In an embodiment herein, cell cycle proteins of the cell cycle family and cell cycle proteins from other organisms are cloned and expressed as outlined below. Thus, probe or degenerate polymerase chain reaction (PCR) primer sequences may be used to find other related cell cycle proteins from humans or other organisms. As will be appreciated by those in the art, particularly useful probe and/or PCR primer sequences include the unique areas of the cell cycle nucleic acid sequence. As is generally known in the art, preferred PCR primers are from about 15 to about 35 nucleotides in length, with-from about 20 to about 30 being preferred, and may contain inosine as needed. The conditions for the PCR reaction are well known in the art. It is therefore also understood that provided along with the sequences in the sequences listed herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant cell cycle nucleic acid can be further-used as a probe to identify and isolate other cell cycle nucleic acids. It can also be used as a "precursor" nucleic acid to make modified or variant cell cycle nucleic acids and proteins.

Using the nucleic acids of the present invention which encode a cell cycle protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the cell cycle protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the cell cycle protein; for example, transcriptional and translational regulatory nucleic acid sequences from Bacillus are preferably used to express the cell cycle protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

Cell cycle proteins of the present invention are produced by culturing a host cell transformed with an expression vector containing nucleic acid encoding a cell cycle protein, under the appropriate conditions to induce or cause expression of the cell cycle protein. The conditions appropriate for cell cycle protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, Saccharomyces cerevisiae and other yeasts, *E. coli, Bacillus subtilis*, SF9 cells, C129 cells, 293 cells, Neurospora, BHK, CHO, COS, and HeLa cells, fibroblasts, Schwanoma cell lines, immortalized mammalian myeloid and lymphoid cell lines, tumor lines.

In a preferred embodiment, the cell cycle proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for cell cycle protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, cell cycle proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of cell cycle protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the tip and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the cell cycle protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, cell cycle proteins are produced in insect cells. Expression vectors for the transformation of insect cells, and in particular, baculovirus-based expression vectors, are well known in the art.

In a preferred embodiment, cell cycle protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The cell cycle protein may also be made as a fusion protein, using techniques well known in the art. Thus, for example, for the creation of monoclonal antibodies, if the desired epitope is small, the cell cycle protein may be fused to a carrier protein to form an immunogen. Alternatively, the cell cycle protein may be made as a fusion protein to increase expression, or for other reasons. For example, when the cell cycle protein is a cell cycle peptide, the nucleic acid encoding the peptide may be linked to other nucleic acid for expression purposes. Similarly, cell cycle proteins of the invention can be linked to protein labels, such as green fluorescent protein (GFP), red fluorescent protein (RFP), blue fluorescent protein (BFP), yellow fluorescent protein (YFP), etc.

In one embodiment, the cell cycle nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the cell cycle protein is purified or isolated after expression. Cell cycle proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the cell cycle protein may be purified using a standard anti-cell cycle antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the cell cycle protein. In some instances no purification will be necessary.

Once expressed and purified if necessary, the cell cycle proteins and nucleic acids are useful in a number of applications.

The nucleotide sequences (or their complement) encoding cell cycle proteins have various applications in the art of molecular biology, including uses as hybridization probes, in chromosome and gene mapping and in the generation of anti-sense RNA and DNA. Cell cycle protein nucleic acid will also be useful for the preparation of cell cycle proteins by the recombinant techniques described herein.

The full-length native sequence cell cycle protein gene, or portions thereof, may be used as hybridization probes for a cDNA library to isolate other genes (for instance, those encoding naturally-occurring variants of cell cycle protein or cell cycle protein from other species) which have a desired sequence identity to the cell cycle protein coding sequence. Optionally, the length of the probes will be about 20 to about 50 bases. The hybridization probes may be derived from the nucleotide sequences herein or from genomic sequences including promoters, enhancer elements and introns of native sequences as provided herein. By way of example, a screening method will comprise isolating the coding region of the cell cycle protein gene using the known DNA sequence to synthesize a selected probe of about 40 bases. Hybridization probes may be labeled by a variety of labels, including radionucleotides such as $^{32}$p or $^{35}$S, or enzymatic labels such as alkaline phosphatase coupled to the probe via avidin/biotin coupling systems. Labeled probes having a sequence complementary to that of the cell cycle protein gene of the present invention can be used to screen libraries of human cDNA, genomic DNA or mRNA to determine which members of such libraries the probe hybridizes.

Nucleotide sequences encoding a cell cycle protein can also be used to construct hybridization probes for mapping the gene which encodes that cell cycle protein and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Nucleic acids which encode cell cycle protein or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a cell cycle protein can be used to clone genomic DNA encoding a cell cycle protein in accordance with established techniques and the genomic sequences used to generate transgenic animals that contain cells which express the desired DNA. Methods for generating transgenic animals, particularly animals such as mice or rats, have become conventional in the art and are described, for example, in U.S. Pat. Nos. 4,736,866 and 4,870,009. Typically, particular cells would be targeted for the cell cycle protein transgene incorporation with tissue-specific enhancers. Transgenic animals that include a copy of a transgene encoding a cell cycle protein introduced into the germ line of the animal at an embryonic stage can be used to examine the effect of increased expression of the desired nucleic acid. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of the cell cycle protein can be used to construct a cell cycle protein "knock out" animal which has a defective or altered gene encoding a cell cycle protein as a result of homologous recombination between the endogenous gene encoding a cell cycle protein and altered genomic DNA encoding a cell cycle protein introduced into an embryonic cell of the animal. For example, cDNA encoding a cell cycle protein can be used to clone genomic DNA encoding a cell cycle protein in accordance with established techniques. A portion of the genomic DNA encoding a cell cycle protein can be deleted or replaced with another gene, such as a gene encoding a selectable marker which can be used to monitor integration. Typically, several kilobases of unaltered flanking DNA (both at the 5' and 3' ends) are included in the vector [see e.g., Thomas, et al., *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li, et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the cell cycle protein.

It is understood that the models described herein can be varied. For example, "knock-in" models can be formed, or the models can be cell-based rather than animal models.

Nucleic acid encoding the cell cycle polypeptides, antagonists or agonists may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik, et al., *Proc. Natl. Acad. Sci. USA*, 83:4143–4146 [1986]). The oligonucleotides can be modified to enhance their uptake, e.g. by substituting their negatively charged phosphodiester groups by uncharged groups. There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau, et al., *Trends in Biotechnology*, 11:205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu, et al., *J. Biol. Chem.*, 262:4429–4432 (1987); and Wagner, et al., *Proc. Natl. Acad. Sci. USA*, 87:3410–3414 (1990). For review of gene marking and gene therapy protocols see Anderson, et al., *Science* 256:808–813 (1992).

In a preferred embodiment, the cell cycle proteins, nucleic acids, variants, modified proteins, cells and/or transgenics containing the said nucleic acids or proteins are used in screening assays. Identification of the cell cycle protein provided herein permits the design of drug screening assays for compounds that bind or interfere with the binding to the cell cycle protein and for compounds which modulate cell cycle activity.

The assays described herein preferably utilize the human cell cycle protein, although other mammalian proteins may also be used, including rodents (mice, rats, hamsters, guinea pigs, etc.), farm animals (cows, sheep, pigs, horses, etc.) and primates. These latter embodiments may be preferred in the development of animal models of human disease. In some embodiments, as outlined herein, variant or derivative cell cycle proteins may be used, including deletion cell cycle proteins as outlined above.

In a preferred embodiment, the methods comprise combining a cell cyle protein and a candidate bioactive agent, and determining the binding of the candidate agent to the cell cycle protein. In other embodiments, further discussed below, binding interference or bioactivity is determined.

The term "candidate bioactive agent" or "exogeneous compound" as used herein describes any molecule, e.g., protein, small organic molecule, carbohydrates (including polysaccharides), polynucleotide, lipids, etc. Generally a plurality of assay mixtures are run in parallel with different agent concentrations to obtain a differential response to the various concentrations. Typically, one of these concentrations serves as a negative control, ie., at zero concentration or below the level of detection. In addition, positive controls, i.e. the use of agents known to alter cell cycling, may be used. For example, p21 is a molecule known to arrest cells in the G1 cell phase, by binding G1 cyclin-CDK complexes.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, a library of different candidate bioactive agents are used. Preferably, the library should provide a sufficiently structurally diverse population of randomized agents to effect a probabilistically sufficient range of diversity to allow binding to a particular target.

Accordingly, an interaction library should be large enough so that at least one of its members will have a structure that gives it affinity for the target. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $\mathbf{10}^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $\mathbf{10}^6$, preferably at least $10^7$, more preferably at least 10" and most preferably at least $10^9$ different sequences are simultaneously analyzed in the subject methods. Preferred methods maximize library size and diversity.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Chemical blocking groups or other chemical substituents may also be added.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., *Tetrahedron*, 49(10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta,* 26:141 (1986)), phosphorothioate (Mag, et al., *Nucleic Acids Res.*, 19:1437 (1991); and U.S. Pat. No. 5,644,048), phosphorodithioate (Briu, et al., *J. Am. Chem. Soc.*, 111:2321 (1989)), O-methylphophoroamidite linkages (see Eckstein, Oligonucleotides and Analogues: A Practical Approach, Oxford University Press), and peptide nucleic acid backbones and linkages (see Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et al., *Nature*, 380:207 (1996), all of which are incorporated by reference)). Other analog nucleic acids include those with positive backbones (Denpcy, et al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowshi, et al., *Angew. Chem. Intl. Ed. English*, 30:423 (1991); Letsinger, et al., *J. Am. Chem. Soc.*, 110:4470 (1988); Letsinger, et al., *Nucleoside & Nucleotide*, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); *Tetrahedron Lett.*, 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., *Chem. Soc. Rev.*, pp. 169–176 (1995)). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties, a wide variety of which are available in the literature.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, which provide the candidate bioactive agents in a conformationally restricted or stable form; b) targeting sequences, which allow the localization of the candidate bioactive agent into a subcellular or extracellular compartment; c) rescue sequences which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; or f any combination of a), b), c), d), and e), as well as linker sequences as needed.

In one embodiment of the methods described herein, portions of cell cycle proteins are utilized; in a preferred embodiment, portions having cell cycle activity are used. Cell cycle activity is described further below and includes binding activity to Traf or Nck or cell cycle protein modulators as further described below. In addition, the assays described herein may utilize either isolated cell cycle proteins or cells comprising the cell cycle proteins.

Generally, in a preferred embodiment of the methods herein, for example for binding assays, the cell cycle protein or the candidate agent is non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. In some embodiments, Traf2 or Nck can be used. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used; examples of such are described below.

In a preferred embodiment, the cell cycle protein is bound to the support, and a candidate bioactive agent is added to the assay. Alternatively, the candidate agent is bound to the support and the cell cycle protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the cell cycle protein may be done in a number of ways. In a preferred embodiment, the candidate bioactive agent is labelled, and binding determined directly. For example, this may be done by attaching all or a portion of the cell cycle protein to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}I$, or with fluorophores. Alternatively, more than one component may be labeled with different labels; using $^{125}I$ for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. cell cycle protein), such as an antibody, peptide, binding partner, ligand, etc. In a preferred embodiment, the competitor is Traf, preferably Traf2, or Nck. Under certain circumstances, there may be competitive binding as between the bioactive agent and the binding moiety, with the binding moiety displacing the bioactive agent. This assay can be used to determine candidate agents which interfere with binding between cell cycle proteins and Traf2 or Nck. "Interference of binding" as used herein means that native binding of the cell cycle protein differs in the presence of the candidate agent. The binding can be eliminated or can be with a reduced affinity. Therefore, in one embodiment, interference is caused by, for example, a conformation change, rather than direct competition for the native binding site.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the cell cycle protein and thus is capable of binding to, and potentially modulating, the activity of the cell cycle protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the cell cycle protein with a higher affinity. Thus, if the candidate bioactive agent is labeled, the presence of the label on the support, coupled with a lack of competitor binding, may indicate that the candidate agent is capable of binding to the cell cycle protein.

In a preferred embodiment, the methods comprise differential screening to identity bioactive agents that are capable of modulating the activity of the cell cycle proteins. Such assays can be done with the cell cycle protein or cells comprising said cell cycle protein. In one embodiment, the methods comprise combining an cell cycle protein and a competitor in a first sample. A second sample comprises a candidate bioactive agent, an cell cycle protein and a competitor. The binding of the competitor is determined for both samples, and a change, or difference in binding between the two samples indicates the presence of an agent capable of binding to the cell cycle protein and potentially modulating its activity. That is, if the binding of the competitor is different in the second sample relative to the first sample, the agent is capable of binding to the cell cycle protein.

Alternatively, a preferred embodiment utilizes differential screening to identify drug candidates that bind to the native cell cycle protein, but cannot bind to modified cell cycle proteins. The structure of the cell cycle protein may be modeled, and used in rational drug design to synthesize agents that interact with that site. Drug candidates that affect cell cycle bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of cell cycle may also be done. In a preferred embodiment, methods for screening for a bioactive agent capable of modulating the activity of cell cycle comprise the steps of adding a candidate bioactive agent to a sample of a cell cycle protein (or cells comprising a cell cycle protein) and determining an alteration in the biological activity of the cell cycle protein. "Modulating the activity of a cell cycle protein" includes an increase in activity, a decrease in activity, or a change in the type or kind of activity present. Thus, in this embodiment, the candidate agent should both bind to cell cycle (although this may not be necessary), and alter its biological or biochemical activity as defined herein. The methods include both in vitro screening methods, as are generally outlined above, and in vivo screening of cells for alterations in the presence, distribution, activity or amount of cell cycle protein.

Thus, in this embodiment, the methods comprise combining an cell cycle sample and a candidate bioactive agent, and evaluating the effect on the cell cycle. By "cell cycle activity" or "cell cycle protein activitiy" or grammatical equivalents herein is meant at least one of the cell cycle protein's biological activities, including, but not limited to, its ability to affect the cell cycle, bind to Traf2, bind to Nck, activate the JNK pathway, disrupt of F-actin upon overexpression, inhibit cell spreading upon overexpression, phosphorylate targets, phosphorylate Gelsolin, and regulate of the cytoskeleton. In some embodiments, fragments of the cell cycle protein are preferred, particularly fragments having one or more cell cycle protein activities.

In a preferred embodiment, the activity of the cell cycle protein is decreased; in another preferred embodiment, the activity of the cell cycle protein is increased. Thus, bioactive agents that are antagonists are preferred in some embodiments, and bioactive agents that are agonists may be preferred in other embodiments. As used herein, increased or overexpressed means an increase of at least 10%, more preferably 25–50%, more preferably 50%–75%, and more preferably at least a 100% to 500% increase over the native state. As used herein, decreased or underexpressed means a decrease of at least 10%, more preferably 25–50%, more preferably 50%–75%, and more preferably at least a 100% to 500% decrease over the native state, i.e., compared to without administeration of the cell cycle proteins, nucleic acids or candidate agents as described herein.

In a preferred embodiment, the invention provides methods for screening for bioactive agents capable of modulating the activity of an cell cycle protein. The methods comprise adding a candidate bioactive agent, as defined above, to a cell comprising cell cycle proteins. Preferred cell types include almost any cell. The cells contain a recombinant nucleic acid that encodes an cell cycle protein. In a preferred embodiment, a library of candidate agents are tested on a plurality of cells.

Detection of cell cycle regulation may be done as will be appreciated by those in the art. In one embodiment, indicators of the cell cycle are used. There are a number of parameters that may be evaluated or assayed to allow the detection of alterations in cell cycle regulation, including, but not limited to, cell viability assays, assays to determine whether cells are arrested at a particular cell cycle stage ("cell proliferation assays"), and assays to determine at which cell stage the cells have arrested ("cell phase assays"). By assaying or measuring one or more of these parameters, it is possible to detect not only alterations in cell cycle regulation, but alterations of different steps of the cell cycle regulation pathway. This may be done to evaluate native cells, for example to quantify the aggressiveness of a tumor cell type, or to evaluate the effect of candidate drug agents that are being tested for their effect on cell cycle regulation. In this manner, rapid, accurate screening of candidate agents may be performed to identify agents that modulate cell cycle regulation.

Thus, the present compositions and methods are useful to elucidate bioactive agents that can cause a cell or a population of cells to either move out of one growth phase and into another, or arrest in a growth phase. In some embodiments, the cells are arrested in a particular growth phase,and it is desirable to either get them out of that phase or into a new phase. Alternatively, it may be desirable to force a cell to arrest in a phase, for example G1, rather than continue to move through the cell cycle. Similarly, it may be desirable in some circumstances to accelerate a non-arrested but slowly moving population of cells into either the next phase or just through the cell cycle, or to delay the onset of the next phase. For example, it may be possible to alter the activities of certain enzymes, for example kinases, phosphatases, proteases or ubiquitination enzymes, that contribute to initiating cell phase changes.

In a preferred embodiment, the methods outlined herein are done on cells that are not arrested in the G1 phase; that is, they are rapidly or uncontrollably growing and replicating, such as tumor cells. In this manner, candidate agents are evaluated to find agents that can alter the cell cycle regulation, i.e. cause the cells to arrest at cell cycle checkpoints, such as in G1 (although arresting in other phases such as S, G2 or M are also desirable). Alternatively, candidate agents are evaluated to find agents that can cause proliferation of a population of cells, i.e. that allow cells that are generally arrested in G1 to start proliferating again; for example, peripheral blood cells, terminally differentiated cells, stem cells in culture, etc.

Accordingly, the invention provides methods for screening for alterations in cell cycle regulation of a population of cells. By "alteration" or "modulation" (used herein interchangeably), is generally meant one of two things. In a preferred embodiment, the alteration results in a change in the cell cycle of a cell, i.e. a proliferating cell arrests in any one of the phases, or an arrested cell moves out of its arrested phase and starts the cell cycle, as compared to another cell or in the same cell under different conditions. Alternatively, the progress of a cell through any particular phase may be altered; that is, there may be an acceleration or delay in the length of time it takes for the cells to move thorough a particular growth phase. For example, the cell may be normally undergo a G1 phase of several hours; the addition of an agent may prolong the G1 phase.

The measurements can be determined wherein all of the conditions are the same for each measurement, or under various conditions, with or without bioactive agents, or at different stages of the cell cycle process. For example, a measurement of cell cycle regulation can be determined in a cell or cell population wherein a candidate bioactive agent is present and wherein the candidate bioactive agent is absent. In another example, the measurements of cell cycle regulation are determined wherein the condition or environment of the cell or populations of cells differ from one another. For example, the cells may be evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In another example, the measurements of cell cycle regulation are determined at different stages of the cell cycle process. In yet another example, the measurements of cell cycle regulation are taken wherein the conditions are the same, and the alterations are between one cell or cell population and another cell or cell population.

By a "population of cells" or "library of cells" herein is meant at least two cells, with at least about $10^3$ being preferred, at least about $10^6$ being particularly preferred, and at least about $10^8$ to $10^9$ being especially preferred. The population or sample can contain a mixture of different cell types from either primary or secondary cultures although samples containing only a single cell type are preferred, for example, the sample can be from a cell line, particularly tumor cell lines, as outlined below. The cells may be in any cell phase, either synchronously or not, including M, G1, S, and G2. In a preferred embodiment, cells that are replicating or proliferating are used; this may allow the use of retroviral vectors for the introduction of candidate bioactive agents. Alternatively, non-replicating cells may be used, and other vectors (such as adenovirus and lentivirus vectors) can be used. In addition, although not required, the cells are compatible with dyes and antibodies.

Preferred cell types for use in the invention include, but are not limited to, mammalian cells, including animal (rodents, including mice, rats, hamsters and gerbils), primates, and human cells, particularly including tumor cells of all types, including breast, skin, lung, cervix, colonrectal, leukemia, brain, etc.

In a preferred embodiment, the methods comprise assaying one or more of several different cell parameters, including, but not limited to, cell viability, cell proliferation, and cell phase. Other parameters which can be assayed, singuraly or jointly include Traf2 activity modulation, Nck activity modulation, JNK pathway activity, F-actin disruption, cell spreading, phosphorylation of Gelsolin, and cytoskeleton activity, particularly including mitosis and cytokinesis.

In a preferred embodiment, cell viability is assayed, to ensure that a lack of cellular change is due to experimental conditions (i.e. the introduction of a candidate bioactive agent) not cell death. There are a variety of suitable cell viability assays which can be used, including, but not limited to, light scattering, viability dye staining, and exclusion dye staining.

In a preferred embodiment, a light scattering assay is used as the viability assay, as is well known in the art. For example, when viewed in the FACS, cells have particular characteristics as measured by their forward and 90 degree (side) light scatter properties. These scatter properties represent the size, shape and granule content of the cells. These properties account for two parameters to be measured as a readout for the viability. Briefly, the DNA of dying or dead cells generally condenses, which alters the 90° scatter; similarly, membrane blebbing can alter the forward scatter. Alterations in the intensity of light scattering, or the cell-refractive index indicate alterations in viability.

Thus, in general, for light scattering assays, a live cell population of a particular cell type is evaluated to determine it's forward and side scattering properties. This sets a standard for scattering that can subsequently be used.

In a preferred embodiment, the viability assay utilizes a viability dye. There are a number of known viability dyes that stain dead or dying cells, but do not stain growing cells. For example, annexin V is a member of a protein family which displays specific binding to phospholipid (phosphotidylserine) in a divalent ion dependent manner. This protein has been widely used for the measurement of apoptosis (programmed cell death) as cell surface exposure of phosphatidylserine is a hallmark early signal of this process. Suitable viability dyes include, but are not limited to, annexin, ethidium homodimer-1, DEAD Red, propidium iodide, SYTOX Green, etc., and others known in the art; see the Molecular Probes Handbook of Fluorescent Probes and Research Chemicals, Haugland, Sixth Edition, hereby incorporated by reference; see Apoptosis Assay on page 285 in particular, and Chapter 16.

Protocols for viability dye staining for cell viability are known, see Molecular Probes catalog, supra. In this embodiment, the viability dye such as annexin is labeled, either directly or indirectly, and combined with a cell population. Annexin is commercially available, i.e., from PharMingen, San Diego, Calif., or Caltag Laboratories, Millbrae, Calif. Preferably, the viability dye is provided in a solution wherein the dye is in a concentration of about 100 ng/ml to about 500 ng/ml, more preferably, about 500 ng/ml to about 1 $\mu$g/ml, and most preferably, from about 1 $\mu$g/ml to about 5 $\mu$g/ml. In a preferred embodiment, the viability dye is directly labeled; for example, annexin may be labeled with a fluorochrome such as fluorecein isothiocyanate (FITC), Alexa dyes, TRITC, AMCA, APC, tri-color, Cy-5, and others known in the art or commercially available. In an alternate preferred embodiment, the viability dye is labeled with a first label, such as a hapten such as biotin, and a secondary fluorescent label is used, such as fluorescent streptavidin. Other first and second labeling pairs can be used as will be appreciated by those in the art.

Once added, the viability dye is allowed to incubate with the cells for a period of time, and washed, if necessary. The cells are then sorted as outlined below to remove the non-viable cells.

In a preferred embodiment, exclusion dye staining is used as the viability assay. Exclusion dyes are those which are excluded from living cells, i.e. they are not taken up passively (they do not permeate the cell membrane of a live cell). However, due to the permeability of dead or dying cells, they are taken up by dead cells. Generally, but not always, the exclusion dyes bind to DNA, for example via intercalation. Preferably, the exclusion dye does not fluoresce, or fluoresces poorly, in the absence of DNA; this eliminates the need for a wash step. Alternatively, exclusion dyes that require the use of a secondary label may also be used. Preferred exclusion dyes include, but are not limited to, ethidium bromide; ethidium homodimer-1; propidium iodine; SYTOX green nucleic acid stain; Calcein AM, BCECF AM; fluorescein diacetate; TOTO® and TO-PRO™ (from Molecular Probes; supra, see chapter 16) and others known in the art.

Protocols for exclusion dye staining for cell viability are known, see the Molecular Probes catalog, supra. In general, the exclusion dye is added to the cells at a concentration of from about 100 ng/ml to about 500 ng/ml, more preferably, about 500 ng/ml to about 1 μg/ml, and most preferably, from about 0.1 μg/ml to about 5 μg/ml, with about 0.5 μg/ml being particularly preferred. The cells and the exclusion dye are incubated for some period of time, washed, if necessary, and then the cells sorted as outlined below, to remove non-viable cells from the population.

In addition, there are other cell viability assays which may be run, including for example enzymatic assays, which can measure extracellular enzymatic activity of either live cells (i.e. secreted proteases, etc.), or dead cells (i.e. the presence of intracellular enzymes in the media; for example, intracellular proteases, mitochondrial enzymes, etc.). See the Molecular Probes Handbook of Fluorescent Probes and Research Chemicals, Haugland, Sixth Edition, hereby incorporated by reference; see chapter 16 in particular.

In a preferred embodiment, at least one cell viability assay is run, with at least two different cell viability assays being preferred, when the fluors are compatible. When only 1 viability assay is run, a preferred embodiment utilizes light scattering assays (both forward and side scattering). When two viability assays are run, preferred embodiments utilize light scattering and dye exclusion, with light scattering and viability dye staining also possible, and all three being done in some cases as well. Viability assays thus allow the separation of viable cells from non-viable or dying cells.

In addition to a cell viability assay, a preferred embodiment utilizes a cell proliferation assay. By "proliferation assay" herein is meant an assay that allows the determination that a cell population is either proliferating, i.e. replicating, or not replicating.

In a preferred embodiment, the proliferation assay is a dye inclusion assay. A dye inclusion assay relies on dilution effects to distinguish between cell phases. Briefly, a dye (generally a fluorescent dye as outlined below) is introduced to cells and taken up by the cells. Once taken up, the dye is trapped in the cell, and does not diffuse out. As the cell population divides, the dye is proportionally diluted. That is, after the introduction of the inclusion dye, the cells are allowed to incubate for some period of time; cells that lose fluorescence over time are dividing, and the cells that remain fluorescent are arrested in a non-growth phase.

Generally, the introduction of the inclusion dye may be done in one of two ways. Either the dye cannot passively enter the cells (e.g. it is charged), and the cells must be treated to take up the dye; for example through the use of a electric pulse. Alternatively, the dye can passively enter the cells, but once taken up, it is modified such that it cannot diffuse out of the cells. For example, enzymatic modification of the inclusion dye may render it charged, and thus unable to diffuse out of the cells. For example, the Molecular Probes CellTracker™ dyes are fluorescent chloromethyl derivatives that freely diffuse into cells, and then glutathione S-transferase-mediated reaction produces membrane impermeant dyes.

Suitable inclusion dyes include, but are not limited to, the Molecular Probes line of CellTracker™ dyes, including, but not limited to CellTracker™ Blue, CellTracker™ Yellow-Green, CellTracker™ Green, CellTracker™ Orange, PKH26 (Sigma), and others known in the art; see the Molecular Probes Handbook, supra; chapter 15 in particular.

In general, inclusion dyes are provided to the cells at a concentration ranging from about 100 ng/ml to about 5 μg/ml, with from about 500 ng/ml to about 1 μg/ml being preferred. A wash step may or may not be used. In a preferred embodiment, a candidate bioactive agent is combined with the cells as described herein. The cells and the inclusion dye are incubated for some period of time, to allow cell division and thus dye dilution. The length of time will depend on the cell cycle time for the particular cells; in general, at least about 2 cell divisions are preferred, with at least about 3 being particularly preferred and at least about 4 being especially preferred. The cells are then sorted as outlined below, to create populations of cells that are replicating and those that are not. As will be appreciated by those in the art, in some cases, for example when screening for anti-proliferation agents, the bright (i.e. fluorescent) cells are collected; in other embodiments, for example for screening for proliferation agents, the low fluorescence cells are collected. Alterations are determined by measuring the fluorescence at either different time points or in different cell populations, and comparing the determinations to one another or to standards.

In a preferred embodiment, the proliferation assay is an antimetabolite assay. In general, antimetabolite assays find the most use when agents that cause cellular arrest in G1 or G2 resting phase is desired. In an antimetabolite proliferation assay, the use of a toxic antimetabolite that will kill dividing cells will result in survival of only those cells that are not dividing. Suitable antimetabolites include, but are not limited to, standard chemotherapeutic agents such as methotrexate, cisplatin, taxol, hydroxyurea, nucleotide analogs such as AraC, etc. In addition, antimetabolite assays may include the use of genes that cause cell death upon expression.

The concentration at which the antimetabolite is added will depend on the toxicity of the particular antimetabolite, and will be determined as is known in the art. The antimetabolite is added and the cells are generally incubated for some period of time; again, the exact period of time will depend on the characteristics and identity of the antimetabolite as well as the cell cycle time of the particular cell population. Generally, a time sufficient for at least one cell division to occur.

In a preferred embodiment, at least one proliferation assay is run, with more than one being preferred. Thus, a proliferation assay results in a population of proliferating cells and a population of arrested cells. Moreover, other proliferation assays may be used, i.e., colorimetric assays known in the art.

In a preferred embodiment, either after or simultaneously with one or more of the proliferation assays outlined above, at least one cell phase assay is done. A "cell phase," assay determines at which cell phase the cells are arrested, M, G1, S, or G2.

In a preferred embodiment, the cell phase assay is a DNA binding dye assay. Briefly, a DNA binding dye is introduced to the cells, and taken up passively. Once inside the cell, the DNA binding dye binds to DNA, generally by intercalation, although in some cases, the dyes can be either major or minor groove binding compounds. The amount of dye is thus directly correlated to the amount of DNA in the cell, which varies by cell phase; G2 and M phase cells have twice the DNA content of G1 phase cells, and S phase cells have an intermediate amount, depending on at what point in S phase the cells are. Suitable DNA binding dyes are permanent, and include, but are not limited to, Hoechst 33342 and 33258, acridine orange, 7-AAD, LDS 751, DAPI, and SYTO 16, Molecular Probes Handbook, supra; chapters 8 and 16 in particular.

In general, the DNA binding dyes are added in concentrations ranging from about 1 μg/ml to about 5 μg/ml. The dyes are added to the cells and allowed to incubate for some period of time; the length of time will depend in part on the dye chosen. In one embodiment, measurements are taken immediately after addition of the dye. The cells are then sorted as outlined below, to create populations of cells that contain different amounts of dye, and thus different amounts of DNA; in this way, cells that are replicating are separated from those that are not. As will be appreciated by those in the art, in some cases, for example when screening for anti-proliferation agents, cells with the least fluorescence (and thus a single copy of the genome) can be separated from those that are replicating and thus contain more than a single genome of DNA. Alterations are determined by measuring the fluorescence at either different time points or in different cell populations, and comparing the determinations to one another or to standards.

In a preferred embodiment, the cell phase assay is a cyclin destruction assay. In this embodiment, prior to screening (and generally prior to the introduction of a candidate bioactive agent, as outlined below), a fusion nucleic acid is introduced to the cells. The fusion nucleic acid comprises nucleic acid encoding a cyclin destruction box and a nucleic acid encoding a detectable molecule. "Cyclin destruction boxes" are known in the art and are sequences that cause destruction via the ubiquitination pathway of proteins containing the boxes during particular cell phases. That is, for example, G1 cyclins may be stable during G1 phase but degraded during S phase due to the presence of a G1 cyclin destruction box. Thus, by linking a cyclin destruction box to a detectable molecule, for example green fluorescent protein, the presence or absence of the detectable molecule can serve to identify the cell phase of the cell population. In a preferred embodiment, multiple boxes are used, preferably each with a different fluor, such that detection of the cell phase can occur.

A number of cyclin destruction boxes are known in the art, for example, cyclin A has a destruction box comprising the sequence RTVLGVIGD; the destruction box of cyclin B1 comprises the sequence RTALGDIGN. See G1, otzer, et al., *Nature*, 349:132–138 (1991). Other destruction boxes are known as well: YMTVSIIDRFMQDSCVPKKMLQLVGVT (rat cyclin B); KFRLLQETMYMTVSIIDRFMQNSCVPKK (mouse cyclin B); RAILIDWLIQVQMKFRLLQETMYMTVS (mouse cyclin B1); DRFLQAQLVCRKKLQWGITALLLASK (mouse cyclin B2); and MSVLRGKLQLVGTAAMLL (mouse cyclin A2).

The nucleic acid encoding the cyclin destruction box is operably linked to nucleic acid encoding a detectable molecule. The fusion proteins are constructed by methods known in the art. For example, the nucleic acids encoding the destruction box is ligated to a nucleic acid encoding a detectable molecule. "By detectable molecule" herein is meant a molecule that allows a cell or compound comprising the detectable molecule to be distinguished from one that does not contain it, i.e., an epitope, sometimes called an antigen TAG, a specific enzyme, or a fluorescent molecule. Preferred fluorescent molecules include but are not limited to green fluorescent protein (GFP), blue fluorescent protein (BFP), yellow fluorescent protein (YFP), red fluorescent protein (RFP), and enzymes including luciferase and β-galactosidase. When antigen TAGs are used, preferred embodiments utilize cell surface antigens. The epitope is preferably any detectable peptide which is not generally found on the cytoplasmic membrane, although in some instances, if the epitope is one normally found on the cells, increases may be detected, although this is generally not preferred. Similarly, enzymatic detectable molecules may also be used; for example, an enzyme that generates a novel or chromogenic product.

Accordingly, the results of sorting after cell phase assays generally result in at least two populations of cells that are in different cell phases.

The proteins and nucleic acids provided herein can also be used for screening purposes wherein the protein-protein interactions of the cell cycle proteins can be identified. Genetic systems have been described to detect protein-protein interactions. The first work was done in yeast systems, namely the "yeast two-hybrid" system. The basic system requires a protein-protein interaction in order to turn on transcription of a reporter gene. Subsequent work was done in mammalian cells. See Fields, et al., *Nature*, 340:245 (1989); Vasavada, et al., *PNAS USA*, 88:10686 (1991); Fearon, et al., *PNAS USA*, 89:7958 (1992); Dang, et al., *Mol. Cell. Biol.*, 11:954 (1991); Chien, et al., *PNAS USA*, 88:9578 (1991); and U.S. Pat. Nos. 5,283,173, 5,667,973, 5,468,614, 5,525,490, and 5,637,463. A preferred system is described in Ser. Nos. 09/050,863, filed Mar. 30, 1998 and Ser. No. 09/359,081 filed Jul. 22, 1999, entitled "Mammalian Protein Interaction Cloning System". For use in conjunction with these systems, a particularly useful shuttle vector is described in Ser. No. 09/133,944, filed Aug. 14, 1998, entitled "Shuttle Vectors".

In general, two nucleic acids are transformed into a cell, where one is a "bait" such as the gene encoding a cell cycle protein or a portion thereof, and the other encodes a test candidate. Only if the two expression products bind to one another will an indicator, such as a fluorescent protein, be expressed. Expression of the indicator indicates when a test candidate binds to the cell cycle protein and can be identified as an cell cycle protein. Using the same system and the identified cell cycle proteins the reverse can be performed. Namely, the cell cycle proteins provided herein can be used to identify new baits, or agents which interact with cell cycle proteins. Additionally, the two-hybrid system can be used wherein a test candidate is added in addition to the bait and the cell cycle protein encoding nucleic acids to determine agents which interfere with the bait, such as Traf2 or Nck, and the cell cycle protein.

In one embodiment, a mammalian two-hybrid system is preferred. Mammalian systems provide post-translational modifications of proteins which may contribute significantly to their ability to interact. In addition, a mammalian two-hybrid system can be used in a wide variety of mammalian cell types to mimic the regulation, induction, processing, etc. of specific proteins within a particular cell type. For example, proteins involved in a disease state (i.e., cancer, apoptosis related disorders) could be tested in the relevant disease cells. Similarly, for testing of random proteins, assaying them under the relevant cellular conditions will give the highest positive results. Furthermore, the mammalian cells can be tested under a variety of experimental conditions that may affect intracellular protein-protein interactions, such as in the presence of hormones, drugs, growth factors and cytokines, radiation, chemotherapeutics, cellular and chemical stimuli, etc., that may contribute to conditions which can effect protein-protein interactions, particularly those involved in cancer.

Assays involving binding such as the two-hybrid system may take into account non-specific binding proteins (NSB).

Expression in various cell types, and assays for cell cycle activity are described above. The activity assays, such as having an effect on Traf2 or Nck binding, cytoskeleton regulation, phosphorylation activity, disruption of F-actin or JNK pathway activation, can be performed to confirm the activity of cell cycle proteins which have already been identified by their sequence identity/similarity or binding to Traf2 or Nck as well as to further confirm the activity of lead compounds identified as modulators of the cell cycle proteins provided herein such as Tnik.

The components provided herein for the assays provided herein may also be combined to form kits. The kits can be based on the use of the protein and/or the nucleic acid encoding the cell cycle proteins. In one embodiment, other components are provided in the kit. Such components include one or more of packaging, instructions, antibodies, and labels. Additional assays such as those used in diagnostics are further described below.

In this way, bioactive agents are identified. Compounds with pharmacological activity are able to enhance or interfere with the activity of the cell cycle protein. The compounds having the desired pharmacological activity may be administered in a physiologically acceptable carrier to a host, as further described below.

The present discovery relating to the role of cell cycle proteins in the cell cycle thus provides methods for inducing or preventing cell proliferation in cells. In a preferred embodiment, the cell cycle proteins, and particularly cell cycle protein fragments, are useful in the study or treatment of conditions which are mediated by the cell cycle proteins, i.e. to diagnose, treat or prevent cell cycle associated disorders. Thus, "cell cycle associated disorders" or "disease state" include conditions involving both insufficient or excessive cell proliferation, preferably, cancer.

Thus, in one embodiment, cell cycle regulation in cells or organisms are provided. In one embodiment, the methods comprise administering to a cell or individual in need thereof, a cell cycle protein in a therapeutic amount. Alternatively, an anti-cell cycle antibody that reduces or eliminates the biological activity of the endogeneous cell cycle protein is administered. In another embodiment, a bioactive agent as identified by the methods provided herein is administered. Alternatively, the methods comprise administering to a cell or individual a recombinant nucleic acid encoding an cell cycle protein. As will be appreciated by those in the art, this may be accomplished in any number of ways. In a preferred embodiment, the activity of cell cycle is increased by increasing the amount of cell cycle in the cell, for example by overexpressing the endogeneous cell cycle or by administering a gene encoding a cell cycle protein, using known gene-therapy techniques, for example. In a preferred embodiment, the gene therapy techniques include the incorporation of the exogeneous gene using enhanced homologous recombination (EHR), for example as described in PCT/US93/03868, hereby incorporated by reference in its entirety.

Without being bound by theory, it appears that cell cycle protein is an important protein in the cell cycle. Accordingly, disorders based on mutant or variant cell cycle genes may be determined. In one embodiment, the invention provides methods for identifying cells containing variant cell cycle genes comprising determining all or part of the sequence of at least one endogeneous cell cycle genes in a cell. As will be appreciated by those in the art, this may be done using any number of sequencing techniques. In a preferred embodiment, the invention provides methods of identifying the cell cycle genotype of an individual comprising determining all or part of the sequence of at least one cell cycle gene of the individual. This is generally done in at least one tissue of the individual, and may include the evaluation of a number of tissues or different samples of the same tissue. The method may include comparing the sequence of the sequenced cell cycle gene to a known cell cycle gene, i.e. a wild-type gene.

The sequence of all or part of the cell cycle gene can then be compared to the sequence of a known cell cycle gene to determine if any differences exist. This can be done using any number of known sequence identity programs, such as Bestfit, etc. In a preferred embodiment, the presence of a difference in the sequence between the cell cycle gene of the patient and the known cell cycle gene is indicative of a disease state or a propensity for a disease state.

In one embodiment, the invention provides methods for diagnosing a cell cycle related condition in an individual. The methods comprise measuring the activity of cell cycle in a tissue from the individual or patient, which may include a measurement of the amount or specific activity of a cell cycle protein. This activity is compared to the activity of cell cycle from either a unaffected second individual or from an unaffected tissue from the first individual. When these activities are different, the first individual may be at risk for a cell cycle associated disorder. In this way, for example, monitoring of various disease conditions may be done, by monitoring the levels of the protein or the expression of mRNA therefor. Similarly, expression levels may correlate to the prognosis.

In one aspect, the expression levels of cell cycle protein genes are determined in different patient samples or cells for which either diagnosis or prognosis information is desired. Gene expression monitoring is done on genes encoding cell cycle proteins. In one aspect, the expression levels of cell cycle protein genes are determined for different cellular states, such as normal cells and cells undergoing apoptosis or transformation. By comparing cell cycle protein gene expression levels in cells in different states, information including both up- and down-regulation of cell cycle protein genes is obtained, which can be used in a number of ways. For example, the evaluation of a particular treatment regime may be evaluated: does a chemotherapeutic drug act to improve the long-term prognosis in a particular patient. Similarly, diagnosis may be done or confirmed by comparing patient samples. Furthermore, these gene expression levels allow screening of drug candidates with an eye to mimicking or altering a particular expression level. This may be done by making biochips comprising sets of important cell cycle protein genes, such as those of the present invention, which can then be used in these screens. These methods can also be done on the protein basis; that is, protein expression levels of the cell cycle proteins can be evaluated for diagnostic purposes or to screen candidate agents. In addition, the cell cycle protein nucleic acid sequences can be administered for gene therapy purposes, including the administration of antisense nucleic acids, or the cell cycle proteins administered as therapeutic drugs.

Cell cycle protein sequences bound to biochips include both nucleic acid and amino acid sequences as defined above. In a preferred embodiment, nucleic acid probes to cell cycle protein nucleic acids (both the nucleic acid sequences having the sequences outlined in the Figures and/or the complements thereof) are made. The nucleic acid probes attached to the biochip are designed to be substantially complementary to the cell cycle protein nucleic acids, i.e. the target sequence (either the target sequence of the sample or to other probe sequences, for example in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A "nucleic acid probe" is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. In some embodiments, much longer nucleic acids can be used, up to hundreds of bases (e.g., whole genes).

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination. bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. "By substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably show fluorescence.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo-or hetero-bifunctional linkers as are well known (see 1994 Pierce Chemical Company catalog, technical section on cross-linkers, pages 155–200, incorporated herein by reference). In addition, in some cases, additional linkers, such as alkyl groups (including substituted and heteroalkyl groups) may be used.

In this embodiment, oligonucleotides, corresponding to the nucleic acid probe, are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affimetrix GeneChip™ technology.

"Differential expression," or grammatical equivalents as used herein, refers to both qualitative as well as quantitative differences in the genes' temporal and/or cellular expression patterns within and among the cells. Thus, a differentially expressed gene can qualitatively have its expression altered, including an activation or inactivation, in, for example, normal versus apoptotic cell. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either unregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart, *Nature Biotechnology*, 14:1675–1680 (1996), hereby expressly incorporated by reference. Other techniques include, but are not limited to, quantitative reverse transcriptase PCR, Northern analysis and RNase protection.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the cell cycle protein and standard immunoassays (ELISAs, etc.) or other techniques, including mass spectroscopy assays, 2D gel electrophoresis assays, etc.

In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding an cell cycle protein is detected by binding the digoxygenin with an anti-digoxygenin secondary antibody and developed with nitro blue tetrazolium and 5-bromo4-chloro-3-indoyl phosphate.

In another preferred method, expression of cell cycle protein is performed using in situ imaging techniques employing antibodies to cell cycle proteins. In this method cells are contacted with from one to many antibodies to the cell cycle protein(s). Following washing to remove non-specific antibody binding, the presence of the antibody or antibodies is detected. In one embodiment the antibody is detected by incubating with a secondary antibody that contains a detectable label. In another method the primary antibody to the cell cycle protein(s) contains a detectable label. In another preferred embodiment each one of multiple primary antibodies contains a distinct and detectable label. This method finds particular use in simultaneous screening for a plurality of cell cycle proteins. The label may be detected in a fluorometer which has the ability to detect and distinguish emissions of different wavelengths. In addition, a fluorescence activated cell sorter (FACS) can be used in this method. As will be appreciated by one of ordinary skill in the art, numerous other histological imaging techniques are useful in the invention and the antibodies can be used in ELISA, immunoblotting (Western blotting), immunoprecipitation, BIACORE technology, and the like.

In one embodiment, the cell cycle proteins of the present invention may be used to generate. polyclonal and monoclonal antibodies to cell cycle proteins, which are useful as described herein. Similarly, the cell cycle proteins can be coupled, using standard technology, to affinity chromatography columns. These columns may then be used to purify cell cycle antibodies. In a preferred embodiment, the antibodies are generated to epitopes unique to the cell cycle protein; that is, the antibodies show little or no cross-reactivity to other proteins. These antibodies find use in a number of applications. For example, the cell cycle antibodies may be coupled to standard affinity chromatography columns and used to purify cell cycle proteins as further described below. The antibodies may also be used as blocking polypeptides, as outlined above, since they will specifically bind to the cell cycle protein.

The anti-cell cycle protein antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the cell cycle protein or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid a, synthetic trehalose dicorynomycolate). The immunization protocol may be selected by one skilled in the art without undue experimentation.

The anti-cell cycle protein antibodies may, alternatively, be monoclonal antibodies. Monoclonal antibodies may be prepared using hybridoma methods, such as those described by Kohler, et al., *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the cell cycle protein or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur, et al., *Monoclonal Antibody Production Techniques and Applications*, Marcel Dekker, Inc., New York, pp. 51–63 (1987)].

The culture medium in which the hybridoma cells are cultured can then be assayed for the presence of monoclonal antibodies directed against cell cycle protein. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson, et al., *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein a-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison, et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The anti-cell cycle protein antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones, et al., *Nature*, 321:522–525 (1986); Riechmann, et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones, et al., *Nature*, 321:522–525 (1986); Riechmann, et al., *Nature*, 332:323–327 (1988); Verhoeyen, et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom, et al, *J. Mol. Biol.*, 227:381 (1991); Marks, et al., *J. Mol. Biol*, 222:581 (1991)1. The techniques of Cole, et al. and Boerner, et al. are also available for the preparation of human monoclonal antibodies (Cole, et al., *Monoclonal Antibodies and Cancer Therapy*, Alan R. Liss, p. 77 (1985); Boerner, et al., *J. Immunol.*, 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks, et al., *Bio/Technology*, 10:779–783 (1992); Lonberg, et al., *Nature*, 368:856–859 (1994); Morrison, *Nature*, 368:812–13 (1994); Fishwild, et al., *Nature Biotechnology*, 14:845–51 (1996); Neuberger, *Nature Biotechnology*, 14:826 (1996); Lonberg, et al., *Intern. Rev. Immunol.*, 13:65–93 (1995).

Bispecific antibodies are monoclonal, preferably human or humanized, antibodies that have binding specificities for at least two different antigens. In the present case, one of the binding specificities is for the cell cycle protein, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein, et al., *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker, et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavychain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh, et al., *Methods in Enzymology*, 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The anti-cell cycle protein antibodies of the invention have various utilities. For example, anti-cell cycle protein antibodies may be used in diagnostic assays for an cell cycle protein, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: a Manual of Techniques*, CRC Press, Inc. pp. 147–158 (1987)]. The antibodies used in the diagnostic assays can be labeled with a detectable moiety. The detectable moiety should be capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter, et al., *Nature*, 144:945 (1962); David, et al., *Biochemistry*, 13:1014 (1974); Pain, et al., *J. Immunol. Meth.*, 40:219 (1981); and Nygren, *J. Histochem and Cytochem.*, 30:407 (1982).

Anti-Cell cycle protein antibodies also are useful for the affinity purification of cell cycle protein from recombinant cell culture or natural sources. In this process, the antibodies against cell cycle protein are immobilized on a suitable support, such a Sephadex resin or filter paper, using methods well known in the art. The immobilized antibody then is contacted with a sample containing the cell cycle protein to be purified, and thereafter the support is washed with a suitable solvent that will remove substantially all the material in the sample except the cell cycle protein, which is bound to the immobilized antibody. Finally, the support is washed with another suitable solvent that will release the cell cycle protein from the antibody.

The anti-cell cycle protein antibodies may also be used in treatment. In one embodiment, the genes encoding the antibodies are provided, such that the antibodies bind to and modulate the cell cycle protein within the cell.

In one embodiment, a therapeutically effective dose of an cell cycle protein, agonist or antagonist is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for cell cycle protein degradation, systemic versus localized delivery, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the cell cycle protein, agonist or antagonist of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the composition may be directly applied as a solution or spray. Depending upon the manner of introduction, the compounds may be formulated in a variety of ways. The concentration of therapeutically active compound in the formulation may vary from about 0.1–100 wt. %.

The pharmaceutical compositions of the present invention comprise an cell cycle protein, agonist or antagonist (including antibodies and bioactive agents as described herein) in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic-bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

Combinations of the compositions may be administered. Moreover, the compositions may be administered in combination with other therapeutics, including growth factors or chemotherapeutics and/or radiation. Targeting agents (i.e. ligands for receptors on cancer cells) may also be combined with the compositions provided herein.

In one embodiment provided herein, the antibodies are used for immunotherapy, thus, methods of immunotherapy are provided. By "immunotherapy" is meant treatment of cell cycle protein related disorders with an antibody raised against a cell cycle protein. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with an cell cycle protein antigen to which antibodies are raised. As appreciated by one of ordinary skill in the art, the cell cycle protein antigen may be provided by injecting an cell cycle protein against which antibodies are desired to be raised into a recipient, or contacting the recipient with an cell cycle protein nucleic acid, capable of expressing the cell cycle protein antigen, under conditions for expression of the cell cycle protein antigen.

In a preferred embodiment, a therapeutic compound is conjugated to an antibody, preferably an cell cycle protein antibody. The therapeutic compound may be a cytotoxic agent. In this method, targeting the cytotoxic agent to apoptotic cells or tumor tissue or cells, results in a reduction in the number of afflicted cells, thereby reducing symptoms associated with apoptosis, cancer cell cycle protein related disorders. Cytotoxic agents are numerous and varied and include, but are not limited to, cytotoxic drugs or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies raised against cell cycle proteins, or binding of a radionuclide to a chelating agent that has been covalently attached to the antibody.

In a preferred embodiment, cell cycle protein genes are administered as DNA vaccines, either single nucleic acids or combinations of cell cycle protein genes. Naked DNA vaccines are generally known in the art; see Brower, *Nature Biotechnology*, 16:1304–1305 (1998). Methods for the use of nucleic acids as DNA vaccines are well known to one of ordinary skill in the art, and include placing an cell cycle protein gene or portion of an cell cycle protein nucleic acid under the control of a promoter for expression in a patient. The cell cycle protein gene used for DNA vaccines can encode full-length cell cycle proteins, but more preferably encodes portions of the cell cycle proteins including peptides derived from the cell cycle protein. In a preferred embodiment a patient is immunized with a DNA vaccine comprising a plurality of nucleotide sequences derived from a cell cycle protein gene. Similarly, it is possible to immunize a patient with a plurality of cell cycle protein genes or portions thereof, as defined herein. Without being bound by theory, following expression of the polypeptide encoded by the DNA vaccine, cytotoxic T-cells, helper T-cells and antibodies are induced which recognize and destroy or eliminate cells expressing cell cycle proteins.

In a preferred embodiment, the DNA vaccines include a gene encoding an adjuvant molecule with the DNA vaccine. Such adjuvant molecules include cytokines that increase the immunogenic response to the cell cycle protein encoded by the DNA vaccine. Additional or alternative adjuvants are known to those of ordinary skill in the art and find use in the invention.

The following example serves to more fully describe the manner of using the above-described invention, as well as to set forth the best modes contemplated for carrying out various aspects of the invention. It is understood that this example in no way serve to limit the true scope of this invention, but rather are presented for illustrative purposes. All references cited herein are expressly incorporated by reference in their entirety. Moreover, all sequences displayed, cited by reference or accession number in the references are incorporated by reference herein.

EXAMPLE 1

Cloning, Tissue Distribution, Binding, Activation and Regulation Functions of Tnik Antibodies and cytokines—Antibodies used in this report include: anti-HA mAb (Babco) and pAb (Santa Cruz Biotechnology); anti-FLAG mAb (Sigma) and pAb (Santa Cruz); anti-Myc mAb (Babco); anti-Traf2 pAb (Santa Cruz); anti-NCK mAb (Transduction Labs); anti-β-actin mAb (Sigma). TNFα was purchased from Calbiochem.

Cloning of full length Tnik and Northern blotting—Using yeast two-hybrid screening, overlapping cDNA fragments were identified that interacted with Traf2 and NCK. The sequences of the fragments were contained in a partial cDNA clone, KIAA0551 (Accession number AB01123), at GenBank. Antisense oligos TGCGCTTATATTCCAGAAGTAGAGCT and CTGTCTCTGCTCCTCCTCTA were designed according to the 5' end sequence of KIAA0551 and the full length Tnik cDNA was cloned from reverse transcribed human brain mRNA by RACE-PCR. Northern blotting was performed on human multi-tissue Northern blot according to the manufacturer's recommendations (Clontech). A PCR product amplified from nucleotide 1264 to nucleotide 2427 of Tnik coding region was used as a probe.

Plasmid construction—Full length human Tnik was cloned into pCI (Promega) derived expression vector pYCI under the control of the CMV promoter with an HA epitope tag (AYPYDVPDYA (SEQ ID NO:25)) inserted on the N-terminus by PCR. A kinase mutant form of Tnik was constructed using the QuikChange mutagenesis kit (Stratagene) with Oligos AGCTTGCAGCCATCAGGGTTATGGATGTCAC (SEQ ID NO:26) and GTGACATCCATAACCTTGATGGCTGCAAGCT (SEQ ID NO:27) to change the highly conserved lysine 54 in the kinase domain to arginine. Full length human Traf2 was cloned into pYCI with a FLAG epitope tag (DYKDDDDKG (SEQ ID NO:28)) inserted on the N-terminus by PCR. Full length human NCK was similarly cloned into pYCI with a FLAG epitope tag at the N-terminus. Myc-JNK2 and Myc-ERK1 were constructed in the pCR3.1 vector with a Myc epitope tag (ASMEQKLISEEDLN (SEQ ID NO:29)) inserted on the N-terminus of JNK2 and ERK1, respectively. All the truncation mutants were constructed by PCR. For construction of the GFP-Tnik fusion protein, full length Tnik was PCR amplified from pYCI-Tnik and inserted in frame onto the 3' end of GFP. All constructs were verified by DNA sequencing. construction of the GFP-Tnik fusion protein, full length Tnik was PCR amplified from pYCI-Tnik and inserted in frame onto the 3' end of GFP. All constructs were verified by DNA sequencing.

Cell culture, transfection of Phoenix-A cells and immunoprecipitation—Phoenix-A cells (derivatives of 293 cells) (Coligan, et al., *Current Protocols in Immunology* [*supplement*], 31:10.28.1–10.28.17 (1999)) were grown in Dulbecco's modified Eagle's medium supplemented with 10% fetal bovine serum. Transfection of Phoenix-A cells was performed using the standard calcium phosphate method (Coligan, et al., *Current Protocols in Immunology* [*supplement*], 31:10.28.1–10.28.17 (1999)). Either $4\times10^5$ cells in a 6-well plate or $3\times10^6$ cells in a 100 mm tissue culture dish were seeded 16 hours before transfection. 3 μg of DNA was used in the transfection for each well of a 6-well plate, and 10 μg DNA was used for each 100 mm dish. Media was changed 8 hours after transfection. Cells were lysed in lysis buffer (1% NP-40, 20 mM Tris-HCl, pH 8.0, 150 mM NaCl) with protease inhibitors (Boehringer Mannheim) and analyzed 24 hours after transfection. Cell lysates were cleared by centrifugation (14,000 RPM×10 min). For immunoprecipitation studies, cell lysates (2×106 cells/lane) were rotated with 2–3 μg of desired antibodies and 20 μl 50% slurry of protein A Sepharose (Pharmacia) for 1.5 hrs. Immune complexes were precipitated and the pellets washed three times with lysis buffer. Washed precipitates were subjected to SDS-PAGE analysis and Western blotting. Supersignal and Supersignal West Duro substrates (Piers) were used as detection systems for the Western blotting.

In vitro kinase assays—For the JNK in vitro kinase assay, Myc-JNK2 was co-transfected into Phoenix-A cells with Tnik mutants, Traf2 or MEKK as described above. 24 hours after transfection, cells were lysed with lysis buffer supplemented with 20 mM β-glycerophospate, 1 mM NaF, 1 mM $Na_3VO_4$ and protease inhibitors. Myc-JNK2 was precipitated from clarified cell lysates with an anti-Myc mAb and the pellets were washed three times with lysis buffer and two times with kinase buffer (20 mM HEPES, pH 7.4, 10 mM $MnCl_2$, 10 mM $MgCl_2$, 20 mM β-glycerophosphate, 1 mM NaF, 1 mM $Na_3VO_4$, 0.5 mM DTT). For the kinase reactions, immunoprecipitates were incubated with 1 μg glutathion S-transferase (GST) c-Jun (1–79) (Santa Cruz Biotechnology) in 20 μl kinase buffer supplemented with 1 μM PKI peptide (Sigma), 10 μM ATP, 5 μCi y-$p^{32}$ ATP for 20 minutes at 30 ° C. Kinase reactions were stopped by addition of 20 μl 2×SDS sample buffer (Norvex), heated at 95° C. for 5 minutes and then loaded onto SDS-PAGE. ERK and p38 in vitro kinase assays were conducted in a similar fashion. For ERK kinase assays, an anti-Myc mAb was used to immunoprecipitate Myc-ERK1 and Myelin Basic Protein (MBP, Sigma) was used as an exogenous substrate. For p38 kinase assays, an anti-FLAG mAb was used to immunoprecipitate FLAG-p38 and GST-ATF2 (Santa Cruz) was used as an exogenous substrate. For in vitro kinase assays on Tnik, 3 μg wild type HA-Tnik or 3 μg kinase mutant form of HA-Tnik was expressed in Phoenix-A cells and immunoprecipitated with an anti-HA antibody. Immune complexes were subjected to kinase assays as described above in the absence or presence of 0.5 μg Gelsolin as an exogenous substrate.

Fluorescent microscopy—Phoenix-A cells seeded in 6-well plates were co-transfected with GFP and Tnik constructs as described above. 24 hours after transfection, cells were observed using a Nikon Eclipse TE 300 fluorescent microscope. For detection of apoptosis, Hoechst 33258 (sigma?) was added to transfected Phoenix-A cells (final concentration 5 μg/ml) and the cells were incubated for 30 min at 37° C. before microscopic observation.

Determination of actin distribution—$4\times10^5$ Phoenix-A cells in 6-well plate were transfected with 3 μg of control vector, HA-Tnik(WT) or HA-Tnik(KM). 24 hours after transfection, culture media were carefully removed. Cells were lysed directly on the plate using 250 μl Triton X-100 lysis buffer (1% Triton X-100, 150 mM NaCl, 20 mM Tris-HCl, pH 7.4) with protease inhibitors. Cell lysates were centrifuged at 14,000 RPM for 10 min. Supernatants represented the Triton X-100 soluble fraction. Pellets were washed once with 500 μl Triton X-100 lysis buffer and dissolved in 500 μl of 1×SDS sample buffer. DNA was sheared by sonication. This represented the Triton X-100 insoluble fraction. Triton X-100 soluble and insoluble fractions derived from the same number of cells were resolved on SDS-PAGE and blotted with an anti-o-actin mAb to determine the content of F- and G-actin.

Molecular cloning of Tnik—Using a human brain cDNA library and a T/B cell library in our yeast two-hybrid pathway mapping effort, we identified a novel Germinal Center Kinase family member that interacted with both TRAF2 and NCK. The 5' end sequence was cloned from cDNAs prepared from human brain mRNA by RACE-PCR and full length cDNA clones of were obtained by RT-PCR. (FIG. 1).

The longest Tnik clone was encoded by a polypeptide of 1360 amino acids: It had an N-terminal kinase domain, an intermediate domain and a C-terminal Germinal Center Kinase Homology (GCKH) region. It shared about 90% amino acid identity with a previously cloned GCK family member, NCK Interacting Kinase (NIK), in both the kinase domain and the GCKH domain (Su, et al., *EMBO J.*, 16:1279–1290 (1997)). However, Tnik was only 40% identical to NIK in the intermediate region (FIG. 1, 3). Two shorter clones of Tnik were also obtained: one lacked nucleotides 1338–1424 (amino acids 447–475) and nucleotides 2383–2406 (amino acids 795–802), and the other lacked those two regions plus nucleotides 1609–1773 (aa 537–591) (FIG. 3).

Primers encompassing these three alternatively spliced regions were designed and used for PCR from spleen, heart and brain cDNAs. The relative amounts of the different isoforms, seen as multiple bands amplified from both spleen and brain, varied among the different tissues (FIG. 2). Amplified DNA fragments were cloned into a TA cloning vector and the inserts sequenced. All eight combinations from the alternative splicing of these three regions were identified. These eight spliced isoforms of Tnik were designated as Tnik, to $Tnik_8$ (FIG. 3). $Tnik_1$ was used in all the experiments described herein.

To determine kinase activity, a putative kinase mutant form of Tnik, designated as Tnik(KM), was constructed with a conserved lysine (Lys-54) residue in the ATP binding pocket mutated to arginine. An HA epitope tag was inserted on the N-terminal portion of Tnik(WT) and Tnik(KM). Both proteins were transiently expressed in Phoenix-A cells, and the expressed proteins were subjected to immunoprecipitation and an in vitro kinase assay. A strong phosphorylated band at 150 kD was detected in the Tnik(WT) expressed lane, but not in the Tnik(KM) expressed lane (FIG. 4, lanes 1, 2). Immunoblotting with an anti-HA antibody showed equal levels of expression of both Tnik(WT) and Tnik(KM) at 150 kD (FIG. 4, lanes 3, 4). Therefore, the phosphorylated band in the in vitro kinase assay represented autophosphorylated Tnik, and the Tnik(KM) mutant was deficient in protein kinase activity.

Tissue distribution of Tnik—The expression pattern of the Tnik message was examined by human multi-tissue Northern blot. Since Tnik shared high homology with NIK, a probe corresponding to nucleotides 1264–2427 of Tnik was used to rule out any potential cross-hybridization. This region shared only 40% amino acid identity with NIK. Three major bands of sizes 6.5 kb, 7.5 kb and 9.5 kb were detected (FIG. 5). Alternative splicing in the coding region described above is unlikely to account for the size differences among the three messages, since the largest isoform is only 273 bps bigger than the smallest isoform. Alternative splicing in the untranslated region or alternative usage of polyA sites could be possible explanations. This phenomenon is not unique to Tnik. NIK and HGK also have multiple message sizes. Tnik is ubiquitously expressed, with higher levels of message detected in heart, brain and skeletal muscle. Interestingly, heart and skeletal muscle predominantly expressed the 6.5 kb form; placenta, kidney and pancreas predominantly expressed the 7.5 kb form; brain, lung and liver expressed all three forms at a similar level. It is currently unknown whether these messages have different functional roles.

Interaction of Tnik with TRAF2 and NCK—To confirm the interaction of Tnik with TRAF2, N-terminal HA-tagged Tnik was transiently expressed in Phoenix-A cells and HA-Tnik was immunoprecipitated by an anti-HA antibody. The immune complexes were resolved on SDS-PAGE and immunoblotted with an anti-TRAF2 antibody. Endogenous TRAF2 specifically co-immunoprecipitated with HA-Tnik (FIG. 6, top panel). To map the interaction domain on Tnik that mediated its interaction with TRAF2, we constructed several truncated forms of HA-tagged Tnik (FIG. 7) and co-expressed them with FLAG-tagged TRAF2. Anti-HA immunoprecipitates were then blotted with an anti-FLAG antibody to detect the co-immunoprecipitated FLAG-TRAF2. Tnik(WT), Tnik(N2), Tnik(C1) and Tnik(M) all co-immunoprecipitated with FLAG-TRAF2, suggesting that the intermediate domain of Tnik is sufficient for Tnik to interact with TRAF2 (FIG. 8, top panel, lanes 1, 3, 4, 6). However, Tnik(C2) consistently showed weak interaction with TRAF2 (lane 5), suggesting that the GCKH domain was also involved in the interaction with TRAF2. Tnik(N1), the Tnik mutant with only the kinase domain, failed to interact with TRAF2 (lane 2). Expression levels of the transfected proteins were controlled by immunoblotting cell lysates with anti-HA and anti-FLAG antibodies (FIG. 8, middle and bottom panels). In addition, $Tnik_8$, the shortest form of Tnik, was still able to interact with Traf2 (data not shown), suggesting that the three alternatively spliced exons were not required for TniK to interact with Traf2.

We then mapped the domains on TRAF2 that mediated the interaction with Tnik. FLAG-tagged TRAF2 mutants (FIG. 9) were co-expressed with HA-Tnik and the lysates were subjected to anti-HA immunoprecipitation. The immune complexes were then blotted with an anti-FLAG antibody. TRAF2(Wr), TRAF2(87–501) and TRAF2 (272–501) were all able to co-immunoprecipitate with HA-Tnik, while TRAF2(1–272) failed to interact with HA-Tnik (FIG. 10, top panel). Immunoblotting cell lysates with anti-HA and anti-FLAG antibodies showed comparable expression levels of the transfected proteins (FIG. 10, middle and bottom panels). This result suggested that the TRAF domain is required for TRAF2 to interact with Tnik. However, since the interaction of full-length TRAF2 with Tnik is stronger then that of either TRAF2(87–501) or TRAF2(272–501), the N-terminal ring finger may directly contribute to the interaction or may stabilize the configuration of the TRAF2 molecule to facilitate this interaction.

Interaction of Tnik with NCK—The interaction of Tnik with NCK was investigated in a similar fashion. Following transient expression of HA-Tnik in Phoenix-A cells, the cell lysates were immunoprecipitated with an anti-HA antibody and blotted with an anti-NCK antibody. Endogenous NCK specifically co-immunoprecipitated with HA-Tnik (FIG. 11, top panel). To map the domains on Tnik required for this interaction, HA-tagged Tnik mutants were co-expressed with FLAG-tagged NCK and the HA-Tnik mutants were immunoprecipitated with an anti-HA antibody. The immune complexes were then blotted with an anti-FLAG antibody. Tnik(WT), Tnik(N2), Tnik(C1) and Tnik(M) were all able to associate with NCK, suggesting that the intermediate domain is also sufficient for Tnik to bind NCK (FIG. 12, top panel, lanes 1, 3, 4, 6). Neither the GCKH domain nor the kinase domain showed any detectable binding to NCK (lanes 2, 5). Immunoblotting cell lysates with anti-HA and anti-FLAG antibodies showed equivalent levels of expression of the transfected preoteins (FIG. 12, middle and bottom panels).

Activation of JNK2 by Tnik—We further examined whether Tnik was able to activate the JNK pathway. 1 $\mu$g, 2 $\mu$g or 3 $\mu$g of Tnik expression plasmid was co-transfected into Phoenix-A cells with Myc-JNK2. 24 hours after transfection, Myc-JNK2 was immunoprecipitated from cell lysates and its kinase activity measured using GST-cJun (1–79) as a substrate. Co-transfection of Tnik enhanced JNK2 kinase activity in a dose dependent fashion (FIG. 13, top panel, lanes1, 3–5). When 3 $\mu$g of Tnik was transfected, JNK2 activity was enhanced 3–4 fold. A similar magnitude of JNK2 activation was observed when cells were treated for 15 minutes with 100 ng/ml of TNF (lanes 1, 2 and 5). Also consistent with published result (Natoli, et al., *Science*, 275:200–203 (1997)), TRAF2 potently activated JNK2 activity (lane 6). The expression levels of Myc-JNK2 were controlled by immunoblotting cell lysates with an anti-Myc antibody (FIG. 13, bottom panel).

To determine whether Tnik can also activate the ERK and p38 pathways, Myc-ERK1 and FLAG-p38 were co-transfected into Phoenix-A cells with different doses of Tnik. The transfected kinases were then immunoprecipitated from cell lysates and the kinase activities measured using MBP and GST-ATF2 as exogenous substrates. In contrast to JNK2, neither ERK1 nor p38 was activated by Tnik overexpression, while co-transfection of MEKK1 potently activated both kinases (FIG. 14, 15). In addition, Tnik did not activate NF-KB (data not shown).

To further investigate the mechanism of this activation, the cohort of Tnik mutants were co-transfected into Phoenix-A cells with Myc-JNK2 and the ability of these mutants to up-regulate JNK2 kinase activity was examined by the in vitro kinase assay. Tnik(WT), Tnik(KM), Tnik(C1) and Tnik(C2) were all able to activate Myc-JNK2, while Tnik(N1), Tnik(N2), Tnik(M) were not (FIG. 16). This result suggested that the C-terminal GCKH region is both necessary and sufficient for activation of the JNK pathway, while the kinase domain is dispensable.

Regulation of the cytoskeleton by Tnik—When Tnik was overexpressed in Phoenix-A cells, the cells showed a striking morphological change. In control GFP transfected cells, more than 80% of GFP positive cells were adherent and well-spread (FIG. 6A, top row, left panel). In contrast, in Tnik and GFP co-transfected cells, more than 80% of GFP positive cells showed inhibited cell spreading. These cells rounded up and lost attachment to the plate (FIG. 6A, top row, right panel). Similar morphologic change was also observed in Hela and NIH-3T3 cells transfected with Tnik (data not shown). We then transfected the cohort of Tnik mutants into Phoenix-A cells to determine which domain of Tnik was involved in inducing the morphologic change. Tnik(KM), Tnik(C1) and Tnik(C2), which lacked the kinase activity, failed to induce the morphologic change (left column, middle and bottom panels and data not shown), while Tnik(N1) and Tnik(N2) were both competent in inducing the inhibition of cell spreading (FIG. 6A, right column, middle panel and data not shown). Therefore, the kinase domain, rather than the GCKH domain required for JNK activation, was both necessary and sufficient for Tnik to regulate cell spreading. This result suggested that the JNK pathway was not involved in this regulation. Consistent with this hypothesis, overexpression of Myc-JNK failed to inhibit cell spreading (FIG. 6A, right column, bottom panel). Since JNK has been implicated in inducing apoptosis in some cells (Basu, et al., *Oncogene*, 17:3277–3285 (1998)), we examined whether cells transfected with Tnik were undergoing apoptosis. Nuclei of phoenix-A cells transfected with control vector, Tnik(WT), Tnik(KM) or RIP were stained with Hoechst 33258(FIG. 6B). No apoptotic body was observed in vector, Tnik(WT) or Tnik(KM) transfected cells, while apototic bodies were readily detected in greater than 60% of cells transfected with a control RIP cDNA(FIG. 6B). In addition, no activation of caspases was observed in Tnik transfected cells (data not shown). Taken together, these results suggested that Tnik did not induce apotosis in transfected phoenix-A cells.

These observations raised the possibility that overexpression of Tnik might have disrupted intracellular F-actin structure. We therefore examined actin distribution in the Triton X-100 soluble (G-actin) and insoluble (F-actin) fractions in control vector, Tnik and Tnik(KM) transfected Phoenix-A cells. Overexpression of wild type Tnik, but not Tnik(KM), resulted in the enhanced distribution of actin in Triton X-100 soluble fraction, consistent with the reduced spreading observed in these cells (FIG. 6C). We hypothesized that overexpression of Tnik may lead to phosphorylation of cytoskeletal components. Recently, a GCK family protein kinase that could phosphorylate the actin-fragmenting protein Severin was purified and cloned from Dictyostelium (Eichinger, et al., *J. Biol. Chem.*, 273:12952–12959 (1998)). We therefore decided to test whether Tnik was able to phosphorylate the mammalian Severin homologue, Gelsolin (Yin, et al., *Nature*, 281:583–586 (1979)). Tnik and Tnik(KM) were expressed in Phoenix-A cells, immunoprecipitated and incubated in an in vitro kinase assay with purified Gelsolin. Wild type Tnik, but not the kinase mutant form of Tnik, phosphorylated Gelsolin in vitro (FIG. 6D).

Unlike any other GCK family members, both the kinase mutant form of Tnik and the GCKH domain of Tnik were as effective as the wild type protein in JNK2 activation, and the kinase domain alone of Tnik was virtually ineffective (FIG. 16). This result suggested that the C-terminal GCKH domain was solely responsible for the activation. This is in contrast to other GCK family kinases, which activate the JNK pathway either using the kinase domain alone, as is seen with GCKR, HGK and HPK1, or using the kinase domain plus the GCKH region, which is seen with GCK, GLK and NIK (Pombo, et al., *Nature*, 377:750–754 (1995); Shi, et al., *J. Biol. Chem.*, 272:32102–32107 (1997); Kiefer, et al., *EMBO J.*, 15:7013–7025 (1996); Diener, et al., *Proc. Natl. Acad. Sci. USA*, 94:9687–9692 (1997); Yao, et al., *J. Biol. Chem.*, 274:2118–2125 (1999); Su, et al., *EMBO J.*, 16:1279–1290, (1997)). The GCKH domain of NIK interacted with MEKK1, and the dominant negative mutant of MEKK1 inhibited NIK induced JNK activation (Su, et al., EMBO J., 16:1279–1290 (1997)). Given the high level of sequence identity between the GCKH of NIK and the GCKH of Tnik, Tnik likely activated the JNK pathway through MEKK1.

NIK was cloned by its ability to interact with the adapter protein NCK. It associated with NCK SH3 domains via two PxxPxR sequences in the intermediate domain, PCPPSR (SEQ ID NO:30) (aa 574–579) and PRVPVR (SEQ ID NO:31) (aa 611–616). Both sequences were required for efficient interaction (Su, et al., *EMBO J.*, 16:1279–1290 (1997)). Similar to NIK, Tnik also interacted with NCK via the intermediate domain. However, PCPPSR (SEQ ID NO:30) is not conserved in Tnik. Instead, Tnik contained two other PxxPxR sequences, PNLPPR (SEQ ID NO:32) (aa 562–567) and PPLPTR (SEQ ID NO:36) (aa 647–652), in addition to the conserved PKVPQR (SEQ ID NO:33) (aa 670–675). Tnik likely interacted with NCK through the cooperative interaction with these three PxxPxR sequences. NCK is an adapter protein involved in many growth factor receptor mediated signal transduction pathways (McCarthy, *Bioessays*, 20:913–921 (1998)). It has been proposed that the NIK-NCK interaction may recruit NIK to receptor or non-receptor tyrosine kinases to regulate MEKKI (Su, et al., *EMBO J.*, 16:1279–1290 (1997)). Tnik may be recruited in a similar fashion.

Tnik also interacts via its intermediate domain with the TRAF domain of TRAF2. Both GCK and GCKR have been previously reported to interact with TRAF2 and it has been suggested that they mediate TRAF2 induced JNK activation (Pombo, et al., *Nature*, 377:750–754 (1995); Diener, et al., *Proc. Natl. Acad. Sci. USA*, 94:9687–9692 (1997); Yuasa, et al., *J. Biol. Chem.*, 273:22681–22692 (1998)). More recently, a Drosophila GCK family member, Misshapen (Msn), has been reported to interact with D-TRAF1 and mediate D-TRAF1 induced JNK activation (Liu, et al., *Curr. Biol.*, 9:101–104 (1998)). Msn has highest homology to NIK and Tnik. Similar to NIK and Tnik, Msn also interacted with Dock, the Drosophila homologue of NCK (Liu, et al., *Curr. Biol.*, 9:101–104 (1998)). In Drosophila, deficiency in Dock results in defective photoreceptor guidance (Garrity, et al., *Cell*, 85:639–650 (1996)), and in mammalian cells, NCK interacts with WASP, a CDC42 effector protein involved in the regulation of cytoskeleton (Symons, et al., *Cell*, 84:723–734 (1996); Rivero-Lezcano, et al., *Mol. Cell Biol.*, 15:5725–5731 (1995)). These findings strongly suggest that the NCK pathway is closely linked to the cytoskeletal changes. Consistently, Msn deficiency leads to defective dorsal closure that requires extensive cell migration and cell shape changes in addition to the activation of the JNK pathway (Treisman, et al., *Gene*, 186:119–125 (1997)). Interaction of Msn with Dock may regulate these cell shape changes. Tnik may participate in the regulation of a similar pathway in mammalian cells.

Supporting this hypothesis, overexpression of Tnik inhibited cell spreading in Phoenix-A cells, NIH-3T3 cells and Hela cells (FIG. 6 and data not shown). This effect is likely due to the disruption of filamentous actin structure. No F-actin fiber could be detected by staining with TRITC-Phalloidin of NIH-3T3 cells transfected with a GFP-Tnik fusion protein, while F-actin fibers were abundant in cells transfected with GFP alone (data not shown). Consistent with this notion, overexpression of Tnik resulted in a decreased proportion of actin in the Triton X-100 insoluble fraction (FIG. 19). The Triton X-100 insoluble fraction contains the filamentous actin pool, while the Triton X-100 soluble fraction contains the globular actin monomers. This is the first evidence that a mammalian GCK family member exerts an effect on cytoskeletal organization. A Dictyostelium GCK member was recently cloned that can phosphorylate the Dictyostelium actin fragmenting protein, Severin, in vitro (Eichinger, et al., *J. Biol. Chem.*, 273:12952–12959 (1998)). Interestingly, Tnik can phosphorylate the mammalian Severin homologue, Gelsolin, in vitro (FIG. 20). Gelsolin is also an F-actin fragmenting and capping enzyme that can reduce the content of F-actin. This result suggests that Tnik regulates F-actin assembly through Gelsolin or other related actin severing enzymes. This is consistent with the result that the kinase domain of Tnik is responsible for the regulation of cell spreading (FIG. 17). The mammalian p21-activated kinase, PAK1, which is distantly related to GCK family members and an effector protein of small G proteins Rac1 and CDC42, has been reported to regulate actin cytoskeleton organization. One proposed mechanism of the regulation is through phosphorylation and inhibition of the Myosin Light Chain Kinase (Sanders, et al., *Science*, 283:2083–2085 (1999)). Overexpression of a constitutively active form of PAK1 also resulted in the inhibition of cell spreading (Garrity, et al., *Cell*, 85:639–650 (1996)), an effect similar to that caused by overexpression of Tnik (FIG. 17 and 18).

We claim:

1. An isolated nucleic acid encoding a TNFK protein, comprising a nucleotide sequence selected from the group consisting of SEQ ID NOs:2–8.

2. An isolated nucleic acid encoding a TNIK protein, comprising a nucleotide sequence encoding an amino acid sequence selected from the group consisting of SEQ ID NOs: 9–15.

3. An expression vector, comprising the isolated nucleic acid according to claim 1 or 2, operably linked to regulatory sequences recognized by a host cell transformed with said expression vector.

4. A host cell or progeny thereof, wherein said host cell is transfected with the isolated nucleic acid according to claim 1 or 2, and wherein said host cell or progeny thereof comprises said isolated nucleic acid following said transfection.

5. A host cell or progeny thereof, wherein said host cell is transfected with the expression vector according to claim 3, and wherein said host cell or progeny thereof comprises said expression vector following said transfection.

6. A process for producing a TNIK protein, comprising culturing the host cell or progeny thereof according to claim 4 or 5 under conditions suitable for expression of said TNIK protein.

7. The process according to claim 6, further comprising recovering said TNIK protein.

8. The isolated nucleic acid according to claim 1, wherein said nucleic acid comprises SEQ ID NO:2.

9. The isolated nucleic acid according to claim 1, wherein said nucleic acid comprises SEQ ID NO:3.

10. The isolated nucleic acid according to claim 1, wherein said nucleic acid comprises SEQ ID NO:4.

11. The isolated nucleic acid according to claim 1, wherein said nucleic acid comprises SEQ ID NO:5.

12. The isolated nucleic acid according to claim 1, wherein said nucleic acid comprises SEQ ID NO:6.

13. The isolated nucleic acid according to claim 1, wherein said nucleic acid comprises SEQ ID NO:7.

14. The isolated nucleic acid according to claim 1, wherein said nucleic acid comprises SEQ ID NO:8.

15. The isolated nucleic acid according to claim 2, wherein said nucleotide sequence encodes SEQ ID NO:9.

16. The isolated nucleic acid according to claim 2, wherein said nucleotide sequence encodes SEQ ID NO.10.

17. The isolated nucleic acid according to claim 3, wherein said nucleotide sequence encodes SEQ ID NO:11.

18. The isolated nucleic acid according to claim 2, wherein said nucleotide sequence encodes SEQ ID NO:12.

19. The isolated nucleic acid according to claim 2, wherein said nucleotide sequence encodes SEQ ID NO:13.

20. The isolated nucleic acid according to claim 2, wherein said nucleotide sequence encodes SEQ ID NO:14.

21. The isolated nucleic acid according to claim 2, wherein said nucleotide sequence encodes SEQ ID NO:15.

22. A process for producing a TNIK protein, comprising culturing the host cell or progeny thereof according to claim 5 under conditions suitable for expression of said TNIK protein.

23. The process according to claim 22, further comprising recovering said TNIK protein.

* * * * *

SEQUENCE LISTING

```
<160> NUMBER OF SEQ ID NOS: 36

<210> SEQ ID NO 1
<211> LENGTH: 4083
<212> TYPE: DNA
<213> ORGANISM: Artificial Sequence
<220> FEATURE:
<223> OTHER INFORMATION: synthetic

<400> SEQUENCE: 1

atggcgagcg actccccggc tcgaagcctg gatgaaatag atctctcggc tctgagggac     60

cctgcaggga tctttgaatt ggtggaactt gttggaaatg gaacatacgg gcaagtttat    120

aagggtcgtc atgtcaaaac gggccagctt gcagccatca aggttatgga tgtcacaggg    180

gatgaagagg aagaaatcaa acaagaaatt aacatgttga agaaatattc tcatcaccgg    240

aatattgcta catactatgg tgcttttatc aaaaagaacc caccaggcat ggatgaccaa    300

ctttggttgg tgatggagtt ttgtggtgct ggctctgtca ccgacctgat caagaacaca    360

aaaggtaaca cgttgaaaga ggagtggatt gcatacatct gcagggaaat cttacggggg    420

ctgagtcacc tgcaccagca taaagtgatt catcgagata ttaaagggca aaatgtcttg    480

ctgactgaaa atgcagaagt taaactagtg gactttggag tcagtgctca gcttgatcga    540

acagtgggca ggaggaatac tttcattgga actccctact ggatggcacc agaagttatt    600

gcctgtgatg aaaacccaga tgccacatat gatttcaaga gtgacttgtg gtctttgggt    660

atcaccgcca ttgaaatggc agaaggtgct ccccctctct gtgacatgca ccccatgaga    720

gctctcttcc tcatcccccg gaatccagcg cctcggctga agtctaagaa gtggtcaaaa    780
```

-continued

```
aaattccagt catttattga gagctgcttg gtaaagaatc acagccagcg accagcaaca    840
gaacaattga tgaagcatcc atttatacga gaccaaccta atgagcgaca ggtccgcatt    900
caactcaagg accatattga tagaacaaag aagaagcgag gagaaaaaga tgagacagag    960
tatgagtaca gtggaagtga ggaagaagag gaggagaatg actcaggaga gcccagctcc   1020
atcctgaatc tgccagggga gtcgacgctg cggagggact ttctgaggct gcagctggcc   1080
aacaaggagc gttctgaggc cctacggagg cagcagctgg agcagcagca gcgggagaat   1140
gaggagcaca agcggcagct gctggccgag cgtcagaagc gcatcgagga gcagaaagag   1200
cagaggcggc ggctggagga gcaacaaagg cgagagaagg agctgcggaa gcagcaggag   1260
agggagcagc gccggcacta tgaggagcag atgcgccggg aggaggagag gaggcgtgcg   1320
gagcatgaac aggaatacat caggcgacag ttagaggagg agcagagaca gttagagatc   1380
ttgcagcagc agctactgca tgaacaagct ctacttctgg aatataagcg caaacaattg   1440
gaagaacaga gacaagcaga aagactgcag aggcagctaa agcaagaaag agactactta   1500
gtttcccttc agcatcagcg gcaggagcag aggcctgtgg agaagaagcc actgtaccat   1560
tacaaagaag gaatgagtcc tagtgagaag ccagcatggg ccaaggaggt agaagaacgg   1620
tcaaggctca accggcaaag ttcccctgcc atgcctcaca aggttgccaa caggatatct   1680
gaccccaacc tgcccccaag gtcggagtcc ttcagcatta gtggagttca gcctgctcga   1740
acacccccca tgctcagacc agtcgatccc cagatcccac atctggtagc tgtaaaatcc   1800
cagggacctg ccttgaccgc ctcccagtca gtgcacgagc agcccacaaa gggcctctct   1860
gggtttcagg aggctctgaa cgtgacctcc caccgcgtgg agatgccacg ccagaactca   1920
gatcccacct cggaaaatcc tcctctcccc actcgcattg aaaagtttga ccgaagctct   1980
tggttacgac aggaagaaga cattccacca aaggtgcctc aaagaacaac ttctatatcc   2040
ccagcattag ccagaaagaa ttctcctggg aatggtagtg ctctgggacc cagactagga   2100
tctcaaccca tcagagcaag caaccctgat ctccggagaa ctgagcccat cttggagagc   2160
cccttgcaga ggaccagcag tggcagttcc tccagctcca gcacccctag ctcccagccc   2220
agctcccaag gaggctccca gcctggatca caagcaggat ccagtgaacg caccagagtt   2280
cgagccaaca gtaagtcaga aggatcacct gtgcttcccc atgagcctgc caaggtgaaa   2340
ccagaagaat ccagggacat tacccggccc agtcgaccag ctagctacaa aaaagctata   2400
gatgaggatc tgacggcatt agccaaagaa ctaagagaac tccggattga agaaacaaac   2460
cgcccaatga agaaggtgac tgattactcc tcctccagtg aggagtcaga aagtagcgag   2520
gaagaggagg aagatggaga gagcgagacc catgatggga cagtggctgt cagcgacata   2580
cccagactga taccaacagg agctccaggc agcaacgagc agtacaatgt gggaatggtg   2640
gggacgcatg ggctggagac ctctcatgcg gacagtttca gcggcagtat ttcaagagaa   2700
ggaaccttga tgattagaga gacgtctgga gagaagaagc gatctggcca cagtgacagc   2760
aatggctttg ctggccacat caacctccct gacctggtgc agcagagcca ttctccagct   2820
ggaaccccga ctgagggact ggggcgcgtc tcaacccatt cccaggagat ggactctggg   2880
actgaatatg gcatggggag cagcaccaaa gcctccttca ccccctttgt ggaccccaga   2940
gtataccaga cgtctcccac tgatgaagat gaagaggatg aggaatcatc agccgcagct   3000
ctgtttacta gcgaacttct taggcaagaa caggccaaac tcaatgaagc aagaaagatt   3060
tcggtggtaa atgtaaaccc aaccaacatt cggcctcata gcgacacacc agaaatcaga   3120
```

-continued

```
aaatacaaga aacgattcaa ctcagaaata ctttgtgcag ctctgtgggg tgtaaacctt   3180

ctggtgggga ctgaaaatgg cctgatgctt ttggaccgaa gtgggcaagg caaagtctat   3240

aatctgatca accggaggcg atttcagcag atggatgtgc tagagggact gaatgtcctt   3300

gtgacaattt caggaaagaa gaataagcta cgagtttact atctttcatg gttaagaaac   3360

agaatactac ataatgaccc agaagtagaa aagaaacaag gctggatcac tgttggggac   3420

ttggaaggct gtatacatta taaagttgtt aaatatgaaa ggatcaaatt tttggtgatt   3480

gccttaaaga atgctgtgga aatatatgct tgggctccta aaccgtatca taaattcatg   3540

gcatttaagt cttttgcaga tctccagcac aagcctctgc tagttgatct cacggtagaa   3600

gaaggtcaaa gattaaaggt tatttttggt tcacacactg gtttccatgt aattgatgtt   3660

gattcaggaa actcttatga tatctacata ccatctcata ttcagggcaa tatcactcct   3720

catgctattg tcatcttgcc taaaacagat ggaatggaaa tgcttgtttg ctatgaggat   3780

gagggggtgt atgtaaacac ctatggccgg ataactaagg atgtggtgct ccaatgggga   3840

gaaatgccca cgtctgtggc ctacattcat tccaatcaga taatgggctg gggcgagaaa   3900

gctattgaga tccggtcagt ggaaacagga catttggatg gagtatttat gcataagcga   3960

gctcaaaggt taaagtttct atgtgaaaga aatgataagg tattttttgc atccgtgcga   4020

tctggaggaa gtagccaagt gtttttcatg accctcaaca gaaattccat gatgaactgg   4080

taa                                                                 4083
```

```
<210> SEQ ID NO 2
<211> LENGTH: 3996
<212> TYPE: DNA
<213> ORGANISM: Artificial Sequence
<220> FEATURE:
<223> OTHER INFORMATION: synthetic

<400> SEQUENCE: 2

atggcgagcg actccccggc tcgaagcctg gatgaaatag atctctcggc tctgagggac     60

cctgcaggga tctttgaatt ggtggaactt gttggaaatg gaacatacgg gcaagtttat    120

aagggtcgtc atgtcaaaac gggccagctt gcagccatca aggttatgga tgtcacaggg    180

gatgaagagg aagaaatcaa acaagaaatt aacatgttga agaaatattc tcatcaccgg    240

aatattgcta catactatgg tgcttttatc aaaaagaacc caccaggcat ggatgaccaa    300

ctttggttgg tgatggagtt ttgtggtgct ggctctgtca ccgacctgat caagaacaca    360

aaaggtaaca cgttgaaaga ggagtggatt gcatacatct gcagggaaat cttacggggg    420

ctgagtcacc tgcaccagca taaagtgatt catcgagata ttaaagggca aaatgtcttg    480

ctgactgaaa atgcagaagt taaactagtg gactttggag tcagtgctca gcttgatcga    540

acagtgggca ggaggaatac tttcattgga actccctact ggatggcacc agaagttatt    600

gcctgtgatg aaaacccaga tgccacatat gatttcaaga gtgacttgtg gtctttgggt    660

atcaccgcca ttgaaatggc agaaggtgct ccccctctct gtgacatgca ccccatgaga    720

gctctcttcc tcatcccccg gaatccagcg cctcggctga agtctaagaa gtggtcaaaa    780

aaattccagt catttattga gagctgcttg gtaaagaatc acagccagcg accagcaaca    840

gaacaattga tgaagcatcc atttatacga gaccaaccta atgagcgaca ggtccgcatt    900

caactcaagg accatattga tagaacaaag aagaagcgag gagaaaaaga tgagacagag    960

tatgagtaca gtggaagtga ggaagaagag gaggagaatg actcaggaga gcccagctcc   1020

atcctgaatc tgccagggga gtcgacgctg cggagggact ttctgaggct gcagctggcc   1080
```

-continued

```
aacaaggagc gttctgaggc cctacggagg cagcagctgg agcagcagca gcgggagaat   1140
gaggagcaca agcggcagct gctggccgag cgtcagaagc gcatcgagga gcagaaagag   1200
cagaggcggc ggctggagga gcaacaaagg cgagagaagg agctgcggaa gcagcaggag   1260
agggagcagc gccggcacta tgaggagcag atgcgccggg aggaggagag gaggcgtgcg   1320
gagcatgaac aggaatataa gcgcaaacaa ttggaagaac agagacaagc agaaagactg   1380
cagaggcagc taaagcaaga aagagactac ttagtttccc ttcagcatca gcggcaggag   1440
cagaggcctg tggagaagaa gccactgtac cattacaaag aaggaatgag tcctagtgag   1500
aagccagcat gggccaagga ggtagaagaa cggtcaaggc tcaaccggca aagttcccct   1560
gccatgcctc acaaggttgc caacaggata tctgacccca acctgccccc aaggtcggag   1620
tccttcagca ttagtggagt tcagcctgct cgaacacccc ccatgctcag accagtcgat   1680
ccccagatcc cacatctggt agctgtaaaa tcccagggac ctgccttgac cgcctcccag   1740
tcagtgcacg agcagcccac aaagggcctc tctgggtttc aggaggctct gaacgtgacc   1800
tcccaccgcg tggagatgcc acgccagaac tcagatccca cctcggaaaa tcctcctctc   1860
cccactcgca ttgaaaagtt tgaccgaagc tcttggttac gacaggaaga agacattcca   1920
ccaaaggtgc ctcaaagaac aacttctata tccccagcat tagccagaaa gaattctcct   1980
gggaatggta gtgctctggg acccagacta ggatctcaac ccatcagagc aagcaaccct   2040
gatctccgga gaactgagcc catcttggag agccccttgc agaggaccag cagtggcagt   2100
tcctccagct ccagcacccc tagctcccag cccagctccc aaggaggctc ccagcctgga   2160
tcacaagcag gatccagtga acgcaccaga gttcgagcca acagtaagtc agaaggatca   2220
cctgtgcttc cccatgagcc tgccaaggtg aaaccagaag aatccaggga cattacccgg   2280
cccagtcgac cagctagcta caaaaaagct atagatgagg atctgacggc attagccaaa   2340
gaactaagag aactccggat tgaagaaaca aaccgcccaa tgaagaaggt gactgattac   2400
tcctcctcca gtgaggagtc agaaagtagc gaggaagagg aggaagatgg agagagcgag   2460
acccatgatg ggacagtggc tgtcagcgac atacccagac tgataccaac aggagctcca   2520
ggcagcaacg agcagtacaa tgtgggaatg gtggggacgc atgggctgga gacctctcat   2580
gcggacagtt tcagcggcag tatttcaaga gaaggaacct tgatgattag agagacgtct   2640
ggagagaaga agcgatctgg ccacagtgac agcaatggct ttgctggcca catcaacctc   2700
cctgacctgg tgcagcagag ccattctcca gctggaaccc cgactgaggg actggggcgc   2760
gtctcaaccc attcccagga gatggactct gggactgaat atggcatggg gagcagcacc   2820
aaagcctcct tcacccctt tgtggacccc agagtatacc agacgtctcc cactgatgaa   2880
gatgaagagg atgaggaatc atcagccgca gctctgttta ctagcgaact tcttaggcaa   2940
gaacaggcca aactcaatga agcaagaaag atttcggtgg taaatgtaaa cccaaccaac   3000
attcggcctc atagcgacac accagaaatc agaaaataca agaaacgatt caactcagaa   3060
atactttgtg cagctctgtg ggtgtaaac cttctggtgg ggactgaaaa tggcctgatg   3120
cttttggacc gaagtgggca aggcaaagtc tataatctga tcaaccggag gcgatttcag   3180
cagatggatg tgctagaggg actgaatgtc cttgtgacaa tttcaggaaa gaagaataag   3240
ctacgagttt actatctttc atggttaaga aacagaatac tacataatga cccagaagta   3300
gaaaagaaac aaggctggat cactgttggg gacttggaag gctgtataca ttataaagtt   3360
gttaaatatg aaaggatcaa atttttggtg attgccttaa agaatgctgt ggaaatatat   3420
```

-continued

```
gcttgggctc ctaaaccgta tcataaattc atggcattta agtcttttgc agatctccag   3480

cacaagcctc tgctagttga tctcacggta gaagaaggtc aaagattaaa ggttattttt   3540

ggttcacaca ctggtttcca tgtaattgat gttgattcag gaaactctta tgatatctac   3600

ataccatctc atattcaggg caatatcact cctcatgcta ttgtcatctt gcctaaaaca   3660

gatggaatgg aaatgcttgt ttgctatgag gatgaggggg tgtatgtaaa cacctatggc   3720

cggataacta aggatgtggt gctccaatgg ggagaaatgc ccacgtctgt ggcctacatt   3780

cattccaatc agataatggg ctggggcgag aaagctattg agatccggtc agtggaaaca   3840

ggacatttgg atggagtatt tatgcataag cgagctcaaa ggttaaagtt tctatgtgaa   3900

agaaatgata aggtattttt tgcatccgtg cgatctggag gaagtagcca agtgtttttc   3960

atgaccctca acagaaattc catgatgaac tggtaa                             3996
```

```
<210> SEQ ID NO 3
<211> LENGTH: 3918
<212> TYPE: DNA
<213> ORGANISM: Artificial Sequence
<220> FEATURE:
<223> OTHER INFORMATION: synthetic

<400> SEQUENCE: 3

atggcgagcg actccccggc tcgaagcctg gatgaaatag atctctcggc tctgagggac     60

cctgcaggga tctttgaatt ggtggaactt gttggaaatg gaacatacgg gcaagtttat    120

aagggtcgtc atgtcaaaac gggccagctt gcagccatca aggttatgga tgtcacaggg    180

gatgaagagg aagaaatcaa acaagaaatt aacatgttga agaaatattc tcatcaccgg    240

aatattgcta catactatgg tgcttttatc aaaaagaacc caccaggcat ggatgaccaa    300

ctttggttgg tgatggagtt ttgtggtgct ggctctgtca ccgacctgat caagaacaca    360

aaaggtaaca cgttgaaaga ggagtggatt gcatacatct gcagggaaat cttacggggg    420

ctgagtcacc tgcaccagca taaagtgatt catcgagata ttaaagggca aaatgtcttg    480

ctgactgaaa atgcagaagt taaactagtg gactttggag tcagtgctca gcttgatcga    540

acagtgggca ggaggaatac tttcattgga actccctact ggatggcacc agaagttatt    600

gcctgtgatg aaaacccaga tgccacatat gatttcaaga gtgacttgtg gtctttgggt    660

atcaccgcca ttgaaatggc agaaggtgct ccccctctct gtgacatgca ccccatgaga    720

gctctcttcc tcatcccccg gaatccagcg cctcggctga agtctaagaa gtggtcaaaa    780

aaattccagt catttattga gagctgcttg gtaaagaatc acagccagcg accagcaaca    840

gaacaattga tgaagcatcc atttatacga gaccaaccta atgagcgaca ggtccgcatt    900

caactcaagg accatattga tagaacaaag aagaagcgag gagaaaaaga tgagacagag    960

tatgagtaca gtggaagtga ggaagaagag gaggagaatg actcaggaga gcccagctcc   1020

atcctgaatc tgccagggga gtcgacgctg cggagggact ttctgaggct gcagctggcc   1080

aacaaggagc gttctgaggc cctacggagg cagcagctgg agcagcagca gcgggagaat   1140

gaggagcaca agcggcagct gctggccgag cgtcagaagc gcatcgagga gcagaaagag   1200

cagaggcggc ggctggagga gcaacaaagg cgagagaagg agctgcggaa gcagcaggag   1260

agggagcagc gccggcacta tgaggagcag atgcgccggg aggaggagag gaggcgtgcg   1320

gagcatgaac aggaatacat caggcgacag ttagaggagg agcagagaca gttagagatc   1380

ttgcagcagc agctactgca tgaacaagct ctacttctgg aatataagcg caaacaattg   1440

gaagaacaga gacaagcaga aagactgcag aggcagctaa agcaagaaag agactactta   1500
```

-continued

```
gtttcccttc agcatcagcg gcaggagcag aggcctgtgg agaagaagcc actgtaccat   1560
tacaaagaag gaatgagtcc tagtgagaag ccagcatggg ccaaggagat cccacatctg   1620
gtagctgtaa aatcccaggg acctgccttg accgcctccc agtcagtgca cgagcagccc   1680
acaaagggcc tctctgggtt tcaggaggct ctgaacgtga cctcccaccg cgtggagatg   1740
ccacgccaga actcagatcc cacctcggaa aatcctcctc tccccactcg cattgaaaag   1800
tttgaccgaa gctcttggtt acgacaggaa gaagacattc caccaaaggt gcctcaaaga   1860
acaacttcta tatccccagc attagccaga aagaattctc ctgggaatgg tagtgctctg   1920
ggacccagac taggatctca acccatcaga gcaagcaacc ctgatctccg gagaactgag   1980
cccatcttgg agagcccctt gcagaggacc agcagtggca gttcctccag ctccagcacc   2040
cctagctccc agcccagctc ccaaggaggc tcccagcctg gatcacaagc aggatccagt   2100
gaacgcacca gagttcgagc caacagtaag tcagaaggat cacctgtgct tccccatgag   2160
cctgccaagg tgaaaccaga agaatccagg gacattaccc ggcccagtcg accagctagc   2220
tacaaaaaag ctatagatga ggatctgacg gcattagcca aagaactaag agaactccgg   2280
attgaagaaa caaaccgccc aatgaagaag gtgactgatt actcctcctc cagtgaggag   2340
tcagaaagta gcgaggaaga ggaggaagat ggagagagcg agacccatga tgggacagtg   2400
gctgtcagcg acatacccag actgatacca acaggagctc caggcagcaa cgagcagtac   2460
aatgtgggaa tggtggggac gcatgggctg gagacctctc atgcggacag tttcagcggc   2520
agtatttcaa gagaaggaac cttgatgatt agagagacgt ctggagagaa gaagcgatct   2580
ggccacagtg acagcaatgg ctttgctggc cacatcaacc tccctgacct ggtgcagcag   2640
agccattctc cagctggaac ccgactgag ggactggggc gcgtctcaac ccattcccag   2700
gagatggact ctgggactga atatggcatg gggagcagca ccaaagcctc cttcaccccc   2760
tttgtggacc ccagagtata ccagacgtct cccactgatg aagatgaaga ggatgaggaa   2820
tcatcagccg cagctctgtt tactagcgaa cttcttaggc aagaacaggc caaactcaat   2880
gaagcaagaa agatttcggt ggtaaatgta aacccaacca acattcggcc tcatagcgac   2940
acaccagaaa tcagaaaata caagaaacga ttcaactcag aaatactttg tgcagctctg   3000
tggggtgtaa accttctggt ggggactgaa aatggcctga tgcttttgga ccgaagtggg   3060
caaggcaaag tctataatct gatcaaccgg aggcgatttc agcagatgga tgtgctagag   3120
ggactgaatg tccttgtgac aatttcagga aagaagaata agctacgagt ttactatctt   3180
tcatggttaa gaaacagaat actacataat gacccagaag tagaaaagaa acaaggctgg   3240
atcactgttg gggacttgga aggctgtata cattataaag ttgttaaata tgaaaggatc   3300
aaatttttgg tgattgcctt aaagaatgct gtggaaatat atgcttgggc tcctaaaccg   3360
tatcataaat tcatggcatt taagtctttt gcagatctcc agcacaagcc tctgctagtt   3420
gatctcacgg tagaagaagg tcaaagatta aaggttattt ttggttcaca cactggtttc   3480
catgtaattg atgttgattc aggaaactct tatgatatct acataccatc tcatattcag   3540
ggcaatatca ctcctcatgc tattgtcatc ttgcctaaaa cagatggaat ggaaatgctt   3600
gtttgctatg aggatgaggg ggtgtatgta aacacctatg gccggataac taaggatgtg   3660
gtgctccaat ggggagaaat gcccacgtct gtggcctaca ttcattccaa tcagataatg   3720
ggctggggcg agaaagctat tgagatccgg tcagtggaaa caggacattt ggatggagta   3780
tttatgcata agcgagctca aaggttaaag tttctatgtg aaagaaatga taaggtattt   3840
```

-continued

```
tttgcatccg tgcgatctgg aggaagtagc caagtgtttt tcatgaccct caacagaaat   3900

tccatgatga actggtaa                                                 3918


<210> SEQ ID NO 4
<211> LENGTH: 4059
<212> TYPE: DNA
<213> ORGANISM: Artificial Sequence
<220> FEATURE:
<223> OTHER INFORMATION: synthetic

<400> SEQUENCE: 4

atggcgagcg actccccggc tcgaagcctg gatgaaatag atctctcggc tctgagggac     60

cctgcaggga tctttgaatt ggtggaactt gttggaaatg gaacatacgg gcaagtttat    120

aagggtcgtc atgtcaaaac gggccagctt gcagccatca aggttatgga tgtcacaggg    180

gatgaagagg aagaaatcaa acaagaaatt aacatgttga agaaatattc tcatcaccgg    240

aatattgcta catactatgg tgcttttatc aaaaagaacc caccaggcat ggatgaccaa    300

ctttggttgg tgatggagtt ttgtggtgct ggctctgtca ccgacctgat caagaacaca    360

aaaggtaaca cgttgaaaga ggagtggatt gcatacatct gcagggaaat cttacggggg    420

ctgagtcacc tgcaccagca taaagtgatt catcgagata ttaaagggca aaatgtcttg    480

ctgactgaaa atgcagaagt taaactagtg gactttggag tcagtgctca gcttgatcga    540

acagtgggca ggaggaatac tttcattgga actccctact ggatggcacc agaagttatt    600

gcctgtgatg aaaacccaga tgccacatat gatttcaaga gtgacttgtg gtctttgggt    660

atcaccgcca ttgaaatggc agaaggtgct cccccctctct gtgacatgca ccccatgaga    720

gctctcttcc tcatcccccg gaatccagcg cctcggctga agtctaagaa gtggtcaaaa    780

aaattccagt catttattga gagctgcttg gtaaagaatc acagccagcg accagcaaca    840

gaacaattga tgaagcatcc atttatacga gaccaaccta atgagcgaca ggtccgcatt    900

caactcaagg accatattga tagaacaaag aagaagcgag gagaaaaaga tgagacagag    960

tatgagtaca gtggaagtga ggaagaagag gaggagaatg actcaggaga gcccagctcc   1020

atcctgaatc tgccagggga gtcgacgctg cggagggact ttctgaggct gcagctggcc   1080

aacaaggagc gttctgaggc cctacggagg cagcagctgg agcagcagca gcgggagaat   1140

gaggagcaca agcggcagct gctggccgag cgtcagaagc gcatcgagga gcagaaagag   1200

cagaggcggc ggctggagga gcaacaaagg cgagagaagg agctgcggaa gcagcaggag   1260

agggagcagc gccggcacta tgaggagcag atgcgccggg aggaggagag gaggcgtgcg   1320

gagcatgaac aggaatacat caggcgacag ttagaggagg agcagagaca gttagagatc   1380

ttgcagcagc agctactgca tgaacaagct ctacttctgg aatataagcg caaacaattg   1440

gaagaacaga gacaagcaga aagactgcag aggcagctaa agcaagaaag agactactta   1500

gtttcccttc agcatcagcg gcaggagcag aggcctgtgg agaagaagcc actgtaccat   1560

tacaaagaag gaatgagtcc tagtgagaag ccagcatggg ccaaggaggt agaagaacgg   1620

tcaaggctca accggcaaag ttcccctgcc atgcctcaca aggttgccaa caggatatct   1680

gaccccaacc tgcccccaag gtcggagtcc ttcagcatta gtggagttca gcctgctcga   1740

acaccccccca tgctcagacc agtcgatccc cagatcccac atctggtagc tgtaaaatcc   1800

cagggacctg ccttgaccgc ctcccagtca gtgcacgagc agcccacaaa gggcctctct   1860

gggtttcagg aggctctgaa cgtgacctcc caccgcgtgg agatgccacg ccagaactca   1920

gatcccacct cggaaaatcc tcctctcccc actcgcattg aaaagtttga ccgaagctct   1980
```

```
tggttacgac aggaagaaga cattccacca aaggtgcctc aaagaacaac ttctatatcc   2040
ccagcattag ccagaaagaa ttctcctggg aatggtagtg ctctgggacc cagactagga   2100
tctcaaccca tcagagcaag caaccctgat ctccggagaa ctgagcccat cttggagagc   2160
cccttgcaga ggaccagcag tggcagttcc tccagctcca gcacccctag ctcccagccc   2220
agctcccaag gaggctccca gcctggatca caagcaggat ccagtgaacg caccagagtt   2280
cgagccaaca gtaagtcaga aggatcacct gtgcttcccc atgagcctgc caaggtgaaa   2340
ccagaagaat ccagggacat tacccggccc agtcgaccag ctgatctgac ggcattagcc   2400
aaagaactaa gagaactccg gattgaagaa acaaaccgcc caatgaagaa ggtgactgat   2460
tactcctcct ccagtgagga gtcagaaagt agcgaggaag aggaggaaga tggagagagc   2520
gagacccatg atgggacagt ggctgtcagc gacataccca gactgatacc aacaggagct   2580
ccaggcagca acgagcagta caatgtggga atggtgggga cgcatgggct ggagacctct   2640
catgcggaca gtttcagcgg cagtatttca agagaaggaa ccttgatgat tagagagacg   2700
tctggagaga agaagcgatc tggccacagt gacagcaatg gctttgctgg ccacatcaac   2760
ctccctgacc tggtgcagca gagccattct ccagctggaa ccccgactga gggactgggg   2820
cgcgtctcaa cccattccca ggagatggac tctgggactg aatatggcat ggggagcagc   2880
accaaagcct ccttcacccc ctttgtggac cccagagtat accagacgtc tcccactgat   2940
gaagatgaag aggatgagga atcatcagcc gcagctctgt ttactagcga acttcttagg   3000
caagaacagg ccaaactcaa tgaagcaaga aagatttcgg tggtaaatgt aaacccaacc   3060
aacattcggc ctcatagcga cacaccagaa atcagaaaat acaagaaacg attcaactca   3120
gaaatacttt gtgcagctct gtggggtgta aaccttctgg tggggactga aaatggcctg   3180
atgcttttgg accgaagtgg gcaaggcaaa gtctataatc tgatcaaccg gaggcgattt   3240
cagcagatgg atgtgctaga gggactgaat gtccttgtga caatttcagg aaagaagaat   3300
aagctacgag tttactatct ttcatggtta agaaacagaa tactacataa tgacccagaa   3360
gtagaaaaga aacaaggctg gatcactgtt ggggacttgg aaggctgtat acattataaa   3420
gttgttaaat atgaaaggat caaatttttg gtgattgcct taaagaatgc tgtggaaata   3480
tatgcttggg ctcctaaacc gtatcataaa ttcatggcat ttaagtcttt tgcagatctc   3540
cagcacaagc ctctgctagt tgatctcacg gtagaagaag gtcaaagatt aaaggttatt   3600
tttggttcac acactggttt ccatgtaatt gatgttgatt caggaaactc ttatgatatc   3660
tacataccat ctcatattca gggcaatatc actcctcatg ctattgtcat cttgcctaaa   3720
acagatggaa tggaaatgct tgtttgctat gaggatgagg gggtgtatgt aaacacctat   3780
ggccggataa ctaaggatgt ggtgctccaa tggggagaaa tgcccacgtc tgtggcctac   3840
attcattcca atcagataat gggctggggc gagaaagcta ttgagatccg gtcagtggaa   3900
acaggacatt tggatggagt atttatgcat aagcgagctc aaaggttaaa gtttctatgt   3960
gaaagaaatg ataaggtatt ttttgcatcc gtgcgatctg gaggaagtag ccaagtgttt   4020
ttcatgaccc tcaacagaaa ttccatgatg aactggtaa                          4059
```

```
<210> SEQ ID NO 5
<211> LENGTH: 3831
<212> TYPE: DNA
<213> ORGANISM: Artificial Sequence
<220> FEATURE:
<223> OTHER INFORMATION: synthetic
```

-continued

<400> SEQUENCE: 5

```
atggcgagcg actccccggc tcgaagcctg gatgaaatag atctctcggc tctgagggac      60
cctgcaggga tctttgaatt ggtggaactt gttggaaatg gaacatacgg gcaagtttat     120
aagggtcgtc atgtcaaaac gggccagctt gcagccatca aggttatgga tgtcacaggg     180
gatgaagagg aagaaatcaa acaagaaatt aacatgttga agaaatattc tcatcaccgg     240
aatattgcta catactatgg tgcttttatc aaaaagaacc caccaggcat ggatgaccaa     300
ctttggttgg tgatggagtt ttgtggtgct ggctctgtca ccgacctgat caagaacaca     360
aaaggtaaca cgttgaaaga ggagtggatt gcatacatct gcagggaaat cttacggggg     420
ctgagtcacc tgcaccagca taaagtgatt catcgagata ttaaagggca aaatgtcttg     480
ctgactgaaa atgcagaagt taaactagtg gactttggag tcagtgctca gcttgatcga     540
acagtgggca ggaggaatac tttcattgga actccctact ggatggcacc agaagttatt     600
gcctgtgatg aaaacccaga tgccacatat gatttcaaga gtgacttgtg gtctttgggt     660
atcaccgcca ttgaaatggc agaaggtgct ccccctctct gtgacatgca ccccatgaga     720
gctctcttcc tcatcccccg gaatccagcg cctcggctga agtctaagaa gtggtcaaaa     780
aaattccagt catttattga gagctgcttg gtaaagaatc acagccagcg accagcaaca     840
gaacaattga tgaagcatcc atttatacga gaccaaccta atgagcgaca ggtccgcatt     900
caactcaagg accatattga tagaacaaag aagaagcgag gagaaaaaga tgagacagag     960
tatgagtaca gtggaagtga ggaagaagag gaggagaatg actcaggaga gcccagctcc    1020
atcctgaatc tgccagggga gtcgacgctg cggagggact ttctgaggct gcagctggcc    1080
aacaaggagc gttctgaggc cctacggagg cagcagctgg agcagcagca gcgggagaat    1140
gaggagcaca agcggcagct gctggccgag cgtcagaagc gcatcgagga gcagaaagag    1200
cagaggcggc ggctggagga gcaacaaagg cgagagaagg agctgcggaa gcagcaggag    1260
agggagcagc gccggcacta tgaggagcag atgcgccggg aggaggagag gaggcgtgcg    1320
gagcatgaac aggaatataa gcgcaaacaa ttggaagaac agagacaagc agaaagactg    1380
cagaggcagc taaagcaaga aagagactac ttagtttccc ttcagcatca gcggcaggag    1440
cagaggcctg tggagaagaa gccactgtac cattacaaag aaggaatgag tcctagtgag    1500
aagccagcat gggccaagga gatcccacat ctggtagctg taaaatccca gggacctgcc    1560
ttgaccgcct cccagtcagt gcacgagcag cccacaaagg gcctctctgg gtttcaggag    1620
gctctgaacg tgacctccca ccgcgtggag atgccacgcc agaactcaga tcccacctcg    1680
gaaaatcctc ctctccccac tcgcattgaa aagtttgacc gaagctcttg gttacgacag    1740
gaagaagaca ttccaccaaa ggtgcctcaa agaacaactt ctatatcccc agcattagcc    1800
agaaagaatt ctcctgggaa tggtagtgct ctgggaccca gactaggatc tcaacccatc    1860
agagcaagca accctgatct ccggagaact gagcccatct tggagagccc cttgcagagg    1920
accagcagtg gcagttcctc cagctccagc acccctagct cccagcccag ctcccaagga    1980
ggctcccagc ctggatcaca agcaggatcc agtgaacgca ccagagttcg agccaacagt    2040
aagtcagaag gatcacctgt gcttccccat gagcctgcca aggtgaaacc agaagaatcc    2100
agggacatta cccggcccag tcgaccagct agctacaaaa aagctataga tgaggatctg    2160
acggcattag ccaaagaact aagagaactc cggattgaag aaacaaaccg cccaatgaag    2220
aaggtgactg attactcctc ctccagtgag gagtcagaaa gtagcgagga agaggaggaa    2280
gatggagaga gcgagaccca tgatgggaca gtggctgtca gcgacatacc cagactgata    2340
```

-continued

```
ccaacaggag ctccaggcag caacgagcag tacaatgtgg gaatggtggg gacgcatggg   2400
ctggagacct ctcatgcgga cagtttcagc ggcagtattt caagagaagg aaccttgatg   2460
attagagaga cgtctggaga gaagaagcga tctggccaca gtgacagcaa tggctttgct   2520
ggccacatca acctccctga cctggtgcag cagagccatt ctccagctgg aaccccgact   2580
gagggactgg ggcgcgtctc aacccattcc caggagatgg actctgggac tgaatatggc   2640
atggggagca gcaccaaagc ctccttcacc ccctttgtgg accccagagt ataccagacg   2700
tctcccactg atgaagatga agaggatgag gaatcatcag ccgcagctct gtttactagc   2760
gaacttctta ggcaagaaca ggccaaactc aatgaagcaa gaaagatttc ggtggtaaat   2820
gtaaacccaa ccaacattcg gcctcatagc gacacaccag aaatcagaaa atacaagaaa   2880
cgattcaact cagaaatact ttgtgcagct ctgtggggtg taaaccttct ggtggggact   2940
gaaaatggcc tgatgctttt ggaccgaagt gggcaaggca aagtctataa tctgatcaac   3000
cggaggcgat ttcagcagat ggatgtgcta gagggactga atgtccttgt gacaatttca   3060
ggaaagaaga ataagctacg agtttactat ctttcatggt taagaaacag aatactacat   3120
aatgacccag aagtagaaaa gaaacaaggc tggatcactg ttggggactt ggaaggctgt   3180
atacattata aagttgttaa atatgaaagg atcaaatttt tggtgattgc cttaaagaat   3240
gctgtggaaa tatatgcttg ggctcctaaa ccgtatcata aattcatggc atttaagtct   3300
tttgcagatc tccagcacaa gcctctgcta gttgatctca cggtagaaga aggtcaaaga   3360
ttaaaggtta tttttggttc acacactggt ttccatgtaa ttgatgttga ttcaggaaac   3420
tcttatgata tctacatacc atctcatatt cagggcaata tcactcctca tgctattgtc   3480
atcttgccta aaacagatgg aatggaaatg cttgtttgct atgaggatga gggggtgtat   3540
gtaaacacct atggccggat aactaaggat gtggtgctcc aatggggaga aatgcccacg   3600
tctgtggcct acattcattc caatcagata atgggctggg gcgagaaagc tattgagatc   3660
cggtcagtgg aaacaggaca tttggatgga gtatttatgc ataagcgagc tcaaaggtta   3720
aagtttctat gtgaaagaaa tgataaggta ttttttgcat ccgtgcgatc tggaggaagt   3780
agccaagtgt tttcatgacc cctcaacaga aattccatga tgaactggta a            3831
```

<210> SEQ ID NO 6
<211> LENGTH: 3972
<212> TYPE: DNA
<213> ORGANISM: Artificial Sequence
<220> FEATURE:
<223> OTHER INFORMATION: synthetic

<400> SEQUENCE: 6

```
atggcgagcg actccccggc tcgaagcctg gatgaaatag atctctcggc tctgagggac     60
cctgcaggga tctttgaatt ggtggaactt gttggaaatg gaacatacgg gcaagtttat    120
aagggtcgtc atgtcaaaac gggccagctt gcagccatca aggttatgga tgtcacaggg    180
gatgaagagg aagaaatcaa acaagaaatt aacatgttga agaaatattc tcatcaccgg    240
aatattgcta catactatgg tgcttttatc aaaaagaacc caccaggcat ggatgaccaa    300
ctttggttgg tgatggagtt ttgtggtgct ggctctgtca ccgacctgat caagaacaca    360
aaaggtaaca cgttgaaaga ggagtggatt gcatacatct gcagggaaat cttacggggg    420
ctgagtcacc tgcaccagca taaagtgatt catcgagata ttaaagggca aaatgtcttg    480
ctgactgaaa atgcagaagt taaactagtg gactttggag tcagtgctca gcttgatcga    540
```

-continued

```
acagtgggca ggaggaatac tttcattgga actccctact ggatggcacc agaagttatt    600
gcctgtgatg aaaacccaga tgccacatat gatttcaaga gtgacttgtg gtctttgggt    660
atcaccgcca ttgaaatggc agaaggtgct cccccctctct gtgacatgca ccccatgaga    720
gctctcttcc tcatccccccg gaatccagcg cctcggctga agtctaagaa gtggtcaaaa    780
aaattccagt catttattga gagctgcttg gtaaagaatc acagccagcg accagcaaca    840
gaacaattga tgaagcatcc atttatacga gaccaaccta atgagcgaca ggtccgcatt    900
caactcaagg accatattga tagaacaaag aagaagcgag gagaaaaaga tgagacagag    960
tatgagtaca gtggaagtga ggaagaagag gaggagaatg actcaggaga gcccagctcc   1020
atcctgaatc tgccagggga gtcgacgctg cggagggact tctgaggct gcagctggcc   1080
aacaaggagc gttctgaggc cctacggagg cagcagctgg agcagcagca gcgggagaat   1140
gaggagcaca agcggcagct gctggccgag cgtcagaagc gcatcgagga gcagaaagag   1200
cagaggcggc ggctggagga gcaacaaagg cgagagaagg agctgcggaa gcagcaggag   1260
agggagcagc gccggcacta tgaggagcag atgcgccggg aggaggagag gaggcgtgcg   1320
gagcatgaac aggaatataa gcgcaaacaa ttggaagaac agagacaagc agaaagactg   1380
cagaggcagc taaagcaaga aagagactac ttagtttccc ttcagcatca gcggcaggag   1440
cagaggcctg tggagaagaa gccactgtac cattacaaag aaggaatgag tcctagtgag   1500
aagccagcat gggccaagga ggtagaagaa cggtcaaggc tcaaccggca aagttcccct   1560
gccatgcctc acaaggttgc caacaggata tctgacccca acctgccccc aaggtcggag   1620
tccttcagca ttagtggagt tcagcctgct cgaacacccc ccatgctcag accagtcgat   1680
ccccagatcc cacatctggt agctgtaaaa tcccagggac ctgccttgac cgcctcccag   1740
tcagtgcacg agcagcccac aaagggcctc tctgggtttc aggaggctct gaacgtgacc   1800
tcccaccgcg tggagatgcc acgccagaac tcagatccca cctcggaaaa tcctcctctc   1860
cccactcgca ttgaaaagtt tgaccgaagc tcttggttac gacaggaaga agacattcca   1920
ccaaaggtgc ctcaaagaac aacttctata tccccagcat tagccagaaa gaattctcct   1980
gggaatggta gtgctctggg acccagacta ggatctcaac ccatcagagc aagcaaccct   2040
gatctccgga gaactgagcc catcttggag agccccttgc agaggaccag cagtggcagt   2100
tcctccagct ccagcacccc tagctcccag cccagctccc aaggaggctc ccagcctgga   2160
tcacaagcag gatccagtga acgcaccaga gttcgagcca acagtaagtc agaaggatca   2220
cctgtgcttc cccatgagcc tgccaaggtg aaaccagaag aatccaggga cattacccgg   2280
cccagtcgac cagctgatct gacggcatta gccaaagaac taagagaact ccggattgaa   2340
gaaacaaacc gcccaatgaa gaaggtgact gattactcct cctccagtga ggagtcagaa   2400
agtagcgagg aagaggagga agatggagag agcgagaccc atgatgggac agtggctgtc   2460
agcgacatac ccagactgat accaacagga gctccaggca gcaacgagca gtacaatgtg   2520
ggaatggtgg ggacgcatgg gctggagacc tctcatgcgg acagtttcag cggcagtatt   2580
tcaagagaag gaaccttgat gattagagag acgtctggag agaagaagcg atctggccac   2640
agtgacagca atggctttgc tggccacatc aacctccctg acctggtgca gcagagccat   2700
tctccagctg gaaccccgac tgagggactg gggcgcgtct caacccattc ccaggagatg   2760
gactctggga ctgaatatgg catggggagc agcaccaaag cctccttcac cccctttgtg   2820
gaccccagag tataccagac gtctcccact gatgaagatg aagaggatga ggaatcatca   2880
gccgcagctc tgtttactag cgaacttctt aggcaagaac aggccaaact caatgaagca   2940
```

-continued

```
agaaagattt cggtggtaaa tgtaaaccca accaacattc ggcctcatag cgacacacca   3000
gaaatcagaa aatacaagaa acgattcaac tcagaaatac tttgtgcagc tctgtggggt   3060
gtaaaccttc tggtggggac tgaaaatggc ctgatgcttt tggaccgaag tgggcaaggc   3120
aaagtctata atctgatcaa ccggaggcga tttcagcaga tggatgtgct agagggactg   3180
aatgtccttg tgacaatttc aggaaagaag aataagctac gagtttacta tctttcatgg   3240
ttaagaaaca gaatactaca taatgaccca gaagtagaaa agaaacaagg ctggatcact   3300
gttggggact tggaaggctg tatacattat aaagttgtta aatatgaaag gatcaaattt   3360
ttggtgattg ccttaaagaa tgctgtggaa atatatgctt gggctcctaa accgtatcat   3420
aaattcatgg catttaagtc ttttgcagat ctccagcaca agcctctgct agttgatctc   3480
acggtagaag aaggtcaaag attaaaggtt atttttggtt cacacactgg tttccatgta   3540
attgatgttg attcaggaaa ctcttatgat atctacatac catctcatat tcagggcaat   3600
atcactcctc atgctattgt catcttgcct aaaacagatg gaatggaaat gcttgtttgc   3660
tatgaggatg aggggtgta tgtaaacacc tatggccgga taactaagga tgtggtgctc    3720
caatggggag aaatgcccac gtctgtggcc tacattcatt ccaatcagat aatgggctgg   3780
ggcgagaaag ctattgagat ccggtcagtg gaaacaggac atttggatgg agtatttatg   3840
cataagcgag ctcaaaggtt aaagtttcta tgtgaaagaa atgataaggt atttttgca    3900
tccgtgcgat ctggaggaag tagccaagtg tttttcatga ccctcaacag aaattccatg   3960
atgaactggt aa                                                        3972
```

```
<210> SEQ ID NO 7
<211> LENGTH: 3894
<212> TYPE: DNA
<213> ORGANISM: Artificial Sequence
<220> FEATURE:
<223> OTHER INFORMATION: synthetic

<400> SEQUENCE: 7

atggcgagcg actccccggc tcgaagcctg gatgaaatag atctctcggc tctgagggac     60
cctgcaggga tctttgaatt ggtggaactt gttggaaatg gaacatacgg gcaagtttat    120
aagggtcgtc atgtcaaaac gggccagctt gcagccatca aggttatgga tgtcacaggg    180
gatgaagagg aagaaatcaa acaagaaatt aacatgttga agaaatattc tcatcaccgg    240
aatattgcta catactatgg tgcttttatc aaaaagaacc caccaggcat ggatgaccaa    300
ctttggttgg tgatggagtt ttgtggtgct ggctctgtca ccgacctgat caagaacaca    360
aaaggtaaca cgttgaaaga ggagtggatt gcatacatct gcagggaaat cttacggggg    420
ctgagtcacc tgcaccagca taaagtgatt catcgagata ttaaagggca aaatgtcttg    480
ctgactgaaa atgcagaagt taaactagtg gactttggag tcagtgctca gcttgatcga    540
acagtgggca ggaggaatac tttcattgga actccctact ggatggcacc agaagttatt    600
gcctgtgatg aaaacccaga tgccacatat gatttcaaga gtgacttgtg gtctttgggt    660
atcaccgcca ttgaaatggc agaaggtgct ccccctctct gtgacatgca ccccatgaga    720
gctctcttcc tcatccccccg gaatccagcg cctcggctga agtctaagaa gtggtcaaaa    780
aaattccagt catttattga gagctgcttg gtaaagaatc acagccagcg accagcaaca    840
gaacaattga tgaagcatcc atttatacga gaccaaccta atgagcgaca ggtccgcatt    900
caactcaagg accatattga tagaacaaag aagaagcgag gagaaaaaga tgagacagag    960
```

-continued

```
tatgagtaca gtggaagtga ggaagaagag gaggagaatg actcaggaga gcccagctcc   1020
atcctgaatc tgccagggga gtcgacgctg cggagggact ttctgaggct gcagctggcc   1080
aacaaggagc gttctgaggc cctacggagg cagcagctgg agcagcagca gcgggagaat   1140
gaggagcaca agcggcagct gctggccgag cgtcagaagc gcatcgagga gcagaaagag   1200
cagaggcggc ggctggagga gcaacaaagg cgagagaagg agctgcggaa gcagcaggag   1260
agggagcagc gccggcacta tgaggagcag atgcgccggg aggaggagag gaggcgtgcg   1320
gagcatgaac aggaatacat caggcgacag ttagaggagg agcagagaca gttagagatc   1380
ttgcagcagc agctactgca tgaacaagct ctacttctgg aatataagcg caaacaattg   1440
gaagaacaga gacaagcaga aagactgcag aggcagctaa agcaagaaag agactactta   1500
gtttcccttc agcatcagcg gcaggagcag aggcctgtgg agaagaagcc actgtaccat   1560
tacaaagaag gaatgagtcc tagtgagaag ccagcatggg ccaaggagat cccacatctg   1620
gtagctgtaa aatcccaggg acctgccttg accgcctccc agtcagtgca cgagcagccc   1680
acaaagggcc tctctgggtt tcaggaggct ctgaacgtga cctcccaccg cgtggagatg   1740
ccacgccaga actcagatcc cacctcggaa aatcctcctc tccccactcg cattgaaaag   1800
tttgaccgaa gctcttggtt acgacaggaa gaagacattc caccaaaggt gcctcaaaga   1860
acaacttcta tatccccagc attagccaga aagaattctc ctgggaatgg tagtgctctg   1920
ggacccagac taggatctca acccatcaga gcaagcaacc ctgatctccg gagaactgag   1980
cccatcttgg agagcccctt gcagaggacc agcagtggca gttcctccag ctccagcacc   2040
cctagctccc agcccagctc ccaaggaggc tcccagcctg gatcacaagc aggatccagt   2100
gaacgcacca gagttcgagc caacagtaag tcagaaggat cacctgtgct tccccatgag   2160
cctgccaagg tgaaaccaga agaatccagg gacattaccc ggcccagtcg accagctgat   2220
ctgacggcat tagccaaaga actaagagaa ctccggattg aagaaacaaa ccgcccaatg   2280
aagaaggtga ctgattactc ctcctccagt gaggagtcag aaagtagcga ggaagaggag   2340
gaagatggag agagcgagac ccatgatggg acagtggctg tcagcgacat acccagactg   2400
ataccaacag gagctccagg cagcaacgag cagtacaatg tgggaatggt ggggacgcat   2460
gggctggaga cctctcatgc ggacagtttc agcggcagta tttcaagaga aggaaccttg   2520
atgattagag agacgtctgg agagaagaag cgatctggcc acagtgacag caatggcttt   2580
gctggccaca tcaacctccc tgacctggtg cagcagagcc attctccagc tggaaccccg   2640
actgagggac tggggcgcgt ctcaacccat tcccaggaga tggactctgg gactgaatat   2700
ggcatgggga gcagcaccaa agcctccttc accccctttg tggaccccag agtataccag   2760
acgtctccca ctgatgaaga tgaagaggat gaggaatcat cagccgcagc tctgtttact   2820
agcgaacttc ttaggcaaga acaggccaaa ctcaatgaag caagaaagat ttcggtggta   2880
aatgtaaacc caaccaacat tcggcctcat agcgacacac cagaaatcag aaaatacaag   2940
aaacgattca actcagaaat actttgtgca gctctgtggg gtgtaaacct tctggtgggg   3000
actgaaaatg gcctgatgct tttggaccga agtgggcaag gcaaagtcta taatctgatc   3060
aaccggaggc gatttcagca gatggatgtg ctagagggac tgaatgtcct tgtgacaatt   3120
tcaggaaaga agaataagct acgagtttac tatctttcat ggttaagaaa cagaatacta   3180
cataatgacc cagaagtaga aaagaaacaa ggctggatca ctgttgggga cttggaaggc   3240
tgtatacatt ataaagttgt taaatatgaa aggatcaaat ttttggtgat tgccttaaag   3300
aatgctgtgg aaatatatgc ttgggctcct aaaccgtatc ataaattcat ggcatttaag   3360
```

```
tcttttgcag atctccagca caagcctctg ctagttgatc tcacggtaga agaaggtcaa   3420

agattaaagg ttatttttgg ttcacacact ggtttccatg taattgatgt tgattcagga   3480

aactcttatg atatctacat accatctcat attcagggca atatcactcc tcatgctatt   3540

gtcatcttgc ctaaaacaga tggaatggaa atgcttgttt gctatgagga tgagggggtg   3600

tatgtaaaca cctatggccg gataactaag gatgtggtgc tccaatgggg agaaatgccc   3660

acgtctgtgg cctacattca ttccaatcag ataatgggct ggggcgagaa agctattgag   3720

atccggtcag tggaaacagg acatttggat ggagtattta tgcataagcg agctcaaagg   3780

ttaaagtttc tatgtgaaag aaatgataag gtatttttttg catccgtgcg atctggagga   3840

agtagccaag tgtttttcat gaccctcaac agaaattcca tgatgaactg gtaa          3894
```

<210> SEQ ID NO 8
<211> LENGTH: 3807
<212> TYPE: DNA
<213> ORGANISM: Artificial Sequence
<220> FEATURE:
<223> OTHER INFORMATION: synthetic

<400> SEQUENCE: 8

```
atggcgagcg actccccggc tcgaagcctg gatgaaatag atctctcggc tctgagggac     60

cctgcaggga tctttgaatt ggtggaactt gttggaaatg gaacatacgg gcaagtttat    120

aagggtcgtc atgtcaaaac gggccagctt gcagccatca aggttatgga tgtcacaggg    180

gatgaagagg aagaaatcaa acaagaaatt aacatgttga agaaatattc tcatcaccgg    240

aatattgcta catactatgg tgcttttatc aaaaagaacc caccaggcat ggatgaccaa    300

ctttggttgg tgatggagtt ttgtggtgct ggctctgtca ccgacctgat caagaacaca    360

aaaggtaaca cgttgaaaga ggagtggatt gcatacatct gcagggaaat cttacggggg    420

ctgagtcacc tgcaccagca taaagtgatt catcgagata ttaaagggca aaatgtcttg    480

ctgactgaaa atgcagaagt taaactagtg gactttggag tcagtgctca gcttgatcga    540

acagtgggca ggaggaatac tttcattgga actccctact ggatggcacc agaagttatt    600

gcctgtgatg aaaacccaga tgccacatat gatttcaaga gtgacttgtg gtctttgggt    660

atcaccgcca ttgaaatggc agaaggtgct cccccctctct gtgacatgca ccccatgaga    720

gctctcttcc tcatcccccg gaatccagcg cctcggctga agtctaagaa gtggtcaaaa    780

aaattccagt catttattga gagctgcttg gtaaagaatc acagccagcg accagcaaca    840

gaacaattga tgaagcatcc atttatacga gaccaaccta atgagcgaca ggtccgcatt    900

caactcaagg accatattga tagaacaaag aagaagcgag gagaaaaaga tgagacagag    960

tatgagtaca gtggaagtga ggaagaagag gaggagaatg actcaggaga gcccagctcc   1020

atcctgaatc tgccagggga gtcgacgctg cggagggact ttctgaggct gcagctggcc   1080

aacaaggagc gttctgaggc cctacggagg cagcagctgg agcagcagca gcgggagaat   1140

gaggagcaca agcggcagct gctggccgag cgtcagaagc gcatcgagga gcagaaagag   1200

cagaggcggc ggctggagga gcaacaaagg cgagagaagg agctgcggaa gcagcaggag   1260

agggagcagc gccggcacta tgaggagcag atgcgccggg aggaggagag gaggcgtgcg   1320

gagcatgaac aggaatataa gcgcaaacaa ttggaagaac agagacaagc agaaagactg   1380

cagaggcagc taaagcaaga aagagactac ttagtttccc ttcagcatca gcggcaggag   1440

cagaggcctg tggagaagaa gccactgtac cattacaaag aaggaatgag tcctagtgag   1500
```

-continued

```
aagccagcat gggccaagga gatcccacat ctggtagctg taaaatccca gggacctgcc   1560
ttgaccgcct cccagtcagt gcacgagcag cccacaaagg gcctctctgg gtttcaggag   1620
gctctgaacg tgacctccca ccgcgtggag atgccacgcc agaactcaga tcccacctcg   1680
gaaaatcctc ctctccccac tcgcattgaa aagtttgacc gaagctcttg gttacgacag   1740
gaagaagaca ttccaccaaa ggtgcctcaa agaacaactt ctatatcccc agcattagcc   1800
agaaagaatt ctcctgggaa tggtagtgct ctgggaccca gactaggatc tcaacccatc   1860
agagcaagca accctgatct ccggagaact gagcccatct tggagagccc cttgcagagg   1920
accagcagtg gcagttcctc cagctccagc acccctagct cccagcccag ctcccaagga   1980
ggctcccagc ctggatcaca agcaggatcc agtgaacgca ccagagttcg agccaacagt   2040
aagtcagaag gatcacctgt gcttccccat gagcctgcca aggtgaaacc agaagaatcc   2100
agggacatta cccggcccag tcgaccagct gatctgacgg cattagccaa agaactaaga   2160
gaactccgga ttgaagaaac aaaccgccca atgaagaagg tgactgatta ctcctcctcc   2220
agtgaggagt cagaaagtag cgaggaagag gaggaagatg gagagagcga gacccatgat   2280
gggacagtgg ctgtcagcga catacccaga ctgataccaa caggagctcc aggcagcaac   2340
gagcagtaca atgtgggaat ggtggggacg catgggctgg agacctctca tgcggacagt   2400
ttcagcggca gtatttcaag agaaggaacc ttgatgatta gagagacgtc tggagagaag   2460
aagcgatctg gccacagtga cagcaatggc tttgctggcc acatcaacct ccctgacctg   2520
gtgcagcaga gccattctcc agctggaacc ccgactgagg gactggggcg cgtctcaacc   2580
cattcccagg agatggactc tgggactgaa tatggcatgg ggagcagcac caaagcctcc   2640
ttcacccccct ttgtggaccc cagagtatac cagacgtctc ccactgatga agatgaagag   2700
gatgaggaat catcagccgc agctctgttt actagcgaac ttcttaggca agaacaggcc   2760
aaactcaatg aagcaagaaa gatttcggtg gtaaatgtaa acccaaccaa cattcggcct   2820
catagcgaca caccagaaat cagaaaatac aagaaacgat tcaactcaga aatactttgt   2880
gcagctctgt ggggtgtaaa ccttctggtg gggactgaaa atggcctgat gcttttggac   2940
cgaagtgggc aaggcaaagt ctataatctg atcaaccgga ggcgatttca gcagatggat   3000
gtgctagagg gactgaatgt ccttgtgaca atttcaggaa agaagaataa gctacgagtt   3060
tactatcttt catggttaag aaacagaata ctacataatg acccagaagt agaaaagaaa   3120
caaggctgga tcactgttgg ggacttggaa ggctgtatac attataaagt tgttaaatat   3180
gaaaggatca aatttttggt gattgcctta aagaatgctg tggaaatata tgcttgggct   3240
cctaaaccgt atcataaatt catggcattt aagtcttttg cagatctcca gcacaagcct   3300
ctgctagttg atctcacggt agaagaaggt caaagattaa aggttatttt tggttcacac   3360
actggtttcc atgtaattga tgttgattca ggaaactctt atgatatcta cataccatct   3420
catattcagg gcaatatcac tcctcatgct attgtcatct tgcctaaaac agatggaatg   3480
gaaatgcttg tttgctatga ggatgagggg gtgtatgtaa acacctatgg ccggataact   3540
aaggatgtgg tgctccaatg ggggagaaatg cccacgtctg tggcctacat tcattccaat   3600
cagataatgg gctggggcga gaaagctatt gagatccggt cagtggaaac aggacatttg   3660
gatggagtat ttatgcataa gcgagctcaa aggttaaagt ttctatgtga aagaaatgat   3720
aaggtatttt ttgcatccgt gcgatctgga ggaagtagcc aagtgttttt catgaccctc   3780
aacagaaatt ccatgatgaa ctggtaa                                        3807
```

-continued

<210> SEQ ID NO 9
<211> LENGTH: 1332
<212> TYPE: PRT
<213> ORGANISM: Artificial Sequence
<220> FEATURE:
<223> OTHER INFORMATION: synthetic

<400> SEQUENCE: 9

```
Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Gly Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
        115                 120                 125

Trp Ile Ala Tyr Ile Cys Arg Glu Ile Leu Arg Gly Leu Ser His Leu
    130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Phe Lys Ser Asp Leu Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Lys Lys Lys Arg Gly Glu Lys Asp Glu Thr Glu
305                 310                 315                 320

Tyr Glu Tyr Ser Gly Ser Glu Glu Glu Glu Glu Glu Asn Asp Ser Gly
                325                 330                 335

Glu Pro Ser Ser Ile Leu Asn Leu Pro Gly Glu Ser Thr Leu Arg Arg
            340                 345                 350

Asp Phe Leu Arg Leu Gln Leu Ala Asn Lys Glu Arg Ser Glu Ala Leu
        355                 360                 365

Arg Arg Gln Gln Leu Glu Gln Gln Gln Arg Glu Asn Glu Glu His Lys
```

-continued

```
    370                 375                 380

Arg Gln Leu Leu Ala Glu Arg Gln Lys Arg Ile Glu Glu Gln Lys Glu
385                 390                 395                 400

Gln Arg Arg Arg Leu Glu Glu Gln Gln Arg Arg Glu Lys Glu Leu Arg
                405                 410                 415

Lys Gln Gln Glu Arg Glu Gln Arg Arg His Tyr Glu Glu Gln Met Arg
            420                 425                 430

Arg Glu Glu Glu Arg Arg Arg Ala Glu His Glu Gln Glu Tyr Lys Arg
        435                 440                 445

Lys Gln Leu Glu Glu Gln Arg Gln Ala Glu Arg Leu Gln Arg Gln Leu
    450                 455                 460

Lys Gln Glu Arg Asp Tyr Leu Val Ser Leu Gln His Gln Arg Gln Glu
465                 470                 475                 480

Gln Arg Pro Val Glu Lys Lys Pro Leu Tyr His Tyr Lys Glu Gly Met
                485                 490                 495

Ser Pro Ser Glu Lys Pro Ala Trp Ala Lys Glu Val Glu Glu Arg Ser
            500                 505                 510

Arg Leu Asn Arg Gln Ser Ser Pro Ala Met Pro His Lys Val Ala Asn
        515                 520                 525

Arg Ile Ser Asp Pro Asn Leu Pro Pro Arg Ser Glu Ser Phe Ser Ile
    530                 535                 540

Ser Gly Val Gln Pro Ala Arg Thr Pro Pro Met Leu Arg Pro Val Asp
545                 550                 555                 560

Pro Gln Ile Pro His Leu Val Ala Val Lys Ser Gln Gly Pro Ala Leu
                565                 570                 575

Thr Ala Ser Gln Ser Val His Glu Gln Pro Thr Lys Gly Leu Ser Gly
            580                 585                 590

Phe Gln Glu Ala Leu Asn Val Thr Ser His Arg Val Glu Met Pro Arg
        595                 600                 605

Gln Asn Ser Asp Pro Thr Ser Glu Asn Pro Pro Leu Pro Thr Arg Ile
    610                 615                 620

Glu Lys Phe Asp Arg Ser Ser Trp Leu Arg Gln Glu Glu Asp Ile Pro
625                 630                 635                 640

Pro Lys Val Pro Gln Arg Thr Thr Ser Ile Ser Pro Ala Leu Ala Arg
                645                 650                 655

Lys Asn Ser Pro Gly Asn Gly Ser Ala Leu Gly Pro Arg Leu Gly Ser
            660                 665                 670

Gln Pro Ile Arg Ala Ser Asn Pro Asp Leu Arg Arg Thr Glu Pro Ile
        675                 680                 685

Leu Glu Ser Pro Leu Gln Arg Thr Ser Ser Gly Ser Ser Ser Ser Ser
    690                 695                 700

Ser Thr Pro Ser Ser Gln Pro Ser Ser Gln Gly Gly Ser Gln Pro Gly
705                 710                 715                 720

Ser Gln Ala Gly Ser Ser Glu Arg Thr Arg Val Arg Ala Asn Ser Lys
                725                 730                 735

Ser Glu Gly Ser Pro Val Leu Pro His Glu Pro Ala Lys Val Lys Pro
            740                 745                 750

Glu Glu Ser Arg Asp Ile Thr Arg Pro Ser Arg Pro Ala Ser Tyr Lys
        755                 760                 765

Lys Ala Ile Asp Glu Asp Leu Thr Ala Leu Ala Lys Glu Leu Arg Glu
    770                 775                 780

Leu Arg Ile Glu Glu Thr Asn Arg Pro Met Lys Lys Val Thr Asp Tyr
785                 790                 795                 800
```

```
Ser Ser Ser Ser Glu Glu Ser Glu Ser Ser Glu Glu Glu Glu Glu Asp
                805                 810                 815

Gly Glu Ser Glu Thr His Asp Gly Thr Val Ala Val Ser Asp Ile Pro
            820                 825                 830

Arg Leu Ile Pro Thr Gly Ala Pro Gly Ser Asn Glu Gln Tyr Asn Val
        835                 840                 845

Gly Met Val Gly Thr His Gly Leu Glu Thr Ser His Ala Asp Ser Phe
    850                 855                 860

Ser Gly Ser Ile Ser Arg Glu Gly Thr Leu Met Ile Arg Glu Thr Ser
865                 870                 875                 880

Gly Glu Lys Lys Arg Ser Gly His Ser Asp Ser Asn Gly Phe Ala Gly
                885                 890                 895

His Ile Asn Leu Pro Asp Leu Val Gln Gln Ser His Ser Pro Ala Gly
            900                 905                 910

Thr Pro Thr Glu Gly Leu Gly Arg Val Ser Thr His Ser Gln Glu Met
        915                 920                 925

Asp Ser Gly Thr Glu Tyr Gly Met Gly Ser Ser Thr Lys Ala Ser Phe
    930                 935                 940

Thr Pro Phe Val Asp Pro Arg Val Tyr Gln Thr Ser Pro Thr Asp Glu
945                 950                 955                 960

Asp Glu Glu Asp Glu Glu Ser Ser Ala Ala Ala Leu Phe Thr Ser Glu
                965                 970                 975

Leu Leu Arg Gln Glu Gln Ala Lys Leu Asn Glu Ala Arg Lys Ile Ser
            980                 985                 990

Val Val Asn Val Asn Pro Thr Asn  Ile Arg Pro His Ser  Asp Thr Pro
        995                 1000                1005

Glu Ile  Arg Lys Tyr Lys Lys  Arg Phe Asn Ser Glu  Ile Leu Cys
    1010                1015                1020

Ala Ala  Leu Trp Gly Val Asn  Leu Leu Val Gly Thr  Glu Asn Gly
    1025                1030                1035

Leu Met  Leu Leu Asp Arg Ser  Gly Gln Gly Lys Val  Tyr Asn Leu
    1040                1045                1050

Ile Asn  Arg Arg Arg Phe Gln  Gln Met Asp Val Leu  Glu Gly Leu
    1055                1060                1065

Asn Val  Leu Val Thr Ile Ser  Gly Lys Lys Asn Lys  Leu Arg Val
    1070                1075                1080

Tyr Tyr  Leu Ser Trp Leu Arg  Asn Arg Ile Leu His  Asn Asp Pro
    1085                1090                1095

Glu Val  Glu Lys Lys Gln Gly  Trp Ile Thr Val Gly  Asp Leu Glu
    1100                1105                1110

Gly Cys  Ile His Tyr Lys Val  Val Lys Tyr Glu Arg  Ile Lys Phe
    1115                1120                1125

Leu Val  Ile Ala Leu Lys Asn  Ala Val Glu Ile Tyr  Ala Trp Ala
    1130                1135                1140

Pro Lys  Pro Tyr His Lys Phe  Met Ala Phe Lys Ser  Phe Ala Asp
    1145                1150                1155

Leu Gln  His Lys Pro Leu Leu  Val Asp Leu Thr Val  Glu Glu Gly
    1160                1165                1170

Gln Arg  Leu Lys Val Ile Phe  Gly Ser His Thr Gly  Phe His Val
    1175                1180                1185

Ile Asp  Val Asp Ser Gly Asn  Ser Tyr Asp Ile Tyr  Ile Pro Ser
    1190                1195                1200
```

His Ile Gln Gly Asn Ile Thr Pro His Ala Ile Val Ile Leu Pro
1205 1210 1215

Lys Thr Asp Gly Met Glu Met Leu Val Cys Tyr Glu Asp Glu Gly
1220 1225 1230

Val Tyr Val Asn Thr Tyr Gly Arg Ile Thr Lys Asp Val Val Leu
1235 1240 1245

Gln Trp Gly Glu Met Pro Thr Ser Val Ala Tyr Ile His Ser Asn
1250 1255 1260

Gln Ile Met Gly Trp Gly Glu Lys Ala Ile Glu Ile Arg Ser Val
1265 1270 1275

Glu Thr Gly His Leu Asp Gly Val Phe Met His Lys Arg Ala Gln
1280 1285 1290

Arg Leu Lys Phe Leu Cys Glu Arg Asn Asp Lys Val Phe Phe Ala
1295 1300 1305

Ser Val Arg Ser Gly Gly Ser Ser Gln Val Phe Phe Met Thr Leu
1310 1315 1320

Asn Arg Asn Ser Met Met Asn Trp Glx
1325 1330

<210> SEQ ID NO 10
<211> LENGTH: 1306
<212> TYPE: PRT
<213> ORGANISM: Artificial Sequence
<220> FEATURE:
<223> OTHER INFORMATION: synthetic

<400> SEQUENCE: 10

Met Ala Ser Asp Ser Pro Ala Arg Ser Leu Asp Glu Ile Asp Leu Ser
1 5 10 15

Ala Leu Arg Asp Pro Ala Gly Ile Phe Glu Leu Val Glu Leu Val Gly
20 25 30

Asn Gly Thr Tyr Gly Gln Val Tyr Lys Gly Arg His Val Lys Thr Gly
35 40 45

Gln Leu Ala Ala Ile Lys Val Met Asp Val Thr Gly Asp Glu Glu Glu
50 55 60

Glu Ile Lys Gln Glu Ile Asn Met Leu Lys Lys Tyr Ser His His Arg
65 70 75 80

Asn Ile Ala Thr Tyr Tyr Gly Ala Phe Ile Lys Lys Asn Pro Pro Gly
85 90 95

Met Asp Asp Gln Leu Trp Leu Val Met Glu Phe Cys Gly Ala Gly Ser
100 105 110

Val Thr Asp Leu Ile Lys Asn Thr Lys Gly Asn Thr Leu Lys Glu Glu
115 120 125

Trp Ile Ala Tyr Ile Cys Arg Glu Ile Leu Arg Gly Leu Ser His Leu
130 135 140

His Gln His Lys Val Ile His Arg Asp Ile Lys Gly Gln Asn Val Leu
145 150 155 160

Leu Thr Glu Asn Ala Glu Val Lys Leu Val Asp Phe Gly Val Ser Ala
165 170 175

Gln Leu Asp Arg Thr Val Gly Arg Arg Asn Thr Phe Ile Gly Thr Pro
180 185 190

Tyr Trp Met Ala Pro Glu Val Ile Ala Cys Asp Glu Asn Pro Asp Ala
195 200 205

Thr Tyr Asp Phe Lys Ser Asp Leu Trp Ser Leu Gly Ile Thr Ala Ile
210 215 220

-continued

```
Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Lys Lys Lys Arg Gly Glu Lys Asp Glu Thr Glu
305                 310                 315                 320

Tyr Glu Tyr Ser Gly Ser Glu Glu Glu Glu Glu Glu Asn Asp Ser Gly
                325                 330                 335

Glu Pro Ser Ser Ile Leu Asn Leu Pro Gly Glu Ser Thr Leu Arg Arg
            340                 345                 350

Asp Phe Leu Arg Leu Gln Leu Ala Asn Lys Glu Arg Ser Glu Ala Leu
        355                 360                 365

Arg Arg Gln Gln Leu Glu Gln Gln Gln Arg Glu Asn Glu Glu His Lys
    370                 375                 380

Arg Gln Leu Leu Ala Glu Arg Gln Lys Arg Ile Glu Glu Gln Lys Glu
385                 390                 395                 400

Gln Arg Arg Arg Leu Glu Glu Gln Gln Arg Arg Glu Lys Glu Leu Arg
                405                 410                 415

Lys Gln Gln Glu Arg Glu Gln Arg Arg His Tyr Glu Glu Gln Met Arg
            420                 425                 430

Arg Glu Glu Glu Arg Arg Arg Ala Glu His Glu Gln Glu Tyr Ile Arg
        435                 440                 445

Arg Gln Leu Glu Glu Glu Gln Arg Gln Leu Glu Ile Leu Gln Gln Gln
    450                 455                 460

Leu Leu His Glu Gln Ala Leu Leu Leu Glu Tyr Lys Arg Lys Gln Leu
465                 470                 475                 480

Glu Glu Gln Arg Gln Ala Glu Arg Leu Gln Arg Gln Leu Lys Gln Glu
                485                 490                 495

Arg Asp Tyr Leu Val Ser Leu Gln His Gln Arg Gln Glu Gln Arg Pro
            500                 505                 510

Val Glu Lys Lys Pro Leu Tyr His Tyr Lys Glu Gly Met Ser Pro Ser
        515                 520                 525

Glu Lys Pro Ala Trp Ala Lys Glu Ile Pro His Leu Val Ala Val Lys
    530                 535                 540

Ser Gln Gly Pro Ala Leu Thr Ala Ser Gln Ser Val His Glu Gln Pro
545                 550                 555                 560

Thr Lys Gly Leu Ser Gly Phe Gln Glu Ala Leu Asn Val Thr Ser His
                565                 570                 575

Arg Val Glu Met Pro Arg Gln Asn Ser Asp Pro Thr Ser Glu Asn Pro
            580                 585                 590

Pro Leu Pro Thr Arg Ile Glu Lys Phe Asp Arg Ser Ser Trp Leu Arg
        595                 600                 605

Gln Glu Glu Asp Ile Pro Pro Lys Val Pro Gln Arg Thr Thr Ser Ile
    610                 615                 620

Ser Pro Ala Leu Ala Arg Lys Asn Ser Pro Gly Asn Gly Ser Ala Leu
625                 630                 635                 640

Gly Pro Arg Leu Gly Ser Gln Pro Ile Arg Ala Ser Asn Pro Asp Leu
```

-continued

```
                645                 650                 655

Arg Arg Thr Glu Pro Ile Leu Glu Ser Pro Leu Gln Arg Thr Ser Ser
            660                 665                 670

Gly Ser Ser Ser Ser Ser Ser Thr Pro Ser Ser Gln Pro Ser Ser Gln
        675                 680                 685

Gly Gly Ser Gln Pro Gly Ser Gln Ala Gly Ser Ser Glu Arg Thr Arg
    690                 695                 700

Val Arg Ala Asn Ser Lys Ser Glu Gly Ser Pro Val Leu Pro His Glu
705                 710                 715                 720

Pro Ala Lys Val Lys Pro Glu Glu Ser Arg Asp Ile Thr Arg Pro Ser
                725                 730                 735

Arg Pro Ala Ser Tyr Lys Lys Ala Ile Asp Glu Asp Leu Thr Ala Leu
            740                 745                 750

Ala Lys Glu Leu Arg Glu Leu Arg Ile Glu Glu Thr Asn Arg Pro Met
        755                 760                 765

Lys Lys Val Thr Asp Tyr Ser Ser Ser Ser Glu Glu Ser Glu Ser Ser
    770                 775                 780

Glu Glu Glu Glu Glu Asp Gly Glu Ser Glu Thr His Asp Gly Thr Val
785                 790                 795                 800

Ala Val Ser Asp Ile Pro Arg Leu Ile Pro Thr Gly Ala Pro Gly Ser
                805                 810                 815

Asn Glu Gln Tyr Asn Val Gly Met Val Gly Thr His Gly Leu Glu Thr
            820                 825                 830

Ser His Ala Asp Ser Phe Ser Gly Ser Ile Ser Arg Glu Gly Thr Leu
        835                 840                 845

Met Ile Arg Glu Thr Ser Gly Glu Lys Lys Arg Ser Gly His Ser Asp
    850                 855                 860

Ser Asn Gly Phe Ala Gly His Ile Asn Leu Pro Asp Leu Val Gln Gln
865                 870                 875                 880

Ser His Ser Pro Ala Gly Thr Pro Thr Glu Gly Leu Gly Arg Val Ser
                885                 890                 895

Thr His Ser Gln Glu Met Asp Ser Gly Thr Glu Tyr Gly Met Gly Ser
            900                 905                 910

Ser Thr Lys Ala Ser Phe Thr Pro Phe Val Asp Pro Arg Val Tyr Gln
        915                 920                 925

Thr Ser Pro Thr Asp Glu Asp Glu Glu Asp Glu Glu Ser Ser Ala Ala
    930                 935                 940

Ala Leu Phe Thr Ser Glu Leu Leu Arg Gln Glu Gln Ala Lys Leu Asn
945                 950                 955                 960

Glu Ala Arg Lys Ile Ser Val Val Asn Val Asn Pro Thr Asn Ile Arg
                965                 970                 975

Pro His Ser Asp Thr Pro Glu Ile Arg Lys Tyr Lys Lys Arg Phe Asn
            980                 985                 990

Ser Glu Ile Leu Cys Ala Ala Leu  Trp Gly Val Asn Leu  Leu Val Gly
        995                 1000                1005

Thr Glu  Asn Gly Leu Met Leu  Leu Asp Arg Ser Gly  Gln Gly Lys
    1010                1015                1020

Val Tyr  Asn Leu Ile Asn Arg  Arg Arg Phe Gln Gln  Met Asp Val
    1025                1030                1035

Leu Glu  Gly Leu Asn Val Leu  Val Thr Ile Ser Gly  Lys Lys Asn
    1040                1045                1050

Lys Leu  Arg Val Tyr Tyr Leu  Ser Trp Leu Arg Asn  Arg Ile Leu
    1055                1060                1065
```

```
His Asn  Asp Pro Glu Val Glu  Lys Lys Gln Gly Trp  Ile Thr Val
    1070                 1075                 1080

Gly Asp  Leu Glu Gly Cys Ile  His Tyr Lys Val Val  Lys Tyr Glu
    1085                 1090                 1095

Arg Ile  Lys Phe Leu Val Ile  Ala Leu Lys Asn Ala  Val Glu Ile
    1100                 1105                 1110

Tyr Ala  Trp Ala Pro Lys Pro  Tyr His Lys Phe Met  Ala Phe Lys
    1115                 1120                 1125

Ser Phe  Ala Asp Leu Gln His  Lys Pro Leu Leu Val  Asp Leu Thr
    1130                 1135                 1140

Val Glu  Glu Gly Gln Arg Leu  Lys Val Ile Phe Gly  Ser His Thr
    1145                 1150                 1155

Gly Phe  His Val Ile Asp Val  Asp Ser Gly Asn Ser  Tyr Asp Ile
    1160                 1165                 1170

Tyr Ile  Pro Ser His Ile Gln  Gly Asn Ile Thr Pro  His Ala Ile
    1175                 1180                 1185

Val Ile  Leu Pro Lys Thr Asp  Gly Met Glu Met Leu  Val Cys Tyr
    1190                 1195                 1200

Glu Asp  Glu Gly Val Tyr Val  Asn Thr Tyr Gly Arg  Ile Thr Lys
    1205                 1210                 1215

Asp Val  Val Leu Gln Trp Gly  Glu Met Pro Thr Ser  Val Ala Tyr
    1220                 1225                 1230

Ile His  Ser Asn Gln Ile Met  Gly Trp Gly Glu Lys  Ala Ile Glu
    1235                 1240                 1245

Ile Arg  Ser Val Glu Thr Gly  His Leu Asp Gly Val  Phe Met His
    1250                 1255                 1260

Lys Arg  Ala Gln Arg Leu Lys  Phe Leu Cys Glu Arg  Asn Asp Lys
    1265                 1270                 1275

Val Phe  Phe Ala Ser Val Arg  Ser Gly Gly Ser Ser  Gln Val Phe
    1280                 1285                 1290

Phe Met  Thr Leu Asn Arg Asn  Ser Met Met Asn Trp  Glx
    1295                 1300                 1305


<210> SEQ ID NO 11
<211> LENGTH: 1353
<212> TYPE: PRT
<213> ORGANISM: Artificial Sequence
<220> FEATURE:
<223> OTHER INFORMATION: synthetic

<400> SEQUENCE: 11

Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Gly Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
            100                 105                 110
```

-continued

```
Val Thr Asp Leu Ile Lys Asn Thr Lys Gly Asn Thr Leu Lys Glu Glu
        115                 120                 125

Trp Ile Ala Tyr Ile Cys Arg Glu Ile Leu Arg Gly Leu Ser His Leu
    130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Phe Lys Ser Asp Leu Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Lys Lys Lys Arg Gly Glu Lys Asp Glu Thr Glu
305                 310                 315                 320

Tyr Glu Tyr Ser Gly Ser Glu Glu Glu Glu Glu Glu Asn Asp Ser Gly
                325                 330                 335

Glu Pro Ser Ser Ile Leu Asn Leu Pro Gly Glu Ser Thr Leu Arg Arg
            340                 345                 350

Asp Phe Leu Arg Leu Gln Leu Ala Asn Lys Glu Arg Ser Glu Ala Leu
        355                 360                 365

Arg Arg Gln Gln Leu Glu Gln Gln Gln Arg Glu Asn Glu Glu His Lys
    370                 375                 380

Arg Gln Leu Leu Ala Glu Arg Gln Lys Arg Ile Glu Glu Gln Lys Glu
385                 390                 395                 400

Gln Arg Arg Arg Leu Glu Glu Gln Gln Arg Arg Glu Lys Glu Leu Arg
                405                 410                 415

Lys Gln Gln Glu Arg Glu Gln Arg Arg His Tyr Glu Glu Gln Met Arg
            420                 425                 430

Arg Glu Glu Glu Arg Arg Arg Ala Glu His Glu Gln Glu Tyr Ile Arg
        435                 440                 445

Arg Gln Leu Glu Glu Glu Gln Arg Gln Leu Glu Ile Leu Gln Gln Gln
    450                 455                 460

Leu Leu His Glu Gln Ala Leu Leu Leu Glu Tyr Lys Arg Lys Gln Leu
465                 470                 475                 480

Glu Glu Gln Arg Gln Ala Glu Arg Leu Gln Arg Gln Leu Lys Gln Glu
                485                 490                 495

Arg Asp Tyr Leu Val Ser Leu Gln His Gln Arg Gln Glu Gln Arg Pro
            500                 505                 510

Val Glu Lys Lys Pro Leu Tyr His Tyr Lys Glu Gly Met Ser Pro Ser
        515                 520                 525
```

-continued

```
Glu Lys Pro Ala Trp Ala Lys Glu Val Glu Glu Arg Ser Arg Leu Asn
    530                 535                 540

Arg Gln Ser Ser Pro Ala Met Pro His Lys Val Ala Asn Arg Ile Ser
545                 550                 555                 560

Asp Pro Asn Leu Pro Pro Arg Ser Glu Ser Phe Ser Ile Ser Gly Val
                565                 570                 575

Gln Pro Ala Arg Thr Pro Pro Met Leu Arg Pro Val Asp Pro Gln Ile
            580                 585                 590

Pro His Leu Val Ala Val Lys Ser Gln Gly Pro Ala Leu Thr Ala Ser
        595                 600                 605

Gln Ser Val His Glu Gln Pro Thr Lys Gly Leu Ser Gly Phe Gln Glu
    610                 615                 620

Ala Leu Asn Val Thr Ser His Arg Val Glu Met Pro Arg Gln Asn Ser
625                 630                 635                 640

Asp Pro Thr Ser Glu Asn Pro Pro Leu Pro Thr Arg Ile Glu Lys Phe
                645                 650                 655

Asp Arg Ser Ser Trp Leu Arg Gln Glu Glu Asp Ile Pro Pro Lys Val
            660                 665                 670

Pro Gln Arg Thr Thr Ser Ile Ser Pro Ala Leu Ala Arg Lys Asn Ser
        675                 680                 685

Pro Gly Asn Gly Ser Ala Leu Gly Pro Arg Leu Gly Ser Gln Pro Ile
    690                 695                 700

Arg Ala Ser Asn Pro Asp Leu Arg Arg Thr Glu Pro Ile Leu Glu Ser
705                 710                 715                 720

Pro Leu Gln Arg Thr Ser Ser Gly Ser Ser Ser Ser Ser Thr Pro
                725                 730                 735

Ser Ser Gln Pro Ser Ser Gln Gly Gly Ser Gln Pro Gly Ser Gln Ala
            740                 745                 750

Gly Ser Ser Glu Arg Thr Arg Val Arg Ala Asn Ser Lys Ser Glu Gly
        755                 760                 765

Ser Pro Val Leu Pro His Glu Pro Ala Lys Val Lys Pro Glu Glu Ser
    770                 775                 780

Arg Asp Ile Thr Arg Pro Ser Arg Pro Ala Asp Leu Thr Ala Leu Ala
785                 790                 795                 800

Lys Glu Leu Arg Glu Leu Arg Ile Glu Glu Thr Asn Arg Pro Met Lys
                805                 810                 815

Lys Val Thr Asp Tyr Ser Ser Ser Ser Glu Glu Ser Glu Ser Ser Glu
            820                 825                 830

Glu Glu Glu Glu Asp Gly Glu Ser Glu Thr His Asp Gly Thr Val Ala
        835                 840                 845

Val Ser Asp Ile Pro Arg Leu Ile Pro Thr Gly Ala Pro Gly Ser Asn
    850                 855                 860

Glu Gln Tyr Asn Val Gly Met Val Gly Thr His Gly Leu Glu Thr Ser
865                 870                 875                 880

His Ala Asp Ser Phe Ser Gly Ser Ile Ser Arg Glu Gly Thr Leu Met
                885                 890                 895

Ile Arg Glu Thr Ser Gly Glu Lys Lys Arg Ser Gly His Ser Asp Ser
            900                 905                 910

Asn Gly Phe Ala Gly His Ile Asn Leu Pro Asp Leu Val Gln Gln Ser
        915                 920                 925

His Ser Pro Ala Gly Thr Pro Thr Glu Gly Leu Gly Arg Val Ser Thr
    930                 935                 940

His Ser Gln Glu Met Asp Ser Gly Thr Glu Tyr Gly Met Gly Ser Ser
```

-continued

```
945                 950                 955                 960

Thr Lys Ala Ser Phe Thr Pro Phe Val Asp Pro Arg Val Tyr Gln Thr
                965                 970                 975

Ser Pro Thr Asp Glu Asp Glu Glu Asp Glu Glu Ser Ser Ala Ala Ala
            980                 985                 990

Leu Phe Thr Ser Glu Leu Leu Arg  Gln Glu Gln Ala Lys  Leu Asn Glu
        995                 1000                1005

Ala Arg  Lys Ile Ser Val Val  Asn Val Asn Pro Thr  Asn Ile Arg
    1010                 1015                 1020

Pro His  Ser Asp Thr Pro Glu  Ile Arg Lys Tyr Lys  Lys Arg Phe
    1025                 1030                 1035

Asn Ser  Glu Ile Leu Cys Ala  Ala Leu Trp Gly Val  Asn Leu Leu
    1040                 1045                 1050

Val Gly  Thr Glu Asn Gly Leu  Met Leu Leu Asp Arg  Ser Gly Gln
    1055                 1060                 1065

Gly Lys  Val Tyr Asn Leu Ile  Asn Arg Arg Arg Phe  Gln Gln Met
    1070                 1075                 1080

Asp Val  Leu Glu Gly Leu Asn  Val Leu Val Thr Ile  Ser Gly Lys
    1085                 1090                 1095

Lys Asn  Lys Leu Arg Val Tyr  Tyr Leu Ser Trp Leu  Arg Asn Arg
    1100                 1105                 1110

Ile Leu  His Asn Asp Pro Glu  Val Glu Lys Lys Gln  Gly Trp Ile
    1115                 1120                 1125

Thr Val  Gly Asp Leu Glu Gly  Cys Ile His Tyr Lys  Val Val Lys
    1130                 1135                 1140

Tyr Glu  Arg Ile Lys Phe Leu  Val Ile Ala Leu Lys  Asn Ala Val
    1145                 1150                 1155

Glu Ile  Tyr Ala Trp Ala Pro  Lys Pro Tyr His Lys  Phe Met Ala
    1160                 1165                 1170

Phe Lys  Ser Phe Ala Asp Leu  Gln His Lys Pro Leu  Leu Val Asp
    1175                 1180                 1185

Leu Thr  Val Glu Glu Gly Gln  Arg Leu Lys Val Ile  Phe Gly Ser
    1190                 1195                 1200

His Thr  Gly Phe His Val Ile  Asp Val Asp Ser Gly  Asn Ser Tyr
    1205                 1210                 1215

Asp Ile  Tyr Ile Pro Ser His  Ile Gln Gly Asn Ile  Thr Pro His
    1220                 1225                 1230

Ala Ile  Val Ile Leu Pro Lys  Thr Asp Gly Met Glu  Met Leu Val
    1235                 1240                 1245

Cys Tyr  Glu Asp Glu Gly Val  Tyr Val Asn Thr Tyr  Gly Arg Ile
    1250                 1255                 1260

Thr Lys  Asp Val Val Leu Gln  Trp Gly Glu Met Pro  Thr Ser Val
    1265                 1270                 1275

Ala Tyr  Ile His Ser Asn Gln  Ile Met Gly Trp Gly  Glu Lys Ala
    1280                 1285                 1290

Ile Glu  Ile Arg Ser Val Glu  Thr Gly His Leu Asp  Gly Val Phe
    1295                 1300                 1305

Met His  Lys Arg Ala Gln Arg  Leu Lys Phe Leu Cys  Glu Arg Asn
    1310                 1315                 1320

Asp Lys  Val Phe Phe Ala Ser  Val Arg Ser Gly Gly  Ser Ser Gln
    1325                 1330                 1335

Val Phe  Phe Met Thr Leu Asn  Arg Asn Ser Met Met  Asn Trp Glx
    1340                 1345                 1350
```

```
<210> SEQ ID NO 12
<211> LENGTH: 1277
<212> TYPE: PRT
<213> ORGANISM: Artificial Sequence
<220> FEATURE:
<223> OTHER INFORMATION: synthetic

<400> SEQUENCE: 12

Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Gly Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
        115                 120                 125

Trp Ile Ala Tyr Ile Cys Arg Glu Ile Leu Arg Gly Leu Ser His Leu
    130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Phe Lys Ser Asp Leu Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Lys Lys Lys Arg Gly Glu Lys Asp Glu Thr Glu
305                 310                 315                 320

Tyr Glu Tyr Ser Gly Ser Glu Glu Glu Glu Glu Glu Asn Asp Ser Gly
                325                 330                 335

Glu Pro Ser Ser Ile Leu Asn Leu Pro Gly Glu Ser Thr Leu Arg Arg
            340                 345                 350

Asp Phe Leu Arg Leu Gln Leu Ala Asn Lys Glu Arg Ser Glu Ala Leu
        355                 360                 365
```

```
Arg Arg Gln Gln Leu Glu Gln Gln Gln Arg Glu Asn Glu Glu His Lys
    370                 375                 380

Arg Gln Leu Leu Ala Glu Arg Gln Lys Arg Ile Glu Glu Gln Lys Glu
385                 390                 395                 400

Gln Arg Arg Arg Leu Glu Glu Gln Gln Arg Arg Glu Lys Glu Leu Arg
                405                 410                 415

Lys Gln Gln Glu Arg Glu Gln Arg Arg His Tyr Glu Glu Gln Met Arg
            420                 425                 430

Arg Glu Glu Glu Arg Arg Arg Ala Glu His Glu Gln Glu Tyr Lys Arg
        435                 440                 445

Lys Gln Leu Glu Glu Gln Arg Gln Ala Glu Arg Leu Gln Arg Gln Leu
    450                 455                 460

Lys Gln Glu Arg Asp Tyr Leu Val Ser Leu Gln His Gln Arg Gln Glu
465                 470                 475                 480

Gln Arg Pro Val Glu Lys Lys Pro Leu Tyr His Tyr Lys Glu Gly Met
                485                 490                 495

Ser Pro Ser Glu Lys Pro Ala Trp Ala Lys Glu Ile Pro His Leu Val
            500                 505                 510

Ala Val Lys Ser Gln Gly Pro Ala Leu Thr Ala Ser Gln Ser Val His
        515                 520                 525

Glu Gln Pro Thr Lys Gly Leu Ser Gly Phe Gln Glu Ala Leu Asn Val
    530                 535                 540

Thr Ser His Arg Val Glu Met Pro Arg Gln Asn Ser Asp Pro Thr Ser
545                 550                 555                 560

Glu Asn Pro Pro Leu Pro Thr Arg Ile Glu Lys Phe Asp Arg Ser Ser
                565                 570                 575

Trp Leu Arg Gln Glu Glu Asp Ile Pro Pro Lys Val Pro Gln Arg Thr
            580                 585                 590

Thr Ser Ile Ser Pro Ala Leu Ala Arg Lys Asn Ser Pro Gly Asn Gly
        595                 600                 605

Ser Ala Leu Gly Pro Arg Leu Gly Ser Gln Pro Ile Arg Ala Ser Asn
    610                 615                 620

Pro Asp Leu Arg Arg Thr Glu Pro Ile Leu Glu Ser Pro Leu Gln Arg
625                 630                 635                 640

Thr Ser Ser Gly Ser Ser Ser Ser Ser Ser Thr Pro Ser Ser Gln Pro
                645                 650                 655

Ser Ser Gln Gly Gly Ser Gln Pro Gly Ser Gln Ala Gly Ser Ser Glu
            660                 665                 670

Arg Thr Arg Val Arg Ala Asn Ser Lys Ser Glu Gly Ser Pro Val Leu
        675                 680                 685

Pro His Glu Pro Ala Lys Val Lys Pro Glu Glu Ser Arg Asp Ile Thr
    690                 695                 700

Arg Pro Ser Arg Pro Ala Ser Tyr Lys Lys Ala Ile Asp Glu Asp Leu
705                 710                 715                 720

Thr Ala Leu Ala Lys Glu Leu Arg Glu Leu Arg Ile Glu Glu Thr Asn
                725                 730                 735

Arg Pro Met Lys Lys Val Thr Asp Tyr Ser Ser Ser Ser Glu Glu Ser
            740                 745                 750

Glu Ser Ser Glu Glu Glu Glu Glu Asp Gly Glu Ser Glu Thr His Asp
        755                 760                 765

Gly Thr Val Ala Val Ser Asp Ile Pro Arg Leu Ile Pro Thr Gly Ala
    770                 775                 780
```

-continued

```
Pro Gly Ser Asn Glu Gln Tyr Asn Val Gly Met Val Gly Thr His Gly
785                 790                 795                 800

Leu Glu Thr Ser His Ala Asp Ser Phe Ser Gly Ser Ile Ser Arg Glu
                805                 810                 815

Gly Thr Leu Met Ile Arg Glu Thr Ser Gly Glu Lys Lys Arg Ser Gly
            820                 825                 830

His Ser Asp Ser Asn Gly Phe Ala Gly His Ile Asn Leu Pro Asp Leu
        835                 840                 845

Val Gln Gln Ser His Ser Pro Ala Gly Thr Pro Thr Glu Gly Leu Gly
    850                 855                 860

Arg Val Ser Thr His Ser Gln Glu Met Asp Ser Gly Thr Glu Tyr Gly
865                 870                 875                 880

Met Gly Ser Ser Thr Lys Ala Ser Phe Thr Pro Phe Val Asp Pro Arg
                885                 890                 895

Val Tyr Gln Thr Ser Pro Thr Asp Glu Asp Glu Glu Asp Glu Glu Ser
            900                 905                 910

Ser Ala Ala Ala Leu Phe Thr Ser Glu Leu Leu Arg Gln Glu Gln Ala
        915                 920                 925

Lys Leu Asn Glu Ala Arg Lys Ile Ser Val Val Asn Val Asn Pro Thr
    930                 935                 940

Asn Ile Arg Pro His Ser Asp Thr Pro Glu Ile Arg Lys Tyr Lys Lys
945                 950                 955                 960

Arg Phe Asn Ser Glu Ile Leu Cys Ala Ala Leu Trp Gly Val Asn Leu
                965                 970                 975

Leu Val Gly Thr Glu Asn Gly Leu Met Leu Leu Asp Arg Ser Gly Gln
            980                 985                 990

Gly Lys Val Tyr Asn Leu Ile Asn  Arg Arg Arg Phe Gln  Gln Met Asp
        995                 1000                1005

Val Leu  Glu Gly Leu Asn Val  Leu Val Thr Ile Ser  Gly Lys Lys
    1010                1015                1020

Asn Lys  Leu Arg Val Tyr Tyr  Leu Ser Trp Leu Arg  Asn Arg Ile
    1025                1030                1035

Leu His  Asn Asp Pro Glu Val  Glu Lys Lys Gln Gly  Trp Ile Thr
    1040                1045                1050

Val Gly  Asp Leu Glu Gly Cys  Ile His Tyr Lys Val  Val Lys Tyr
    1055                1060                1065

Glu Arg  Ile Lys Phe Leu Val  Ile Ala Leu Lys Asn  Ala Val Glu
    1070                1075                1080

Ile Tyr  Ala Trp Ala Pro Lys  Pro Tyr His Lys Phe  Met Ala Phe
    1085                1090                1095

Lys Ser  Phe Ala Asp Leu Gln  His Lys Pro Leu Leu  Val Asp Leu
    1100                1105                1110

Thr Val  Glu Glu Gly Gln Arg  Leu Lys Val Ile Phe  Gly Ser His
    1115                1120                1125

Thr Gly  Phe His Val Ile Asp  Val Asp Ser Gly Asn  Ser Tyr Asp
    1130                1135                1140

Ile Tyr  Ile Pro Ser His Ile  Gln Gly Asn Ile Thr  Pro His Ala
    1145                1150                1155

Ile Val  Ile Leu Pro Lys Thr  Asp Gly Met Glu Met  Leu Val Cys
    1160                1165                1170

Tyr Glu  Asp Glu Gly Val Tyr  Val Asn Thr Tyr Gly  Arg Ile Thr
    1175                1180                1185

Lys Asp  Val Val Leu Gln Trp  Gly Glu Met Pro Thr  Ser Val Ala
```

-continued

```
    1190                1195                1200

Tyr Ile  His Ser Asn Gln Ile  Met Gly Trp Gly Glu  Lys Ala Ile
    1205                1210                1215

Glu Ile  Arg Ser Val Glu Thr  Gly His Leu Asp Gly  Val Phe Met
    1220                1225                1230

His Lys  Arg Ala Gln Arg Leu  Lys Phe Leu Cys Glu  Arg Asn Asp
    1235                1240                1245

Lys Val  Phe Phe Ala Ser Val  Arg Ser Gly Gly Ser  Ser Gln Val
    1250                1255                1260

Phe Phe  Met Thr Leu Asn Arg  Asn Ser Met Met Asn  Trp Glx
    1265                1270                1275


<210> SEQ ID NO 13
<211> LENGTH: 1324
<212> TYPE: PRT
<213> ORGANISM: Artificial Sequence
<220> FEATURE:
<223> OTHER INFORMATION: synthetic

<400> SEQUENCE: 13

Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Gly Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
        115                 120                 125

Trp Ile Ala Tyr Ile Cys Arg Glu Ile Leu Arg Gly Leu Ser His Leu
    130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Phe Lys Ser Asp Leu Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
```

```
        275                 280                 285

Ile Arg Asp Gln Pro Asn Glu Arg Gln Val Arg Ile Gln Leu Lys Asp
    290                 295                 300

His Ile Asp Arg Thr Lys Lys Lys Arg Gly Glu Lys Asp Glu Thr Glu
305                 310                 315                 320

Tyr Glu Tyr Ser Gly Ser Glu Glu Glu Glu Glu Glu Asn Asp Ser Gly
                325                 330                 335

Glu Pro Ser Ser Ile Leu Asn Leu Pro Gly Glu Ser Thr Leu Arg Arg
            340                 345                 350

Asp Phe Leu Arg Leu Gln Leu Ala Asn Lys Glu Arg Ser Glu Ala Leu
        355                 360                 365

Arg Arg Gln Gln Leu Glu Gln Gln Gln Arg Glu Asn Glu Glu His Lys
    370                 375                 380

Arg Gln Leu Leu Ala Glu Arg Gln Lys Arg Ile Glu Glu Gln Lys Glu
385                 390                 395                 400

Gln Arg Arg Arg Leu Glu Glu Gln Gln Arg Arg Glu Lys Glu Leu Arg
                405                 410                 415

Lys Gln Gln Glu Arg Glu Gln Arg Arg His Tyr Glu Glu Gln Met Arg
            420                 425                 430

Arg Glu Glu Glu Arg Arg Arg Ala Glu His Glu Gln Glu Tyr Lys Arg
        435                 440                 445

Lys Gln Leu Glu Glu Gln Arg Gln Ala Glu Arg Leu Gln Arg Gln Leu
    450                 455                 460

Lys Gln Glu Arg Asp Tyr Leu Val Ser Leu Gln His Gln Arg Gln Glu
465                 470                 475                 480

Gln Arg Pro Val Glu Lys Lys Pro Leu Tyr His Tyr Lys Glu Gly Met
                485                 490                 495

Ser Pro Ser Glu Lys Pro Ala Trp Ala Lys Glu Val Glu Glu Arg Ser
            500                 505                 510

Arg Leu Asn Arg Gln Ser Ser Pro Ala Met Pro His Lys Val Ala Asn
        515                 520                 525

Arg Ile Ser Asp Pro Asn Leu Pro Pro Arg Ser Glu Ser Phe Ser Ile
    530                 535                 540

Ser Gly Val Gln Pro Ala Arg Thr Pro Pro Met Leu Arg Pro Val Asp
545                 550                 555                 560

Pro Gln Ile Pro His Leu Val Ala Val Lys Ser Gln Gly Pro Ala Leu
                565                 570                 575

Thr Ala Ser Gln Ser Val His Glu Gln Pro Thr Lys Gly Leu Ser Gly
            580                 585                 590

Phe Gln Glu Ala Leu Asn Val Thr Ser His Arg Val Glu Met Pro Arg
        595                 600                 605

Gln Asn Ser Asp Pro Thr Ser Glu Asn Pro Pro Leu Pro Thr Arg Ile
    610                 615                 620

Glu Lys Phe Asp Arg Ser Ser Trp Leu Arg Gln Glu Glu Asp Ile Pro
625                 630                 635                 640

Pro Lys Val Pro Gln Arg Thr Thr Ser Ile Ser Pro Ala Leu Ala Arg
                645                 650                 655

Lys Asn Ser Pro Gly Asn Gly Ser Ala Leu Gly Pro Arg Leu Gly Ser
            660                 665                 670

Gln Pro Ile Arg Ala Ser Asn Pro Asp Leu Arg Arg Thr Glu Pro Ile
        675                 680                 685

Leu Glu Ser Pro Leu Gln Arg Thr Ser Ser Gly Ser Ser Ser Ser Ser
    690                 695                 700
```

```
Ser Thr Pro Ser Ser Gln Pro Ser Ser Gln Gly Gly Ser Gln Pro Gly
705                 710                 715                 720

Ser Gln Ala Gly Ser Ser Glu Arg Thr Arg Val Arg Ala Asn Ser Lys
                725                 730                 735

Ser Glu Gly Ser Pro Val Leu Pro His Glu Pro Ala Lys Val Lys Pro
            740                 745                 750

Glu Glu Ser Arg Asp Ile Thr Arg Pro Ser Arg Pro Ala Asp Leu Thr
        755                 760                 765

Ala Leu Ala Lys Glu Leu Arg Glu Leu Arg Ile Glu Glu Thr Asn Arg
    770                 775                 780

Pro Met Lys Lys Val Thr Asp Tyr Ser Ser Ser Ser Glu Glu Ser Glu
785                 790                 795                 800

Ser Ser Glu Glu Glu Glu Glu Asp Gly Glu Ser Glu Thr His Asp Gly
                805                 810                 815

Thr Val Ala Val Ser Asp Ile Pro Arg Leu Ile Pro Thr Gly Ala Pro
            820                 825                 830

Gly Ser Asn Glu Gln Tyr Asn Val Gly Met Val Gly Thr His Gly Leu
        835                 840                 845

Glu Thr Ser His Ala Asp Ser Phe Ser Gly Ser Ile Ser Arg Glu Gly
    850                 855                 860

Thr Leu Met Ile Arg Glu Thr Ser Gly Glu Lys Lys Arg Ser Gly His
865                 870                 875                 880

Ser Asp Ser Asn Gly Phe Ala Gly His Ile Asn Leu Pro Asp Leu Val
                885                 890                 895

Gln Gln Ser His Ser Pro Ala Gly Thr Pro Thr Glu Gly Leu Gly Arg
            900                 905                 910

Val Ser Thr His Ser Gln Glu Met Asp Ser Gly Thr Glu Tyr Gly Met
        915                 920                 925

Gly Ser Ser Thr Lys Ala Ser Phe Thr Pro Phe Val Asp Pro Arg Val
    930                 935                 940

Tyr Gln Thr Ser Pro Thr Asp Glu Asp Glu Glu Asp Glu Glu Ser Ser
945                 950                 955                 960

Ala Ala Ala Leu Phe Thr Ser Glu Leu Leu Arg Gln Glu Gln Ala Lys
                965                 970                 975

Leu Asn Glu Ala Arg Lys Ile Ser Val Val Asn Val Asn Pro Thr Asn
            980                 985                 990

Ile Arg Pro His Ser Asp Thr Pro  Glu Ile Arg Lys Tyr  Lys Lys Arg
        995                 1000                1005

Phe Asn  Ser Glu Ile Leu Cys  Ala Ala Leu Trp Gly  Val Asn Leu
    1010                1015                1020

Leu Val  Gly Thr Glu Asn Gly  Leu Met Leu Leu Asp  Arg Ser Gly
    1025                1030                1035

Gln Gly  Lys Val Tyr Asn Leu  Ile Asn Arg Arg Arg  Phe Gln Gln
    1040                1045                1050

Met Asp  Val Leu Glu Gly Leu  Asn Val Leu Val Thr  Ile Ser Gly
    1055                1060                1065

Lys Lys  Asn Lys Leu Arg Val  Tyr Tyr Leu Ser Trp  Leu Arg Asn
    1070                1075                1080

Arg Ile  Leu His Asn Asp Pro  Glu Val Glu Lys Lys  Gln Gly Trp
    1085                1090                1095

Ile Thr  Val Gly Asp Leu Glu  Gly Cys Ile His Tyr  Lys Val Val
    1100                1105                1110
```

-continued

```
Lys Tyr  Glu Arg Ile Lys Phe  Leu Val Ile Ala Leu  Lys Asn Ala
    1115                 1120                 1125

Val Glu  Ile Tyr Ala Trp Ala  Pro Lys Pro Tyr His  Lys Phe Met
    1130                 1135                 1140

Ala Phe  Lys Ser Phe Ala Asp  Leu Gln His Lys Pro  Leu Leu Val
    1145                 1150                 1155

Asp Leu  Thr Val Glu Glu Gly  Gln Arg Leu Lys Val  Ile Phe Gly
    1160                 1165                 1170

Ser His  Thr Gly Phe His Val  Ile Asp Val Asp Ser  Gly Asn Ser
    1175                 1180                 1185

Tyr Asp  Ile Tyr Ile Pro Ser  His Ile Gln Gly Asn  Ile Thr Pro
    1190                 1195                 1200

His Ala  Ile Val Ile Leu Pro  Lys Thr Asp Gly Met  Glu Met Leu
    1205                 1210                 1215

Val Cys  Tyr Glu Asp Glu Gly  Val Tyr Val Asn Thr  Tyr Gly Arg
    1220                 1225                 1230

Ile Thr  Lys Asp Val Val Leu  Gln Trp Gly Glu Met  Pro Thr Ser
    1235                 1240                 1245

Val Ala  Tyr Ile His Ser Asn  Gln Ile Met Gly Trp  Gly Glu Lys
    1250                 1255                 1260

Ala Ile  Glu Ile Arg Ser Val  Glu Thr Gly His Leu  Asp Gly Val
    1265                 1270                 1275

Phe Met  His Lys Arg Ala Gln  Arg Leu Lys Phe Leu  Cys Glu Arg
    1280                 1285                 1290

Asn Asp  Lys Val Phe Phe Ala  Ser Val Arg Ser Gly  Gly Ser Ser
    1295                 1300                 1305

Gln Val  Phe Phe Met Thr Leu  Asn Arg Asn Ser Met  Met Asn Trp
    1310                 1315                 1320

Glx


<210> SEQ ID NO 14
<211> LENGTH: 1298
<212> TYPE: PRT
<213> ORGANISM: Artificial Sequence
<220> FEATURE:
<223> OTHER INFORMATION: synthetic

<400> SEQUENCE: 14

Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Gly Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
        115                 120                 125

Trp Ile Ala Tyr Ile Cys Arg Glu Ile Leu Arg Gly Leu Ser His Leu
```

-continued

```
    130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Phe Lys Ser Asp Leu Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Lys Lys Lys Arg Gly Glu Lys Asp Glu Thr Glu
305                 310                 315                 320

Tyr Glu Tyr Ser Gly Ser Glu Glu Glu Glu Glu Glu Asn Asp Ser Gly
                325                 330                 335

Glu Pro Ser Ser Ile Leu Asn Leu Pro Gly Glu Ser Thr Leu Arg Arg
            340                 345                 350

Asp Phe Leu Arg Leu Gln Leu Ala Asn Lys Glu Arg Ser Glu Ala Leu
        355                 360                 365

Arg Arg Gln Gln Leu Glu Gln Gln Gln Arg Glu Asn Glu Glu His Lys
    370                 375                 380

Arg Gln Leu Leu Ala Glu Arg Gln Lys Arg Ile Glu Glu Gln Lys Glu
385                 390                 395                 400

Gln Arg Arg Arg Leu Glu Glu Gln Gln Arg Arg Glu Lys Glu Leu Arg
                405                 410                 415

Lys Gln Gln Glu Arg Glu Gln Arg Arg His Tyr Glu Glu Gln Met Arg
            420                 425                 430

Arg Glu Glu Glu Arg Arg Arg Ala Glu His Glu Gln Glu Tyr Ile Arg
        435                 440                 445

Arg Gln Leu Glu Glu Glu Gln Arg Gln Leu Glu Ile Leu Gln Gln Gln
    450                 455                 460

Leu Leu His Glu Gln Ala Leu Leu Leu Glu Tyr Lys Arg Lys Gln Leu
465                 470                 475                 480

Glu Glu Gln Arg Gln Ala Glu Arg Leu Gln Arg Gln Leu Lys Gln Glu
                485                 490                 495

Arg Asp Tyr Leu Val Ser Leu Gln His Gln Arg Gln Glu Gln Arg Pro
            500                 505                 510

Val Glu Lys Lys Pro Leu Tyr His Tyr Lys Glu Gly Met Ser Pro Ser
        515                 520                 525

Glu Lys Pro Ala Trp Ala Lys Glu Ile Pro His Leu Val Ala Val Lys
    530                 535                 540

Ser Gln Gly Pro Ala Leu Thr Ala Ser Gln Ser Val His Glu Gln Pro
545                 550                 555                 560
```

-continued

```
Thr Lys Gly Leu Ser Gly Phe Gln Glu Ala Leu Asn Val Thr Ser His
                565                 570                 575

Arg Val Glu Met Pro Arg Gln Asn Ser Asp Pro Thr Ser Glu Asn Pro
            580                 585                 590

Pro Leu Pro Thr Arg Ile Glu Lys Phe Asp Arg Ser Ser Trp Leu Arg
        595                 600                 605

Gln Glu Glu Asp Ile Pro Pro Lys Val Pro Gln Arg Thr Thr Ser Ile
    610                 615                 620

Ser Pro Ala Leu Ala Arg Lys Asn Ser Pro Gly Asn Gly Ser Ala Leu
625                 630                 635                 640

Gly Pro Arg Leu Gly Ser Gln Pro Ile Arg Ala Ser Asn Pro Asp Leu
                645                 650                 655

Arg Arg Thr Glu Pro Ile Leu Glu Ser Pro Leu Gln Arg Thr Ser Ser
            660                 665                 670

Gly Ser Ser Ser Ser Ser Ser Thr Pro Ser Ser Gln Pro Ser Ser Gln
        675                 680                 685

Gly Gly Ser Gln Pro Gly Ser Gln Ala Gly Ser Ser Glu Arg Thr Arg
    690                 695                 700

Val Arg Ala Asn Ser Lys Ser Glu Gly Ser Pro Val Leu Pro His Glu
705                 710                 715                 720

Pro Ala Lys Val Lys Pro Glu Glu Ser Arg Asp Ile Thr Arg Pro Ser
                725                 730                 735

Arg Pro Ala Asp Leu Thr Ala Leu Ala Lys Glu Leu Arg Glu Leu Arg
            740                 745                 750

Ile Glu Glu Thr Asn Arg Pro Met Lys Lys Val Thr Asp Tyr Ser Ser
        755                 760                 765

Ser Ser Glu Glu Ser Glu Ser Ser Glu Glu Glu Glu Glu Asp Gly Glu
    770                 775                 780

Ser Glu Thr His Asp Gly Thr Val Ala Val Ser Asp Ile Pro Arg Leu
785                 790                 795                 800

Ile Pro Thr Gly Ala Pro Gly Ser Asn Glu Gln Tyr Asn Val Gly Met
                805                 810                 815

Val Gly Thr His Gly Leu Glu Thr Ser His Ala Asp Ser Phe Ser Gly
            820                 825                 830

Ser Ile Ser Arg Glu Gly Thr Leu Met Ile Arg Glu Thr Ser Gly Glu
        835                 840                 845

Lys Lys Arg Ser Gly His Ser Asp Ser Asn Gly Phe Ala Gly His Ile
    850                 855                 860

Asn Leu Pro Asp Leu Val Gln Gln Ser His Ser Pro Ala Gly Thr Pro
865                 870                 875                 880

Thr Glu Gly Leu Gly Arg Val Ser Thr His Ser Gln Glu Met Asp Ser
                885                 890                 895

Gly Thr Glu Tyr Gly Met Gly Ser Ser Thr Lys Ala Ser Phe Thr Pro
            900                 905                 910

Phe Val Asp Pro Arg Val Tyr Gln Thr Ser Pro Thr Asp Glu Asp Glu
        915                 920                 925

Glu Asp Glu Glu Ser Ser Ala Ala Ala Leu Phe Thr Ser Glu Leu Leu
    930                 935                 940

Arg Gln Glu Gln Ala Lys Leu Asn Glu Ala Arg Lys Ile Ser Val Val
945                 950                 955                 960

Asn Val Asn Pro Thr Asn Ile Arg Pro His Ser Asp Thr Pro Glu Ile
                965                 970                 975
```

-continued

```
Arg Lys Tyr Lys Lys Arg Phe Asn Ser Glu Ile Leu Cys Ala Ala Leu
            980                 985                 990

Trp Gly Val Asn Leu Leu Val Gly  Thr Glu Asn Gly Leu  Met Leu Leu
        995                 1000                 1005

Asp Arg  Ser Gly Gln Gly Lys  Val Tyr Asn Leu Ile  Asn Arg Arg
    1010                 1015                 1020

Arg Phe  Gln Gln Met Asp Val  Leu Glu Gly Leu Asn  Val Leu Val
    1025                 1030                 1035

Thr Ile  Ser Gly Lys Lys Asn  Lys Leu Arg Val Tyr  Tyr Leu Ser
    1040                 1045                 1050

Trp Leu  Arg Asn Arg Ile Leu  His Asn Asp Pro Glu  Val Glu Lys
    1055                 1060                 1065

Lys Gln  Gly Trp Ile Thr Val  Gly Asp Leu Glu Gly  Cys Ile His
    1070                 1075                 1080

Tyr Lys  Val Val Lys Tyr Glu  Arg Ile Lys Phe Leu  Val Ile Ala
    1085                 1090                 1095

Leu Lys  Asn Ala Val Glu Ile  Tyr Ala Trp Ala Pro  Lys Pro Tyr
    1100                 1105                 1110

His Lys  Phe Met Ala Phe Lys  Ser Phe Ala Asp Leu  Gln His Lys
    1115                 1120                 1125

Pro Leu  Leu Val Asp Leu Thr  Val Glu Glu Gly Gln  Arg Leu Lys
    1130                 1135                 1140

Val Ile  Phe Gly Ser His Thr  Gly Phe His Val Ile  Asp Val Asp
    1145                 1150                 1155

Ser Gly  Asn Ser Tyr Asp Ile  Tyr Ile Pro Ser His  Ile Gln Gly
    1160                 1165                 1170

Asn Ile  Thr Pro His Ala Ile  Val Ile Leu Pro Lys  Thr Asp Gly
    1175                 1180                 1185

Met Glu  Met Leu Val Cys Tyr  Glu Asp Glu Gly Val  Tyr Val Asn
    1190                 1195                 1200

Thr Tyr  Gly Arg Ile Thr Lys  Asp Val Val Leu Gln  Trp Gly Glu
    1205                 1210                 1215

Met Pro  Thr Ser Val Ala Tyr  Ile His Ser Asn Gln  Ile Met Gly
    1220                 1225                 1230

Trp Gly  Glu Lys Ala Ile Glu  Ile Arg Ser Val Glu  Thr Gly His
    1235                 1240                 1245

Leu Asp  Gly Val Phe Met His  Lys Arg Ala Gln Arg  Leu Lys Phe
    1250                 1255                 1260

Leu Cys  Glu Arg Asn Asp Lys  Val Phe Phe Ala Ser  Val Arg Ser
    1265                 1270                 1275

Gly Gly  Ser Ser Gln Val Phe  Phe Met Thr Leu Asn  Arg Asn Ser
    1280                 1285                 1290

Met Met  Asn Trp Glx
    1295


<210> SEQ ID NO 15
<211> LENGTH: 1269
<212> TYPE: PRT
<213> ORGANISM: Artificial Sequence
<220> FEATURE:
<223> OTHER INFORMATION: synthetic

<400> SEQUENCE: 15

Met Ala Ser Asp Ser Pro Ala Arg Ser Leu Asp Glu Ile Asp Leu Ser
1               5                   10                  15
```

-continued

```
Ala Leu Arg Asp Pro Ala Gly Ile Phe Glu Leu Val Glu Leu Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Gly Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
        115                 120                 125

Trp Ile Ala Tyr Ile Cys Arg Glu Ile Leu Arg Gly Leu Ser His Leu
    130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Phe Lys Ser Asp Leu Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Lys Lys Lys Arg Gly Glu Lys Asp Glu Thr Glu
305                 310                 315                 320

Tyr Glu Tyr Ser Gly Ser Glu Glu Glu Glu Glu Glu Asn Asp Ser Gly
                325                 330                 335

Glu Pro Ser Ser Ile Leu Asn Leu Pro Gly Glu Ser Thr Leu Arg Arg
            340                 345                 350

Asp Phe Leu Arg Leu Gln Leu Ala Asn Lys Glu Arg Ser Glu Ala Leu
        355                 360                 365

Arg Arg Gln Gln Leu Glu Gln Gln Gln Arg Glu Asn Glu Glu His Lys
    370                 375                 380

Arg Gln Leu Leu Ala Glu Arg Gln Lys Arg Ile Glu Glu Gln Lys Glu
385                 390                 395                 400

Gln Arg Arg Arg Leu Glu Glu Gln Gln Arg Arg Glu Lys Glu Leu Arg
                405                 410                 415

Lys Gln Gln Glu Arg Glu Gln Arg Arg His Tyr Glu Glu Gln Met Arg
            420                 425                 430

Arg Glu Glu Glu Arg Arg Arg Ala Glu His Glu Gln Glu Tyr Lys Arg
```

-continued

```
        435                 440                 445

Lys Gln Leu Glu Glu Gln Arg Gln Ala Glu Arg Leu Gln Arg Gln Leu
    450                 455                 460

Lys Gln Glu Arg Asp Tyr Leu Val Ser Leu Gln His Gln Arg Gln Glu
465                 470                 475                 480

Gln Arg Pro Val Glu Lys Lys Pro Leu Tyr His Tyr Lys Glu Gly Met
                485                 490                 495

Ser Pro Ser Glu Lys Pro Ala Trp Ala Lys Glu Ile Pro His Leu Val
            500                 505                 510

Ala Val Lys Ser Gln Gly Pro Ala Leu Thr Ala Ser Gln Ser Val His
        515                 520                 525

Glu Gln Pro Thr Lys Gly Leu Ser Gly Phe Gln Glu Ala Leu Asn Val
    530                 535                 540

Thr Ser His Arg Val Glu Met Pro Arg Gln Asn Ser Asp Pro Thr Ser
545                 550                 555                 560

Glu Asn Pro Pro Leu Pro Thr Arg Ile Glu Lys Phe Asp Arg Ser Ser
                565                 570                 575

Trp Leu Arg Gln Glu Glu Asp Ile Pro Pro Lys Val Pro Gln Arg Thr
            580                 585                 590

Thr Ser Ile Ser Pro Ala Leu Ala Arg Lys Asn Ser Pro Gly Asn Gly
        595                 600                 605

Ser Ala Leu Gly Pro Arg Leu Gly Ser Gln Pro Ile Arg Ala Ser Asn
    610                 615                 620

Pro Asp Leu Arg Arg Thr Glu Pro Ile Leu Glu Ser Pro Leu Gln Arg
625                 630                 635                 640

Thr Ser Ser Gly Ser Ser Ser Ser Ser Ser Thr Pro Ser Ser Gln Pro
                645                 650                 655

Ser Ser Gln Gly Gly Ser Gln Pro Gly Ser Gln Ala Gly Ser Ser Glu
            660                 665                 670

Arg Thr Arg Val Arg Ala Asn Ser Lys Ser Glu Gly Ser Pro Val Leu
        675                 680                 685

Pro His Glu Pro Ala Lys Val Lys Pro Glu Glu Ser Arg Asp Ile Thr
    690                 695                 700

Arg Pro Ser Arg Pro Ala Asp Leu Thr Ala Leu Ala Lys Glu Leu Arg
705                 710                 715                 720

Glu Leu Arg Ile Glu Glu Thr Asn Arg Pro Met Lys Lys Val Thr Asp
                725                 730                 735

Tyr Ser Ser Ser Ser Glu Glu Ser Glu Ser Ser Glu Glu Glu Glu Glu
            740                 745                 750

Asp Gly Glu Ser Glu Thr His Asp Gly Thr Val Ala Val Ser Asp Ile
        755                 760                 765

Pro Arg Leu Ile Pro Thr Gly Ala Pro Gly Ser Asn Glu Gln Tyr Asn
    770                 775                 780

Val Gly Met Val Gly Thr His Gly Leu Glu Thr Ser His Ala Asp Ser
785                 790                 795                 800

Phe Ser Gly Ser Ile Ser Arg Glu Gly Thr Leu Met Ile Arg Glu Thr
                805                 810                 815

Ser Gly Glu Lys Lys Arg Ser Gly His Ser Asp Ser Asn Gly Phe Ala
            820                 825                 830

Gly His Ile Asn Leu Pro Asp Leu Val Gln Gln Ser His Ser Pro Ala
        835                 840                 845

Gly Thr Pro Thr Glu Gly Leu Gly Arg Val Ser Thr His Ser Gln Glu
    850                 855                 860
```

```
Met Asp Ser Gly Thr Glu Tyr Gly Met Gly Ser Ser Thr Lys Ala Ser
865                 870                 875                 880

Phe Thr Pro Phe Val Asp Pro Arg Val Tyr Gln Thr Ser Pro Thr Asp
                885                 890                 895

Glu Asp Glu Glu Asp Glu Glu Ser Ser Ala Ala Ala Leu Phe Thr Ser
            900                 905                 910

Glu Leu Leu Arg Gln Glu Gln Ala Lys Leu Asn Glu Ala Arg Lys Ile
        915                 920                 925

Ser Val Val Asn Val Asn Pro Thr Asn Ile Arg Pro His Ser Asp Thr
    930                 935                 940

Pro Glu Ile Arg Lys Tyr Lys Lys Arg Phe Asn Ser Glu Ile Leu Cys
945                 950                 955                 960

Ala Ala Leu Trp Gly Val Asn Leu Leu Val Gly Thr Glu Asn Gly Leu
                965                 970                 975

Met Leu Leu Asp Arg Ser Gly Gln Gly Lys Val Tyr Asn Leu Ile Asn
            980                 985                 990

Arg Arg Arg Phe Gln Gln Met Asp  Val Leu Glu Gly Leu  Asn Val Leu
        995                 1000                1005

Val Thr  Ile Ser Gly Lys Lys  Asn Lys Leu Arg Val  Tyr Tyr Leu
    1010                1015                1020

Ser Trp  Leu Arg Asn Arg Ile  Leu His Asn Asp Pro  Glu Val Glu
    1025                1030                1035

Lys Lys  Gln Gly Trp Ile Thr  Val Gly Asp Leu Glu  Gly Cys Ile
    1040                1045                1050

His Tyr  Lys Val Val Lys Tyr  Glu Arg Ile Lys Phe  Leu Val Ile
    1055                1060                1065

Ala Leu  Lys Asn Ala Val Glu  Ile Tyr Ala Trp Ala  Pro Lys Pro
    1070                1075                1080

Tyr His  Lys Phe Met Ala Phe  Lys Ser Phe Ala Asp  Leu Gln His
    1085                1090                1095

Lys Pro  Leu Leu Val Asp Leu  Thr Val Glu Glu Gly  Gln Arg Leu
    1100                1105                1110

Lys Val  Ile Phe Gly Ser His  Thr Gly Phe His Val  Ile Asp Val
    1115                1120                1125

Asp Ser  Gly Asn Ser Tyr Asp  Ile Tyr Ile Pro Ser  His Ile Gln
    1130                1135                1140

Gly Asn  Ile Thr Pro His Ala  Ile Val Ile Leu Pro  Lys Thr Asp
    1145                1150                1155

Gly Met  Glu Met Leu Val Cys  Tyr Glu Asp Glu Gly  Val Tyr Val
    1160                1165                1170

Asn Thr  Tyr Gly Arg Ile Thr  Lys Asp Val Val Leu  Gln Trp Gly
    1175                1180                1185

Glu Met  Pro Thr Ser Val Ala  Tyr Ile His Ser Asn  Gln Ile Met
    1190                1195                1200

Gly Trp  Gly Glu Lys Ala Ile  Glu Ile Arg Ser Val  Glu Thr Gly
    1205                1210                1215

His Leu  Asp Gly Val Phe Met  His Lys Arg Ala Gln  Arg Leu Lys
    1220                1225                1230

Phe Leu  Cys Glu Arg Asn Asp  Lys Val Phe Phe Ala  Ser Val Arg
    1235                1240                1245

Ser Gly  Gly Ser Ser Gln Val  Phe Phe Met Thr Leu  Asn Arg Asn
    1250                1255                1260
```

-continued

```
Ser Met  Met Asn Trp Glx
    1265


<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Arg Thr Val Leu Gly Val Ile Gly Asp
1               5


<210> SEQ ID NO 17
<211> LENGTH: 9
<212> TYPE: PRT
<213> ORGANISM: Artificial Sequence
<220> FEATURE:
<223> OTHER INFORMATION: synthetic

<400> SEQUENCE: 17

Arg Thr Ala Leu Gly Asp Ile Gly Asn
1               5


<210> SEQ ID NO 18
<211> LENGTH: 27
<212> TYPE: PRT
<213> ORGANISM: Rattus sp.

<400> SEQUENCE: 18

Tyr Met Thr Val Ser Ile Ile Asp Arg Phe Met Gln Asp Ser Cys Val
1               5                   10                  15

Pro Lys Lys Met Leu Gln Leu Val Gly Val Thr
            20                  25


<210> SEQ ID NO 19
<211> LENGTH: 28
<212> TYPE: PRT
<213> ORGANISM: Mus sp.

<400> SEQUENCE: 19

Lys Phe Arg Leu Leu Gln Glu Thr Met Tyr Met Thr Val Ser Ile Ile
1               5                   10                  15

Asp Arg Phe Met Gln Asn Ser Cys Val Pro Lys Lys
            20                  25


<210> SEQ ID NO 20
<211> LENGTH: 27
<212> TYPE: PRT
<213> ORGANISM: Mus sp.

<400> SEQUENCE: 20

Arg Ala Ile Leu Ile Asp Trp Leu Ile Gln Val Gln Met Lys Phe Arg
1               5                   10                  15

Leu Leu Gln Glu Thr Met Tyr Met Thr Val Ser
            20                  25


<210> SEQ ID NO 21
<211> LENGTH: 27
<212> TYPE: PRT
<213> ORGANISM: Mus sp.

<400> SEQUENCE: 21
```

-continued

```
Asp Arg Phe Leu Gln Ala Gln Leu Val Cys Arg Lys Lys Leu Gln Val
1               5                   10                  15

Val Gly Ile Thr Ala Leu Leu Leu Ala Ser Lys
            20                  25


<210> SEQ ID NO 22
<211> LENGTH: 18
<212> TYPE: PRT
<213> ORGANISM: Mus sp.

<400> SEQUENCE: 22

Met Ser Val Leu Arg Gly Lys Leu Gln Leu Val Gly Thr Ala Ala Met
1               5                   10                  15

Leu Leu


<210> SEQ ID NO 23
<211> LENGTH: 26
<212> TYPE: DNA
<213> ORGANISM: Artificial Sequence
<220> FEATURE:
<223> OTHER INFORMATION: synthetic

<400> SEQUENCE: 23

tgcgcttata ttccagaagt agagct                                            26


<210> SEQ ID NO 24
<211> LENGTH: 20
<212> TYPE: DNA
<213> ORGANISM: Artificial Sequence
<220> FEATURE:
<223> OTHER INFORMATION: synthetic

<400> SEQUENCE: 24

ctgtctctgc tcctcctcta                                                   20


<210> SEQ ID NO 25
<211> LENGTH: 10
<212> TYPE: PRT
<213> ORGANISM: Artificial Sequence
<220> FEATURE:
<223> OTHER INFORMATION: synthetic

<400> SEQUENCE: 25

Ala Tyr Pro Tyr Asp Val Pro Asp Tyr Ala
1               5                   10


<210> SEQ ID NO 26
<211> LENGTH: 31
<212> TYPE: DNA
<213> ORGANISM: Artificial Sequence
<220> FEATURE:
<223> OTHER INFORMATION: synthetic

<400> SEQUENCE: 26

agcttgcagc catcagggtt atggatgtca c                                      31


<210> SEQ ID NO 27
<211> LENGTH: 31
<212> TYPE: DNA
<213> ORGANISM: Artificial Sequence
<220> FEATURE:
<223> OTHER INFORMATION: synthetic

<400> SEQUENCE: 27

gtgacatcca taaccttgat ggctgcaagc t                                      31
```

<210> SEQ ID NO 28
<211> LENGTH: 9
<212> TYPE: PRT
<213> ORGANISM: Artificial Sequence
<220> FEATURE:
<223> OTHER INFORMATION: synthetic

<400> SEQUENCE: 28

Asp Tyr Lys Asp Asp Asp Asp Lys Gly
1 5

<210> SEQ ID NO 29
<211> LENGTH: 14
<212> TYPE: PRT
<213> ORGANISM: Artificial Sequence
<220> FEATURE:
<223> OTHER INFORMATION: synthetic

<400> SEQUENCE: 29

Ala Ser Met Glu Gln Lys Leu Ile Ser Glu Glu Asp Leu Asn
1 5 10

<210> SEQ ID NO 30
<211> LENGTH: 6
<212> TYPE: PRT
<213> ORGANISM: Artificial Sequence
<220> FEATURE:
<223> OTHER INFORMATION: synthetic

<400> SEQUENCE: 30

Pro Cys Pro Pro Ser Arg
1 5

<210> SEQ ID NO 31
<211> LENGTH: 6
<212> TYPE: PRT
<213> ORGANISM: Artificial Sequence
<220> FEATURE:
<223> OTHER INFORMATION: synthetic

<400> SEQUENCE: 31

Pro Arg Val Pro Val Arg
1 5

<210> SEQ ID NO 32
<211> LENGTH: 6
<212> TYPE: PRT
<213> ORGANISM: Artificial Sequence
<220> FEATURE:
<223> OTHER INFORMATION: synthetic

<400> SEQUENCE: 32

Pro Asn Leu Pro Pro Arg
1 5

<210> SEQ ID NO 33
<211> LENGTH: 6
<212> TYPE: PRT
<213> ORGANISM: Artificial Sequence
<220> FEATURE:
<223> OTHER INFORMATION: synthetic

<400> SEQUENCE: 33

Pro Lys Val Pro Gln Arg
1 5

<210> SEQ ID NO 34
<211> LENGTH: 1360
<212> TYPE: PRT
<213> ORGANISM: Artificial Sequence
<220> FEATURE:
<223> OTHER INFORMATION: synthetic

<400> SEQUENCE: 34

```
Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Gly Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
        115                 120                 125

Trp Ile Ala Tyr Ile Cys Arg Glu Ile Leu Arg Gly Leu Ser His Leu
    130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Phe Lys Ser Asp Leu Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Lys Lys Lys Arg Gly Glu Lys Asp Glu Thr Glu
305                 310                 315                 320

Tyr Glu Tyr Ser Gly Ser Glu Glu Glu Glu Glu Glu Asn Asp Ser Gly
                325                 330                 335

Glu Pro Ser Ser Ile Leu Asn Leu Pro Gly Glu Ser Thr Leu Arg Arg
            340                 345                 350

Asp Phe Leu Arg Leu Gln Leu Ala Asn Lys Glu Arg Ser Glu Ala Leu
        355                 360                 365
```

-continued

```
Arg Arg Gln Gln Leu Glu Gln Gln Gln Arg Glu Asn Glu Glu His Lys
    370                 375                 380

Arg Gln Leu Leu Ala Glu Arg Gln Lys Arg Ile Glu Glu Gln Lys Glu
385                 390                 395                 400

Gln Arg Arg Arg Leu Glu Glu Gln Gln Arg Arg Glu Lys Glu Leu Arg
                405                 410                 415

Lys Gln Gln Glu Arg Glu Gln Arg Arg His Tyr Glu Glu Gln Met Arg
            420                 425                 430

Arg Glu Glu Glu Arg Arg Arg Ala Glu His Glu Gln Glu Tyr Ile Arg
        435                 440                 445

Arg Gln Leu Glu Glu Glu Gln Arg Gln Leu Glu Ile Leu Gln Gln Gln
    450                 455                 460

Leu Leu His Glu Gln Ala Leu Leu Leu Glu Tyr Lys Arg Lys Gln Leu
465                 470                 475                 480

Glu Glu Gln Arg Gln Ala Glu Arg Leu Gln Arg Gln Leu Lys Gln Glu
                485                 490                 495

Arg Asp Tyr Leu Val Ser Leu Gln His Gln Arg Gln Glu Gln Arg Pro
            500                 505                 510

Val Glu Lys Lys Pro Leu Tyr His Tyr Lys Glu Gly Met Ser Pro Ser
        515                 520                 525

Glu Lys Pro Ala Trp Ala Lys Glu Val Glu Glu Arg Ser Arg Leu Asn
    530                 535                 540

Arg Gln Ser Ser Pro Ala Met Pro His Lys Val Ala Asn Arg Ile Ser
545                 550                 555                 560

Asp Pro Asn Leu Pro Pro Arg Ser Glu Ser Phe Ser Ile Ser Gly Val
                565                 570                 575

Gln Pro Ala Arg Thr Pro Pro Met Leu Arg Pro Val Asp Pro Gln Ile
            580                 585                 590

Pro His Leu Val Ala Val Lys Ser Gln Gly Pro Ala Leu Thr Ala Ser
        595                 600                 605

Gln Ser Val His Glu Gln Pro Thr Lys Gly Leu Ser Gly Phe Gln Glu
    610                 615                 620

Ala Leu Asn Val Thr Ser His Arg Val Glu Met Pro Arg Gln Asn Ser
625                 630                 635                 640

Asp Pro Thr Ser Glu Asn Pro Pro Leu Pro Thr Arg Ile Glu Lys Phe
                645                 650                 655

Asp Arg Ser Ser Trp Leu Arg Gln Glu Glu Asp Ile Pro Pro Lys Val
            660                 665                 670

Pro Gln Arg Thr Thr Ser Ile Ser Pro Ala Leu Ala Arg Lys Asn Ser
        675                 680                 685

Pro Gly Asn Gly Ser Ala Leu Gly Pro Arg Leu Gly Ser Gln Pro Ile
    690                 695                 700

Arg Ala Ser Asn Pro Asp Leu Arg Arg Thr Glu Pro Ile Leu Glu Ser
705                 710                 715                 720

Pro Leu Gln Arg Thr Ser Ser Gly Ser Ser Ser Ser Ser Ser Thr Pro
                725                 730                 735

Ser Ser Gln Pro Ser Ser Gln Gly Gly Ser Gln Pro Gly Ser Gln Ala
            740                 745                 750

Gly Ser Ser Glu Arg Thr Arg Val Arg Ala Asn Ser Lys Ser Glu Gly
        755                 760                 765

Ser Pro Val Leu Pro His Glu Pro Ala Lys Val Lys Pro Glu Glu Ser
    770                 775                 780

Arg Asp Ile Thr Arg Pro Ser Arg Pro Ala Ser Tyr Lys Lys Ala Ile
```

-continued

```
785                 790                 795                 800

Asp Glu Asp Leu Thr Ala Leu Ala Lys Glu Leu Arg Glu Leu Arg Ile
                805                 810                 815

Glu Glu Thr Asn Arg Pro Met Lys Lys Val Thr Asp Tyr Ser Ser Ser
            820                 825                 830

Ser Glu Glu Ser Glu Ser Ser Glu Glu Glu Glu Asp Gly Glu Ser
        835                 840                 845

Glu Thr His Asp Gly Thr Val Ala Val Ser Asp Ile Pro Arg Leu Ile
    850                 855                 860

Pro Thr Gly Ala Pro Gly Ser Asn Glu Gln Tyr Asn Val Gly Met Val
865                 870                 875                 880

Gly Thr His Gly Leu Glu Thr Ser His Ala Asp Ser Phe Ser Gly Ser
                885                 890                 895

Ile Ser Arg Glu Gly Thr Leu Met Ile Arg Glu Thr Ser Gly Glu Lys
            900                 905                 910

Lys Arg Ser Gly His Ser Asp Ser Asn Gly Phe Ala Gly His Ile Asn
        915                 920                 925

Leu Pro Asp Leu Val Gln Gln Ser His Ser Pro Ala Gly Thr Pro Thr
    930                 935                 940

Glu Gly Leu Gly Arg Val Ser Thr His Ser Gln Glu Met Asp Ser Gly
945                 950                 955                 960

Thr Glu Tyr Gly Met Gly Ser Ser Thr Lys Ala Ser Phe Thr Pro Phe
                965                 970                 975

Val Asp Pro Arg Val Tyr Gln Thr Ser Pro Thr Asp Glu Asp Glu Glu
            980                 985                 990

Asp Glu Glu Ser Ser Ala Ala Ala  Leu Phe Thr Ser Glu  Leu Leu Arg
        995                 1000                1005

Gln Glu  Gln Ala Lys Leu Asn  Glu Ala Arg Lys Ile  Ser Val Val
    1010                1015                1020

Asn Val  Asn Pro Thr Asn Ile  Arg Pro His Ser Asp  Thr Pro Glu
    1025                1030                1035

Ile Arg  Lys Tyr Lys Lys Arg  Phe Asn Ser Glu Ile  Leu Cys Ala
    1040                1045                1050

Ala Leu  Trp Gly Val Asn Leu  Leu Val Gly Thr Glu  Asn Gly Leu
    1055                1060                1065

Met Leu  Leu Asp Arg Ser Gly  Gln Gly Lys Val Tyr  Asn Leu Ile
    1070                1075                1080

Asn Arg  Arg Arg Phe Gln Gln  Met Asp Val Leu Glu  Gly Leu Asn
    1085                1090                1095

Val Leu  Val Thr Ile Ser Gly  Lys Lys Asn Lys Leu  Arg Val Tyr
    1100                1105                1110

Tyr Leu  Ser Trp Leu Arg Asn  Arg Ile Leu His Asn  Asp Pro Glu
    1115                1120                1125

Val Glu  Lys Lys Gln Gly Trp  Ile Thr Val Gly Asp  Leu Glu Gly
    1130                1135                1140

Cys Ile  His Tyr Lys Val Val  Lys Tyr Glu Arg Ile  Lys Phe Leu
    1145                1150                1155

Val Ile  Ala Leu Lys Asn Ala  Val Glu Ile Tyr Ala  Trp Ala Pro
    1160                1165                1170

Lys Pro  Tyr His Lys Phe Met  Ala Phe Lys Ser Phe  Ala Asp Leu
    1175                1180                1185

Gln His  Lys Pro Leu Leu Val  Asp Leu Thr Val Glu  Glu Gly Gln
    1190                1195                1200
```

```
Arg Leu  Lys Val Ile Phe Gly  Ser His Thr Gly Phe  His Val Ile
    1205                 1210                 1215

Asp Val  Asp Ser Gly Asn Ser  Tyr Asp Ile Tyr Ile  Pro Ser His
    1220                 1225                 1230

Ile Gln  Gly Asn Ile Thr Pro  His Ala Ile Val Ile  Leu Pro Lys
    1235                 1240                 1245

Thr Asp  Gly Met Glu Met Leu  Val Cys Tyr Glu Asp  Glu Gly Val
    1250                 1255                 1260

Tyr Val  Asn Thr Tyr Gly Arg  Ile Thr Lys Asp Val  Val Leu Gln
    1265                 1270                 1275

Trp Gly  Glu Met Pro Thr Ser  Val Ala Tyr Ile His  Ser Asn Gln
    1280                 1285                 1290

Ile Met  Gly Trp Gly Glu Lys  Ala Ile Glu Ile Arg  Ser Val Glu
    1295                 1300                 1305

Thr Gly  His Leu Asp Gly Val  Phe Met His Lys Arg  Ala Gln Arg
    1310                 1315                 1320

Leu Lys  Phe Leu Cys Glu Arg  Asn Asp Lys Val Phe  Phe Ala Ser
    1325                 1330                 1335

Val Arg  Ser Gly Gly Ser Ser  Gln Val Phe Phe Met  Thr Leu Asn
    1340                 1345                 1350

Arg Asn  Ser Met Met Asn Trp
    1355                 1360


<210> SEQ ID NO 35
<211> LENGTH: 1233
<212> TYPE: PRT
<213> ORGANISM: Artificial Sequence
<220> FEATURE:
<223> OTHER INFORMATION: synthetic

<400> SEQUENCE: 35

Met Ala Asn Asp Ser Pro Ala Lys Ser Leu Val Glu Ile Asp Leu Ser
1               5                   10                  15

Ser Leu Arg Asp Pro Ala Gly Ile Phe Glu Val Val Glu Leu Val Gly
            20                  25                  30

Asn Gly Thr Tyr Gly Gln Val Tyr Lys Gly Arg His Val Lys Thr Val
        35                  40                  45

Thr Ala Ala Ile Lys Val Met Asp Val Thr Gly Asp Glu Glu Glu Glu
    50                  55                  60

Ile Thr Leu Glu Ile Asn Met Leu Lys Lys Tyr Ser His His Arg Asn
65                  70                  75                  80

Ile Ala Thr Tyr Tyr Gly Ala Phe Ile Lys Lys Ser Pro Pro Gly His
                85                  90                  95

Asp Asp Gln Leu Trp Leu Val Met Glu Phe Cys Gly Ala Gly Ser Ile
            100                 105                 110

Thr Asp Leu Ile Val Asn Thr Lys Gly Asn Thr Leu Lys Glu Asp Trp
        115                 120                 125

Ile Ala Tyr Ile Ser Arg Glu Ile Leu Arg Gly Leu Ala His Leu His
    130                 135                 140

Ile His His Val Ile His Arg Asp Ile Lys Gly Gln Asn Val Leu Leu
145                 150                 155                 160

Thr Glu Asn Ala Glu Val Lys Leu Val Asp Phe Gly Val Ser Ala Gln
                165                 170                 175

Leu Asp Arg Thr Val Gly Arg Arg Asn Thr Phe Ile Gly Thr Pro Tyr
            180                 185                 190
```

-continued

```
Trp Met Ala Pro Glu Val Ile Ala Cys Asp Glu Asn Pro Asp Ala Thr
        195                 200                 205

Tyr Asp Tyr Arg Ser Asp Leu Trp Ser Cys Gly Ile Thr Ala Ile Glu
    210                 215                 220

Met Ala Glu Gly Cys Pro Pro Leu Cys Asp Met His Pro Met Arg Ala
225                 230                 235                 240

Leu Phe Leu Ile Pro Arg Asn Pro Pro Pro Arg Leu Lys Ser Lys Lys
                245                 250                 255

Trp Ser Lys Lys Phe Phe Ser Phe Ile Glu Gly Cys Leu Val Lys Asn
            260                 265                 270

Tyr Met Gln Arg Pro Ser Thr Glu Gln Leu Leu Lys His Pro Phe Ile
        275                 280                 285

Arg Asp Gln Pro Asn Glu Arg Gln Val Arg Ile Gln Leu Lys Asp His
    290                 295                 300

Ile Asp Arg Thr Arg Lys Lys Arg Gly Glu Lys Asp Glu Thr Glu Tyr
305                 310                 315                 320

Glu Tyr Ser Gly Ser Glu Glu Glu Glu Glu Glu Val Pro Glu Glu Gln
                325                 330                 335

Glu Gly Glu Pro Ser Ser Ile Val Asn Val Pro Gly Glu Ser Thr Leu
            340                 345                 350

Arg Arg Asp Phe Leu Arg Leu Gln Gln Glu Asn Lys Glu Arg Ser Glu
        355                 360                 365

Ala Leu Arg Arg Gln Gln Leu Ser Gln Glu Gln Leu Arg Glu Gln Glu
    370                 375                 380

Glu Tyr Lys Arg Gln Leu Leu Ala Glu Arg Gln Lys Arg Ile Glu Cys
385                 390                 395                 400

Gln Lys Glu Gln Arg Arg Arg Leu Glu Glu Gln Gln Arg Arg Glu Arg
                405                 410                 415

Glu Ala Arg Arg Gln Gln Glu Arg Glu Gln Arg Arg Arg Glu Gln Glu
            420                 425                 430

Glu Lys Arg Arg Leu Glu Glu Leu Glu Arg Arg Arg Lys Glu Glu Glu
        435                 440                 445

Glu Arg Arg Arg Ala Glu Glu Glu Arg Arg Arg Val Glu Arg Glu Gln
    450                 455                 460

Glu Tyr Ile Arg Arg Gln Leu Glu Glu Glu Gln Arg His Leu Glu Ile
465                 470                 475                 480

Leu Gln Gln Gln Leu Leu Gln Glu Gln Ala Met Leu Leu His Asp His
                485                 490                 495

Arg His Pro His Ala Gln Gln Gln Pro Pro Pro Pro Gln Gln Gln Asp
            500                 505                 510

Arg Ser Lys Pro Ser Ser His Ala Pro Glu Pro Lys Pro His Tyr Asp
        515                 520                 525

Pro Ala Asp Asn Ala Arg Glu Val Gln Trp Ser His Leu Ala Ser Leu
    530                 535                 540

Lys Asn Asn Val Ser Pro Val Ser Arg Ser His Ser Phe Ser Asp Val
545                 550                 555                 560

Pro Ser Lys Phe Ala Ala His His His Leu Arg Ser Gln Asp Pro Cys
                565                 570                 575

Pro Pro Ser Arg Ser Glu Gly Leu Ser Gln Ser Ser Asp Ser Lys Ser
            580                 585                 590

Glu Val Pro Glu Pro Thr Arg Gln Lys Ala Trp Ser Arg Ser Asp Ser
        595                 600                 605
```

-continued

```
Asp Glu Val Pro Pro Arg Val Pro Val Arg Thr Thr Ser Arg Ser Pro
    610                 615                 620

Val Leu Ser Arg Arg Asp Ser Pro Leu Gln Gly Gly Gly Asn Ser Gln
625                 630                 635                 640

Ala Gly Gln Arg Asn Ser Thr Ser Ser Ile Glu Pro Pro Leu Leu Trp
                645                 650                 655

Glu Arg Val Glu Lys Leu Val Pro Arg Pro Gly Ser Gly Ser Ser Ser
            660                 665                 670

Gly Ser Ser Asn Ser Gly Ser Gln Pro Gly Ser His Pro Cys Ser Gln
        675                 680                 685

Ser Gly Ser Gly Glu Arg Phe Arg Val Arg Ser Ser Ser Lys Ser Glu
    690                 695                 700

Gly Ser Pro Ser Pro Arg Gln Glu Ser Ala Ala Lys Lys Pro Asp Asp
705                 710                 715                 720

Lys Lys Glu Val Phe Arg Ser Leu Lys Pro Ala Gly Glu Val Asp Leu
                725                 730                 735

Thr Ala Leu Ala Lys Glu Leu Arg Ala Val Glu Asp Val Arg Pro Pro
            740                 745                 750

His Lys Val Thr Asp Tyr Ser Ser Ser Ser Glu Glu Ser Gly Thr Thr
        755                 760                 765

Asp Glu Phe Glu Glu Pro Val His Gln Glu Gly Ala Asp Asp Ser Thr
    770                 775                 780

Ser Gly Pro Glu Asp Thr Arg Ala Ala Ser Pro Asn Leu Ser Asn Gly
785                 790                 795                 800

Glu Thr Glu Ser Val Lys Thr Met Ile Val His Asp Asp Val Glu Ser
                805                 810                 815

Glu Pro Ala Met Thr Pro Ser Lys Glu Gly Thr Leu Ile Val Arg Gln
            820                 825                 830

Thr Gln Ser Ala Ser Ser Thr Leu Gln Lys His Lys Ser Ser Ser Ser
        835                 840                 845

Phe Thr Pro Asp Phe Thr Asp Pro Arg Leu Leu Leu Gln Ile Ser Pro
    850                 855                 860

Ser Gly Thr Thr Val Thr Ser Val Val Gly Phe Ser Cys Asp Gly Leu
865                 870                 875                 880

Arg Pro Glu Ala Ile Arg Gln Asp Pro Thr Arg Lys Gly Ser Val Val
                885                 890                 895

Asn Val Asn Pro Thr Asn Thr Arg Pro Gln Ser Asp Thr Pro Glu Ile
            900                 905                 910

Arg Lys Tyr Lys Lys Arg Phe Asn Ser Glu Ile Leu Cys Ala Ala Leu
        915                 920                 925

Trp Gly Val Asn Leu Leu Val Gly Thr Glu Ser Gly Leu Met Leu Leu
    930                 935                 940

Asp Arg Ser Gly Gln Gly Lys Val Tyr Pro Leu Ile Ser Arg Arg Arg
945                 950                 955                 960

Phe Gln Gln Met Asp Val Leu Glu Gly Leu Asn Val Leu Val Thr Ile
                965                 970                 975

Ser Gly Lys Lys Asp Lys Leu Arg Val Tyr Tyr Leu Ser Trp Leu Arg
            980                 985                 990

Asn Arg Ile Leu His Asn Asp Pro  Glu Val Glu Lys Lys  Gln Gly Trp
        995                 1000                 1005

Thr Thr  Val Gly Asp Leu Glu  Gly Cys Val His Tyr  Lys Val Val
    1010                 1015                 1020

Lys Tyr  Glu Arg Ile Lys Phe  Leu Val Ile Ala Leu  Lys Ser Ser
```

-continued

```
    1025                1030                1035

Val Glu  Val Tyr Ala Trp Ala  Pro Lys Pro Tyr His  Lys Phe Met
    1040                1045                1050

Ala Phe  Lys Ser Phe Gly Glu  Leu Leu His Lys Pro  Leu Leu Val
    1055                1060                1065

Asp Leu  Thr Val Glu Glu Gly  Gln Arg Leu Lys Val  Ile Tyr Gly
    1070                1075                1080

Ser Cys  Ala Gly Phe His Ala  Val Asp Val Asp Ser  Gly Ser Val
    1085                1090                1095

Tyr Asp  Ile Tyr Leu Pro Thr  His Ile Gln Cys Ser  Ile Lys Pro
    1100                1105                1110

His Ala  Ile Tyr Ile Leu Pro  Asn Thr Asp Gly Met  Glu Leu Leu
    1115                1120                1125

Val Cys  Tyr Glu Asp Glu Gly  Val Tyr Val Asn Thr  Tyr Gly Arg
    1130                1135                1140

Ile Thr  Lys Asp Val Val Leu  Gln Trp Gly Glu Met  Pro Thr Ser
    1145                1150                1155

Val Ala  Tyr Ile His Ser Asn  Gln Thr Met Gly Trp  Gly Glu Lys
    1160                1165                1170

Ala Ile  Glu Ile Arg Ser Val  Glu Thr Gly His Leu  Asp Gly Val
    1175                1180                1185

Phe Met  His Lys Arg Ala Gln  Arg Leu Lys Phe Leu  Cys Gly Arg
    1190                1195                1200

Asn Asp  Lys Val Phe Phe Ser  Ser Val Arg Ser Gly  Gly Ser Ser
    1205                1210                1215

Gln Val  Tyr Phe Met Thr Leu  Gly Arg Thr Ser Leu  Leu Ser Trp
    1220                1225                1230


<210> SEQ ID NO 36
<211> LENGTH: 6
<212> TYPE: PRT
<213> ORGANISM: Artificial Sequence
<220> FEATURE:
<223> OTHER INFORMATION: synthetic

<400> SEQUENCE: 36

Pro Pro Leu Pro Thr Arg
1               5
```